US007818181B2

(12) United States Patent  (10) Patent No.: US 7,818,181 B2
Green                      (45) Date of Patent:     Oct. 19, 2010

(54) MEDICAL PRACTICE PATTERN TOOL

(75) Inventor: Robert A. Green, Rochester, NY (US)

(73) Assignee: Focused Medical Analytics LLC, Rochester, NY (US)

( * ) Notice: Subject to any disclaimer, the term of this patent is extended or adjusted under 35 U.S.C. 154(b) by 1116 days.

(21) Appl. No.: 11/392,179

(22) Filed: Mar. 29, 2006

(65) Prior Publication Data

US 2007/0106533 A1    May 10, 2007

Related U.S. Application Data

(60) Provisional application No. 60/731,917, filed on Oct. 31, 2005.

(51) Int. Cl.
    G06Q 10/00    (2006.01)
    G06Q 50/00    (2006.01)
(52) U.S. Cl. ......................................................... 705/2
(58) Field of Classification Search .................. 705/2, 705/3, 4; 364/401
    See application file for complete search history.

(56) References Cited

U.S. PATENT DOCUMENTS

| 4,835,372 | A |   | 5/1989  | Combrich        |
|-----------|---|---|---------|-----------------|
| 5,359,509 | A |   | 10/1994 | Little          |
| 5,471,382 | A |   | 11/1995 | Tallman         |
| 5,544,044 | A |   | 8/1996  | Leatherman      |
| 5,557,514 | A | * | 9/1996  | Seare et al. ........ 705/2 |
| 5,583,758 | A |   | 12/1996 | McIlroy         |
| 5,764,923 | A |   | 6/1998  | Tallman         |
| 5,835,897 | A |   | 11/1998 | Dang            |
| 5,845,254 | A |   | 12/1998 | Lockwood        |
| 5,933,809 | A |   | 8/1999  | Hunt            |
| 5,953,704 | A |   | 9/1999  | McIlroy         |
| 5,964,700 | A |   | 10/1999 | Tallman         |
| 6,047,259 | A |   | 4/2000  | Campbell        |
| 6,049,794 | A |   | 4/2000  | Jacobs          |
| 6,061,657 | A |   | 5/2000  | Whiting-O'Keefe |
| 6,208,974 | B1 |  | 3/2001  | Campbell        |
| 6,223,164 | B1 |  | 4/2001  | Seare           |
| 6,282,531 | B1 |  | 8/2001  | Haughton        |
| 6,353,817 | B1 |  | 3/2002  | Jacobs          |
| 6,370,511 | B1 |  | 4/2002  | Dang            |
| 6,574,742 | B1 |  | 6/2003  | Jamroga         |
| 2001/0025137 | A1 | | 9/2001 | Webb           |
| 2002/0019753 | A1 | | 2/2002 | Boden          |
| 2002/0059080 | A1 | | 5/2002 | Kasirer        |

(Continued)

FOREIGN PATENT DOCUMENTS

WO    WO9117510 A1    11/1991

(Continued)

OTHER PUBLICATIONS

"Measuring Provider Efficiency Version 1.0"; Dec. 31, 2004; Bridges to Excellence & The Leapfrog Group.*

(Continued)

Primary Examiner—Gerald J. O'Connor
Assistant Examiner—John A Pauls
(74) Attorney, Agent, or Firm—Hiscock & Barclay, LLP

(57) ABSTRACT

The invention is a business process embodied in a software algorithm that determines difference in practice patterns among physicians for the main cost components of given conditions.

31 Claims, 8 Drawing Sheets

U.S. PATENT DOCUMENTS

| | | |
|---|---|---|
| 2002/0111826 A1 | 8/2002 | Potter |
| 2002/0120472 A1 | 8/2002 | Dvorak |
| 2002/0123909 A1 | 9/2002 | Salisbury |
| 2002/0165738 A1 | 11/2002 | Dang |
| 2002/0173987 A1 | 11/2002 | Dang |
| 2002/0173988 A1 | 11/2002 | Dang |
| 2002/0173989 A1 | 11/2002 | Dang |
| 2002/0173992 A1 | 11/2002 | Dang |
| 2003/0104470 A1 | 6/2003 | Fors |
| 2004/0006278 A1 | 1/2004 | Webb |
| 2004/0039600 A1 | 2/2004 | Kramer |
| 2004/0039710 A1 | 2/2004 | McMillan |
| 2004/0111291 A1 | 6/2004 | Dust |
| 2004/0128078 A1 | 7/2004 | Haughton |
| 2004/0128163 A1 | 7/2004 | Goodman |
| 2004/0172284 A1 | 9/2004 | Sullivan |
| 2004/0198354 A1 | 10/2004 | Pettine |
| 2005/0010446 A1 | 1/2005 | Lash |
| 2005/0057488 A1 | 3/2005 | White |
| 2005/0086076 A1 | 4/2005 | Dunn |
| 2005/0096785 A1 | 5/2005 | Moncrief |
| 2005/0177400 A1 | 8/2005 | Rosenfeld |
| 2005/0197545 A1 | 9/2005 | Hoggle |

FOREIGN PATENT DOCUMENTS

| | | |
|---|---|---|
| WO | WO9325990 A1 | 12/1993 |
| WO | WO9424929 A1 | 11/1994 |
| WO | WO9506993 A1 | 3/1995 |
| WO | WO9512857 A1 | 5/1995 |
| WO | WO9519604 A3 | 7/1995 |
| WO | WO9600423 A1 | 1/1996 |
| WO | WO9701141 A1 | 1/1997 |
| WO | WO9728445 A1 | 8/1997 |
| WO | WO9802837 A1 | 1/1998 |
| WO | WO9941653 A2 | 8/1999 |
| WO | WO9941653 A3 | 10/1999 |
| WO | WO0135310 A1 | 5/2001 |
| WO | WO0170103 A3 | 9/2001 |
| WO | WO0219221 A1 | 3/2002 |
| WO | WO0244994 A2 | 6/2002 |
| WO | WO02052483 A2 | 7/2002 |
| WO | WO02075612 A1 | 9/2002 |
| WO | WO03065179 A2 | 8/2003 |
| WO | WO2004111766 A2 | 12/2004 |
| WO | WO2005043440 A1 | 5/2005 |
| WO | WO2005062790 A2 | 7/2005 |
| WO | WO2005083619 A2 | 9/2005 |

OTHER PUBLICATIONS

Axene, David V. 'Challenges With Tiered Networks', Society of Actuaries Annual Meeting, New York, New York, Oct. 26, 2004; Retreived from the Internet: http://www.soa.org/files/pdf/056_bk_annual04.pdf.

Kravis, Thomas 'Tiered Networks', Society of Actuaries Annual Meeting, New York, New York, Oct. 26, 2004; Retreived from the Internet: http://www.soa.org/files/pdf/056_bk_annual04.pdf.

Wernicke, Mark D. 'Developing a Tiered Network', Society of Actuaries Annual Meeting, New York, New York, Oct. 26, 2004; Retreived from the Internet: http://www.soa.org/files/pdf/056_bk_annual04.pdf.

Damberg, Cheryl, et al. 'Advancing Physician Performance Measurement', Pacific Business Group on Health, San Francisco, California, Sep. 2005.

'Efficency Measurment Errors, [online] 2003 Cave Consulting Group [retrieved on Apr. 28, 2008]. Retrieved from: http://www.cavegroup.com/efficiency_measurement_errors.html.

Southern California Evidence-based Practice Center—RAND Corporation, Santa Monica, CA, "Identifying, Categorizing, and Evaluating Health Care Efficiency Measures", AHRQ Publication No. 8-0030, Apr. 2008, 214 pages.

Robert A. Greene, MD,FACP, et al., "Review of the Massachusetts Group Insurance Commission Physician Profiling and Network Tiering Plan", Nov. 17, 2006, 52 pages.

* cited by examiner

| Condition, ETG number | | |
|---|---|---|
| Responsible Costs | Rank | % Specialty Responsibility |
| Findings | | |
| Strategy Ideas | | |
| Potential savings | | |
| % of specialty potential savings | | |

Fig. 3

| Internal Medicine | Total cost in top ETGs: | $29,533,536 | % of responsible cost: | 32.5% | Total responsible cost: | $90,944,106 |
|---|---|---|---|---|---|---|
| Benign hypertension, w/o comorbidity, 0281 | | Non-insulin dependent diabetes, with comorbidity, 0029 | | Inflammation of the esophagus, w/o surgery, 0433 | | Insulin dependent diabetes, with comorbidity, 0027 | | Acute sinusitis, 0333 | |
| $5,597,343 | 1 | 6.2% | $5,372,615 | 2 | 5.9% | $3,455,824 | 3 | 3.8% | $2,662,353 | 4 | 2.9% | $2,361,658 | 5 | 2.6% |
| Findings Q5 Rxs CCB, ARB, combos | | Findings Glitazones make all the difference | | Findings PPIs make all the difference | | Findings | | Findings | |
| $1,500,000 | | $750,000 | | | | | | | |
| Family Practice | Total cost in top ETGs: | $12,475,365 | % of responsible cost: | 30.8% | Total responsible cost: | $40,546,870 |
| Non-insulin dependent diabetes, with comorbidity, 0029 | | Benign hypertension, w/o comorbidity, 0281 | | Acute sinusitis, 0333 | | Inflammation of the esophagus, w/o surgery, 0433 | | Tonsillitis, adenoiditis or pharyngitis, w/o surgery, 0331 |
| $1,757,134 | 1 | 4.3% | $1,627,762 | 2 | 4.0% | $1,405,923 | 3 | 3.5% | $1,342,028 | 4 | 3.3% | $1,324,530 | 5 | 3.3% |
| Findings | | Findings | | Findings | | Findings | | Findings | |
| Pediatrics | Total cost in top ETGs: | $16,357,295 | % of responsible cost: | 44.8% | Total responsible cost: | $36,499,904 |
| Tonsillitis, adenoiditis or pharyngitis, w/o surgery, 0331 | | Otitis media, w/o surgery, 0329 | | Uncomplicated neonatal management, 0780 | | Attention Deficit Disorder, 0101 | | Minor inflammation of skin & subcutaneous tissue, 0678 |
| $4,345,301 | 1 | 11.9% | $3,276,141 | 2 | 9.0% | $2,077,717 | 3 | 5.7% | $1,407,302 | 4 | 3.9% | $1,228,858 | 5 | 3.4% |
| Findings | | Findings | | Findings | | Findings | | Findings | |
| Ear, Nose, and Throat | Total cost in top ETGs: | $8,138,919 | % of responsible cost: | 63.6% | Total responsible cost: | $12,878,926 |
| Tonsillitis, adenoiditis or pharyngitis, with surgery, 0330 | | Chronic sinusitis, with surgery, 0334 | | Otitis media, with minor surgery, 0328 | | Chronic sinusitis, w/o surgery, 0335 | | Otitis media, w/o surgery, 0329 |
| $2,338,383 | 1 | 8.2% | $1,249,446 | 2 | 9.7% | $1,101,483 | 3 | 8.6% | $854,013 | 4 | 6.6% | $705,534 | 5 | 5.5% |
| Findings | | Findings | | Findings | | Findings | | Findings | |

Fig. 4

MEDICAL PRACTICE PATTERN TOOL

CROSS-REFERENCE TO RELATED APPLICATIONS

This application claims priority from U.S. Provisional Patent Application Ser. No. 60/731,917, filed Oct. 31, 2005.

FIELD OF THE INVENTION

This invention relates to computer-implemented processes for the analysis of medical practice.

BACKGROUND OF THE INVENTION

Conventional systems, such as the Episode Treatment Group (ETG) software by Symmetry Health Data System, Inc, various risk adjusters, and other measures of physician service use allow managed care organizations to find rates of utilization of given services, determine relative costs of physician care, and bucket costs into categories such as office visits, pharmacy, and facility use. The conventional systems thus might show that there are differences between medical providers, such as one might be more expensive than another; however, they do not take the necessary steps to address what a managed care organization should work on in order to decrease costs of medical care and improve quality. The conventional systems do not identify what the specific cost drivers are that cause differences between the medical providers. Further, the conventional systems do not present data in a way that is clinically relevant and easy to present in graphic form to facilitate the discussion of medical appropriateness and allow clinical judgment as to whether the service is under utilized, over utilized, or mis-used, based on medical evidence for or against the service in question. In other words, the conventional systems do not connect cost containment to quality improvement.

The conventional approaches therefore require a priori hypotheses about cost drivers and then extensive drilldowns and other data analysis to discover the cost drivers. The user must ask specific questions, hypothesizing which services might be cost drivers, for example: "Find out if lab testing is a factor in hypertension care, and then find which tests and who is using them." Such analyses typically take a number of hundred person-hours of work, develop over a time frame of weeks to months, and may lead down dead ends. For example, an analysis of hypertension cost drivers took approximately four weeks in real time to complete, and found that pharmacy was the only factor differentiating costs of care among physicians. A comprehensive analysis investigating the cost drivers for a plurality of conditions in a number of different specialties would be quite cumbersome using the conventional methods and the results would likely be out of date when the analysis is completed.

Several references are related to the evaluation and comparison of healthcare providers according to costs, quality of care, and effectiveness. Some of the references are related to determining the proper treatment for a patient. For instance, PCT publication number WO 96/00423 A1 by MEDICODE, INC. compares individual medical practitioners or a group of medical practitioners against a statistical norm or trend. The comparison is made by converting medical providers billing data into a historical database. The application also discusses the determination of episodes of care and providing reports on the results. The application does not compare the services performed by the medical providers to determine what services stand out as the cause for the differences between the medical providers or the groups of medical providers.

U.S. Application publication No. 2002/0111826 A1 by Potter, et al. compares actual costs of episodes of care against budgeted costs to evaluate medical practitioners and to manage health care costs. Potter, et al. does not teach a timely and comprehensive analysis investigating the underlying cost drivers for a plurality of conditions in a number of different specialties.

U.S. Pat. No. 5,845,254, issued to Lockwood, et al., teaches a process of determining cost effectiveness of physicians in a group and the qualitative performance level of the group by adjusting the episodes of care by severity. Lockwood, et al. does not identify the cost drivers that cause differences between medical providers.

PCT Publication number WO 91/17510 A1 by HEALTHCHEX, INC. describes a means for processing health care services information relative to certain clinical variables, including age, gender, and diagnosis, and then ranking the data into orders of clinical complexity. The system then determines systematic relationships between medical services rendered to patients, clinical complexity, and cost. The system does not determine what the specific cost drivers are that cause differences between medical providers, nor does it address what an managed care organization should do to decrease costs of medical care and improve quality.

A family of U.S. applications and patents and a PCT application based on U.S. Pat. No. 5,835,897, issued to Dennis K. Dang teaches computer-implemented processes of determining the cost-efficiency and service quality of health care providers. The references in the family discuss episode treatment groups (ETGs) and the ETG grouper software. The application does not compare the services performed by the health care providers to determine what services stand out as the cause for the differences between the health care providers or the groups of health care providers.

U.S. application publication No. 2004/0111291 A1 by Dust, et al. teaches a process of identifying patients likely to generate high cost health care and sending patients to proper health care providers to meet certain requirements set by an employer that provides health care benefits. The method does not identify cost drivers for a plurality of conditions in a number of different specialties.

PCT publication number WO 95/19604 A3 by INFORMED ACCESS SYSTEMS, INC. teaches a process for selecting the appropriate treatment for a patient. The publication does not require a diagnosis; the process sorts potential patients into those that do not need professional medical care and those that do. The level and type of care is then determined for those that need treatment. The process does not compare the costs associated with treatments it recommends to determine the differences between groups of medical providers. Further, the publication does not teach a process for recommending particular services for treating a patient with a particular diagnosis.

PCT publication number WO 99/41653 A2 by IAMETER, INCORPORATED and associated U.S. Pat. No. 6,061,657 teach a process for treating a particular patient for a particular illness including the estimation of charges for the treatment and keeping the actual cost of the treatment close to the estimate. The publication does not teach the identification of specific cost drivers that cause differences between medical providers. The publication also does not provide a medical practice blueprint that includes a timely analysis of several conditions in several specialties that can be used to provide recommendations regarding certain practice patterns.

U.S. Pat. No. 6,223,164, issued to Seare, et al., teaches a system for analyzing historical medical provider billings to statistically establish a normative utilization profile wherein a medical provider's utilization profile is compared with a normative profile. Seare creates a model of the cost of a specific medical episode based on historical treatment patterns and a fee schedule and compares various treatment patterns for a particular diagnosis to the model to determine an allegedly cost-effective treatment approach. Seare also identifies medical providers who provide treatment that does not fall within the statistically established treatment patterns or profiles. Seare does not find the general practice patterns and does not describe the specific differences between the treatment patterns and the models.

Therefore, what is needed is a medical practice analysis tool that efficiently uncovers the true underlying cost drivers. Further what is needed is a tool that can provide a timely analysis of several conditions in several specialties to develop a medical practice blueprint, recommending certain practice patterns over others for the several conditions and specialties.

SUMMARY OF THE INVENTION

The invention comprises, in one form thereof, an algorithm that allows the discovery of the medical practice pattern of physicians or other practitioners stratified according to predefined criteria. For example, the practitioners are stratified according to those who are low, medium, and high users of resources for a given condition. Its input is episodes of care generated by episode grouping software, such as the Episode Treatment Grouper™ of Symmetry Health Data System, Inc. Its output is a series of tables and graphs showing the cost drivers for each stratum of practitioners (e.g. by low to high cost quintiles) and their variation from stratum to stratum.

The invention sifts through the costs at the service level and then shows which services are the significant factors for the condition of interest. The invention readily discovers those while conventional systems require testing of multiple hypotheses and potentially could miss the true cost drivers unless the appropriate questions were asked in the first place. Using conventional systems, a typical analysis of a single condition takes weeks, as noted above. A full analysis using the present invention could be produced in less than 30 minutes with automated formatting of the output data.

The inputs and outputs of the invention are clinically relevant and easy to present in graphic form. This facilitates the discussion of medical appropriateness and allows clinical judgment as to whether the service is under utilized, over utilized, or misused, based on medical evidence for or against the service in question. Therefore the invention allows the connection of cost containment to quality improvement.

The invention includes a method of practice pattern analysis for medical professionals. The method comprises the steps of defining a plurality of episodes of care from any database of medical services organized into episodes of care for a plurality of medical professionals, assigning the medical professionals into strata according to a given characteristic for the defined episodes, recording all medical services provided for each of the episodes of care, normalizing the number of medical services provided and costs by the number of episodes of care in the plurality of episodes, removing all the services having a particular value under a threshold to remove anomalous data, and generating a report of the actual medical services and costs versus a set of expected medical services and costs for each stratum of medical professionals, wherein the report is normalized to the number of episodes of care in the stratum.

More particularly, the invention includes a method of managing medical care performed by a group of medical practitioners. The method comprises the steps of compiling a plurality of episodes of care comprising a plurality of services provided by each practitioner in the group of practitioners; sorting the medical practitioners into strata according to a predefined criterion; and listing the services associated with the medical practitioners in each stratum with a selected service value being included with each of the services. An additional step comprises one of the following: assembling a list of services having a threshold parameter above a threshold defined such that only services that have a significant impact on the selected service value are preserved or comparing an actual selected service value to an expected selected service value for each of the services in each stratum. For the purposes of this description, the selected service value is defined as either the service cost total for all the episodes in each stratum or the service utilization total for all the episodes in each stratum. Other service values may be used in alternative embodiments. The threshold parameter is related to the selected service value. For example, the threshold parameter is equal to the selected service value or a normalized selected service value. The medical practitioners are associated with all the services in the episodes that the practitioner had a significant role for a total role analysis. The step of assembling services includes the steps of determining the threshold parameter for each service by dividing the selected service value in each stratum by the number of episodes in that stratum; setting the minimum threshold for the threshold parameter; and storing the services having a threshold parameter above the threshold in a potential cost drivers table. The step of assembling services may also include the steps of determining an expected selected service value for each of the services in each of the episodes of care; evaluating a threshold parameter by subtracting the selected service values in each stratum from the expected selected service value and dividing the difference by the number of episodes in that stratum; setting the minimum threshold for the threshold parameter; and storing the services having a per episode service value difference above the threshold in a potential cost drivers table.

The threshold parameter may also be evaluated by setting it equal to the selected service value for each service in each stratum, e.g.: the threshold parameter would equal the total cost of a service in each stratum or the total utilization of a service in each stratum. Alternatively, the threshold parameter is determined for each service in each stratum by dividing the service cost total for all the episodes in that stratum by the service utilization total for all the episodes in that stratum. In a further alternative, the threshold parameter is evaluated by subtracting the selected service values in each stratum from the expected selected service value.

The method may further comprise the steps of generating a report comparing among the strata the selected service values for the services in the potential cost drivers table; identifying the service that differentiates the strata; and providing the medical practitioners with a description of how to reduce the difference between the strata. The expected selected service value determination step may include the steps of totaling the selected service value for each service for all the episodes in the analysis to provide an analysis total of the selected service value; determining an analysis average for the selected service value of each service by dividing the analysis total of the selected service value by the sum of the episodes in the analysis; and multiplying the analysis average of the selected service value by the number of episodes in each stratum for each service to provide the expected selected service value. The step of compiling a plurality of episodes may include tracking each service by episodes of care performed by a group of medical practitioners; aggregating the medical services according to given characteristics; and sorting the episodes of care into predefined conditions. Particularly, the episodes of care may be formed using the Symmetry ETG grouper software. The condition analyzed in the method may be a complete ETG, a combination of ETGs, a subset of an ETG, or a combination of subsets of a plurality of ETGs.

The medical practitioners may be separated into strata according to several criteria including, but not limited to, cost, the number of services performed, performance in another condition, geographic region, specialty, type of practice, and size of practice. Medical practitioners having an anomalous selected service value may be removed from the analysis group. The practitioners may be attributed to the episodes according to a number of attribution rules. For example, the practitioner attributed to an episode may be the practitioner with the highest percentage of professional costs of the episode, the practitioner with the highest percentage of generated costs of the episode, all practitioners in the episode who contributed more than a preset percentage of the cost to the episode, a primary care physician associated with the episode, all practitioners with any involvement in the episode, the practitioner that performed a significant procedure in the episode, the practitioner that had the most face-to-face encounters with a patient associated with the episode, or combinations thereof.

An additional analysis includes the further step of analyzing the practice pattern of an individual practitioner in a total role drilldown analysis of a single medical condition. Similarly, the analysis may include the further step of analyzing the practice pattern of an individual practitioner in a total role MPPT meta-drilldown analysis including data from a plurality of medical conditions.

Further, the invention includes a method for providing a group of medical providers with guidelines for decreasing underuse, overuse, or misuse of medical services. The method comprises the steps of identifying a number of medical conditions performed by the group of medical providers; performing a medical practice pattern analysis; analyzing the results of the medical practice pattern analysis to identify a number of cost drivers that differentiate the strata in each condition; and providing the medical practitioners with a description of how to reduce the difference in the cost drivers between the strata in each condition. The step of performing a medical practice pattern analysis includes the further steps of identifying a plurality of episodes of care for the medical providers for a given condition and a plurality of medical services utilized in each episode of care; calculating a total episode cost for each episode of care; organizing the episodes of care into conditions with given characteristics; separating the medical providers for each conditions into strata by a given characteristic; executing a normalizing algorithm in each stratum for each condition with a threshold to identify and remove anomalous services in the episode of care; and producing a report showing a plurality of cost drivers and comparing the main cost drivers between the strata for each episode grouping.

Even further, the invention includes a medical practice pattern analysis report, comprising tables and graphs of a selected service value for a service for a plurality of strata, wherein the selected service value is greater than a threshold set to remove a plurality of other services having a less significant effect on a particular difference between the strata. The selected service value may include, but is not limited to, an absolute cost per episode of the service, an absolute service utilization per episode, a cost difference per episode, a service utilization difference per episode, and a service cost per utilization. A plurality of medical practitioners are attributed to a plurality of episodes including the services, and the strata are defined by a criterion that may include the average cost, average service utilization, performance in another condition, geographic region, specialty, type of practice, and size of practice of the medical practitioners responsible for the services. The graph may display a service that drives the difference between the strata as well as the selected service values for a plurality of services, wherein the selected service values are greater than the threshold.

Still further, the invention includes a medical method blueprint, comprising a plurality of cells, each describing a treatment recommendation for a particular type of episode of care, wherein the recommendation is based on a medical practice pattern analysis that revealed a service as a driver for a difference between a plurality of stratified medical practitioners. The cells may be grouped by specialty. The medical practitioners are stratified by a criterion that may include the average cost, average service utilization, geographic region, specialty, type of practice, and size of practice of the medical practitioners responsible for the services.

The advantages of the algorithm are therefore manifold: first, it uncovers the true underlying cost drivers, and second it does so quickly. Utilization of the algorithm would allow analysis of the top 20 conditions of the 20 largest specialties (400 analyses) in a few hundred person-hours. Conventional methods have been too cumbersome to allow such a systematic analysis. A similar analysis with current techniques could take years, by which time the results would be outdated. Lastly, because of its process of database set up at the front end, the algorithm is not limited to a single episode grouping. Rather, the analysis can be carried out across multiple episode groupings, and even across combinations of episode groupings and subsets of episode groupings.

BRIEF DESCRIPTION OF THE DRAWINGS

The present invention is disclosed with reference to the accompanying drawings, wherein:

FIG. 3 is a blueprint cell according to the present invention;

FIG. 4 is a portion of the medical management blueprint of the present invention;

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
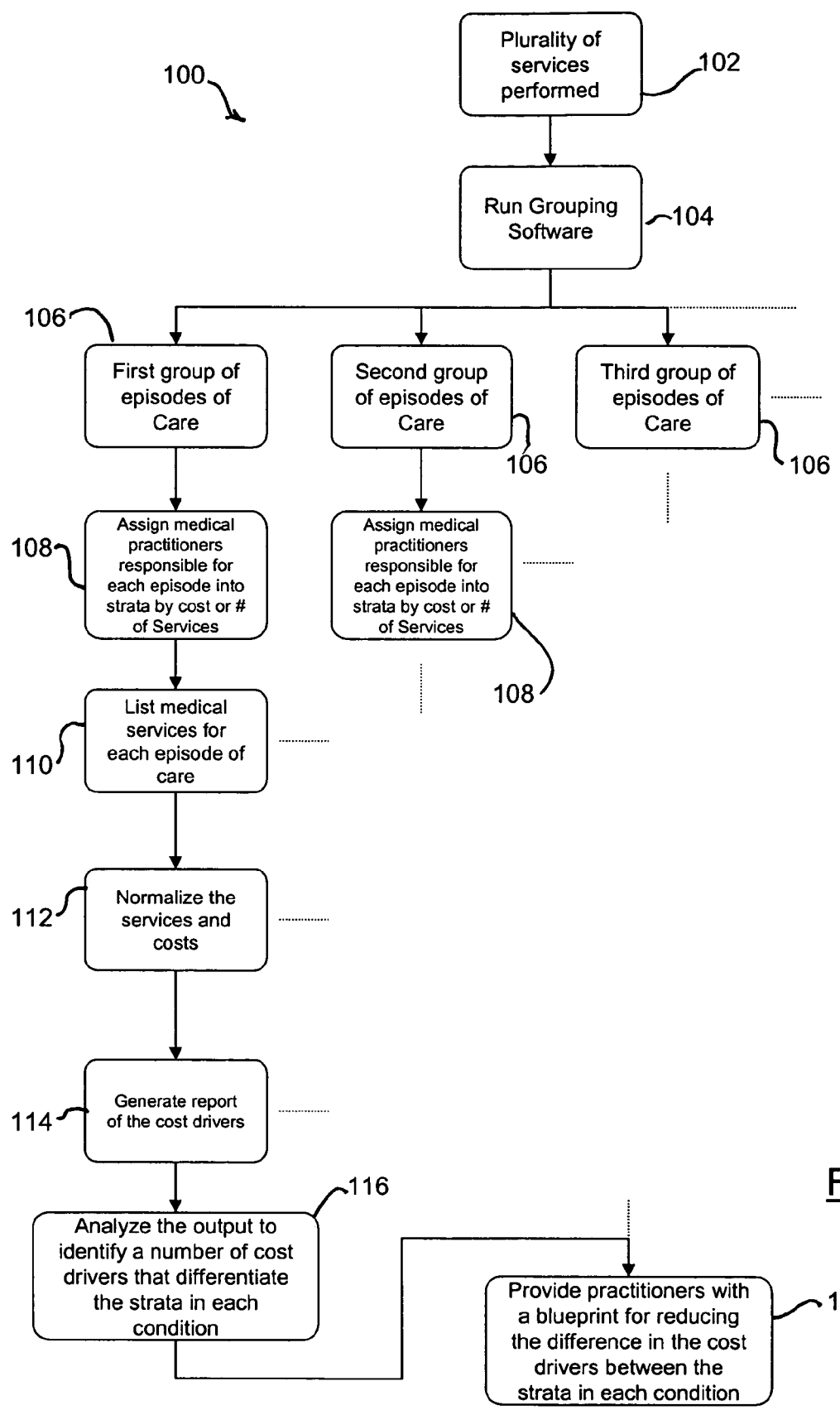
FIG. 1 is a flow diagram of the general process of the present invention.

Referring to FIG. 1, there is shown a flow diagram of the medical practice pattern tool of the present invention. The medical practice pattern tool 100 includes the steps of inputting the services 102 performed by a plurality of medical practitioners into a grouping protocol 104, which identifies episodes of care comprised of the services and groups them into the episodes of care according to a medical services database. The grouping protocol 104 outputs several groups of episodes of care 106 and step 108 assigns medical practitioners into strata by cost or by the number of services performed. Step 110 lists the medical services performed in each episode of care within each stratum. Step 112 analyzes the services by generating an average cost and utilization per stratum, calculating the average cost and utilization per episode across all strata, generating expected cost and utilization for each service according to that average number and the total number of episodes in the service's stratum, generating total cost and utilization differences per episode for each service in each stratum, and removing all services where costs and/or utilization absolute values or differences from expected are below a threshold. In step 114, a report is generated showing the key cost drivers and differences from expected values, which are services having a total cost or utilization absolute value or difference per episode that is greater than or equal to a threshold value. In one embodiment, the reports are output in tables and bar graphs.

More particularly, the medical practice pattern tool 100 tracks services performed by medical practitioners in a given region, specialty, or combination thereof in steps 102 and 104. A medical practitioner is defined as any person that provides care to a patient, including but not limited to physicians, doctors, anesthesiologists, nurse practitioners, nurses, technicians such as radiology technicians, and therapists. In an alternative embodiment, medical practitioner is expanded to medical providers, which may include medical facilities such as clinics and hospitals. The services provided include any care provided to a patient, such as office visits, radiology, pharmaceuticals, and vaccinations. Step 104 assigns the services to episodes of care and determines the responsibility for each episode of care and sorts the episodes of care by pre-defined conditions. An episode of care is defined as all management, ancillary (including lab and radiology), pharmacy, inpatient facility, and surgical (i.e.: professional) services for one patient over a defined time period.

Step 104 may be carried out by any grouping protocol, such as, for example, the ETG grouper software by Symmetry Health Data System, Inc. This should not be construed to exclude other ETG groupers. The Symmetry ETG grouper is described in the family of patents based on U.S. Pat. No. 5,835,897 by Dennis K. Dang, which is herein incorporated by reference. According to Dang, an episode treatment group (ETG) is a clinically homogenous and statistically stable group of similar illness etiology and therapeutic treatment. The ETG grouper method uses service or segment-level claim data as input data and assigns each service to an appropriate episode of care. The Episode Treatment Grouper™ collects these services into an episode and assigns the episode to one of approximately 900 clinically homogeneous conditions or Episode Treatment Groups™ (ETGs™). Examples of ETGs include, for example, benign skin lesions (ETG 0682), allergic rhinitis (ETG 0332), benign hypertension without co-morbidity (ETG 0281), and joint derangement with surgery—knee and lower leg (ETG 0742.02).

ETGs gather all in-patient, ambulatory and ancillary claims into mutually exclusive treatment episodes (otherwise known as episodes of care), regardless of treatment duration, then use clinical algorithms to identify both concurrent and recurrent episodes. The ETG grouper continues to collect information until an absence of treatment is detected for a predetermined period of time commensurate with the episode. For example, a bronchitis episode will have a sixty day window, while a myocardial infarction may have a one year window. Subsequent records of the same nature within the window reset the window for an additional period of time until the patient is asymptomatic for the pre-determined time period.

ETGs can identify a change in the patient's condition and shift the patient's episode from the initially defined ETG to the ETG which includes the change in condition. ETGs identify all providers treating a single illness episode.

Medical claim data is input as data records by data entry into a computer storage device, such as a hard disk drive. The ETG grouper may reside in any of a number of computer system architectures, i.e., it may be run from a stand-alone computer or exist in a client-server system, for example a local area network (LAN) or wide area network (WAN). The ETG grouper and the medical practice pattern tool may be provided in a single software package and installed on a single workstation or server. Alternatively, the grouper and the medical practice pattern tool are separate modules. The grouper output, which is the medical practice pattern tool input, may even be provided by a third party.

Once relevant medical claim data is input, claims data is processed by loading the computer program into the computer system memory. During set-up of the program onto the computer system, the computer program will have previously set pointers to the physical location of the data files and look-up tables written to the computer storage device. Upon initialization of the computer program, the user is prompted to enter an identifier for a first patient. The program then checks for open episodes for the identified patient, sets flags to identify the open episodes and closes any episodes based upon a predetermined time duration from date of episode to current date. After all open episodes for a patient are identified, the new claims data records are read to memory and validated for type of provider, CPT code and ICD-9 (dx) code, then identified as a management, surgery, facility, ancillary, drug or other record. The CPT code is the American Medical Association's list of the Current Procedural Terminology; CPT-4 is the fourth version of this list. The ICD is the International Classification of Diseases published by the World Health Organization. ICD-9 is the ninth revision of this publication.

As used herein, "Management records" are defined as claims which represent a service by a provider engaging in the direct evaluation, management, or treatment of a patient. Examples of management records include office visits and therapeutic services. Management records serve as anchor records because they represent focal points in the patient treatment as well as for related ancillary services. "Ancillary records" are claims which represent services which are incidental to the direct evaluation, management and treatment of the patient. Examples of ancillary records include X-ray and laboratory tests. "Surgery records" are specific surgical professional fee claims. Surgery records also serve as anchor records. "Facility records" are claims for medical care facility usage. Examples of facility records include hospital room charges or outpatient surgical room charges. "Drug records" are specific for pharmaceutical prescription claims. "Other records" are those medical claim records that are not management, surgery, ancillary, facility or drug records.

Invalid records are flagged and logged to an error output file for the user. Valid records are then processed by an ETG Assignor Sub-routine and, based upon diagnosis code, are either matched to existing open episodes for the patient or serve to create new episodes.

Management and surgery records serve as "anchor records." An "anchor record" is a record that originates a diagnosis or a definitive treatment for a given medical condition. Management and surgery records serve as base reference records for facility, ancillary, and drug claim records relating to the diagnosis or treatment that is the subject of the management or surgery record. Only management and surgery records can serve to start a given episode.

If the record is a management record or a surgery record, the diagnosis code in the claim record is compared with prior related open episodes in an existing look-up table for a possible ETG match. If more than one open episode exists, the program selects the most recent open episode. A positive match signifies that the current episode is related to an existing open episode. After the match is determined, the time window is reset for an additional period of time corresponding to the episode. A loop shifts the originally assigned ETG based on the additional or subsequent diagnoses. If any of the additional or subsequent diagnoses is a defined co-morbidity diagnosis, the patient's co-morbidity file is updated. If no match between the first diagnosis code and an open episode is found, a new episode is created.

Grouping prescription drug records requires two tables, a NDC (National Drug Code) by GDC (Generic Drug Code) table and a GDC by ETG table. Because the NDC table has approximately 200,000 entries, it has been found impracticable to directly construct an NDC by ETG table. For this reason the NDC by GDC table serves as a translation table to translate NDCs to GDCs and construct a smaller table based upon GDCs. Reading, then from these tables, the NDC code in the claim data record is read and translated to a GDC code. The program then identifies all valid ETGs for the GDC codes in the claim data record then matches those valid ETGs with active episodes.

The output of the ETG grouper is one or more episode treatment groups, each comprising a list of all the episodes of care in the group. The services that make up the episodes and the practitioners responsible for the services are included in a table. Although the medical practice pattern tool 100 is described using the ETGs defined by Symmetry's ETG grouper, any grouper protocol may be used, such as the Medstat Episode Grouper by Thomson Medstat and the Cave Grouper by the Cave Consulting Group.

Figure 2A:
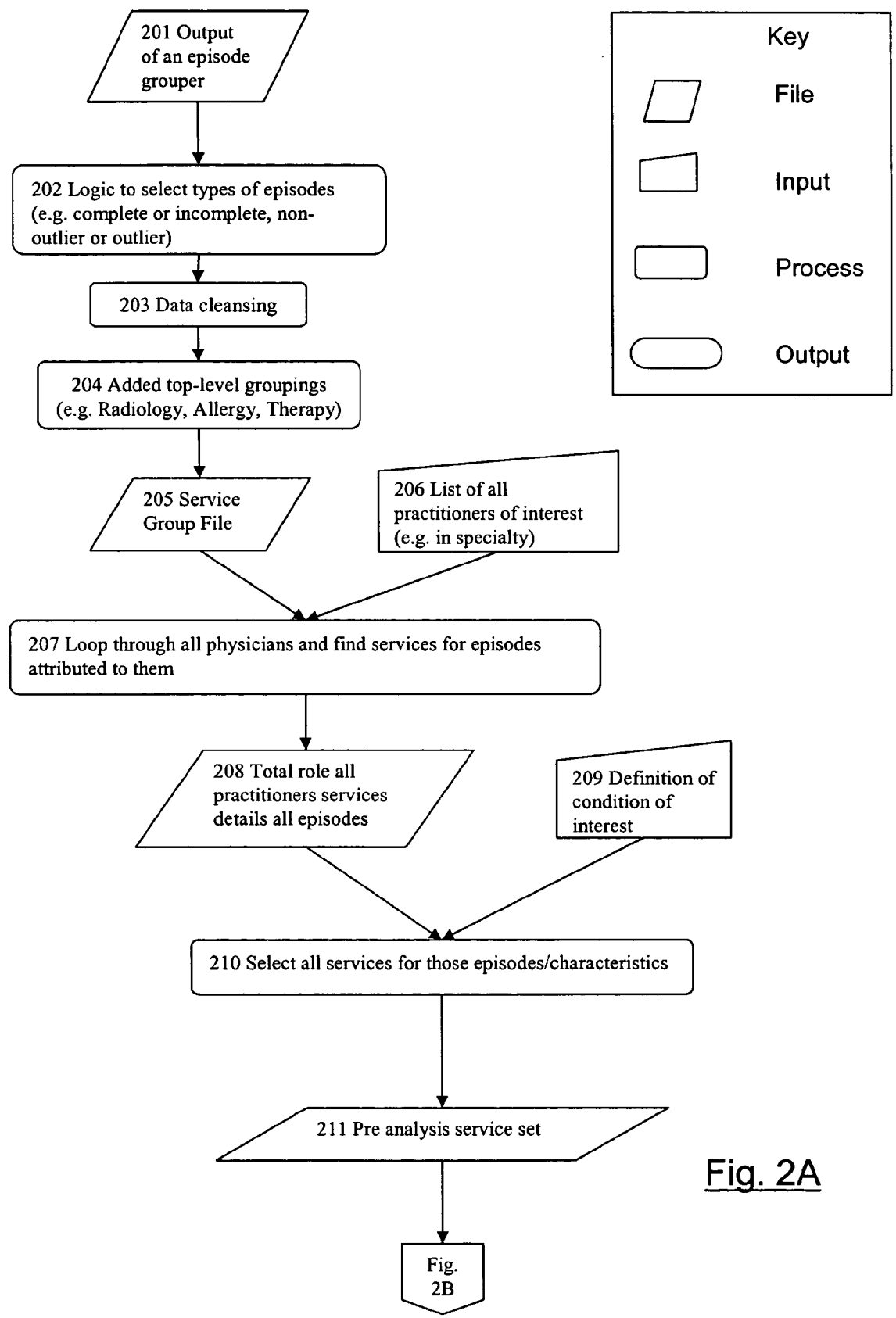
FIGS. 2A and 2B include a more detailed flow diagram of the medical practice pattern tool of the present invention.
Figure 2B:
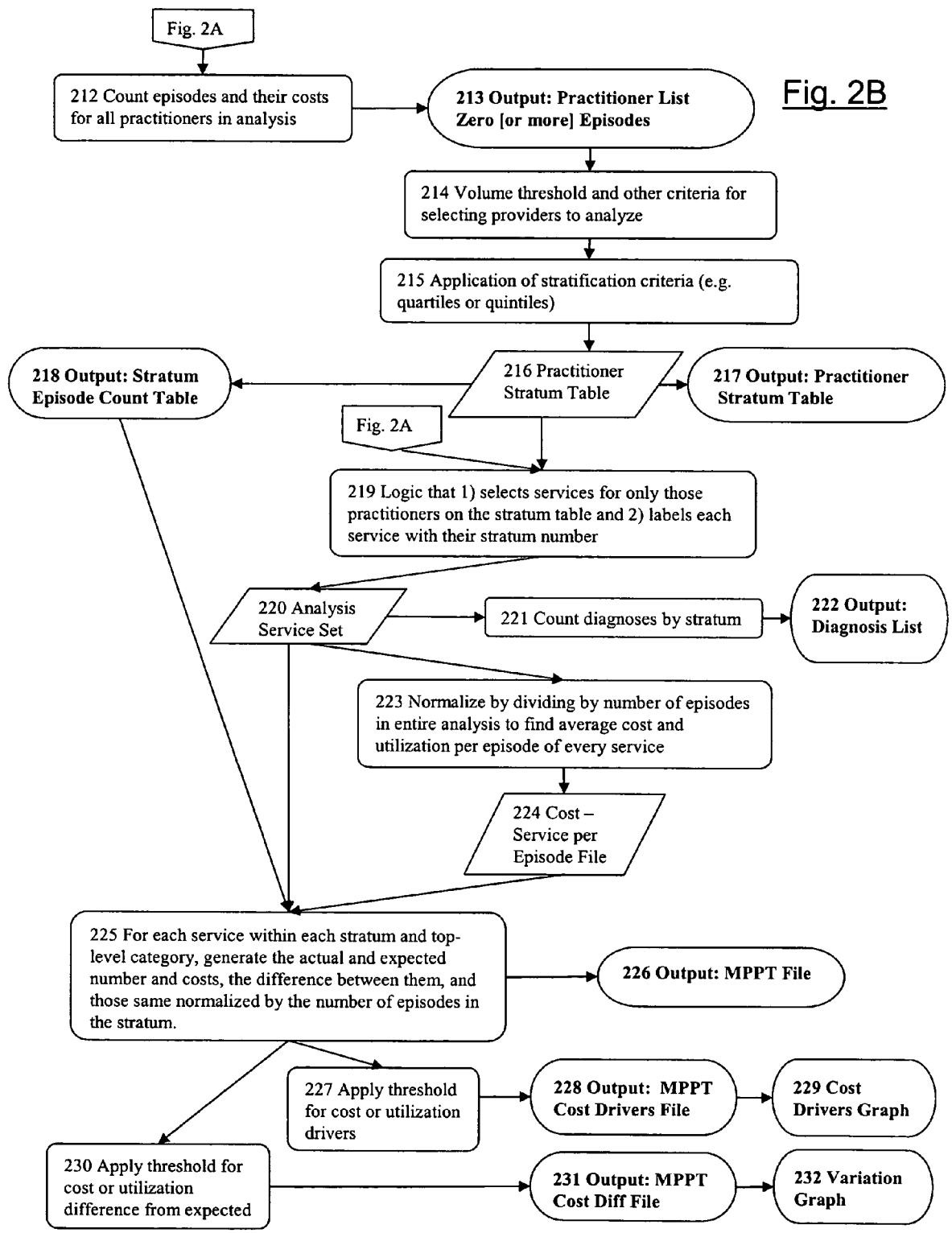

Referring to FIGS. 2A and 2B, the user selects the episodes according to certain general characteristics such as completeness or outlier status in step 202. Complete episodes are episodes in which the predetermined time window described above has passed. Outlier episodes are episodes which exceed given criteria for cost or service level. In the current embodiment, only complete episodes are used. Alternatively a user could choose to examine incomplete episodes or both complete and incomplete episodes. Similarly, in the current embodiment only non-outlier episodes are used. However, a user of the invention could choose to analyze high-cost outlier episodes, for example, in order to find the cost drivers in those episodes (i.e. to determine what made them outliers).

In step 203, the user performs data cleansing as necessary. For example, anesthesia services that are measured in minutes in one institution and in occurrences in another institution could all be converted to occurrences. In another example, outpatient surgery facility fees, which might vary from institution to institution, could be converted into uniform fees to better allow comparison based on utilization rather than particular contracting arrangements.

In step 204, the user performs high level service groupings. For example, the episode grouper may already have grouped services into ancillary costs, management fees, inpatient facility costs, pharmacy, and surgical professional fees. In the current embodiment, the invention assigns services so as to create the additional high level categories of radiology services, physical therapy services, and allergy services (production and administration of vaccine, commonly known as "allergy shots"). The output of step 204 is the service group file 205.

In step 206 the system finds all managing practitioners in the specialty or specialties of interest and creates a list of practitioner IDs. Alternatively a list of practitioners can be provided or created by other means such as by user input. A provider ID list produced by other commercial data processes also may be used for this step. It should be noted that a number of different specialties or practitioners from different specialties may be combined at the user's discretion in order to capture all the practitioners of interest. For example, there may be practitioners in different specialties that perform similar services. The percentage of involvement for each practitioner is calculated for each episode by cycling through each episode, finding and storing all practitioners associated with the episode, calculating and storing each practitioner's percentage of the total of the episode, and outputting a practitioner episode percentage table reporting the roles of the practitioners in each episode. The percentage of involvement is calculated by the total cost that the practitioner contributed to the episode or by the number of services the practitioner ordered in the episode. Alternatively to percentages, other measures of involvement may be used. Any attribution rule may be used to assign episodes to practitioners; however, it should be noted that a practitioner that is deemed to have had a significant role in an episode is assigned all the services in that episode regardless of whether that practitioner was responsible for the service, according to the current embodiment.

A number of alternative attribution rules are described in a white paper from Bridges to Excellence and The Leapfrog Group, "Measuring Provider Efficiency, Version 1.0" [online], Dec. 31, 2004 [retrieved on Jan. 17, 2006]. Retrieved from the Internet: <http://bridgestoexcellence.org/bte/pdf/Measuring_Provider_Efficiency_Versionl_12-31-20041.pdf> pages 38-41. The first method described in the white paper attributes an episode to the one practitioner with the highest percentage of the cost of the episode. This method will generally result in only one practitioner being attributed to an episode even when there are many treating practitioners. Further, the attributed practitioner may not have been responsible for the decisions that led to the costs of the episode. A second method in the white paper is similar to the first method with a minimum threshold for the percentage of the costs of the episode. Particularly, the episode is attributed to the practitioner with the highest percentage of the cost of the episode only if that percentage is over the threshold. This eliminates episodes with highly fragmented care. In a third method described in the white paper, the attribution rule assigns the episodes to the patient's primary care provider regardless of the primary care provider's role in the episode. This method is only applicable when the patients are required to select a primary care provider. The fourth method described in the white paper infers a primary care provider for patients that are not required to select one. The primary care provider is identified by review of the patient's visits to providers for a predefined period, such as 12 months, before the episode. The fifth attribution method described by the white paper assigns all the practitioners involved in an episode to the episode regardless of the percentage of the practitioner's involvement. The white paper's sixth method attributes an episode to the practitioner that performed a significant procedure in the episode. This method only applies to surgical episode types. The seventh method described by the white paper assigns the episode to the practitioner with the most face-to-face encounters with the patient. The attribution is thus not based on dollars. The white paper also describes a method that attributes an episode to the practitioners that had professional fees above a threshold percentage of the cost of the episode. The attribution rule is not to be limited to the above-described attribution methods.

The system then selects all services for all episodes attributed to each practitioner in step 207. A variety of rules may be used for assigning episodes to practitioners, such as, for example, those practitioners who have generated a certain percentage of services at least 25% of the total costs of the episode. The definition of a significant role may be varied to include more or less practitioners as needed for the particular analysis.

The medical practice pattern tool 100 now produces a file 208 comprising all services in all episodes attributed to each practitioner, for each practitioner of interest. The file includes all services with an additional field identifying the practitioner to whom was attributed the episode containing the service. Where an episode has been attributed to more than one practitioner, for example, where two practitioners shared management of the patient, the episode's services are copied and, in the second instance of the episode, the added field has the second practitioner's identifier. It should be noted that multiple practitioners may be assigned the same total role services.

The episodes specific to a condition of interest are then defined by the user of the medical practice pattern tool 100 in step 209. This step may be performed several times to provide analysis on several different groups of episodes of interest using the data compiled in the previous steps. It should be noted that by preserving in file 208 all episodes across all conditions for the entire group of practitioners, great flexibility is retained for analyses, because, at this step, conditions can be created by selecting episodes according to specific criteria not limited by the definitions of the original episode grouper.

The user employs clinical judgment to produce an operational definition of a group of episodes of interest, which may be from one or more ETGs output by the grouper. For example, in the specialty of allergists, the episodes of interest may be related to Allergic Rhinitis in the ETG 0332. A further example in the specialty of orthopedists, the episodes of interest may be Carpal Tunnel Syndrome with and without surgery, combining the ETGs 0174 and 1075. Alternatively, the episodes of interest may be a subset of an ETG defined by ICD-9 or by CPT. For example, in the specialty of dermatologists, benign neoplasm of skin (ETG 0682) could be analyzed without episodes containing the diagnosis of actinic keratoses, which would normally be included in ETG 0682. A further example in the specialty of orthopedics, knee derangement with or without surgery (ETGs 0742.02 and 0743.02), but including only episodes containing arthroscopy. In a further alternative, episodes of interest are defined to include multiple ETGs with multiple limitations. For example, an analysis in the specialty of dermatologists may include dermatitis in ETG 0678, minor inflammation of skin, episodes with diagnoses 690-693 plus ETG 0692, dermatological signs and symptoms, episodes with diagnosis 782.1, rash.

In step 210, the medical practice pattern tool 100 selects the services for the episodes of interest identified in step 209 and outputs a pre-analysis service set file 211 listing the services in the episodes of interest with identifiers for all practitioners to whom those episodes were attributed.

In step 212, the medical practice pattern tool 100 counts the number of episodes and their costs for all practitioners in the analysis and outputs a file 213 showing the episode counts and average cost by practitioner. In step 214, the user then optionally applies a volume threshold and/or other criteria to select a final list of practitioners to analyze. For example, the user may decide that practitioners who see fewer than 5 cases per year have atypical practices and should be excluded from analysis.

In step 215, the user assigns the practitioners into strata. The strata may be defined in numerous ways, such as by the total episode cost (the total cost of the episode regardless of the practitioner's contribution), responsible cost, by specialty, by geographic location (e.g. urban, suburban, rural), by type of practice (e.g. by group size), etc. For example, the physicians are ranked according to cost and separated into percentile groups (quartiles, quintiles, etc). The strata may be divided evenly, or the boundaries between strata may be selected using the user's judgment, for example at natural breaks in the data. In a particular embodiment, the strata are defined for the episodes of interest using the pre-analysis service table, by ranking all the relevant physicians from highest to lowest volume in terms of number of episodes, choosing a lower limit for number of episodes, re-sorting all physicians with greater than or equal to the minimum number of episodes by the average total cost per episode, lowest to highest. Physicians having an average total cost per episode that is unexpectedly high or low compared to the rest of the group of episodes of interest may be removed from the group. Similarly, physicians having a number of episodes that does not fit with the rest of the group are removed. The physicians are then divided into strata, such as cost quintiles. The medical practice pattern tool 100 outputs a practitioner stratum table that lists the practitioners in their respective strata and includes the total role episode count, the responsible role expense, the total role expense, the responsible role average cost per episode, and the total role expense per episode (see Table A4 in the example). The result is step 216, which outputs the practitioner stratum table 217. The medical practice pattern tool 100 also outputs a table 218 of episode count by stratum, which is a table of the number of episodes in each stratum.

In step 219, the medical practice pattern tool 100 then uses the final practitioner stratum table 216 and the pre-analysis service set 211 and selects episodes' services for only those practitioners in the final table 216. Each service is labeled with its attributed practitioner's stratum number. The result is file 220, the analysis service set.

In step 221, the medical practice pattern tool 100 then counts the beginning diagnosis for each episode in the analysis service set and produces a count of diagnoses by stratum, outputting the diagnosis list 222. This list can be used in conjunction with other outputs of the medical practice pattern tool 100 to perform additional analyses, such as determining whether the pattern of medical conditions by specific diagnosis had an effect on costs.

The medical practice pattern tool 100 then in step 223 finds the average cost and utilization for every service across all episodes in the entire analysis. To achieve this, the cost and service utilizations are totaled across all the episodes in the entire group of episodes of interest, which may be known as the analysis total. Each cost and service utilization is normalized by dividing by the total number of episodes in the group of episodes of interest to generate the cost per episode average and the service utilization per episode average across all the episodes in the analysis, which may be known as the analysis average. The number of episodes in the entire group of episodes of interest is the sum of the stratum episode counts in the table 218. The medical practice pattern tool 100 outputs a table of the costs and service utilizations per episode for all episodes of interest, resulting in file 224, the cost-service per episode file.

The medical practice pattern tool 100 then in step 225 determines the expected cost and expected service utilization for each service in each stratum from step 223. For each service, the system multiplies the number of episodes in the current stratum times the service cost per episode and service utilization per episode from the table 224 of costs and services per episode in the entire analysis. The result is the "expected" costs and service utilizations for each service in the current stratum (i.e.: as if the average cost and service utilization across all practitioners of interest had been delivered for the number of episodes in that stratum). In other words, the expected cost and expected utilization for every service in each stratum equals the average cost or utilization for a service across all episodes times that stratum's number of episodes from the stratum episode count table 218.

The medical practice pattern tool 100 then also in step 225 finds the difference between the actual and expected service cost or utilization for each service in each stratum. The expected cost and service utilization are subtracted, respectively, from the actual cost and service utilization of each service to find a cost and utilization difference per service. It should be noted that the actual service cost is defined herein as the sum of the cost of that service over every time the service occurred in a stratum. For example, if a service is consistently $200 and it occurred 100 times in a particular stratum, the total service cost is $20,000 for that stratum. It should be further noted that the service utilization is defined herein as the number of times a service was performed for the episodes in a given stratum. In the above example, the service utilization is 100.

The medical practice pattern tool 100 then generates a list of all the services attributed to the practitioners in the practitioner stratum table and then sorts and normalizes all the resultant services. For each service the tool shows the actual total cost and utilization, the expected cost and utilization, and the differences between the actual and expected costs (and optionally, utilizations). The tool then applies a normalization within each stratum by dividing both the total costs and utilizations and their differences from expected by the number of episodes in that stratum. The resulting output is a table 226, the MPPT file, sorted by stratum, high level category, and then service within each category from highest to lowest difference from expected cost or utilization.

In steps 227 and 230, the user may identify potential cost drivers and generate a report comparing the absolute values of the services. In step 227, the user applies a minimum threshold for the total cost for each service in each stratum or the service utilization for each service in each stratum. The threshold therefore may be, for example, a total cost of $10 per episode or a service utilization of 0.1 per episode. Any service that has a cost or service utilization above the threshold is stored in a potential cost drivers table. Thus, anomalous data are removed. The total service cost or service utilization for each of these potential cost drivers may be displayed in a graph, such as a bar graph, in step 229.

It often makes sense to group certain services together in the graph, for example, pharmaceutical claims. The user may use clinical judgment while examining the services to apply appropriate groupings, e.g.: complex radiology within radiology, antibiotics within pharmacy, consultations within examination and management, etc. Therefore it is beneficial to group the services by type within the strata formed in step 215. Further, in the steps following step 215, it is convenient to calculate the totals for each type of service as if the service type was an individual service. For example, the system calculates the total cost difference per episode for all antibiotics within pharmacy, as well as for the individual services within the pharmacy type.

The important cost differences are determined by setting a threshold for the cost difference per episode and removing the services that are below that threshold in step 230. For example, a cost difference per episode that is less than $2 may be considered to an insignificant difference and services below that threshold would be removed from the list. Thus, anomalous data are removed. The resulting output list, which indicates the total cost difference per quintile episode, groups similar services together within each stratum as discussed in step 227. For example, in allergic rhinitis allergy vaccines ("allergy shots") appear within the ETG category of management costs while other management costs and evaluation are grouped separately. Likewise, all physical therapy services would be grouped together and all anesthesia services would be grouped together. The service group differences from expected can then be displayed as a graph 232 showing the variation from average of each service group for each stratum.

In alternative embodiments, the threshold step may be applied to other values. For instance, the utilization difference may be calculated similarly to the cost difference and the threshold may be applied to the utilization difference or the utilization difference divided by the number of episodes in the stratum. Alternatively, the threshold may be applied to the total cost or utilization. In a further alternative, the threshold is applied to the total cost of a service within a stratum divided by the total utilization of that service in that stratum. So the threshold may be applied to the total cost, the total utilization, the cost per episode, the utilization per episode, the cost difference, the utilization difference, the cost difference per episode, the utilization difference per episode, the cost per utilization, or variations and combinations thereof.

The final output of the medical practice pattern tool 100 comprises a report consisting of tables or graphs, such as bar graphs (outputs 229 and 232), comparing the cost drivers. The graph 232 displays the cost per episode of the cost drivers above and below the expected value for each stratum. The graph readily shows the differences between the strata. Thus step 116 (FIG. 1) is reviewing the table(s) and graph(s) and determining the services that drive the differences between the strata. For example, physicians in the first quintile may use less of service A than the average of the group of episodes of interest, thus showing a negative cost difference per episode for service A, and more of service B than the average of the group of episodes of interest, thus showing a positive cost difference per episode for service B. If the practitioners in the fifth quintile have a positive cost difference per episode for service A and a negative cost difference per episode for service B, and the first quintile is the least expensive quintile, then it stands to reason that physicians that choose to use more of service B and less of service A will have less expensive episodes of care for that group of episodes of interest on average.

It is possible to collect all of the results from several analyses of separate groups of episodes of interest and form a medical management blueprint for practitioners to follow. The blueprint provided in step 118 (FIG. 1) has a separate cell, such as the one shown in FIG. 3, for each analysis performed using the medical practice pattern tool 100. Each cell has a brief description of the episodes of interest, a list of two or three cost drivers, and a recommendation for treatment within that specialty. The description of the episodes of interest will indicate whether a single ETG, a combination of ETGs, or a subset of ETGs was used. The cells are placed in rows according to specialty, as shown by example in FIG. 4. Therefore, after making a diagnosis, a practitioner may consult the blueprint or a listing or guideline derived from the blueprint to determine what services for treating this diagnosis are favored. If the preferred services of the practitioner are not cost drivers in the analysis, then she proceeds according to her discretion. However, if the services are addressed in the blueprint, the practitioner is recommended to use the services utilized by the lower cost quintiles and to not use services that are not utilized by the lower cost quintiles. In addition or alternatively to providing recommendations to the practitioners, the blueprint may recommend that a practitioner or an organization renegotiate a contract with a service provider. For example, the medical practice pattern tool 100 may show that the inpatient physical therapy costs are exceedingly high for a particular hospital and the recommendation is for the managed care organization to renegotiate the costs for the therapy. In a general sense, an organization can use the blueprint to organize its efforts to manage costs.

An advantage of the medical practice pattern tool is that it reveals what services less expensive practitioners use and what services they do not use. It does not simply report which practitioners are expensive and which are inexpensive. Further, the medical practice pattern tool may have counterintuitive results. In particular, the recommendation may be to use a more expensive service over a less expensive service. This may be because the less expensive service is less effective than the more expensive service, or because the less expensive service is used much more frequently, causing higher total costs. For example, for the condition allergic rhinitis it has been found that physicians in the less expensive quintiles use less vaccine ("allergy shots") and more pharmaceuticals to treat allergies while those in the expensive quintiles use more vaccinations and less pharmaceuticals. This result is counterintuitive because pharmaceuticals tend to drive expenses in other conditions.

It is possible for the results of an analysis to be skewed by certain factors. Patient severity could be systematically different from one stratum to another. ETGs are already constructed so as to be cost homogenous, and those that are clinically homogenous minimize the concerns further (e.g. ETG for HTN without complications).

Certain episode groupers include severity adjustment, or severity could be judged by separate analyses (e.g. through one of several standard severity adjustment methods such as age-gender, ERG, DCG, etc). The differences in physician practice patterns are usually apparent and larger than severity differences, due to the construction of ETGs. However, one could group episodes by patient-severity strata and then evaluate the differences in practice according to patient severity.

The invention has a major competitive edge over other analytic tools in the market. First, it discovers the general characteristics of practice patterns, rather than requiring multiple a priori hypotheses and analyses. A key goal of managed care organizations is identifying and defining "best practices."

In addition, the inputs and outputs of the algorithm are clinically relevant and easy to present in graphic form. This facilitates the discussion of medical appropriateness and allows clinical judgment as to whether the service is under utilized, over utilized, or mis-used, based on medical evidence for or against the service in question. Therefore the invention allows the connection of cost containment to quality improvement.

Application of the algorithm shows potential savings of $250,000 to $1,250,000 among conditions in three specialties that have been examined. The potential cost savings for a medium-sized regional insurance plan are $10,000,000 to $30,000,000 per year (2 conditions×20 specialties×$250,000 average at the low end, 3×20×$500,000 average at the high end).

As described, the medical practice pattern tool focuses on the total role rather than the responsible role of a particular medical practitioner. For the purposes of this description, the total role comprises the total cost or utilization of the care of a particular patient, as opposed to the contribution of a single physician of interest, which is the responsible role. The advantage that the total role has over the responsible role is that the total role analysis captures all services in an episode while the responsible role analysis only considers services for which the practitioner of interest is responsible. Thus, if a particular practitioner does not typically order a particular service for a given ETG, and another practitioner typically does order that service, the first practitioner looks less expensive and the service at issue looks like a cost driver. A total role analysis may show that this is an incorrect result. For example, a first general practitioner may typically order an MRI for episodes in a particular ETG prior to sending the patients to a specialist. A second general practitioner may typically send the patients directly to the specialist for episodes in the same ETG, in which case, the specialist is responsible for the MRI. In a responsible role comparison of the two general practitioners, the first general practitioner looks more expensive and the MRI appears to be a cost driver, all else being equal. A total role analysis shows, however, that the MRI was ordered in all episodes regardless of whether the general practitioner or the specialist ordered it, and the MRI is eliminated as a potential cost driver. A responsible role analysis may be desirable in certain circumstances, and one skilled in the art will be able to modify the medical practice pattern tool described to provide such an analysis. Thus, the medical practice pattern tool with a responsible role focus is considered to be within the scope of the invention.

Further to the main MPPT analysis, an individual practitioner's practice pattern is discerned by a total role drilldown and a total role MPPT meta-drilldown. The total role drilldown for a practitioner lists all the services from the episodes in which this practitioner had a significant role. The episodes are from a single condition corresponding to an MPPT analysis, such as a modified ETG. The services are organized by high level category and, within each category, the services are ranked according to the total cost difference (i.e. the expected cost subtracted from the total cost).

The total role MPPT meta-drilldown lists all the services from the episodes in which the physician had a significant role for all the conditions analyzed. In other words, the MPPT analysis may be carried out for several conditions and an individual practitioner may have a significant role in episodes of a plurality of these conditions. The MPPT meta-drilldown combines all the episodes from all the conditions considered. Similarly to the total role drilldown for an individual condition, the services in the MPPT meta-drilldown are organized by high level category and within each category the services are ranked according to the total cost difference (i.e. the expected cost subtracted from the total cost). The expected cost and utilization for each service in the MPPT meta-drilldown is calculated by multiplying the average cost and utilization for the service in each condition (from step 223) times the number of episodes in which the physician had a significant role in that condition, then summing the result over all the conditions considered. This provides a case-mixed service cost and utilization, by service.

The organization and ranking of the services in the total role drilldown and the total role MPPT meta-drilldown thus readily show the physician's variation in one condition and across multiple conditions, respectively. The services that really make a difference to the cost of the physician's practice are revealed by normalizing by the number of episodes, as described in the main MPPT analysis. Most of the physician's services have a cost difference per service of close to $0, while services that truly affect costs have a non-zero cost difference per episode.

EXAMPLE A

In an example, a number of episodes of care for the condition benign neoplasm of the skin, ETG 0682, are analyzed using the medical practice pattern tool. In this example, the medical practitioners are physicians in the specialty of dermatology associated with a medium sized regional managed care organization. The claims data input to the ETG grouper was from a period of two years.

The user chose to analyze complete episodes of care that were not cost outliers. In the data cleansing step the user had substituted uniform fees for outpatient hospital services. In choosing the top-level of groupings the user kept the Symmetry Grouper categories (ancillary, facility, management, pharmacy, and surgery) but split radiology costs out of ancillary to form a separate category. A sample of the resulting service group file 205 is shown in Table A1. Note that the data at this point contains all episodes from all ETGs for the specialty of dermatology.

In the example, the user had previously compiled a list of all dermatologists in the managed care organization and used that list as input 206. The user then found all episodes that were to be attributed to each dermatologist according to the user's chosen attribution rule, and inserted the attributed practitioner's identification number as the final field in the file 208, "total role all practitioners services details all episode," sample shown in Table A2. Note that more than one practitioner could have been attributed in a given episode, and in that case the medical practice pattern tool would have made one or more additional copies of all the services in that episode and appended the second (and third and fourth, and so on as the case might be) practitioner identifier to the copied episode's services. For example, the services with claim IDs 56 through 60 in Table A2, which belong to episode number 1067490, were attributed to physician number CCP010000009 and CCP010000032. Thus, the services for this episode are listed twice with one set attributed to CCP010000009 and the other attributed to CCP010000032.

The user knew from prior experience that ETG 0682 contains episodes of actinic keratosis removal as well as non-actinic keratosis skin lesion removal. Because this mixed two medical conditions, the user, in step 209, specified that the condition of interest was those ETG 0682 episodes that did not contain a diagnosis of actinic keratoses (ICD9 702.xy where x is any fourth digit and y is any fifth digit). The medical practice pattern tool therefore at this step selected only episodes of 0683 without actinic keratosis diagnoses, producing the pre-analysis service set 211. Of the episodes shown in Tables A1 and A2, the episode with claim IDs 66 through 70 included a diagnosis of actinic keratoses and therefore were removed from the analysis.

The medical practice pattern tool at this point counts the episodes and their costs for all practitioners in the pre-analysis service set, producing the file 213, "practitioner zero or more episodes." A sample of the file 213 is shown in Table A3. Note that the practitioners are ordered by volume so that the user can apply optional threshold and other criteria in step 214. In this case the user did not choose to apply any criteria. However, in this step there might have been a volume threshold, for example a minimum of 100 episodes, which would have removed seven practitioners. The user also could have removed any practitioners with an atypical practice, for example, anyone known to specialize in treatment of skin cancers, who might therefore a priori be considered to have more difficult patients referred for care.

In step 215 the decision was made to stratify the practitioners into quartiles according to average total episode cost. Other stratification schemes could have been applied, such as cost quintiles or urban/suburban/rural practice locations. The result was file 217, "practitioner stratum table," as shown in Table A4 The MPPT counted the episodes in each stratum producing the stratum episode count table 218 as shown in Table A5. It is seen that there were a total of 22,358 episodes across all four quartiles, with 6,455 episodes in Quartile 1, 4,443 episodes in Quartile 2, 7,788 episodes in Quartile 3, and 3,672 episodes in Quartile 4.

The MPPT in step 219 would have selected only those services in the pre analysis service set 211 that were in episodes attributed to the physicians in the final practitioner stratum table, producing the analysis service set. In this example, since no physician was eliminated in step 214, the analysis service set was identical to the pre-analysis service set. The MPPT produced a count of diagnoses by stratum, output 222 "diagnosis list", as shown in Table A6.

The MPPT then in step 223 found the costs and service count (utilization) per episode for every service in the analysis service set. A portion of the resulting "cost-service per episode" file 224 is shown in Table A7. Taking as an example service 11400, which is the CPT-4 identifier code for the procedure "excise, benign skin lesion, including margins, except skin tag, trunk/arms/legs," it is seen that the service was performed 512 times in the entire analysis (that is, across the 22,358 episodes of all four quartiles). The total cost was $47,710. Therefore the average cost per episode for all dermatologists of interest (in this case, the entire specialty in the region of the managed care organization) was $47,710 divided by 22,358, or $2.13 per episode and the average utilization per episode was 512 divided by 22,358, or 0.0229 per episode. The other columns in Table A7 simply track the number of episodes in which the service occurred, the average cost of the service per episode in which it actually occurred, and the average number of times the service was ordered per episode in which it actually occurred. If fewer dermatologists were analyzed (e.g. if some were excluded in step 214 for small numbers of episodes or atypical practices), the denominator of 22,358 would have been smaller.

The MPPT then performs the step 225 consisting of listing the services by stratum, top-level category, and then service, counting the actual costs per service and occurrence (utilization) per service within each stratum, generating the expected costs and occurrences, generating the differences between actual and expected, and normalizing those by the number of episodes in the stratum. A portion of the output 226, the MPPT file, is shown in table A8. Continuing the example of service 11400, it is seen that for quartile 1 the service occurred 94 times in 6,455 episodes at a total cost of $10,400. If the service had occurred at the average rate of all analyzed practitioners of 0.0229 per episode, it would have occurred 147.82 times, the expected number of occurrences (0.0229 times 6,455). Similar calculations lead to an expected cost of $13, 774 ($2.13 time 6,455), showing that in quartile 1 the service occurred at a lower rate than expected and a lower cost than expected. The cost difference between actual and expected was $3,734. The MPPT then normalized the actual cost and cost difference to the number of episodes in the quartile, yielding an actual cost per quartile episode of $1.55 (rounded in the table to $2) and a cost difference of $0.58 per episode below expected (rounded to −$1.00).

By similar calculations and reasoning it can be seen that in quartile 1 the service 17000, destruction of premalignant lesion, occurs more often than expected, at an actual cost per quartile episode of $13.37 (rounded to $13) and a cost difference of $1.03 per episode above expected (rounded to $1).

By similar calculations and reasoning it can be seen that in contrast to the lowest cost quartile, the service 11400 in quartile 4 is used at $4 per episode ($2 per episode above expected) and the service 17000 is used at $10 per episode ($3 per episode below average).

Figure 5:
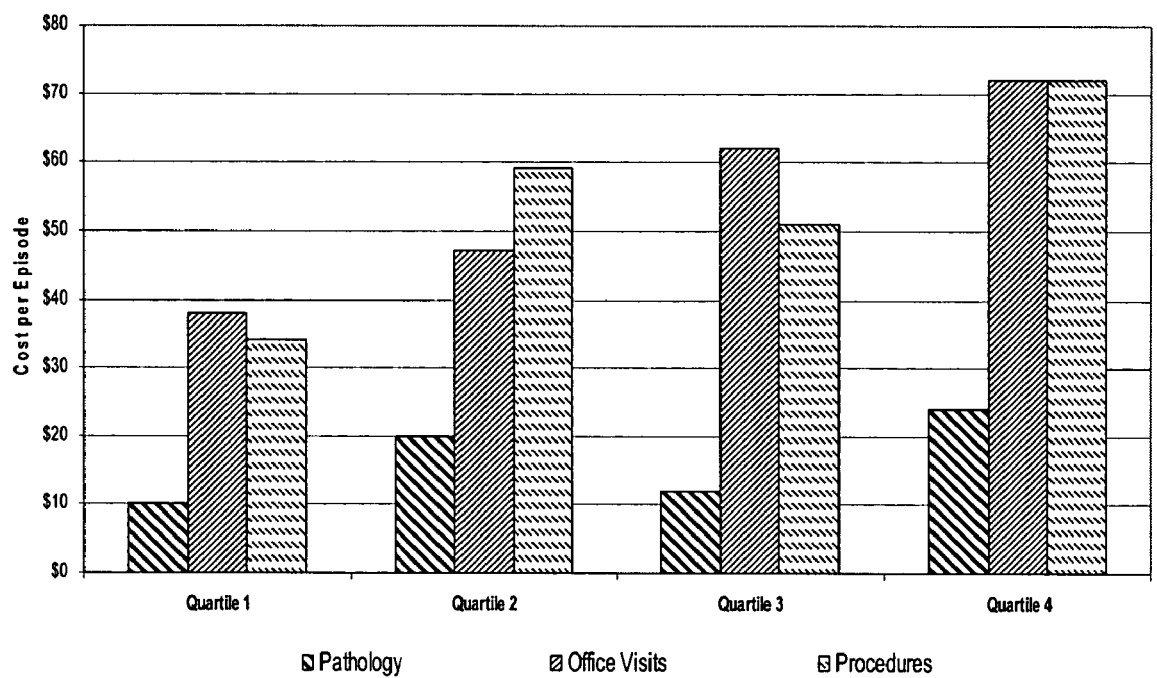
FIGS. 5, 6A, and 6B are bar graph outputs of the medical practice pattern tool according to Example A.

The user now applies thresholds to determine significant drivers of cost and variation. In this example a cost driver threshold of $2 (rounded) per episode was used and all services with costs below that threshold were removed. The medical practice pattern tool in this step removes (for example) all pharmacy and radiology services, showing that they were not significant cost drivers as defined by the user in setting that threshold. An alternative threshold of services per episode could have been used. A portion of the resulting report (file 228) is shown in table A9 and the corresponding graph shown in FIG. 5, which shows the absolute cost per the number of episodes in each stratum for the significant cost drivers. This report shows that the important cost drivers in the condition benign skin lesions are pathology costs, management costs, and procedure costs. Particularly, FIG. 5 shows that Quartile 1 spends much less on office visits and procedures than the more expensive quartiles.

Figure 6A:
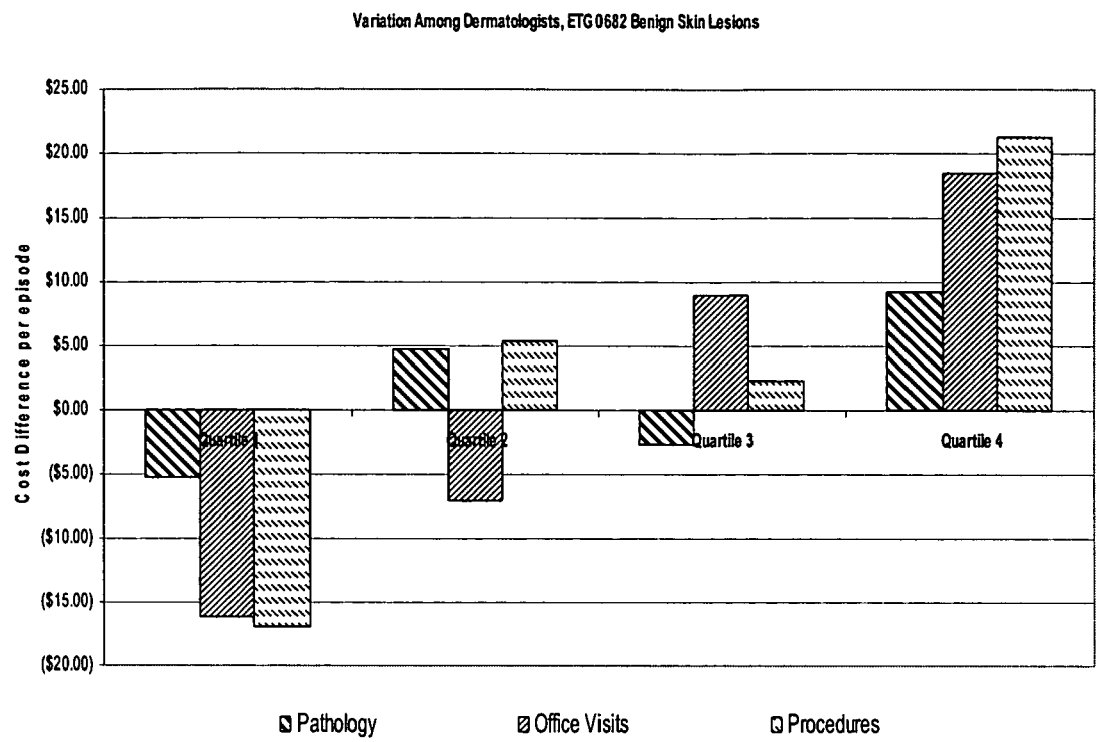
Figure 6B:
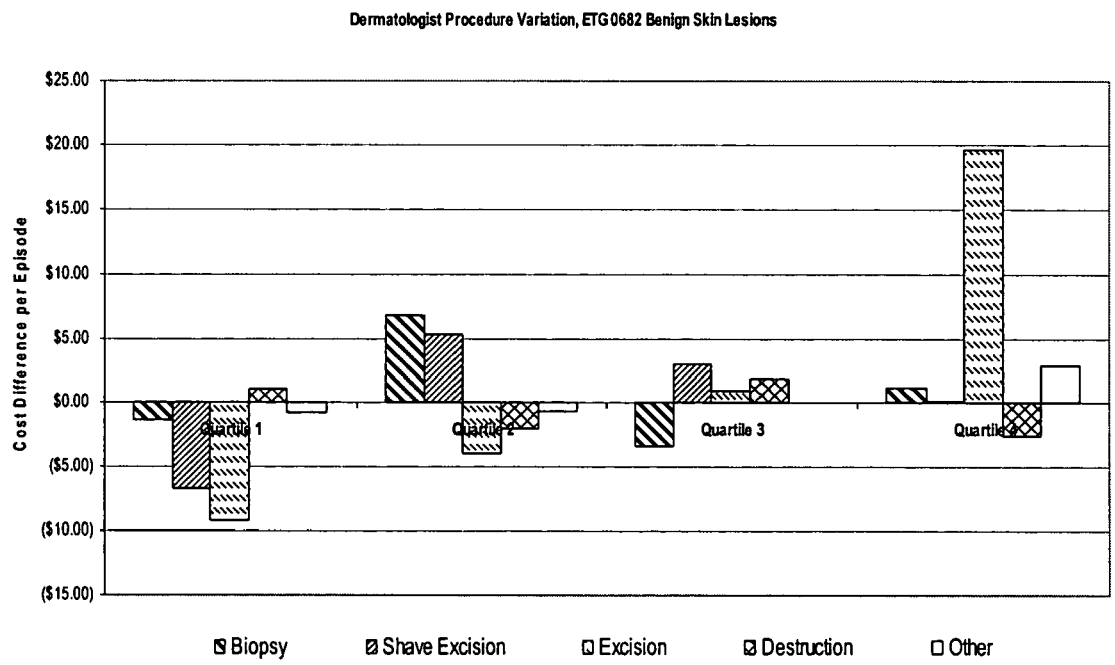

Similarly the user could remove all cost differences under a threshold such as $1 to show that those services were not significant drivers of the variation in care among quartiles. An alternative threshold of service utilization difference could be used. In this example, the user also choose to use a separate cost difference threshold to select all services with a per episode cost difference of over $0.30 (absolute value). FIG. 6A shows the difference between the actual cost and the expected cost per the number of episodes in each stratum for the significant cost drivers. FIG. 6B shows the significant cost drivers within the procedure group of cost drivers: biopsy, shave excision, excision, destruction, and other. The graphs clearly show that Quartile 1 spends much less on office visits and procedures than the more expensive quartiles. More specifically, Quartile 1 spends less on excision procedures and more on destruction than the other quartiles.

It will be noted that in this example under surgical procedures there are several natural groupings of services, such as all excisions, all lesion destructions, etc. The user has sorted and subtotaled the costs for those groupings of services.

The resultant tables and corresponding graphs thus teach that the practice pattern of the lower quartile dermatologists consists of lower pathology costs, office visit costs, and procedure costs compared to those of the higher cost dermatologists, and further that the procedure costs are represented in general by higher excision-type procedures in the highest quartile dermatologists.

Therefore the medical practice pattern tool has uncovered a pattern of variation in care among cost quartiles in the use of office visits and lesion excision versus lesion destruction. This teaches that the practice pattern of the lower cost physicians is to do lesion destruction rather than lesion excision, and further that medical costs can be decreased by a medical guideline that suggests to practitioners to perform lesion destruction instead of excision as often as possible consistent with good medical practice.

One will note that Tables A8 and A9 include several columns that track data that were not necessarily used in the analysis. This data may be useful, however, for additional analysis and for providing context to the recipients of the medical practice pattern tool analysis. Particularly, the "stratum" column lists the stratum designation; for example: S1 is used for stratum 1 and Q1 is used for Quartile or Quintile 1. The "category" column lists the cost category, such as Ancillary (A), which includes labs, other testing, outpatient facility fees, etc., Evaluation and Management (M), which includes office visits, etc., Pharmacy (P), Radiology (R), Inpatient Facility (F), Physical Therapy (T), among others. The "service" column lists the service group designator, e.g. the CPT code, the medication group label, the DRG code, etc. The "procedure description" column simply lists the text description of the service group designator. The "total services" column lists the stratum service usage, which is the total number of times that service was provided for all episodes in the current stratum. The "your services" column lists the number of units of that service provided for all episodes in that stratum performed by the physicians with a significant role. This value is obtained by examining each episode and counting the services generated or ordered by the index physician, for those physicians with a significant role. The "other's services" column lists the number of that service provided for all episodes, obtained by examining each episode and counting the services generated or ordered by practitioners who were not in the significant role relative to the index practitioner.

The "expected services" column lists the number of services that would be expected if performed in this stratum at the average rate of services per episode in the entire analysis (i.e. across all strata). More particularly, the expected services is defined by the service usage for the entire analysis divided by the number of episodes in the analysis and multiplied by the number of episodes in the current stratum. The "stratum (or quartile or quintile) episodes" column lists the number of episodes in that stratum. The "total costs" column lists the actual total costs for all of that service in that stratum. The "your costs" column lists the actual costs for that service in that stratum for the physicians with significant roles. This is the costs for the services usage listed in the "your services" column. The "other costs" column lists the actual costs for all of that service in the current stratum for the other physicians without a significant role. This is the costs for the services usage listed in the "other services" column. The "expected costs" column lists the expected costs for that service, generated in the same manner as the expected services. Particularly, the expected cost is defined by the service cost for the entire analysis divided by the number of episodes in the analysis and multiplied by the number of episodes in the current stratum. The "total cost difference" column lists the total costs minus the expected costs and the "total costs per stratum episode" column lists the total costs divided by the number of episodes in the stratum.

The total cost "difference per stratum episodes" column lists the total costs divided by the number of episodes in the stratum. The "your costs per service" column lists the costs for physicians with a significant role (from the "your costs" column) divided by their number of services (from the "your services" column). The "other costs per svc" column lists the costs of the physicians who were not the significant role physicians for the episodes (from the "other's costs" column) divided by their number of services (from the "other's services" column). The "spec costs per svc" column lists the specialty costs per service, which is the sum of costs of all the physicians in the analysis (from the "total costs" column) divided by the number of that service in the entire analysis (from the "total services" column). The "episodes this service occurred" column lists the total number of episodes in the stratum in which the service was found. Tracking this additional data allows the user to perform additional analyses once the key cost drivers and the expensive practitioners are discovered. For example, the user may perform analyses related to the percentage use of a service by stratum episode, or the cost per service when service was actually used.

When reporting to an individual practitioner in the analysis, further analyses focused on the individual may be carried out. These include the total role drilldown and the total role MPPT meta-drilldown. The total role drilldown for physician #CCP010000014, who was assigned to the fourth quartile in the MPPT analysis, is shown in Table A10, wherein all the services from the episodes in which this physician had a significant role are listed. The episodes are from a single condition corresponding to an MPPT analysis, in this case the benign neoplasm of the skin, without actinic keratoses ETG 0682 of the present example. The services are organized by high level category and, within each category, the services are ranked according to the total cost difference (i.e. the expected cost subtracted from the total cost).

The total role MPPT meta-drilldown is shown by Table A11, which lists all the services from the episodes in which the physician had a significant role for all the conditions analyzed. In other words, the MPPT analysis may be carried out for several conditions (e.g.: ETGs or modified ETGs) and the present physician may have a significant role in episodes of a plurality of these conditions. The MPPT meta-drilldown combines all the episodes from all the conditions considered. Similarly to the total role drilldown, the services in the MPPT meta-drilldown are organized by high level category and within each category the services are ranked according to the total cost difference (i.e. the expected cost subtracted from the total cost). The expected cost and utilization for each service in the MPPT meta-drilldown is calculated by multiplying the average cost and utilization for the service in each condition (from step 223) times the number of episodes in which the physician had a significant role in that condition, then summing the result over all the conditions considered. This provides a case-mixed service cost and utilization, by service.

The organization and ranking of the services in the total role drilldown and the total role MPPT meta-drilldown thus readily show the physician's variation in one condition and across multiple conditions, respectively. The services that really make a difference to the cost of the physician's practice are revealed by normalizing by the number of episodes, as described in the main MPPT analysis. Most of the physician's services have a cost difference per service of close to $0, though services that truly affect costs have a non-zero cost difference per episode. Upon review of Tables A10 and A11, one will note that this physician is high in service number 11400 (excision) and low in service number 17000 (leasion destruction). This is in parallel to the MPPT part of the present example in which the fourth quartile was high in excision and low in lesion destruction, while the lower cost first quartile was low in excision and high in lesion destruction. Further, this physician tends to do more level 3 consults and office visits and fewer than expected level 2 of the same (see category "M" in Table A11).

Therefore, when reporting to the physician that the MPPT analysis indicates that higher quartile physicians tend to do more excisions than destruction, the user may also provide the physician's pattern in the same condition and across all conditions. In this case, the physician follows the fourth quartile pattern for the benign neoplasm of the skin without actinic keratoses condition and across all conditions. Further, the present physician codes much higher for office visits. Thus, the user may provide two concrete actions to lower the physician's costs.

For physicians in the lower quartiles, there may still be areas where they can lower costs and the total role drilldown and the MPPT meta-drilldown may reveal these areas in the physician's pattern. Thus the drilldowns may be valuable for all physicians in the analysis.

EXAMPLE B

In further example, a number of episodes of care for the condition Allergic Rhinitis, ETG 0332, are analyzed using the medical practice pattern tool. In this example, the medical practitioners are physicians in the specialty of allergy associated with a medium sized regional managed care organization. The claims data input to the ETG grouper was from a period of two years. The system develops the practitioner episode percentage table using the output of the ETG grouper, which provides the list of physicians associated with episodes of care in ETG 0332. For each episode, the system calculates the percentage of involvement of each physician by dividing the sum of the costs of the services the physician is responsible for in that episode by the total cost of the episode. The system then calculates and stores the number of episodes for which each physician contributed to at least 25% of the cost; though, it should be noted that other attribution rules may be used. Now the system ranks the physicians and divides them into strata, in this case cost quintiles, as shown in Table B1. As one can see, the physicians are ranked according to the average cost of the episodes in which that physician had a significant role. The quintiles are evenly divided except that physician 10's total role expense per episode fit better in the fourth quintile than the third.

Referring to Table B1, physician 1 has a significant role in 181 episodes in ETG 0332 and the total cost of those episodes is $115,782, translating to about $640 per episode. This places physician 1 in the lowest cost quintile, Q1. Physician 12, on the other hand, has a total cost per episode of about $753, which results in physician 12's placement in a higher cost quintile, Q4. The responsible cost data is also included in Table B1.

The system now calculates the expected cost and service utilization (number of times a service is ordered) for each service in each quintile. The system totals the cost of each service for the entire ETG 0332 and then totals the service utilization for that service over ETG 0332. For instance, service reference number 95004 has an ETG total cost of $84,806 and an ETG total service utilization of 21,600. Each of these totals is then divided by the total number of episodes in the ETG, which is 2506 in the case of ETG 0332. This results in the cost per episode average of $33.84 and the service utilization per episode average of 8.62 for service reference number 95004. The cost per episode average is multiplied times the number of episodes in each quintile to calculate the expected cost of the service for that quintile. For instance, there are 472 episodes in quintile Q1, multiplied times the cost per episode average of 33.84 results in an expected cost of $15,973 for service 95004 in Q1. Similarly, the service utilization per episode average is multiplied times the number of episodes in each quintile to calculate the expected service utilization of the service for that quintile. Thus the expected service utilization for service 95004 in Q1 is 4068.32.

The expected cost and service utilization are reported in Table B2, which lists the services organized by quintile and by type. The services are grouped by type in each quintile with subtotals in Table B2 so that services may be easily grouped in the final analysis. For example, pharmaceuticals in general may be a cost driver and there may be less interest in the details of the specific pharmaceuticals. For each service, the system subtracts the expected cost from the actual cost also reported in Table B2 to calculate the total cost difference. This is divided by the number of episodes in the quintile to result in the total cost difference per quintile episode. For service 95004, the total cost difference is $4,703 and the total cost difference per quintile episode is $10, as reported in Table B2. A negative total cost difference per quintile episode, such as ($1) for service 95015 indicates that the actual cost was lower than the expected cost.

Once the total cost difference per quintile episode is calculated for every service in every quintile, a cost driver threshold is set. In this case, any service with a total cost difference per quintile episode having an absolute value of $2 or greater, is reported in Table B3, still organized by quintile and by type within each quintile.

Figure 7:
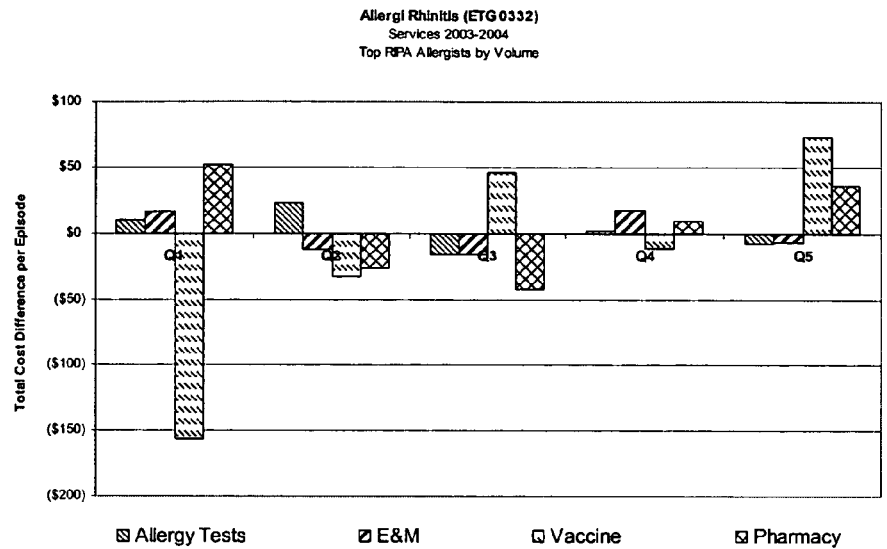
FIGS. 7 and 8 are the bar graph outputs of the medical practice pattern tool according to Example B.
Figure 8:
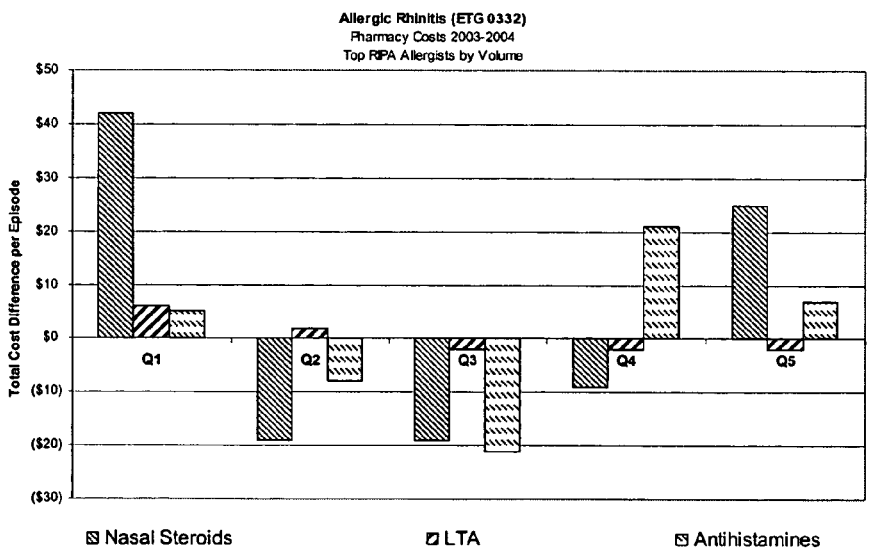

FIG. 7 shows the bar graph of the potential cost drivers from Table B3. The user employs clinical judgment to combine certain services and produce a meaningful graph. For example, if pharmacy is a cost driver in general, a separate graph of the components of the pharmacy group is generated to compare the cost difference per episode of the components. In this example, allergy test services, which were previously grouped and the cost difference per episode totaled in Tables B2 and B3, are graphed in a group; and pharmacy services, which were similarly grouped in Tables B2 and B3, are graphed in a group. Evaluation and management (E&M) services and vaccine services were grouped together in Tables B2 and B3; however, it now makes sense to graph these separately. The cost difference per episode for E&M services, such as service reference numbers 99244, 99214, 99243, and 99213 in quintile Q1, are totaled and graphed. Similarly, the cost difference per episode for vaccine services, such as service reference numbers 95147, 95115, 95165, and 95117 in quintile Q1, are totaled and graphed. Illustrating that even a portion of Table B3 may be graphed to compare the cost difference per episode of certain services, FIG. 8 shows the bar graph of the cost difference per episode of nasal steroid services, leukotriene receptor antagonist (LTA) services, and antihistamines, which are components of the pharmacy group of services.

The results of the medical practice pattern tool analysis of ETG 0332, Allergic Rhinitis, reveals that among allergists the main cost drivers are vaccine costs (the manufacture and administration of "allergy shots"), and to a much lesser extent allergy tests and E&M visits. The lowest cost physicians use much less vaccine but the most medications. They have slightly higher allergy test and office visit costs per episode than other quintiles. The highest cost physicians test and consult less but treat with both vaccines and medications far more. The middle quintile uses more vaccine and less pharmacy, but that quintile is dominated by one physician with that practice pattern.

In pharmacy, nasal steroid costs are the main driver, followed by prescription antihistamines. Leukotriene receptor antagonists (LTAs) were a smaller factor. The lowest cost physicians use the most nasal steroids and LTAs. They use prescription antihistamines moderately. They may be recommending over-the-counter loratadine, which would not appear in claims data. This would be an important question to ask physicians in that quintile.

Other factors besides physician practice choices could be in play. The most obvious would be patient severity. If patients in quintile five were the most severely ill they might need both vaccine and medication. However quintiles 1 and 2 (the lowest cost quintiles) contain two national-level and one international-level expert in allergy and immunology. A priori one would expect them to attract and treat the most severe patients. In addition, the largest allergy group in analysis region has members in all five quintiles, with two of the most senior members in quintiles 1 and 2, and the third senior member in quintile 5.

In summary, the results of the medical practice pattern tool analysis suggest that the most cost-effective allergists test and counsel somewhat more, and use nasal steroids (and perhaps OTC Loratadine) in preference to vaccines. The potential savings, if all physicians followed the quintile 1 practice pattern, are $160,000 per year.

It should be noted that because the service utilization and expected service utilization for each service is included in Table B2, the service utilization difference per episode may be calculated and the analysis may be completed comparing the service utilization difference per episode.

In an alternative embodiment, the analysis is carried out for a set of medical practitioners except that the strata are set up so that each stratum is one practitioner. The result is a comparison of the practice patterns of individuals rather than a comparison of a group of low cost practitioners and higher cost practitioners as described in the previous embodiment.

In a further alternative embodiment, all the conditions of a specialty (e.g. all the ETGs related to dermatology) are combined. In other words, the group of episodes of interest comprises all the episodes in all the dermatology ETGs. The strata are divided such that each stratum includes only one practitioner. The result is the general tendency of a given practitioner, revealing that a particular practitioner uses more or less E&M, procedures, etc. than expected for his specialty.

In an even further embodiment, the stratification of one condition (e.g. a particular ETG) is based on the characteristics of a separate condition. The analysis is then carried out on the cost variation in one condition as it relates to the other condition. For example, one carpal tunnel syndrome (CTS)-related ETG includes surgery and another is without surgery. If the two ETGs are combined, episodes of carpal tunnel treatment with surgery will overshadow episodes without surgery. In other words, the episodes with surgery are much more expensive than episodes without surgery; therefore, the episodes without surgery will very rarely have a sufficient effect to be included in the cost driver analysis and a driver that prevents surgery will likely be missed.

To reveal these cost drivers, the MPPT analysis 100 is carried out on each of the two CTS ETGs separately through step 216 to result in the practitioner stratum tables (output 217) for both ETGs. The system then compares the practitioner stratum tables to reveal each practitioner's rate of carpal tunnel treatment with surgery episodes versus treatment without surgery. The analysis is completed on the ETG for carpal tunnel without surgery by stratifying the practitioners by this surgery rate. The resulting cost differences may reveal a way to avoid surgery, such as steroid injections. The differences may also reveal that a service is a waste of money, for example if steroid injections had no effect on lowering the surgery rate.

There is a similar issue with the treatment of bronchitis. The episodes that start with bronchitis but lead to pneumonia will only appear in the pneumonia episodes. Therefore, similarly to the carpal tunnel example, an alternative stratification method is needed. In this case, the practitioners for the bronchitis ETG are separated into two strata: one with episodes that led to pneumonia and one with episodes that did not lead to pneumonia. The MPPT analysis is then carried out comparing the two strata and potentially revealing a service that reduces the likelihood that a bronchitis episode will result in pneumonia.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims.

TABLE A1

| CLAIM_ID | MEM_ID | SVC_PV | service date | SVC_EXP1 | SVC_EXP2 | CPT | CPT_MOD | DX_1 | DX_2 | PV_TYPE |
|---|---|---|---|---|---|---|---|---|---|---|
| 56 | 855VM1YAM 00 | CCP010000009 | 06-Oct-2003 | $66 | $66 | 17110 | | 238.2 | 078.10 | MD |
| 57 | 855VM1YAM 00 | CCP010000009 | 06-Oct-2003 | $130 | $130 | 99243 | 25 | 238.2 | 078.10 | MD |
| 58 | 855VM1YAM 00 | CCP010000000 | 12-Sep-2003 | $56 | $56 | 99213 | | 216.9 | 244.9 | MD |
| 59 | 855VM1YAM 00 | CCP010000032 | 11-Nov-2003 | $140 | $140 | 11440 | | 238.2 | | MD |
| 60 | 855VM1YAM 00 | CCP010000000 | 11-Nov-2003 | $31 | $31 | 88305 | 90 | 216.9 | | IL |
| 61 | 8RO29B9A4 02 | CCP010000023 | 25-Sep-2003 | $77 | $77 | 11402 | 51 | 216.9 | | MD |
| 62 | 8RO29B9A4 02 | CCP010000023 | 25-Sep-2003 | $77 | $77 | 11402 | 51 | 216.9 | | MD |
| 63 | 8RO29B9A4 02 | CCP010000023 | 25-Sep-2003 | $165 | $165 | 11403 | | 216.9 | | MD |
| 64 | 8RO29B9A4 02 | CCP010000000 | 25-Sep-2003 | $92 | $92 | 88305 | 90 | 238.2 | | IL |
| 65 | 8RO29B9A4 02 | CCP010000023 | 02-Sep-2003 | $86 | $86 | 99242 | | 216.9 | | MD |
| 66 | 94PY71739 01 | CCP010000023 | 21-Mar-2003 | $84 | $84 | 11311 | | 702.11 | | MD |
| 67 | 94PY71739 01 | CCP010000023 | 07-Mar-2003 | $58 | $58 | 17110 | | 702.11 | | MD |
| 68 | 94PY71739 01 | CCP010000000 | 21-Mar-2003 | $31 | $31 | 88305 | 90 | 216.3 | | IL |
| 69 | 94PY71739 01 | CCP010000023 | 25-Apr-2003 | $20 | $20 | 99211 | | 216.9 | | MD |
| 70 | 94PY71739 01 | CCP010000023 | 07-Mar-2003 | $86 | $86 | 99242 | 25 | 702.11 | | MD |

| CLAIM_ID | etgno | epino | REC_TYPE | Responsible Flag | SVC_EXP3 | quantity | visit_type | runid | servicein2 | PV_ID | Episode DATEFROM |
|---|---|---|---|---|---|---|---|---|---|---|---|
| 56 | 0682 | 1067490 | S | .0000 | $66 | 1 | | 2.0000 | X1700 | P010000009 | 12-Sep-2003 |
| 57 | 0682 | 1067490 | M | .0000 | $130 | 1 | C | 2.0000 | 99243 | P010000009 | 12-Sep-2003 |
| 58 | 0682 | 1067490 | M | .0000 | $56 | 1 | F | 2.0000 | 99213 | P010000000 | 12-Sep-2003 |
| 59 | 0682 | 1067490 | S | .0000 | $140 | 1 | | 2.0000 | 11440 | P010000032 | 12-Sep-2003 |
| 60 | 0682 | 1067490 | A | 1.0000 | $31 | 1 | | 2.0000 | 88305 | P010000032 | 12-Sep-2003 |
| 61 | 0682 | 4631697 | S | .0000 | $77 | 1 | | 4.0000 | 11402 | P010000023 | 02-Sep-2003 |
| 62 | 0682 | 4631697 | S | .0000 | $77 | 1 | | 4.0000 | 11402 | P010000023 | 02-Sep-2003 |
| 63 | 0682 | 4631697 | S | .0000 | $165 | 1 | | 4.0000 | 11403 | P010000023 | 02-Sep-2003 |
| 64 | 0682 | 4631697 | A | 1.0000 | $31 | 3 | | 4.0000 | 88305 | P010000023 | 02-Sep-2003 |
| 65 | 0682 | 4631697 | M | .0000 | $86 | 1 | C | 4.0000 | 99242 | P010000023 | 02-Sep-2003 |
| 66 | 0682 | 6782814 | S | .0000 | $84 | 1 | | 5.0000 | 11311 | P010000023 | 07-Mar-2003 |
| 67 | 0682 | 6782814 | S | .0000 | $58 | 1 | | 5.0000 | X1700 | P010000023 | 07-Mar-2003 |
| 68 | 0682 | 6782814 | A | 1.0000 | $31 | 1 | | 5.0000 | 88305 | P010000023 | 07-Mar-2003 |
| 69 | 0682 | 6782814 | M | .0000 | $20 | 1 | F | 5.0000 | 99211 | P010000023 | 07-Mar-2003 |
| 70 | 0682 | 6782814 | M | .0000 | $86 | 1 | C | 5.0000 | 99242 | P010000023 | 07-Mar-2003 |

| CLAIM_ID | Episode DATETHRU | DX_BEGIN | TOT_COST | CPT_ORIG | SVC_GRP | SVC_SET |
|---|---|---|---|---|---|---|
| 56 | 11-Nov-2003 | 216.9 | $423 | X1700 | 17110 | 17110 |
| 57 | 11-Nov-2003 | 216.9 | $423 | 99243 | 99243 | 99243 |
| 58 | 11-Nov-2003 | 216.9 | $423 | 99213 | 99213 | 99213 |
| 59 | 11-Nov-2003 | 216.9 | $423 | 11440 | 11440 | 11440 |
| 60 | 11-Nov-2003 | 216.9 | $423 | 88305 | 88305 | 88305 |
| 61 | 25-Sep-2003 | 216.9 | $497 | 11402 | 11402 | 11402 |
| 62 | 25-Sep-2003 | 216.9 | $497 | 11402 | 11402 | 11402 |
| 63 | 25-Sep-2003 | 216.9 | $497 | 11403 | 11403 | 11403 |
| 64 | 25-Sep-2003 | 216.9 | $497 | 88305 | 88305 | 88305 |
| 65 | 25-Sep-2003 | 216.9 | $497 | 99242 | 99242 | 99242 |
| 66 | 25-Apr-2003 | 702.11 | $279 | 11311 | 11311 | 11311 |
| 67 | 25-Apr-2003 | 702.11 | $279 | X1700 | 17110 | 17110 |
| 68 | 25-Apr-2003 | 702.11 | $279 | 88305 | 88305 | 88305 |
| 69 | 25-Apr-2003 | 702.11 | $279 | 99211 | 99211 | 99211 |
| 70 | 25-Apr-2003 | 702.11 | $279 | 99242 | 99242 | 99242 |

TABLE A2

| CLAIM_ID | MEM_ID | SVC_PV | from date | SVC_EXP1 | SVC_EXP2 | CPT | CPT_MOD | DX_1 | DX_2 | PV_TYPE |
|---|---|---|---|---|---|---|---|---|---|---|
| 56 | 855VM1YAM 00 | CCP010000009 | 06-Oct-2003 | $66 | $66 | 17110 | | 238.2 | 078.10 | MD |
| 57 | 855VM1YAM 00 | CCP010000009 | 06-Oct-2003 | $130 | $130 | 99243 | 25 | 238.2 | 078.10 | MD |
| 58 | 855VM1YAM 00 | CCP010000000 | 12-Sep-2003 | $56 | $56 | 99213 | | 216.9 | 244.9 | MD |
| 59 | 855VM1YAM 00 | CCP010000032 | 11-Nov-2003 | $140 | $140 | 11440 | | 238.2 | | MD |

TABLE A2-continued

| | | | | | | | | | | | |
|---|---|---|---|---|---|---|---|---|---|---|---|
| 60 | 855VM1YAM 00 | CCP010000000 | 11-Nov-2003 | $31 | $31 | 88305 | 90 | 216.9 | | | IL |
| 56 | 855VM1YAM 00 | CCP010000009 | 06-Oct-2003 | $66 | $66 | 17110 | | 238.2 | 078.10 | | MD |
| 57 | 855VM1YAM 00 | CCP010000009 | 06-Oct-2003 | $130 | $130 | 99243 | 25 | 238.2 | 078.10 | | MD |
| 58 | 855VM1YAM 00 | CCP010000000 | 12-Sep-2003 | $56 | $56 | 99213 | | 216.9 | 244.9 | | MD |
| 59 | 855VM1YAM 00 | CCP010000032 | 11-Nov-2003 | $140 | $140 | 11440 | | 238.2 | | | MD |
| 60 | 855VM1YAM 00 | CCP010000000 | 11-Nov-2003 | $31 | $31 | 88305 | 90 | 216.9 | | | IL |
| 61 | 8RO29B9A4 02 | CCP010000023 | 25-Sep-2003 | $77 | $77 | 11402 | 51 | 216.9 | | | MD |
| 62 | 8RO29B9A4 02 | CCP010000023 | 25-Sep-2003 | $77 | $77 | 11402 | 51 | 216.9 | | | MD |
| 63 | 8RO29B9A4 02 | CCP010000023 | 25-Sep-2003 | $165 | $165 | 11403 | | 216.9 | | | MD |
| 64 | 8RO29B9A4 02 | CCP010000000 | 25-Sep-2003 | $92 | $92 | 88305 | 90 | 238.2 | | | IL |
| 65 | 8RO29B9A4 02 | CCP010000023 | 02-Sep-2003 | $86 | $86 | 99242 | | 216.9 | | | MD |
| 66 | 94PY71739 01 | CCP010000023 | 21-Mar-2003 | $84 | $84 | 11311 | | 702.11 | | | MD |
| 67 | 94PY71739 01 | CCP010000023 | 07-Mar-2003 | $58 | $58 | 17110 | | 702.11 | | | MD |
| 68 | 94PY71739 01 | CCP010000000 | 21-Mar-2003 | $31 | $31 | 88305 | 90 | 216.3 | | | IL |
| 69 | 94PY71739 01 | CCP010000023 | 25-Apr-2003 | $20 | $20 | 99211 | | 216.9 | | | MD |
| 70 | 94PY71739 01 | CCP010000023 | 07-Mar-2003 | $86 | $86 | 99242 | 25 | 702.11 | | | MD |

| CLAIM_ID | etgno | epino | REC_TYPE | RESPFLAG | SVC_EXP3 | quantity | visit_type | runid | servicein2 | PV_ID | DATEFROM |
|---|---|---|---|---|---|---|---|---|---|---|---|
| 56 | 0682 | 1067490 | S | .0000 | $66 | 1 | | 2.0000 | X1700 | P010000009 | 12-Sep-2003 |
| 57 | 0682 | 1067490 | M | .0000 | $130 | 1 | C | 2.0000 | 99243 | P010000009 | 12-Sep-2003 |
| 58 | 0682 | 1067490 | M | .0000 | $56 | 1 | F | 2.0000 | 99213 | P010000000 | 12-Sep-2003 |
| 59 | 0682 | 1067490 | S | .0000 | $140 | 1 | | 2.0000 | 11440 | P010000032 | 12-Sep-2003 |
| 60 | 0682 | 1067490 | A | 1.0000 | $31 | 1 | | 2.0000 | 88305 | P010000032 | 12-Sep-2003 |
| 56 | 0682 | 1067490 | S | .0000 | $66 | 1 | | 2.0000 | X1700 | P010000009 | 12-Sep-2003 |
| 57 | 0682 | 1067490 | M | .0000 | $130 | 1 | C | 2.0000 | 99243 | P010000009 | 12-Sep-2003 |
| 58 | 0682 | 1067490 | M | .0000 | $56 | 1 | F | 2.0000 | 99213 | P010000000 | 12-Sep-2003 |
| 59 | 0682 | 1067490 | S | .0000 | $140 | 1 | | 2.0000 | 11440 | P010000032 | 12-Sep-2003 |
| 60 | 0682 | 1067490 | A | 1.0000 | $31 | 1 | | 2.0000 | 88305 | P010000032 | 12-Sep-2003 |
| 61 | 0682 | 4631697 | S | .0000 | $77 | 1 | | 4.0000 | 11402 | P010000023 | 02-Sep-2003 |
| 62 | 0682 | 4631697 | S | .0000 | $77 | 1 | | 4.0000 | 11402 | P010000023 | 02-Sep-2003 |
| 63 | 0682 | 4631697 | S | .0000 | $165 | 1 | | 4.0000 | 11403 | P010000023 | 02-Sep-2003 |
| 64 | 0682 | 4631697 | A | 1.0000 | $31 | 3 | | 4.0000 | 88305 | P010000023 | 02-Sep-2003 |
| 65 | 0682 | 4631697 | M | .0000 | $86 | 1 | C | 4.0000 | 99242 | P010000023 | 02-Sep-2003 |
| 66 | 0682 | 6782814 | S | .0000 | $84 | 1 | | 5.0000 | 11311 | P010000023 | 07-Mar-2003 |
| 67 | 0682 | 6782814 | S | .0000 | $58 | 1 | | 5.0000 | X1700 | P010000023 | 07-Mar-2003 |
| 68 | 0682 | 6782814 | A | 1.0000 | $31 | 1 | | 5.0000 | 88305 | P010000023 | 07-Mar-2003 |
| 69 | 0682 | 6782814 | M | .0000 | $20 | 1 | F | 5.0000 | 99211 | P010000023 | 07-Mar-2003 |
| 70 | 0682 | 6782814 | M | .0000 | $86 | 1 | C | 5.0000 | 99242 | P010000023 | 07-Mar-2003 |

| CLAIM_ID | DATETHRU | DX_BEGIN | TOT_COST | CPT_ORIG | SVC_GRP | SVC_SET | TOTAL_ROLE_ID |
|---|---|---|---|---|---|---|---|
| 56 | 11-Nov-2003 | 216.9 | $423 | X1700 | 17110 | 17110 | CCP010000009 |
| 57 | 11-Nov-2003 | 216.9 | $423 | 99243 | 99243 | 99243 | CCP010000009 |
| 58 | 11-Nov-2003 | 216.9 | $423 | 99213 | 99213 | 99213 | CCP010000009 |
| 59 | 11-Nov-2003 | 216.9 | $423 | 11440 | 11440 | 11440 | CCP010000009 |
| 60 | 11-Nov-2003 | 216.9 | $423 | 88305 | 88305 | 88305 | CCP010000009 |
| 56 | 11-Nov-2003 | 216.9 | $423 | X1700 | 17110 | 17110 | CCP010000032 |
| 57 | 11-Nov-2003 | 216.9 | $423 | 99243 | 99243 | 99243 | CCP010000032 |
| 58 | 11-Nov-2003 | 216.9 | $423 | 99213 | 99213 | 99213 | CCP010000032 |
| 59 | 11-Nov-2003 | 216.9 | $423 | 11440 | 11440 | 11440 | CCP010000032 |
| 60 | 11-Nov-2003 | 216.9 | $423 | 88305 | 88305 | 88305 | CCP010000032 |
| 61 | 25-Sep-2003 | 216.9 | $497 | 11402 | 11402 | 11402 | CCP010000023 |
| 62 | 25-Sep-2003 | 216.9 | $497 | 11402 | 11402 | 11402 | CCP010000023 |
| 63 | 25-Sep-2003 | 216.9 | $497 | 11403 | 11403 | 11403 | CCP010000023 |
| 64 | 25-Sep-2003 | 216.9 | $497 | 88305 | 88305 | 88305 | CCP010000023 |
| 65 | 25-Sep-2003 | 216.9 | $497 | 99242 | 99242 | 99242 | CCP010000023 |
| 66 | 25-Apr-2003 | 702.11 | $279 | 11311 | 11311 | 11311 | CCP010000023 |
| 67 | 25-Apr-2003 | 702.11 | $279 | X1700 | 17110 | 17110 | CCP010000023 |
| 68 | 25-Apr-2003 | 702.11 | $279 | 88305 | 88305 | 88305 | CCP010000023 |
| 69 | 25-Apr-2003 | 702.11 | $279 | 99211 | 99211 | 99211 | CCP010000023 |
| 70 | 25-Apr-2003 | 702.11 | $279 | 99242 | 99242 | 99242 | CCP010000023 |

TABLE A3

Dermatology
Dates of Service Jan. 1, 2003-Dec. 31, 2004 paid Dec. 31, 2004
Total Role benign neoplasm of the skin without actinic keratoses diagnosis 702.xx
etg 0682

| Doctor | total role id | etg of interest episode count | total episodes across all etg's | percent of total episodes | etg of interest doctor responsible dollars | etg of interest doctor total episode dollars | responsible dollars per episode | total episode dollars per episode |
|---|---|---|---|---|---|---|---|---|
| NAME 28 | CCP010000028 | 11 | 136 | 8.1% | $1,202 | $1,416 | $109 | $129 |
| NAME 34 | CCP010000034 | 13 | 111 | 11.7% | $1,534 | $1,801 | $118 | $139 |

TABLE A3-continued

Dermatology  
Dates of Service Jan. 1, 2003-Dec. 31, 2004 paid Dec. 31, 2004  
Total Role benign neoplasm of the skin without actinic keratoses diagnosis 702.xx  
etg 0682

| Doctor | total role id | etg of interest episode count | total episodes across all etg's | percent of total episodes | etg of interest doctor responsible dollars | etg of interest doctor total episode dollars | responsible dollars per episode | total episode dollars per episode |
|---|---|---|---|---|---|---|---|---|
| NAME | 20 CCP010000020 | 16 | 104 | 15.4% | $2,114 | $2,759 | $132 | $172 |
| NAME | 33 CCP010000033 | 17 | 41 | 41.5% | $3,461 | $4,229 | $204 | $249 |
| NAME | 31 CCP010000031 | 18 | 119 | 15.1% | $2,210 | $2,714 | $123 | $151 |
| NAME | 8 CCP010000008 | 48 | 194 | 24.7% | $8,918 | $11,901 | $186 | $248 |
| NAME | 22 CCP010000022 | 53 | 343 | 15.5% | $6,029 | $7,665 | $114 | $145 |
| NAME | 37 CCP010000037 | 114 | 468 | 24.4% | $13,755 | $16,936 | $121 | $149 |
| NAME | 1 CCP010000001 | 124 | 548 | 22.6% | $12,875 | $15,931 | $104 | $128 |
| NAME | 35 CCP010000035 | 164 | 534 | 30.7% | $23,619 | $26,740 | $144 | $163 |
| NAME | 6 CCP010000006 | 196 | 1,159 | 16.9% | $23,183 | $28,251 | $118 | $144 |
| NAME | 36 CCP010000036 | 239 | 1,277 | 18.7% | $26,827 | $33,072 | $112 | $138 |
| NAME | 2 CCP010000002 | 252 | 745 | 33.8% | $24,030 | $25,788 | $95 | $102 |
| NAME | 27 CCP010000027 | 282 | 1,497 | 18.8% | $42,615 | $45,645 | $151 | $162 |
| NAME | 7 CCP010000007 | 285 | 1,342 | 21.2% | $57,853 | $59,968 | $203 | $210 |
| NAME | 24 CCP010000024 | 357 | 1,638 | 21.8% | $51,656 | $55,213 | $145 | $155 |
| NAME | 26 CCP010000026 | 441 | 2,643 | 16.7% | $52,503 | $59,788 | $119 | $136 |
| NAME | 4 CCP010000004 | 448 | 1,328 | 33.7% | $51,131 | $53,399 | $114 | $119 |
| NAME | 13 CCP010000013 | 478 | 2,878 | 16.6% | $89,603 | $99,854 | $187 | $209 |
| NAME | 5 CCP010000005 | 512 | 2,728 | 18.8% | $72,851 | $81,939 | $142 | $160 |
| NAME | 30 CCP010000030 | 516 | 1,685 | 30.6% | $72,469 | $82,939 | $140 | $161 |
| NAME | 23 CCP010000023 | 541 | 2,063 | 26.2% | $109,318 | $112,946 | $202 | $209 |
| NAME | 3 CCP010000003 | 597 | 1,184 | 50.4% | $55,838 | $59,244 | $94 | $99 |
| NAME | 32 CCP010000032 | 617 | 2,590 | 23.8% | $107,442 | $121,776 | $174 | $197 |
| NAME | 29 CCP010000029 | 711 | 2,416 | 29.4% | $88,267 | $99,224 | $124 | $140 |
| NAME | 25 CCP010000025 | 731 | 2,348 | 31.1% | $120,207 | $125,768 | $164 | $172 |
| NAME | 19 CCP010000019 | 817 | 3,774 | 21.6% | $117,096 | $122,392 | $143 | $150 |
| NAME | 11 CCP010000011 | 843 | 2,237 | 37.7% | $85,965 | $94,409 | $102 | $112 |
| NAME | 16 CCP010000016 | 855 | 2,318 | 36.9% | $124,612 | $132,612 | $146 | $155 |
| NAME | 18 CCP010000018 | 881 | 4,108 | 21.4% | $105,119 | $116,862 | $119 | $133 |
| NAME | 14 CCP010000014 | 939 | 2,540 | 37.0% | $165,757 | $173,593 | $177 | $185 |
| NAME | 21 CCP010000021 | 1,162 | 2,689 | 43.2% | $116,606 | $124,819 | $100 | $107 |
| NAME | 15 CCP010000015 | 1,280 | 3,141 | 40.8% | $100,439 | $110,545 | $78 | $86 |
| NAME | 9 CCP010000009 | 1,692 | 4,870 | 34.7% | $224,567 | $255,154 | $133 | $151 |
| NAME | 12 CCP010000012 | 1,738 | 4,776 | 36.4% | $181,431 | $190,528 | $104 | $110 |
| NAME | 10 CCP010000010 | 1,795 | 5,045 | 35.6% | $255,935 | $264,955 | $143 | $148 |
| NAME | 17 CCP010000017 | 2,575 | 5,796 | 44.4% | $376,755 | $387,526 | $146 | $150 |

TABLE A4

Dermatology  
Dates of Service Jan. 1, 2003-Dec. 31, 2004 paid Dec. 31, 2004  
Total Role benign neoplasm of the skin without actinic keratoses diagnosis 702.xx  
etg 0682

| Doctor | total role id | etg of interest episode count | etg of interest doctor responsible dollars | etg of interest doctor total episode dollars | responsible dollars per episode | total episode dollars per episode | cost rank | quartile |
|---|---|---|---|---|---|---|---|---|
| NAME | 15 CCP010000015 | 1,280 | $100,439 | $110,545 | $78 | $86 | 1 | Q1 |
| NAME | 3 CCP010000003 | 597 | $55,838 | $59,244 | $94 | $99 | 2 | Q1 |
| NAME | 2 CCP010000002 | 252 | $24,030 | $25,788 | $95 | $102 | 3 | Q1 |
| NAME | 21 CCP010000021 | 1,162 | $116,606 | $124,819 | $100 | $107 | 4 | Q1 |
| NAME | 12 CCP010000012 | 1,738 | $181,431 | $190,528 | $104 | $110 | 5 | Q1 |
| NAME | 11 CCP010000011 | 843 | $85,965 | $94,409 | $102 | $112 | 6 | Q1 |
| NAME | 4 CCP010000004 | 448 | $51,131 | $53,399 | $114 | $119 | 7 | Q1 |
| NAME | 1 CCP010000001 | 124 | $12,875 | $15,931 | $104 | $128 | 8 | Q1 |
| NAME | 28 CCP010000028 | 11 | $1,202 | $1,416 | $109 | $129 | 9 | Q1 |
| | | | | | | | Q1 Count 9 | |
| NAME | 18 CCP010000018 | 881 | $105,119 | $116,862 | $119 | $133 | 10 | Q2 |
| NAME | 26 CCP010000026 | 441 | $52,503 | $59,788 | $119 | $136 | 11 | Q2 |
| NAME | 36 CCP010000036 | 239 | $26,827 | $33,072 | $112 | $138 | 12 | Q2 |
| NAME | 34 CCP010000034 | 13 | $1,534 | $1,801 | $118 | $139 | 13 | Q2 |
| NAME | 29 CCP010000029 | 711 | $88,267 | $99,224 | $124 | $140 | 14 | Q2 |
| NAME | 6 CCP010000006 | 196 | $23,183 | $28,251 | $118 | $144 | 15 | Q2 |
| NAME | 22 CCP010000022 | 53 | $6,029 | $7,665 | $114 | $145 | 16 | Q2 |
| NAME | 10 CCP010000010 | 1,795 | $255,935 | $264,955 | $143 | $148 | 17 | Q2 |

TABLE A4-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| Doctor | | total role id | etg of interest episode count | etg of interest doctor responsible dollars | etg of interest doctor total episode dollars | responsible dollars per episode | total episode dollars per episode | cost rank | quartile |
|---|---|---|---|---|---|---|---|---|---|
| NAME | 37 | CCP010000037 | 114 | $13,755 | $16,936 | $121 | $149 | 18 | Q2 |
| | | | | | | | | Q2 Count 9 | |
| NAME | 19 | CCP010000019 | 817 | $117,096 | $122,392 | $143 | $150 | 19 | Q3 |
| NAME | 17 | CCP010000017 | 2,575 | $376,755 | $387,526 | $146 | $150 | 20 | Q3 |
| NAME | 31 | CCP010000031 | 18 | $2,210 | $2,714 | $123 | $151 | 21 | Q3 |
| NAME | 9 | CCP010000009 | 1,692 | $224,567 | $255,154 | $133 | $151 | 22 | Q3 |
| NAME | 24 | CCP010000024 | 357 | $51,656 | $55,213 | $145 | $155 | 23 | Q3 |
| NAME | 16 | CCP010000016 | 855 | $124,612 | $132,612 | $146 | $155 | 24 | Q3 |
| NAME | 5 | CCP010000005 | 512 | $72,851 | $81,939 | $142 | $160 | 25 | Q3 |
| NAME | 30 | CCP010000030 | 516 | $72,469 | $82,939 | $140 | $161 | 26 | Q3 |
| NAME | 27 | CCP010000027 | 282 | $42,615 | $45,645 | $151 | $162 | 27 | Q3 |
| NAME | 35 | CCP010000035 | 164 | $23,619 | $26,740 | $144 | $163 | 28 | Q3 |
| | | | | | | | | Q3 Count 10 | |
| NAME | 25 | CCP010000025 | 731 | $120,207 | $125,768 | $164 | $172 | 29 | Q4 |
| NAME | 20 | CCP010000020 | 16 | $2,114 | $2,759 | $132 | $172 | 30 | Q4 |
| NAME | 14 | CCP010000014 | 939 | $165,757 | $173,593 | $177 | $185 | 31 | Q4 |
| NAME | 32 | CCP010000032 | 617 | $107,442 | $121,776 | $174 | $197 | 32 | Q4 |
| NAME | 23 | CCP010000023 | 541 | $109,318 | $112,946 | $202 | $209 | 33 | Q4 |
| NAME | 13 | CCP010000013 | 478 | $89,603 | $99,854 | $187 | $209 | 34 | Q4 |
| NAME | 7 | CCP010000007 | 285 | $57,853 | $59,968 | $203 | $210 | 35 | Q4 |
| NAME | 8 | CCP010000008 | 48 | $8,918 | $11,901 | $186 | $248 | 36 | Q4 |
| NAME | 33 | CCP010000033 | 17 | $3,461 | $4,229 | $204 | $249 | 37 | Q4 |
| | | | 22,358 | | | | | Q4 Count 9 | |
| | | | | | | | | Grand Count 37 | |

TABLE A5

Dermatology
Dates of Service Jan. 1, 2003-Dec. 31, 2004 paid Dec. 31, 2004
Total Role benign neoplasm of the skin without actinic
keratoses diagnosis 702.xx etg 0682
(5 or more episodes)

| Quartile | etg brief name | quartile episode count |
|---|---|---|
| Q1 | benign_lesions_without_actinic keratoses | 6,455 |
| Q2 | benign_lesions_without_actinic keratoses | 4,443 |
| Q3 | benign_lesions_without_actinic keratoses | 7,788 |
| Q4 | benign_lesions_without_actinic keratoses | 3,672 |
| Total of quartile, doctor, episode level | | 22,358 |

TABLE A6

Dermatology
Dates of Service Jan. 1, 2003-Dec. 31, 2004 paid Dec. 31, 2004
Total Role benign neoplasm of the skin without actinic keratoses diagnosis 702.xx
etg 0682

| quartile | begin diagnosis | episode count | diagnosis expense | medium | long |
|---|---|---|---|---|---|
| Q1 | 214.1 | 1 | $387 | LIPOMA OTH SKIN/SUBQ TISSUE | LIPOMA OF OTHER SKIN AND SUBCUTANEOUS TISSUE |
| Q1 | 214.9 | 2 | $480 | LIPOMA UNS SITE | LIPOMA UNSPECIFIED SITE |
| Q1 | 215.9 | 1 | $76 | OTH BENIGN NEO CONNEC SOFT TISS UNS | OTHER BENIGN NEOPLASM OF CONNECTIVE AND OTHER SOFT TISSUE SITE |
| Q1 | 216.0 | 17 | $2,650 | BENIGN NEO SKIN LIP | BENIGN NEOPLASM OF SKIN OF LIP |
| Q1 | 216.1 | 22 | $3,492 | BENIGN NEO EYELID INC CANTHUS | BENIGN NEOPLASM OF EYELID INCLUDING CANTHUS |
| Q1 | 216.2 | 16 | $2,131 | BENIGN NEO EAR SKIN | BENIGN NEOPLASM OF EAR AND EXTERNAL AUDITORY CANAL |

TABLE A6-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| quartile | begin diagnosis | episode count | diagnosis expense | medium | long |
|---|---|---|---|---|---|
| Q1 | 216.3 | 260 | $35,232 | BENIGN NEO SKIN OTH/UNS PARTS FACE | BENIGN NEOPLASM OF SKIN OF OTHER AND UNSPECIFIED PARTS OF FACE |
| Q1 | 216.4 | 177 | $21,392 | BENIGN NEO SCALP/SKIN NECK | BENIGN NEOPLASM OF SCALP AND SKIN OF NECK |
| Q1 | 216.5 | 565 | $78,097 | BENIGN NEO SKIN TRUNK EX SCROTUM | BENIGN NEOPLASM OF SKIN OF TRUNK EXCEPT SCROTUM |
| Q1 | 216.6 | 164 | $23,016 | BEN NEO SKIN UPPER LIMB | BENIGN NEOPLASM OF SKIN OF UPPER LIMB INCLUDING SHOULDER |
| Q1 | 216.7 | 172 | $22,699 | BENIGN NEO SKIN LOWER LIMB INC HIP | BENIGN NEOPLASM OF SKIN OF LOWER LIMB INCLUDING HIP |
| Q1 | 216.8 | 16 | $2,917 | BENIGN NEO OTHER SITES SKIN | BENIGN NEOPLASM OF OTHER SPECIFIED SITES OF SKIN |
| Q1 | 216.9 | 652 | $69,688 | BENIGN NEO SKIN SITE UNS | BENIGN NEOPLASM OF SKIN SITE UNSPECIFIED |
| Q1 | 228.01 | 6 | $884 | HEMANGIOMA SKIN/SUBQ TISSUE | HEMANGIOMA OF SKIN AND SUBCUTANEOUS TISSUE |
| Q1 | 228.1 | 1 | $130 | LYMPHANGIOMA ANY SITE | LYMPHANGIOMA ANY SITE |
| Q1 | 238.2 | 4,334 | $406,694 | UNCERT BEHAVIOR NEO SKIN | NEOPLASM OF UNCERTAIN BEHAVIOR OF SKIN |
| Q1 | 239.2 | 1 | $56 | BONE/SKIN UNSP BEHAVIOR NEO | NEOPLASM OF UNSPECIFIED NATURE OF BONE SOFT TISSUE AND SKIN |
| Q1 | 448.1 | 34 | $6,058 | NEVUS NON-NEOPLASTIC | NEVUS NON-NEOPLASTIC |
| Q2 | 214.0 | 2 | $265 | LIPOMA SKIN/SUBQ TISSUE FACE | LIPOMA OF SKIN AND SUBCUTANEOUS TISSUE OF FACE |
| Q2 | 214.1 | 7 | $1,148 | LIPOMA OTH SKIN/SUBQ TISSUE | LIPOMA OF OTHER SKIN AND SUBCUTANEOUS TISSUE |
| Q2 | 215.8 | 3 | $292 | OTH BEN NEO CONNEC SOFT TISSUE OT | OTHER BENIGN NEOPLASM OF CONNECTIVE AND OTHER SOFT TISSUE OF OTHER SPECIFIED SITES |
| Q2 | 215.9 | 1 | $112 | OTH BENIGN NEO CONNEC SOFT TISS UNS | OTHER BENIGN NEOPLASM OF CONNECTIVE AND OTHER SOFT TISSUE SITE UNSPECIFIED |
| Q2 | 216.0 | 14 | $1,862 | BENIGN NEO SKIN LIP | BENIGN NEOPLASM OF SKIN OF LIP |
| Q2 | 216.1 | 9 | $1,653 | BENIGN NEO EYELID INC CANTHUS | BENIGN NEOPLASM OF EYELID INCLUDING CANTHUS |
| Q2 | 216.2 | 4 | $465 | BENIGN NEO EAR SKIN | BENIGN NEOPLASM OF EAR AND EXTERNAL AUDITORY CANAL |
| Q2 | 216.3 | 179 | $26,569 | BENIGN NEO SKIN OTH/UNS PARTS FACE | BENIGN NEOPLASM OF SKIN OF OTHER AND UNSPECIFIED PARTS OF FACE |
| Q2 | 216.4 | 123 | $18,970 | BENIGN NEO SCALP/SKIN NECK | BENIGN NEOPLASM OF SCALP AND SKIN OF NECK |
| Q2 | 216.5 | 284 | $44,678 | BENIGN NEO SKIN TRUNK EX SCROTUM | BENIGN NEOPLASM OF SKIN OF TRUNK EXCEPT SCROTUM |
| Q2 | 216.6 | 107 | $15,845 | BEN NEO SKIN UPPER LIMB | BENIGN NEOPLASM OF SKIN OF UPPER LIMB INCLUDING SHOULDER |
| Q2 | 216.7 | 103 | $14,578 | BENIGN NEO SKIN LOWER LIMB INC HIP | BENIGN NEOPLASM OF SKIN OF LOWER LIMB INCLUDING HIP |
| Q2 | 216.8 | 56 | $7,571 | BENIGN NEO OTHER SITES SKIN | BENIGN NEOPLASM OF OTHER SPECIFIED SITES OF SKIN |
| Q2 | 216.9 | 816 | $115,075 | BENIGN NEO SKIN SITE UNS | BENIGN NEOPLASM OF SKIN SITE UNSPECIFIED |
| Q2 | 228.01 | 37 | $4,636 | HEMANGIOMA SKIN/SUBQ TISSUE | HEMANGIOMA OF SKIN AND SUBCUTANEOUS TISSUE |
| Q2 | 228.1 | 1 | $171 | LYMPHANGIOMA ANY SITE | LYMPHANGIOMA ANY SITE |
| Q2 | 238.2 | 2,606 | $360,120 | UNCERT BEHAVIOR NEO SKIN | NEOPLASM OF UNCERTAIN BEHAVIOR OF SKIN |
| Q2 | 239.2 | 3 | $837 | BONE/SKIN UNSP BEHAVIOR NEO | NEOPLASM OF UNSPECIFIED NATURE OF BONE SOFT TISSUE AND SKIN |
| Q2 | 448.1 | 72 | $13,707 | NEVUS NON-NEOPLASTIC | NEVUS NON-NEOPLASTIC |
| Q3 | 210.0 | 3 | $486 | BENIGN NEO LIP | BENIGN NEOPLASM OF LIP |
| Q3 | 214.0 | 5 | $1,124 | LIPOMA SKIN/SUBQ TISSUE FACE | LIPOMA OF SKIN AND SUBCUTANEOUS TISSUE OF FACE |
| Q3 | 214.1 | 13 | $2,875 | LIPOMA OTH SKIN/SUBQ TISSUE | LIPOMA OF OTHER SKIN AND SUBCUTANEOUS TISSUE |
| Q3 | 214.8 | 2 | $320 | LIPOMA OTHER SITES | LIPOMA OF OTHER SPECIFIED SITES |
| Q3 | 214.9 | 9 | $1,618 | LIPOMA UNS SITE | LIPOMA UNSPECIFIED SITE |
| Q3 | 215.8 | 1 | $71 | OTH BEN NEO CONNEC SOFT TISSUE OT | OTHER BENIGN NEOPLASM OF CONNECTIVE AND OTHER SOFT TISSUE OF OTHER SPECIFIED SITES |
| Q3 | 215.9 | 2 | $180 | OTH BENIGN NEO CONNEC SOFT TISS UNS | OTHER BENIGN NEOPLASM OF CONNECTIVE AND OTHER SOFT TISSUE SITE |
| Q3 | 216. | 1 | $372 | BENIGN NEOPLASM OF SKIN | BENIGN NEOPLASM OF SKIN |
| Q3 | 216.0 | 9 | $1,376 | BENIGN NEO SKIN LIP | BENIGN NEOPLASM OF SKIN OF LIP |
| Q3 | 216.1 | 16 | $3,892 | BENIGN NEO EYELID INC CANTHUS | BENIGN NEOPLASM OF EYELID INCLUDING CANTHUS |
| Q3 | 216.2 | 13 | $2,583 | BENIGN NEO EAR SKIN | BENIGN NEOPLASM OF EAR AND EXTERNAL AUDITORY CANAL |
| Q3 | 216.3 | 325 | $50,703 | BENIGN NEO SKIN OTH/UNS PARTS FACE | BENIGN NEOPLASM OF SKIN OF OTHER AND UNSPECIFIED PARTS OF FACE |
| Q3 | 216.4 | 111 | $22,575 | BENIGN NEO SCALP/SKIN NECK | BENIGN NEOPLASM OF SCALP AND SKIN OF NECK |
| Q3 | 216.5 | 438 | $74,330 | BENIGN NEO SKIN TRUNK EX SCROTUM | BENIGN NEOPLASM OF SKIN OF TRUNK EXCEPT SCROTUM |
| Q3 | 216.6 | 73 | $13,441 | BEN NEO SKIN UPPER LIMB | BENIGN NEOPLASM OF SKIN OF UPPER LIMB INCLUDING SHOULDER |
| Q3 | 216.7 | 99 | $18,208 | BENIGN NEO SKIN LOWER LIMB INC HIP | BENIGN NEOPLASM OF SKIN OF LOWER LIMB INCLUDING HIP |

TABLE A6-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| quartile | begin diagnosis | episode count | diagnosis expense | medium | long |
|---|---|---|---|---|---|
| Q3 | 216.8 | 28 | $4,922 | BENIGN NEO OTHER SITES SKIN | BENIGN NEOPLASM OF OTHER SPECIFIED SITES OF SKIN |
| Q3 | 216.9 | 1,473 | $218,510 | BENIGN NEO SKIN SITE UNS | BENIGN NEOPLASM OF SKIN SITE UNSPECIFIED |
| Q3 | 228.01 | 96 | $17,043 | HEMANGIOMA SKIN/SUBQ TISSUE | HEMANGIOMA OF SKIN AND SUBCUTANEOUS TISSUE |
| Q3 | 228.1 | 1 | $260 | LYMPHANGIOMA ANY SITE | LYMPHANGIOMA ANY SITE |
| Q3 | 238.2 | 4,980 | $741,410 | UNCERT BEHAVIOR NEO SKIN | NEOPLASM OF UNCERTAIN BEHAVIOR OF SKIN |
| Q3 | 239.2 | 4 | $783 | BONE/SKIN UNSP BEHAVIOR NEO | NEOPLASM OF UNSPECIFIED NATURE OF BONE SOFT TISSUE AND SKIN |
| Q3 | 448.1 | 80 | $15,792 | NEVUS NON-NEOPLASTIC | NEVUS NON-NEOPLASTIC |
| Q4 | 210.0 | 1 | $129 | BENIGN NEO LIP | BENIGN NEOPLASM OF LIP |
| Q4 | 214.0 | 2 | $295 | LIPOMA SKIN/SUBQ TISSUE FACE | LIPOMA OF SKIN AND SUBCUTANEOUS TISSUE OF FACE |
| Q4 | 214.1 | 3 | $620 | LIPOMA OTH SKIN/SUBQ TISSUE | LIPOMA OF OTHER SKIN AND SUBCUTANEOUS TISSUE |
| Q4 | 214.9 | 2 | $473 | LIPOMA UNS SITE | LIPOMA UNSPECIFIED SITE |
| Q4 | 215.8 | 8 | $1,739 | OTH BEN NEO CONNEC SOFT TISSUE OT | OTHER BENIGN NEOPLASM OF CONNECTIVE AND OTHER SOFT TISSUE OF OTHER SPECIFIED SITES |
| Q4 | 215.9 | 7 | $1,477 | OTH BENIGN NEO CONNEC SOFT TISS UNS | OTHER BENIGN NEOPLASM OF CONNECTIVE AND OTHER SOFT TISSUE SITE |
| Q4 | 216.0 | 6 | $1,310 | BENIGN NEO SKIN LIP | BENIGN NEOPLASM OF SKIN OF LIP |
| Q4 | 216.1 | 10 | $2,452 | BENIGN NEO EYELID INC CANTHUS | BENIGN NEOPLASM OF EYELID INCLUDING CANTHUS |
| Q4 | 216.2 | 10 | $1,757 | BENIGN NEO EAR SKIN | BENIGN NEOPLASM OF EAR AND EXTERNAL AUDITORY CANAL |
| Q4 | 216.3 | 106 | $25,030 | BENIGN NEO SKIN OTH/UNS PARTS FACE | BENIGN NEOPLASM OF SKIN OF OTHER AND UNSPECIFIED PARTS OF FACE |
| Q4 | 216.4 | 60 | $13,613 | BENIGN NEO SCALP/SKIN NECK | BENIGN NEOPLASM OF SCALP AND SKIN OF NECK |
| Q4 | 216.5 | 382 | $74,703 | BENIGN NEO SKIN TRUNK EX SCROTUM | BENIGN NEOPLASM OF SKIN OF TRUNK EXCEPT SCROTUM |
| Q4 | 216.6 | 58 | $10,812 | BEN NEO SKIN UPPER LIMB | BENIGN NEOPLASM OF SKIN OF UPPER LIMB INCLUDING SHOULDER |
| Q4 | 216.7 | 59 | $11,764 | BENIGN NEO SKIN LOWER LIMB INC HIP | BENIGN NEOPLASM OF SKIN OF LOWER LIMB INCLUDING HIP |
| Q4 | 216.8 | 82 | $17,728 | BENIGN NEO OTHER SITES SKIN | BENIGN NEOPLASM OF OTHER SPECIFIED SITES OF SKIN |
| Q4 | 216.9 | 1,246 | $244,793 | BENIGN NEO SKIN SITE UNS | BENIGN NEOPLASM OF SKIN SITE UNSPECIFIED |
| Q4 | 228.01 | 89 | $15,747 | HEMANGIOMA SKIN/SUBQ TISSUE | HEMANGIOMA OF SKIN AND SUBCUTANEOUS TISSUE |
| Q4 | 228.1 | 3 | $977 | LYMPHANGIOMA ANY SITE | LYMPHANGIOMA ANY SITE |
| Q4 | 238.2 | 1,403 | $259,521 | UNCERT BEHAVIOR NEO SKIN | NEOPLASM OF UNCERTAIN BEHAVIOR OF SKIN |
| Q4 | 239.2 | 3 | $554 | BONE/SKIN UNSP BEHAVIOR NEO | NEOPLASM OF UNSPECIFIED NATURE OF BONE SOFT TISSUE AND SKIN |
| Q4 | 448.1 | 128 | $27,300 | NEVUS NON-NEOPLASTIC | NEVUS NON-NEOPLASTIC |

TABLE A7

| PAIRED_ETGNO | service group | specialty total role episode occurred in count | specialty total role average expense | specialty total role average services | specialty total role expense | specialty total role services | strata sum episode count | total role expected expense per episode | total role expected services per episode |
|---|---|---|---|---|---|---|---|---|---|
| benign_lesions_without_actinic_keratoses | 00300 | 2 | $290.00 | 1 | $580 | 2 | 22,358 | $0.0259 | .00008945 |
| benign_lesions_without_actinic_keratoses | 00400 | 1 | $225.00 | 1 | $225 | 1 | 22,358 | $0.0101 | .00004473 |
| benign_lesions_without_actinic_keratoses | 00820 | 1 | $315.00 | 1 | $315 | 1 | 22,358 | $0.0141 | .00004473 |
| benign_lesions_without_actinic_keratoses | 0301 | 1 | $ 39.00 | 1 | $39 | 1 | 22,358 | $0.0017 | .00004473 |
| benign_lesions_without_actinic_keratoses | 0320 | 1 | $ 34.00 | 1 | $34 | 1 | 22,358 | $0.0015 | .00004473 |
| benign_lesions_without_actinic_keratoses | 0490 | 1 | $336.00 | 6 | $336 | 6 | 22,358 | $0.0150 | .00026836 |
| benign_lesions_without_actinic_keratoses | 0551 | 1 | $425.00 | 5 | $425 | 5 | 22,358 | $0.0190 | .00022363 |
| benign_lesions_without_actinic_keratoses | 0969 | 1 | $ 8.00 | 2 | $8 | 2 | 22,358 | $0.0004 | .00008945 |
| benign_lesions_without_actinic_keratoses | 10022 | 1 | $100.00 | 1 | $100 | 1 | 22,358 | $0.0045 | .00004473 |
| benign_lesions_without_actinic_keratoses | 11000 | 1 | $ 53.00 | 1 | $53 | 1 | 22,358 | $0.0024 | .00004473 |
| benign_lesions_without_actinic_keratoses | 11042 | 2 | $ 84.50 | 1 | $169 | 2 | 22,358 | $0.0076 | .00008945 |
| benign_lesions_without_actinic_keratoses | 11100 | 1,699 | $ 89.42 | 1 | $151,931 | 1,770 | 22,358 | $6.7954 | .07916629 |
| benign_lesions_without_actinic_keratoses | 11101 | 423 | $ 61.89 | 2 | $26,181 | 636 | 22,358 | $1.1710 | .02844619 |
| benign_lesions_without_actinic_keratoses | 11200 | 3 | $ 50.00 | 1 | $150 | 3 | 22,358 | $0.0067 | .00013418 |
| benign_lesions_without_actinic_keratoses | 11201 | 1 | $140.00 | 4 | $140 | 4 | 22,358 | $0.0063 | .00017891 |
| benign_lesions_without_actinic_keratoses | 11300 | 1,068 | $ 67.39 | 2 | $71,969 | 1,636 | 22,358 | $3.2189 | .07317291 |
| benign_lesions_without_actinic_keratoses | 11301 | 1,858 | $ 90.66 | 1 | $168,438 | 2,724 | 22,358 | $7.5337 | .12183558 |
| benign_lesions_without_actinic_keratoses | 11302 | 475 | $ 96.64 | 1 | $45,904 | 569 | 22,358 | $2.0531 | .02544950 |
| benign_lesions_without_actinic_keratoses | 11303 | 27 | $118.74 | 1 | $3,206 | 32 | 22,358 | $0.1434 | .00143126 |

TABLE A7-continued

| PAIRED_ETGNO | service group | specialty total role episode occurred in count | specialty total role average expense | specialty total role average services | specialty total role expense | specialty total role services | strata sum episode count | total role expected expense per episode | total role expected services per episode |
|---|---|---|---|---|---|---|---|---|---|
| benign_lesions_without_actinic keratoses | 11305 | 471 | $ 64.23 | 2 | $30,250 | 763 | 22,358 | $ 1.3530 | .03412649 |
| benign_lesions_without_actinic keratoses | 11306 | 513 | $102.81 | 2 | $52,741 | 832 | 22,358 | $ 2.3589 | .03721263 |
| benign_lesions_without_actinic keratoses | 11307 | 94 | $ 95.78 | 1 | $9,003 | 99 | 22,358 | $ 0.4027 | .00442795 |
| benign_lesions_without_actinic keratoses | 11308 | 11 | $102.91 | 1 | $1,132 | 11 | 22,358 | $ 0.0506 | .00049199 |
| benign_lesions_without_actinic keratoses | 11310 | 548 | $ 78.14 | 1 | $42,822 | 724 | 22,358 | $ 1.9153 | .03238215 |
| benign_lesions_without_actinic keratoses | 11311 | 561 | $106.09 | 1 | $59,519 | 758 | 22,358 | $ 2.6621 | .03390285 |
| benign_lesions_without_actinic keratoses | 11312 | 106 | $109.69 | 1 | $11,627 | 118 | 22,358 | $ 0.5200 | .00527775 |
| benign_lesions_without_actinic keratoses | 11313 | 3 | $140.00 | 1 | $420 | 3 | 22,358 | $ 0.0188 | .00013418 |
| benign_lesions_without_actinic keratoses | 11400 | 428 | $111.47 | 1 | $47,710 | 512 | 22,358 | $ 2.1339 | .02290008 |
| benign_lesions_without_actinic keratoses | 11401 | 745 | $137.40 | 1 | $102,362 | 966 | 22,358 | $ 4.5783 | .04320601 |
| benign_lesions_without_actinic keratoses | 11402 | 466 | $156.19 | 1 | $72,786 | 531 | 22,358 | $ 3.2555 | .02374989 |
| benign_lesions_without_actinic keratoses | 11403 | 106 | $183.32 | 1 | $19,432 | 119 | 22,358 | $ 0.8691 | .00532248 |
| benign_lesions_without_actinic keratoses | 11404 | 31 | $215.26 | 1 | $6,673 | 34 | 22,358 | $ 0.2985 | .00152071 |
| benign_lesions_without_actinic keratoses | 11406 | 12 | $252.92 | 1 | $3,035 | 13 | 22,358 | $ 0.1357 | .00058145 |
| benign_lesions_without_actinic keratoses | 11420 | 88 | $111.85 | 1 | $9,843 | 110 | 22,358 | $ 0.4402 | .00491994 |
| benign_lesions_without_actinic keratoses | 11421 | 111 | $131.81 | 1 | $14,631 | 122 | 22,358 | $ 0.6544 | .00545666 |
| benign_lesions_without_actinic keratoses | 11422 | 57 | $157.56 | 1 | $8,981 | 63 | 22,358 | $ 0.4017 | .00281778 |
| benign_lesions_without_actinic keratoses | 11423 | 21 | $192.19 | 1 | $4,036 | 23 | 22,358 | $ 0.1805 | .00102871 |
| benign_lesions_without_actinic keratoses | 11424 | 6 | $222.17 | 1 | $1,333 | 6 | 22,358 | $ 0.0596 | .00026836 |
| benign_lesions_without_actinic keratoses | 11426 | 2 | $261.50 | 1 | $523 | 2 | 22,358 | $ 0.0234 | .00008945 |
| benign_lesions_without_actinic keratoses | 11440 | 216 | $148.58 | 1 | $32,093 | 273 | 22,358 | $ 1.4354 | .01221039 |
| benign_lesions_without_actinic keratoses | 11441 | 136 | $165.09 | 1 | $22,452 | 152 | 22,358 | $ 1.0042 | .00679846 |
| benign_lesions_without_actinic keratoses | 11442 | 55 | $178.07 | 1 | $9,794 | 57 | 22,358 | $ 0.4381 | .00254942 |
| benign_lesions_without_actinic keratoses | 11443 | 13 | $242.38 | 1 | $3,151 | 15 | 22,358 | $ 0.1409 | .00067090 |
| benign_lesions_without_actinic keratoses | 11444 | 2 | $293.50 | 1 | $587 | 2 | 22,358 | $ 0.0263 | .00008945 |
| benign_lesions_without_actinic keratoses | 11446 | 1 | $371.00 | 1 | $371 | 1 | 22,358 | $ 0.0166 | .00004473 |
| benign_lesions_without_actinic keratoses | 11600 | 1 | $160.00 | 1 | $160 | 1 | 22,358 | $ 0.0072 | .00004473 |
| benign_lesions_without_actinic keratoses | 11602 | 3 | $162.67 | 1 | $488 | 3 | 22,358 | $ 0.0218 | .00013418 |
| benign_lesions_without_actinic keratoses | 11603 | 2 | $162.00 | 1 | $324 | 2 | 22,358 | $ 0.0145 | .00008945 |
| benign_lesions_without_actinic keratoses | 11604 | 1 | $244.00 | 1 | $244 | 1 | 22,358 | $ 0.0109 | .00004473 |
| benign_lesions_without_actinic keratoses | 11755 | 2 | $ 59.50 | 1 | $119 | 2 | 22,358 | $ 0.0053 | .00008945 |
| benign_lesions_without_actinic keratoses | 11900 | 21 | $ 51.76 | 1 | $1,087 | 23 | 22,358 | $ 0.0486 | .00102871 |
| benign_lesions_without_actinic keratoses | 11901 | 11 | $ 54.36 | 1 | $598 | 11 | 22,358 | $ 0.0267 | .00049199 |
| benign_lesions_without_actinic keratoses | 12031 | 104 | $189.34 | 1 | $19,691 | 116 | 22,358 | $ 0.8807 | .00518830 |
| benign_lesions_without_actinic keratoses | 12032 | 95 | $227.11 | 1 | $21,575 | 99 | 22,358 | $ 0.9650 | .00442795 |
| benign_lesions_without_actinic keratoses | 12051 | 12 | $219.08 | 1 | $2,629 | 12 | 22,358 | $ 0.1176 | .00053672 |
| benign_lesions_without_actinic keratoses | 13101 | 8 | $319.25 | 1 | $2,554 | 8 | 22,358 | $ 0.1142 | .00035781 |
| benign_lesions_without_actinic keratoses | 13131 | 2 | $315.00 | 1 | $630 | 2 | 22,358 | $ 0.0282 | .00008945 |
| benign_lesions_without_actinic keratoses | 17000 | 4,018 | $ 68.66 | 1 | $275,888 | 4,424 | 22,358 | $12.3396 | .19787101 |
| benign_lesions_without_actinic keratoses | 17003 | 2,635 | $ 11.03 | 3 | $29,069 | 7,268 | 22,358 | $ 1.3002 | .32507380 |
| benign_lesions_without_actinic keratoses | 17004 | 33 | $ 62.36 | 1 | $2,058 | 34 | 22,358 | $ 0.0920 | .00152071 |
| benign_lesions_without_actinic keratoses | 17106 | 14 | $367.43 | 1 | $5,144 | 14 | 22,358 | $ 0.2301 | .00062617 |
| benign_lesions_without_actinic keratoses | 17110 | 2,499 | $ 59.61 | 1 | $148,953 | 2,657 | 22,358 | $ 6.6622 | .11883889 |
| benign_lesions_without_actinic keratoses | 17111 | 20 | $ 39.40 | 1 | $788 | 20 | 22,358 | $ 0.0352 | .00089453 |
| benign_lesions_without_actinic keratoses | 17281 | 1 | $144.00 | 1 | $144 | 1 | 22,358 | $ 0.0064 | .00004473 |
| benign_lesions_without_actinic keratoses | 27327 | 1 | $539.00 | 1 | $539 | 1 | 22,358 | $ 0.0241 | .00004473 |
| benign_lesions_without_actinic keratoses | 30100 | 2 | $ 94.50 | 1 | $189 | 2 | 22,358 | $ 0.0085 | .00008945 |
| benign_lesions_without_actinic keratoses | 36415 | 1 | $ 6.00 | 1 | $6 | 1 | 22,358 | $ 0.0003 | .00004473 |
| benign_lesions_without_actinic keratoses | 40490 | 21 | $123.14 | 1 | $2,586 | 23 | 22,358 | $ 0.1157 | .00102871 |
| benign_lesions_without_actinic keratoses | 54050 | 4 | $159.75 | 1 | $639 | 5 | 22,358 | $ 0.0286 | .00022363 |
| benign_lesions_without_actinic keratoses | 54056 | 7 | $160.14 | 1 | $1,121 | 7 | 22,358 | $ 0.0501 | .00031309 |
| benign_lesions_without_actinic keratoses | 54060 | 1 | $278.00 | 1 | $278 | 1 | 22,358 | $ 0.0124 | .00004473 |
| benign_lesions_without_actinic keratoses | 54100 | 2 | $194.00 | 1 | $388 | 2 | 22,358 | $ 0.0174 | .00008945 |
| benign_lesions_without_actinic keratoses | 56605 | 8 | $ 90.00 | 1 | $720 | 8 | 22,358 | $ 0.0322 | .00035781 |
| benign_lesions_without_actinic keratoses | 67810 | 25 | $190.44 | 1 | $4,761 | 28 | 22,358 | $ 0.2129 | .00125235 |
| benign_lesions_without_actinic keratoses | 69100 | 14 | $ 83.14 | 1 | $1,164 | 14 | 22,358 | $ 0.0521 | .00062617 |
| benign_lesions_without_actinic keratoses | 76942 | 2 | $ 98.50 | 1 | $197 | 2 | 22,358 | $ 0.0088 | .00008945 |
| benign_lesions_without_actinic keratoses | 80002 | 4 | $ 5.00 | 1 | $20 | 4 | 22,358 | $ 0.0009 | .00017891 |
| benign_lesions_without_actinic keratoses | 80003 | 2 | $ 5.00 | 1 | $10 | 2 | 22,358 | $ 0.0004 | .00008945 |
| benign_lesions_without_actinic keratoses | 80004 | 1 | $ 5.00 | 1 | $5 | 1 | 22,358 | $ 0.0002 | .00004473 |
| benign_lesions_without_actinic keratoses | 80005 | 2 | $ 5.00 | 1 | $10 | 2 | 22,358 | $ 0.0004 | .00008945 |
| benign_lesions_without_actinic keratoses | 80012 | 1 | $ 6.00 | 1 | $6 | 1 | 22,358 | $ 0.0003 | .00004473 |
| benign_lesions_without_actinic keratoses | 80048 | 78 | $ 3.29 | 1 | $257 | 81 | 22,358 | $ 0.0115 | .00362286 |
| benign_lesions_without_actinic keratoses | 80050 | 27 | $ 14.00 | 1 | $378 | 27 | 22,358 | $ 0.0169 | .00120762 |
| benign_lesions_without_actinic keratoses | 80051 | 2 | $ 4.00 | 1 | $8 | 2 | 22,358 | $ 0.0004 | .00008945 |
| benign_lesions_without_actinic keratoses | 80053 | 119 | $ 5.13 | 1 | $610 | 122 | 22,358 | $ 0.0273 | .00545666 |
| benign_lesions_without_actinic keratoses | 80061 | 91 | $ 8.09 | 1 | $736 | 92 | 22,358 | $ 0.0329 | .00411486 |
| benign_lesions_without_actinic keratoses | 80299 | 3 | $ 13.33 | 1 | $40 | 4 | 22,358 | $ 0.0018 | .00017891 |
| benign_lesions_without_actinic keratoses | 81000 | 8 | $ 5.38 | 1 | $43 | 8 | 22,358 | $ 0.0019 | .00035781 |
| benign_lesions_without_actinic keratoses | 82040 | 4 | $ 5.75 | 1 | $23 | 4 | 22,358 | $ 0.0010 | .00017891 |
| benign_lesions_without_actinic keratoses | 82248 | 20 | $ 2.15 | 1 | $43 | 20 | 22,358 | $ 0.0019 | .00089453 |
| benign_lesions_without_actinic keratoses | 82270 | 39 | $ 3.44 | 1 | $134 | 41 | 22,358 | $ 0.0060 | .00183380 |
| benign_lesions_without_actinic keratoses | 82310 | 2 | $ 4.00 | 1 | $8 | 2 | 22,358 | $ 0.0004 | .00008945 |

TABLE A7-continued

| PAIRED_ETGNO | service group | specialty total role episode occurred in count | specialty total role average expense | specialty total role average services | specialty total role expense | specialty total role services | strata sum episode count | total role expected expense per episode | total role expected services per episode |
|---|---|---|---|---|---|---|---|---|---|
| benign_lesions_without_actinic keratoses | 82565 | 12 | $ 4.75 | 1 | $57 | 13 | 22,358 | $ 0.0025 | .00058145 |
| benign_lesions_without_actinic keratoses | 82947 | 27 | $ 2.26 | 1 | $61 | 27 | 22,358 | $ 0.0027 | .00120762 |
| benign_lesions_without_actinic keratoses | 84075 | 2 | $ 4.00 | 1 | $8 | 2 | 22,358 | $ 0.0004 | .00008945 |
| benign_lesions_without_actinic keratoses | 84100 | 1 | $ 8.00 | 1 | $8 | 1 | 22,358 | $ 0.0004 | .00004473 |
| benign_lesions_without_actinic keratoses | 84155 | 2 | $ 3.00 | 1 | $6 | 2 | 22,358 | $ 0.0003 | .00008945 |
| benign_lesions_without_actinic keratoses | 84436 | 2 | $ 4.00 | 1 | $8 | 2 | 22,358 | $ 0.0004 | .00008945 |
| benign_lesions_without_actinic keratoses | 84439 | 11 | $ 8.00 | 1 | $88 | 11 | 22,358 | $ 0.0039 | .00049199 |
| benign_lesions_without_actinic keratoses | 84443 | 48 | $ 7.00 | 1 | $336 | 48 | 22,358 | $ 0.0150 | .00214688 |
| benign_lesions_without_actinic keratoses | 84450 | 23 | $ 3.48 | 1 | $80 | 24 | 22,358 | $ 0.0036 | .00107344 |
| benign_lesions_without_actinic keratoses | 84460 | 57 | $ 4.54 | 1 | $259 | 63 | 22,358 | $ 0.0116 | .00281778 |
| benign_lesions_without_actinic keratoses | 84478 | 6 | $ 4.00 | 1 | $24 | 8 | 22,358 | $ 0.0011 | .00035781 |
| benign_lesions_without_actinic keratoses | 84520 | 1 | $ 3.00 | 1 | $3 | 1 | 22,358 | $ 0.0001 | .00004473 |
| benign_lesions_without_actinic keratoses | 85013 | 3 | $ 5.00 | 1 | $15 | 3 | 22,358 | $ 0.0007 | .00013418 |
| benign_lesions_without_actinic keratoses | 85014 | 11 | $ 2.18 | 1 | $24 | 12 | 22,358 | $ 0.0011 | .00053672 |
| benign_lesions_without_actinic keratoses | 85018 | 1 | $ 6.00 | 1 | $6 | 1 | 22,358 | $ 0.0003 | .00004473 |
| benign_lesions_without_actinic keratoses | 85025 | 109 | $ 3.57 | 1 | $389 | 127 | 22,358 | $ 0.0174 | .00568029 |
| benign_lesions_without_actinic keratoses | 85027 | 74 | $ 2.27 | 1 | $168 | 76 | 22,358 | $ 0.0075 | .00339923 |
| benign_lesions_without_actinic keratoses | 85044 | 1 | $ 6.00 | 2 | $6 | 2 | 22,358 | $ 0.0003 | .00008945 |
| benign_lesions_without_actinic keratoses | 85045 | 1 | $ 4.00 | 2 | $4 | 2 | 22,358 | $ 0.0002 | .00008945 |
| benign_lesions_without_actinic keratoses | 85049 | 1 | $ 2.00 | 1 | $2 | 1 | 22,358 | $ 0.0001 | .00004473 |
| benign_lesions_without_actinic keratoses | 85610 | 18 | $ 4.83 | 2 | $87 | 29 | 22,358 | $ 0.0039 | .00129707 |
| benign_lesions_without_actinic keratoses | 85651 | 5 | $ 2.00 | 1 | $10 | 5 | 22,358 | $ 0.0004 | .00022363 |
| benign_lesions_without_actinic keratoses | 85652 | 4 | $ 2.00 | 1 | $8 | 4 | 22,358 | $ 0.0004 | .00017891 |
| benign_lesions_without_actinic keratoses | 85730 | 6 | $ 3.00 | 1 | $18 | 6 | 22,358 | $ 0.0008 | .00026836 |
| benign_lesions_without_actinic keratoses | 86140 | 5 | $ 3.00 | 1 | $15 | 5 | 22,358 | $ 0.0007 | .00022363 |
| benign_lesions_without_actinic keratoses | 86141 | 2 | $ 10.00 | 1 | $20 | 2 | 22,358 | $ 0.0009 | .00008945 |
| benign_lesions_without_actinic keratoses | 86580 | 2 | $ 7.50 | 1 | $15 | 2 | 22,358 | $ 0.0007 | .00008945 |
| benign_lesions_without_actinic keratoses | 86618 | 3 | $ 12.00 | 1 | $36 | 3 | 22,358 | $ 0.0016 | .00013418 |
| benign_lesions_without_actinic keratoses | 86644 | 3 | $ 18.67 | 1 | $56 | 4 | 22,358 | $ 0.0025 | .00017891 |
| benign_lesions_without_actinic keratoses | 86645 | 1 | $ 28.00 | 2 | $28 | 2 | 22,358 | $ 0.0013 | .00008945 |
| benign_lesions_without_actinic keratoses | 86777 | 1 | $ 8.00 | 1 | $8 | 1 | 22,358 | $ 0.0004 | .00004473 |
| benign_lesions_without_actinic keratoses | 86850 | 2 | $ 19.50 | 1 | $39 | 2 | 22,358 | $ 0.0017 | .00008945 |
| benign_lesions_without_actinic keratoses | 86900 | 2 | $ 2.00 | 1 | $4 | 2 | 22,358 | $ 0.0002 | .00008945 |
| benign_lesions_without_actinic keratoses | 86901 | 2 | $ 2.00 | 1 | $4 | 2 | 22,358 | $ 0.0002 | .00008945 |
| benign_lesions_without_actinic keratoses | 87101 | 6 | $ 8.00 | 1 | $48 | 6 | 22,358 | $ 0.0021 | .00026836 |
| benign_lesions_without_actinic keratoses | 87106 | 4 | $ 4.00 | 1 | $16 | 4 | 22,358 | $ 0.0007 | .00017891 |
| benign_lesions_without_actinic keratoses | 87340 | 1 | $ 7.00 | 1 | $7 | 1 | 22,358 | $ 0.0003 | .00004473 |
| benign_lesions_without_actinic keratoses | 87390 | 1 | $ 8.00 | 1 | $8 | 1 | 22,358 | $ 0.0004 | .00004473 |
| benign_lesions_without_actinic keratoses | 88106 | 1 | $ 21.00 | 1 | $21 | 1 | 22,358 | $ 0.0009 | .00004473 |
| benign_lesions_without_actinic keratoses | 88173 | 2 | $ 39.50 | 2 | $79 | 3 | 22,358 | $ 0.0035 | .00013418 |
| benign_lesions_without_actinic keratoses | 88304 | 77 | $ 16.25 | 1 | $1,251 | 83 | 22,358 | $ 0.0560 | .00371232 |
| benign_lesions_without_actinic keratoses | 88305 | 6,637 | $ 50.11 | 2 | $332,602 | 10,756 | 22,358 | $14.8762 | .48108060 |
| benign_lesions_without_actinic keratoses | 88307 | 2 | $ 68.00 | 1 | $136 | 2 | 22,358 | $ 0.0061 | .00008945 |
| benign_lesions_without_actinic keratoses | 88312 | 35 | $ 28.37 | 2 | $993 | 62 | 22,358 | $ 0.0444 | .00277306 |
| benign_lesions_without_actinic keratoses | 88321 | 13 | $ 91.54 | 1 | $1,190 | 14 | 22,358 | $ 0.0532 | .00062617 |
| benign_lesions_without_actinic keratoses | 88342 | 16 | $296.63 | 2 | $4,746 | 32 | 22,358 | $ 0.2123 | .00143126 |
| benign_lesions_without_actinic keratoses | 92002 | 1 | $ 76.00 | 1 | $76 | 1 | 22,358 | $ 0.0034 | .00004473 |
| benign_lesions_without_actinic keratoses | 92012 | 1 | $ 68.00 | 1 | $68 | 1 | 22,358 | $ 0.0030 | .00004473 |
| benign_lesions_without_actinic keratoses | 93000 | 17 | $ 30.82 | 1 | $524 | 17 | 22,358 | $ 0.0234 | .00076035 |
| benign_lesions_without_actinic keratoses | 93005 | 5 | $ 51.60 | 1 | $258 | 5 | 22,358 | $ 0.0115 | .00022363 |
| benign_lesions_without_actinic keratoses | 93010 | 5 | $ 27.20 | 1 | $136 | 5 | 22,358 | $ 0.0061 | .00022363 |
| benign_lesions_without_actinic keratoses | 93971 | 1 | $154.00 | 1 | $154 | 1 | 22,358 | $ 0.0069 | .00004473 |
| benign_lesions_without_actinic keratoses | 94010 | 1 | $124.00 | 1 | $124 | 1 | 22,358 | $ 0.0055 | .00004473 |
| benign_lesions_without_actinic keratoses | 94240 | 1 | $125.00 | 1 | $125 | 1 | 22,358 | $ 0.0056 | .00004473 |
| benign_lesions_without_actinic keratoses | 94720 | 2 | $ 82.50 | 1 | $165 | 2 | 22,358 | $ 0.0074 | .00008945 |
| benign_lesions_without_actinic keratoses | 95810 | 1 | $295.00 | 1 | $295 | 1 | 22,358 | $ 0.0132 | .00004473 |
| benign_lesions_without_actinic keratoses | 95816 | 1 | $159.00 | 1 | $159 | 1 | 22,358 | $ 0.0071 | .00004473 |
| benign_lesions_without_actinic keratoses | 95819 | 1 | $116.00 | 1 | $116 | 1 | 22,358 | $ 0.0052 | .00004473 |
| benign_lesions_without_actinic keratoses | 96910 | 1 | $ 59.00 | 1 | $59 | 1 | 22,358 | $ 0.0026 | .00004473 |
| benign_lesions_without_actinic keratoses | 99201 | 1 | $ 38.00 | 1 | $38 | 1 | 22,358 | $ 0.0017 | .00004473 |
| benign_lesions_without_actinic keratoses | 99202 | 93 | $ 70.82 | 1 | $6,586 | 99 | 22,358 | $ 0.2946 | .00442795 |
| benign_lesions_without_actinic keratoses | 99203 | 156 | $108.70 | 1 | $16,957 | 160 | 22,358 | $ 0.7584 | .00715628 |
| benign_lesions_without_actinic keratoses | 99204 | 11 | $143.91 | 1 | $1,583 | 11 | 22,358 | $ 0.0708 | .00049199 |
| benign_lesions_without_actinic keratoses | 99205 | 1 | $164.00 | 1 | $164 | 1 | 22,358 | $ 0.0073 | .00004473 |
| benign_lesions_without_actinic keratoses | 99211 | 11 | $ 24.36 | 1 | $268 | 11 | 22,358 | $ 0.0120 | .00049199 |
| benign_lesions_without_actinic keratoses | 99212 | 1,230 | $ 41.79 | 1 | $51,402 | 1,311 | 22,358 | $ 2.2990 | .05863673 |
| benign_lesions_without_actinic keratoses | 99213 | 6,470 | $ 58.10 | 1 | $375,886 | 6,814 | 22,358 | $16.8121 | .30476787 |
| benign_lesions_without_actinic keratoses | 99214 | 116 | $ 91.59 | 1 | $10,624 | 117 | 22,358 | $ 0.4752 | .00523303 |
| benign_lesions_without_actinic keratoses | 99215 | 4 | $162.50 | 1 | $650 | 5 | 22,358 | $ 0.0291 | .00022363 |
| benign_lesions_without_actinic keratoses | 99233 | 1 | $ 86.00 | 1 | $86 | 1 | 22,358 | $ 0.0038 | .00004473 |
| benign_lesions_without_actinic keratoses | 99241 | 105 | $ 53.00 | 1 | $5,565 | 105 | 22,358 | $ 0.2489 | .00469631 |
| benign_lesions_without_actinic keratoses | 99242 | 2,122 | $ 99.17 | 1 | $210,441 | 2,166 | 22,358 | $ 9.4123 | .09687807 |
| benign_lesions_without_actinic keratoses | 99243 | 4,196 | $131.13 | 1 | $550,225 | 4,264 | 22,358 | $24.6098 | .19071473 |

TABLE A7-continued

| PAIRED_ETGNO | service group | specialty total role episode occurred in count | specialty total role average expense | specialty total role average services | specialty total role expense | specialty total role services | strata sum episode count | total role expected expense per episode | total role expected services per episode |
|---|---|---|---|---|---|---|---|---|---|
| benign_lesions_without_actinic keratoses | 99244 | 15 | $184.33 | 1 | $2,765 | 15 | 22,358 | $0.1237 | .00067090 |
| benign_lesions_without_actinic keratoses | 99245 | 2 | $237.00 | 1 | $474 | 2 | 22,358 | $0.0212 | .00008945 |
| benign_lesions_without_actinic keratoses | 99252 | 1 | $ 79.00 | 1 | $79 | 1 | 22,358 | $0.0035 | .00004473 |
| benign_lesions_without_actinic keratoses | 99253 | 2 | $107.50 | 1 | $215 | 2 | 22,358 | $0.0096 | .00008945 |
| benign_lesions_without_actinic keratoses | 99254 | 1 | $154.00 | 1 | $154 | 1 | 22,358 | $0.0069 | .00004473 |
| benign_lesions_without_actinic keratoses | 99312 | 1 | $ 65.00 | 1 | $65 | 1 | 22,358 | $0.0029 | .00004473 |
| benign_lesions_without_actinic keratoses | 99385 | 5 | $ 56.00 | 1 | $280 | 5 | 22,358 | $0.0125 | .00022363 |
| benign_lesions_without_actinic keratoses | 99386 | 2 | $ 56.00 | 1 | $112 | 2 | 22,358 | $0.0050 | .00008945 |
| benign_lesions_without_actinic keratoses | 99391 | 1 | $ 56.00 | 1 | $56 | 1 | 22,358 | $0.0025 | .00004473 |
| benign_lesions_without_actinic keratoses | 99394 | 3 | $ 56.00 | 1 | $168 | 3 | 22,358 | $0.0075 | .00013418 |
| benign_lesions_without_actinic keratoses | 99395 | 18 | $ 56.00 | 1 | $1,008 | 18 | 22,358 | $0.0451 | .00080508 |
| benign_lesions_without_actinic keratoses | 99396 | 50 | $ 56.00 | 1 | $2,800 | 50 | 22,358 | $0.1252 | .00223634 |
| benign_lesions_without_actinic keratoses | 99601 | 1 | $ 95.00 | 1 | $95 | 1 | 22,358 | $0.0042 | .00004473 |
| benign_lesions_without_actinic keratoses | A0425 | 1 | $ 60.00 | 10 | $60 | 10 | 22,358 | $0.0027 | .00044727 |
| benign_lesions_without_actinic keratoses | A0429 | 1 | $325.00 | 1 | $325 | 1 | 22,358 | $0.0145 | .00004473 |
| benign_lesions_without_actinic keratoses | A4550 | 1 | $ 49.00 | 1 | $49 | 1 | 22,358 | $0.0022 | .00004473 |
| benign_lesions_without_actinic keratoses | A4646 | 3 | $ 73.00 | 1 | $219 | 3 | 22,358 | $0.0098 | .00013418 |
| benign_lesions_without_actinic keratoses | A4649 | 1 | $ 73.00 | 1 | $73 | 1 | 22,358 | $0.0033 | .00004473 |
| benign_lesions_without_actinic keratoses | AS | 6 | $226.17 | 1 | $1,357 | 6 | 22,358 | $0.0607 | .00026836 |
| benign_lesions_without_actinic keratoses | CL | 1 | $163.00 | 2 | $163 | 2 | 22,358 | $0.0073 | .00008945 |
| benign_lesions_without_actinic keratoses | ER | 4 | $123.00 | 1 | $492 | 4 | 22,358 | $0.0220 | .00017891 |
| benign_lesions_without_actinic keratoses | H0A | 2 | $ 48.00 | 28 | $96 | 55 | 22,358 | $0.0043 | .00245997 |
| benign_lesions_without_actinic keratoses | H3A | 799 | $ 20.82 | 16 | $16,635 | 12,963 | 22,358 | $0.7440 | .57979247 |
| benign_lesions_without_actinic keratoses | H6J | 8 | $ 25.13 | 15 | $201 | 117 | 22,358 | $0.0090 | .00523303 |
| benign_lesions_without_actinic keratoses | J2250 | 1 | $ 28.00 | 1 | $28 | 1 | 22,358 | $0.0013 | .00004473 |
| benign_lesions_without_actinic keratoses | J3010 | 1 | $ 1.00 | 1 | $1 | 1 | 22,358 | $0.0000 | .00004473 |
| benign_lesions_without_actinic keratoses | J3301 | 15 | $ 13.53 | 1 | $203 | 21 | 22,358 | $0.0091 | .00093926 |
| benign_lesions_without_actinic keratoses | J7050 | 10 | $ 4.50 | 1 | $45 | 11 | 22,358 | $0.0020 | .00049199 |
| benign_lesions_without_actinic keratoses | J9A | 8 | $ 6.50 | 21 | $52 | 168 | 22,358 | $0.0023 | .00751409 |
| benign_lesions_without_actinic keratoses | L1A | 1 | $161.00 | 3 | $161 | 3 | 22,358 | $0.0072 | .00013418 |
| benign_lesions_without_actinic keratoses | L1B | 3 | $336.33 | 30 | $1,009 | 90 | 22,358 | $0.0451 | .00402540 |
| benign_lesions_without_actinic keratoses | L9B | 133 | $ 62.86 | 26 | $8,361 | 3,440 | 22,358 | $0.3740 | .15385992 |
| benign_lesions_without_actinic keratoses | Q5N | 98 | $125.34 | 27 | $12,283 | 2,666 | 22,358 | $0.5494 | .11924143 |
| benign_lesions_without_actinic keratoses | S0630 | 11 | $ 41.27 | 1 | $454 | 11 | 22,358 | $0.0203 | .00049199 |
| benign_lesions_without_actinic keratoses | S2B | 91 | $ 56.53 | 43 | $5,144 | 3,905 | 22,358 | $0.2301 | .17465784 |
| benign_lesions_without_actinic keratoses | Z2A | 7 | $ 32.57 | 16 | $228 | 114 | 22,358 | $0.0102 | .00509885 |
| benign_lesions_without_actinic keratoses | Z2G | 70 | $201.26 | 29 | $14,088 | 2,036 | 22,358 | $0.6301 | .09106360 |

TABLE A8

Dermatology
Dates of Service Jan. 1, 2003-Dec. 31, 2004 paid Dec. 31, 2004
Total Role benign neoplasm of the skin without actinic keratoses diagnosis 702.xx
etg 0682

| quartile | category | services | service description | Total Svcs | Your Svcs | Other Svcs |
|---|---|---|---|---|---|---|
| Q1 | A | 00300 | ANESTHESIA, HEAD, NECK, POST TRUNK INTEGUMENTARY, MUSCLE NERVES | 2 | 2 | 0 |
| Q1 | A | 94720 | CARBON MONOXIDE DIFFUSING CAPACITY | 2 | 2 | 0 |
| Q1 | A | 94240 | FUNCTIONAL RESIDUAL CAPACITY/VOLUME: HELIUM/NITROGEN OPEN CIRCUIT/OTHER | 1 | 1 | 0 |
| Q1 | A | 94010 | SPIROMETRY W/GRAPHIC RECORD/VITAL CAPACITY/FLOW RATE W/WO MAXIMAL VOLUN | 1 | 1 | 0 |
| Q1 | A | A4646 | | 2 | 0 | 2 |
| Q1 | A | 99601 | HOME INFUSION/SPECIALTY DRUG ADMINISTRATION, PER VISIT (TO 2 HRS); | 1 | 1 | 0 |
| . | . | . | . | . | . | . |
| . | . | . | . | . | . | . |
| . | . | . | . | . | . | . |
| Q1 | A | 88321 | CONSULTATION & REPORT, REFERRED SLIDES PREPARED ELSEWHERE | 1 | 0 | 1 |
| Q1 | A | 88342 | IMMUNOCYTOCHEMISTRY (W/TISSUE IMMUNOPEROXIDASE), EACH ANTIBODY | 3 | 3 | 0 |
| Q1 | A | 88305 | LEVEL IV—SURGICAL PATHOLOGY, GROSS & MICROSCOPIC EXAM | 2,008 | 1,723 | 285 |
| | A Total | | | 2,356 | 1,776 | 580 |
| Q1 | M | 99213 | OFFICE/OP VISIT, EST PT, 2 KEY COMPONENTS: EXPAND PROB HX; EXPAND PROB | 2,356 | 2,184 | 172 |
| Q1 | M | 99214 | OFFICE/OP VISIT, EST PT, 2 KEY COMPONENTS: DETAILED HX; DETAILED EXAM; | 45 | 31 | 14 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | |
|---|---|---|---|---|---|---|
| Q1 | M | 99205 | OFFICE/OP VISIT, NEW PT, 3 KEY COMPONENTS:COMPREHENSIVE HX;COMPREHENSIV | 1 | 0 | 1 |
| . | . | . | . | . | . | . |
| . | . | . | . | . | . | . |
| . | . | . | . | . | . | . |
| Q1 | M | 99241 | OFFICE CONSULTATION, 3 KEY COMPONENTS: PROB FOCUS HX; PROB FOCUS EXAM; | 1 | 1 | 0 |
| Q1 | M | 99202 | OFFICE/OP VISIT, NEW PT, 3 KEY COMPONENTS: EXPAND PROB FOCUS HX; EXPAND | 2 | 0 | 2 |
| Q1 | M | 99203 | OFFICE/OP VISIT, NEW PT, 3 KEY COMPONENTS: DETAILED HX; DETAILED EXAM; | 10 | 3 | 7 |
| Q1 | M | 99212 | OFFICE/OP VISIT, EST PT, 2 KEY COMPONENTS: PROB FOCUS HX; PROB FOCUS EX | 253 | 229 | 24 |
| Q1 | M | 99242 | OFFICE CONSULTATION, 3 KEY COMPONENTS: EXPAND PROB FOCUS HX;EXPAND PROB | 341 | 327 | 14 |
| Q1 | M | 99243 | OFFICE CONSULTATION, 3 KEY COMPONENTS: DETAILED HX; DETAILED EXAM; MED | 536 | 510 | 26 |
| | M Total | | | 3,568 | 3,288 | 280 |
| Q1 | P | L9B | VITAMIN A DERIVATIVES | 1,900 | 1,736 | 164 |
| Q1 | P | H3A | ANALGESICS, NARCOTICS | 4,432 | 795 | 3,637 |
| . | . | . | . | . | . | . |
| . | . | . | . | . | . | . |
| . | . | . | . | . | . | . |
| Q1 | P | J9A | INTESTINAL MOTILITY STIMULANTS | 32 | 0 | 32 |
| Q1 | P | H0A | LOCAL ANESTHETICS | 25 | 0 | 25 |
| Q1 | P | S2B | NSAIDS, CYCLOOXYGENASE INHIBITOR—TYPE | 875 | 200 | 675 |
| | P Total | | | 8,919 | 4,171 | 4,748 |
| Q1 | R | 76942 | US GUIDANCE, NEEDLE PLACEMENT, RADIOLOGICAL S&I | 1 | 0 | 1 |
| | R Total | | | 1 | 0 | 1 |
| Q1 | S | 17000 | DESTRUCTION, BENIGN/PREMALIG LESIONS, EXCEPT SKIN TAGS/ CUTANEOUS VASC P | 1,343 | 1,320 | 23 |
| Q1 | S | 11300 | SHAVING SKIN LESION, TRUNK/ARMS/LEGS; DIAMETER 0.5 CM/< | 524 | 509 | 15 |
| Q1 | S | 17004 | DESTRUCTION, BENIGN/PREMALIG LESIONS, EXCEPT SKIN TAGS/ CUTANEOUS VASC P | 13 | 13 | 0 |
| Q1 | S | 54060 | DESTRUCTION, PENILE LESION, SIMPLE; SURGICAL EXCISION | 1 | 1 | 0 |
| . | . | . | . | . | . | . |
| . | . | . | . | . | . | . |
| . | . | . | . | . | . | . |
| Q1 | S | 11442 | EXCISE, BENIGN SKIN LESION, INCL MARGINS, FACE/EARS/EYELIDS/NOSE/LIPS/M | 3 | 1 | 2 |
| Q1 | S | 11421 | EXCISE BEN SKIN LESION W/MARG, EXCEPT SKIN TAG SCALP/NECK/ HANDS/FEET/GE | 5 | 5 | 0 |
| Q1 | S | 11400 | EXCISE, BENIGN SKIN LESION, INCL MARGINS, EXCEPT SKIN TAG, TRUNK/ARMS/L | 94 | 89 | 5 |
| Q1 | S | 11101 | BX, SKIN, SUBQ/MUCOUS MEMBRANE (SEP PROC); ADD'L LESION | 95 | 86 | 9 |
| Q1 | S | 11100 | BX, SKIN, SUBQ/MUCOUS MEMBRANE; SINGLE LESION | 465 | 448 | 17 |
| Q1 | S | 11310 | SHAVING SKIN LESION, FACE/EARS/EYELIDS/NOSE/LIPS/MUCOUS MEMBRANE; DIAME | 124 | 118 | 6 |
| Q1 | S | 11403 | EXCISE, BENIGN SKIN LESION, INCL MARGINS, EXCEPT SKIN TAG, TRUNK/ARMS/L | 5 | 4 | 1 |
| Q1 | S | 12031 | LAYER CLOSURE, WOUNDS, SCALP/AXILLAE/TRUNK/EXTREMITIES; 2.5 CM/< | 5 | 4 | 1 |
| Q1 | S | 11441 | EXCISE, BENIGN SKIN LESION, INCL MARGINS, FACE/EARS/EYELIDS/NOSE/LIPS/M | 11 | 6 | 5 |
| Q1 | S | 11440 | EXCISE, BENIGN SKIN LESION, INCL MARGINS, FACE/EARS/EYELIDS/NOSE/LIPS/M | 13 | 10 | 3 |
| Q1 | S | 11301 | SHAVING SKIN LESION, TRUNK/ARMS/LEGS; DIAMETER 0.6-1.0 CM | 585 | 573 | 12 |
| Q1 | S | 11302 | SHAVING SKIN LESION, TRUNK/ARMS/LEGS; DIAMETER 1.1-2.0 CM | 50 | 50 | 0 |
| Q1 | S | 11402 | EXCISE, BENIGN SKIN LESION, INCL MARGINS, EXCEPT SKIN TAG, TRUNK/ARMS/L | 67 | 63 | 4 |
| Q1 | S | 11306 | SHAVING SKIN LESION, SCALP/NECK/HANDS/FEET/GENITALIA; DIAMETER 0.6-1.0 | 50 | 47 | 3 |
| Q1 | S | 11311 | SHAVING SKIN LESION, FACE/EARS/EYELIDS/NOSE/LIPS/MUCOUS MEMBRANE; DIAME | 64 | 61 | 3 |
| Q1 | S | 11401 | EXCISE, BENIGN SKIN LESION, INCL MARGINS, EXCEPT SKIN TAG, TRUNK/ARMS/L | 98 | 93 | 5 |
| | S Total | | | 6,616 | 6,446 | 170 |
| | Q1 Total | | | 21,460 | 15,681 | 5,779 |
| Q2 | A | 88305 | LEVEL IV—SURGICAL PATHOLOGY, GROSS & MICROSCOPIC EXAM | 2,823 | 2,414 | 409 |
| Q2 | A | 88342 | IMMUNOCYTOCHEMISTRY (W/TISSUE IMMUNOPEROXIDASE), EACH ANTIBODY | 10 | 5 | 5 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | |
|---|---|---|---|---|---|---|
| Q2 | A | 00820 | ANESTHESIA, PROC, LOWER POSTERIOR ABDOMINAL WALL | 1 | 0 | 1 |
| . | . | . | . | . | . | . |
| . | . | . | . | . | . | . |
| . | . | . | . | . | . | . |
| Q2 | A | 80053 | COMPREHENSIVE METABOLIC PANEL | 22 | 0 | 22 |
| Q2 | A | 84460 | TRANSFERASE; ALANINE AMINO (ALT) (SGPT) | 10 | 0 | 10 |
| Q2 | A | 84443 | THYROID STIMULATING HORMONE (TSH) | 5 | 0 | 5 |
| Q2 | A | 80050 | GENERAL HEALTH PANEL | 2 | 0 | 2 |
| | A Total | | | 3,029 | 2,449 | 580 |
| Q2 | M | 99242 | OFFICE CONSULTATION, 3 KEY COMPONENTS: EXPAND PROB FOCUS HX; EXPAND PROB | 445 | 417 | 28 |
| Q2 | M | 99204 | OFFICE/OP VISIT, NEW PT, 3 KEY COMPONENTS: COMPREHENSIVE HX; COMPREHENSIVE E | 4 | 0 | 4 |
| Q2 | M | 99245 | OFFICE CONSULTATION, 3 KEY COMPONENTS: COMPREHENSIVE HX; COMPREHENSIVE E | 1 | 0 | 1 |
| . | . | . | . | . | . | . |
| . | . | . | . | . | . | . |
| . | . | . | . | . | . | . |
| Q2 | M | 99241 | OFFICE CONSULTATION, 3 KEY COMPONENTS: PROB FOCUS HX; PROB FOCUS EXAM | 3 | 2 | 1 |
| Q2 | M | 99203 | OFFICE/OP VISIT, NEW PT, 3 KEY COMPONENTS: DETAILED HX; DETAILED EXAM; | 13 | 2 | 11 |
| Q2 | M | 99212 | OFFICE/OP VISIT, EST PT, 2 KEY COMPONENTS: PROB FOCUS HX; PROB FOCUS EX | 183 | 150 | 33 |
| Q2 | M | 99243 | OFFICE CONSULTATION, 3 KEY COMPONENTS: DETAILED HX; DETAILED EXAM; MED | 779 | 756 | 23 |
| Q2 | M | 99213 | OFFICE/OP VISIT, EST PT, 2 KEY COMPONENTS: EXPAND PROB HX; EXPAND PROB | 999 | 776 | 223 |
| | M Total | | | 2,485 | 2,114 | 371 |
| Q2 | P | S2B | NSAIDS, CYCLOOXYGENASE INHIBITOR—TYPE | 899 | 132 | 767 |
| Q2 | P | Z2G | IMMUNOMODULATORS | 443 | 385 | 58 |
| . | . | . | . | . | . | . |
| . | . | . | . | . | . | . |
| . | . | . | . | . | . | . |
| Q2 | P | J7050 | Infusion, normal saline solution, 250 cc | 1 | 1 | 0 |
| Q2 | P | Z2A | ANTIHISTAMINES | 8 | 6 | 2 |
| Q2 | P | L9B | VITAMIN A DERIVATIVES | 341 | 267 | 74 |
| | P Total | | | 4,910 | 1,992 | 2,918 |
| Q2 | S | 11100 | BX, SKIN, SUBQ/MUCOUS MEMBRANE; SINGLE LESION | 580 | 567 | 13 |
| Q2 | S | 11302 | SHAVING SKIN LESION, TRUNK/ARMS/LEGS; DIAMETER 1.1-2.0 CM | 236 | 234 | 2 |
| Q2 | S | 11101 | BX, SKIN, SUBQ/MUCOUS MEMBRANE (SEP PROC); ADD'L LESION | 307 | 302 | 5 |
| Q2 | S | 11301 | SHAVING SKIN LESION, TRUNK/ARMS/LEGS; DIAMETER 0.6-1.0 CM | 671 | 654 | 17 |
| Q2 | S | 11305 | SHAVING SKIN LESION, SCALP/NECK/HANDS/FEET/GENITALIA; DIAMETER 0.5 CM/< | 285 | 274 | 11 |
| Q2 | S | 11312 | SHAVING SKIN LESION, FACE/EARS/EYELIDS/NOSE/LIPS/ MUCOUS MEMBRANE; DIAME | 51 | 51 | 0 |
| Q2 | S | 11300 | SHAVING SKIN LESION, TRUNK/ARMS/LEGS; DIAMETER 0.5 CM/< | 374 | 357 | 17 |
| Q2 | S | 11311 | SHAVING SKIN LESION, FACE/EARS/EYELIDS/NOSE/LIPS/ MUCOUS MEMBRANE; DIAME | 167 | 165 | 2 |
| Q2 | S | 11400 | EXCISE, BENIGN SKIN LESION, INCL MARGINS, EXCEPT SKIN TAG, TRUNK/ARMS/L | 97 | 96 | 1 |
| Q2 | S | 11603 | EXCISION, MALIGNANT LESION, INCL MARGINS, TRUNK/ARMS/LEGS; EXCISED DIAM | 2 | 2 | 0 |
| Q2 | S | 11307 | SHAVING SKIN LESION, SCALP/NECK/HANDS/FEET/GENITALIA; DIAMETER 1.1-2.0 | 23 | 23 | 0 |
| . | . | . | . | . | . | . |
| . | . | . | . | . | . | . |
| . | . | . | . | . | . | . |
| Q2 | S | 40490 | BX, LIP | 4 | 4 | 0 |
| Q2 | S | 11900 | INJECTION, INTRALESIONAL; UP TO & INCL 7 LESIONS | 2 | 2 | 0 |
| Q2 | S | 11310 | SHAVING SKIN LESION, FACE/EARS/EYELIDS/NOSE/LIPS/ MUCOUS MEMBRANE; DIAME | 140 | 135 | 5 |
| Q2 | S | 17004 | DESTRUCTION, BENIGN/PREMALIG LESIONS, EXCEPT SKIN TAGS/ CUTANEOUS VASC P | 1 | 1 | 0 |
| Q2 | S | 11420 | EXCISE BENIGN SKIN LESION W/MARG, EXCPT SKIN TAG SCALP/NECK HANDS/FEET/ | 15 | 15 | 0 |
| . | . | . | . | . | . | . |
| . | . | . | . | . | . | . |
| . | . | . | . | . | . | . |
| Q2 | S | 11442 | EXCISE, BENIGN SKIN LESION, INCL MARGINS, FACE/EARS/EYELIDS/NOSE/LIPS/M | 3 | 2 | 1 |
| Q2 | S | 11306 | SHAVING SKIN LESION, SCALP/NECK/HANDS/FEET/GENITALIA; DIAMETER 0.6-1.0 | 144 | 139 | 5 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | |
|---|---|---|---|---|---|---|
| Q2 | S | 11421 | EXCISE BEN SKIN LESION W/MARG, EXCEPT SKIN TAG SCALP/NECK/HANDS/FEET/GE | 8 | 8 | 0 |
| Q2 | S | 11440 | EXCISE, BENIGN SKIN LESION, INCL MARGINS, FACE/EARS/EYELIDS/NOSE/LIPS/M | 35 | 33 | 2 |
| Q2 | S | 12032 | LAYER CLOSURE, WOUNDS, SCALP/AXILLAE/TRUNK/EXTREMITIES; 2.6-7.5 CM | 7 | 5 | 2 |
| Q2 | S | 11403 | EXCISE, BENIGN SKIN LESION, INCL MARGINS, EXCEPT SKIN TAG, TRUNK/ARMS/L | 5 | 5 | 0 |
| Q2 | S | 11441 | EXCISE, BENIGN SKIN LESION, INCL MARGINS, FACE/EARS/EYELIDS/NOSE/LIPS/M | 9 | 7 | 2 |
| Q2 | S | 11401 | EXCISE, BENIGN SKIN LESION, INCL MARGINS, EXCEPT SKIN TAG, TRUNK/ARMS/L | 145 | 136 | 9 |
| Q2 | S | 11402 | EXCISE, BENIGN SKIN LESION, INCL MARGINS, EXCEPT SKIN TAG, TRUNK/ARMS/L | 72 | 69 | 3 |
| Q2 | S | 17000 | DESTRUCTION, BENIGN/PREMALIG LESIONS, EXCEPT SKIN TAGS/CUTANEOUS VASC P | 758 | 722 | 36 |
| | S Total | | | 4,832 | 4,668 | 164 |
| | Q2 Total | | | 15,256 | 11,223 | 4,033 |
| Q3 | A | 0551 | SKILLED NURSING—PER VISIT | 5 | 5 | 0 |
| Q3 | A | 88321 | CONSULTATION & REPORT, REFERRED SLIDES PREPARED ELSEWHERE | 8 | 7 | 1 |
| Q3 | A | 88342 | IMMUNOCYTOCHEMISTRY (W/TISSUE IMMUNOPEROXIDASE), EACH ANTIBODY | 14 | 6 | 8 |
| Q3 | A | 0490 | AMBULATORY SURGICAL CARE GENERAL CLASSIFICATION | 6 | 6 | 0 |
| . | . | . | | . | . | . |
| . | . | . | | . | . | . |
| . | . | . | | . | . | . |
| Q3 | A | AS | Ambulatory Surgery | 2 | 1 | 1 |
| Q3 | A | 88305 | LEVEL IV—SURGICAL PATHOLOGY, GROSS & MICROSCOPIC EXAM | 3,056 | 2,549 | 507 |
| | A Total | | | 3,531 | 2,658 | 873 |
| Q3 | M | 99243 | OFFICE CONSULTATION, 3 KEY COMPONENTS: DETAILED HX; DETAIL EXAM; MED | 2,013 | 1,983 | 30 |
| Q3 | M | 99213 | OFFICE/OP VISIT, EST PT, 2 KEY COMPONENTS: EXPAND PROB HX; EXPAND PROB | 2,464 | 2,063 | 401 |
| Q3 | M | 99241 | OFFICE CONSULTATION, 3 KEY COMPONENTS: PROB FOCUS HX; PROB FOCUS EXAM; | 100 | 99 | 1 |
| Q3 | M | 99212 | OFFICE/OP VISIT, EST PT, 2 KEY COMPONENTS: PROB FOCUS HX; PROB FOCUS EX | 511 | 439 | 72 |
| Q3 | M | 99203 | OFFICE/OP VISIT, NEW PT, 3 KEY COMPONENTS: DETAILED HX; DETAILED EXAM; | 82 | 57 | 25 |
| Q3 | M | 99202 | OFFICE/OP VISIT, NEW PT, 3 KEY COMPONENTS: EXPAND PROB FOCUS HX; EXPAND | 51 | 37 | 14 |
| . | . | . | | . | . | . |
| . | . | . | | . | . | . |
| . | . | . | | . | . | . |
| Q3 | M | 99204 | OFFICE/OP VISIT, NEW PT, 3 KEY COMPONENTS: COMPREHENSIVE HX;COMPREHENSIV | 2 | 0 | 2 |
| Q3 | M | 99244 | OFFICE CONSULTATION, 3 KEY COMPONENTS: COMPREHENSIVE HX; COMPREHENSIVE E | 3 | 1 | 2 |
| Q3 | M | 99214 | OFFICE/OP VISIT, EST PT, 2 KEY COMPONENTS: DETAILED HX; DETAILED EXAM; | 23 | 3 | 20 |
| Q3 | M | 99242 | OFFICE CONSULTATION, 3 KEY COMPONENTS: EXPAND PROB FOCUS HX; EXPAND PROB | 705 | 680 | 25 |
| | M Total | | | 6,002 | 5,364 | 638 |
| Q3 | p | L1B | ACNE AGENTS, SYSTEMIC | 60 | 60 | 0 |
| Q3 | p | L1A | ANTIPSORIATIC AGENTS, SYSTEMIC | 3 | 3 | 0 |
| Q3 | p | Z2A | ANTIHISTAMINES | 60 | 0 | 60 |
| . | . | . | | . | . | . |
| . | . | . | | . | . | . |
| . | . | . | | . | . | . |
| Q3 | p | Z2G | IMMUNOMODULATORS | 564 | 508 | 56 |
| Q3 | p | H3A | ANALGESICS, NARCOTICS | 3,760 | 934 | 2,826 |
| Q3 | p | Q5N | TOPICAL ANTINEOPLASTIC & PREMALIGNANT LESION AGNTS | 580 | 580 | 0 |
| | P Total | | | 7,487 | 3,043 | 4,444 |
| Q3 | S | 11306 | SHAVING SKIN LESION, SCALP/NECK/HANDS/FEET/GENITALIA; DIAMETER 0.6-1.0 | 521 | 518 | 3 |
| Q3 | S | 11311 | SHAVING SKIN LESION, FACE/EARS/EYELIDS/NOSE/LIPS/MUCOUS MEMBRANE; DIAME | 444 | 438 | 6 |
| Q3 | S | 17000 | DESTRUCTION, BENIGN/PREMALIG LESIONS, EXCEPT SKIN TAGS/CUTANEOUS VASC P | 1,711 | 1,683 | 28 |
| Q3 | S | 11301 | SHAVING SKIN LESION, TRUNK/ARMS/LEGS; DIAMETER 0.6-1.0 CM | 1,130 | 1,092 | 38 |
| Q3 | S | 11403 | EXCISE, BENIGN SKIN LESION, INCL MARGINS, EXCEPT SKIN TAG, TRUNK/ARMS/L | 75 | 71 | 4 |
| Q3 | S | 11440 | EXCISE, BENIGN SKIN LESION, INCL MARGINS, FACE/EARS/EYELIDS/NOSE/LIPS/M | 132 | 119 | 13 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | |
|---|---|---|---|---|---|---|
| Q3 | S | 11310 | SHAVING SKIN LESION, FACE/EARS/EYELIDS/NOSE/LIPS/ MUCOUS MEMBRANE; DIAME | 327 | 317 | 10 |
| Q3 | S | 11404 | EXCISE, BENIGN SKIN LESION, INCL MARGINS, EXCEPT SKIN TAG, TRUNK/ARMS/L | 25 | 21 | 4 |
| Q3 | S | 17106 | DESTRUCTION, CUTANEOUS VASCULAR PROLIFERATIVE LESIONS; <10 SQ CM | 12 | 12 | 0 |
| . | . | . | . | . | . | . |
| . | . | . | . | . | . | . |
| . | . | . | . | . | . | . |
| Q3 | S | 11441 | EXCISE, BENIGN SKIN LESION, INCL MARGINS, FACE/EARS/EYELIDS/NOSE/LIPS/M | 63 | 62 | 1 |
| Q3 | S | 12031 | LAYER CLOSURE, WOUNDS, SCALP/AXILLAE/TRUNK/EXTREMITIES; 2 CM/< | 47 | 43 | 4 |
| Q3 | S | 11402 | EXCISE, BENIGN SKIN LESION, INCL MARGINS, EXCEPT SKIN TAG, TRUNK/ARMS/L | 193 | 185 | 8 |
| Q3 | S | 11302 | SHAVING SKIN LESION, TRUNK/ARMS/LEGS; DIAMETER 1.1-2.0 CM | 191 | 187 | 4 |
| Q3 | S | 54056 | DESTRUCTION, PENILE LESION, SIMPLE; CRYOSURGERY | 6 | 6 | 0 |
| Q3 | S | 11424 | EXCISE BEN SKIN LESION W/MARG, EXCEPT SKIN TAG SCALP/NECK/HANDS/FEET/GE | 4 | 4 | 0 |
| Q3 | S | 67810 | BX, EYELID | 8 | 8 | 0 |
| . | . | . | . | . | . | . |
| . | . | . | . | . | . | . |
| . | . | . | . | . | . | . |
| Q3 | S | 11901 | INJECTION, INTRALESIONAL; >7 LESIONS | 7 | 7 | 0 |
| Q3 | S | 11401 | EXCISE, BENIGN SKIN LESION, INCL MARGINS, EXCEPT SKIN TAG, TRUNK/ARMS/L | 335 | 317 | 18 |
| Q3 | S | 11426 | EXCISE BENIGN SKIN LESION W/MARG, EXCEPT SKIN TAG SCALP/NECK/HANDS/FT/G | 1 | 1 | 0 |
| Q3 | S | 17004 | DESTRUCTION, BENIGN/PREMALIG LESIONS, EXCEPT SKIN TAGS/CUTANEOUS/VASC P | 15 | 15 | 0 |
| Q3 | S | 11444 | EXCISE, BENIGN SKIN LESION, INCL MARGINS, FACE/EARS/EYELIDS/NOSE/LIPS/M | 1 | 1 | 0 |
| . | . | . | . | . | . | . |
| . | . | . | . | . | . | . |
| . | . | . | . | . | . | . |
| Q3 | S | 11305 | SHAVING SKIN LESION, SCALP/NECK/HANDS/FEET/GENITALIA; DIAMETER 0.5 CM/< | 167 | 160 | 7 |
| Q3 | S | 11101 | BX, SKIN, SUBQ/MUCOUS MEMBRANE (SEP PROC); ADD'L LESION | 110 | 96 | 14 |
| Q3 | S | 11400 | EXCISE, BENIGN SKIN LESION, INCL MARGINS, EXCEPT SKIN TAG, TRUNK/ARMS/L | 130 | 125 | 5 |
| Q3 | S | 11300 | SHAVING SKIN LESION, TRUNK/ARMS/LEGS; DIAMETER 0.5 CM/< | 259 | 238 | 21 |
| Q3 | S | 11100 | BX, SKIN, SUBQ/MUCOUS MEMBRANE; SINGLE LESION | 367 | 325 | 42 |
| | S Total | | | 9,313 | 8,900 | 413 |
| Q3 Total | | | | 26,333 | 19,965 | 6,368 |
| Q4 | A | 88305 | LEVEL IV—SURGICAL PATHOLOGY, GROSS & MICROSCOPIC EXAM | 2,869 | 2,614 | 255 |
| Q4 | A | AS | Ambulatory Surgery | 2 | 2 | 0 |
| Q4 | A | ER | Emergency | 2 | 2 | 0 |
| Q4 | A | S0630 | Removal of sutures by a physician other than the physician who originall | 5 | 5 | 0 |
| . | . | . | . | . | . | . |
| . | . | . | . | . | . | . |
| . | . | . | . | . | . | . |
| Q4 | A | 85025 | BLOOD COUNT; COMPLETE CBC, AUTOMATED (HGB, HCT, RBC, WBC, & PLATELET) & | 13 | 0 | 13 |
| Q4 | A | 84460 | TRANSFERASE; ALANINE AMINO (ALT) (SGPT) | 3 | 0 | 3 |
| Q4 | A | 80053 | COMPREHENSIVE METABOLIC PANEL | 14 | 0 | 14 |
| Q4 | A | 80061 | LIPID PANEL | 8 | 0 | 8 |
| Q4 | A | 88321 | CONSULTATION & REPORT, REFERRED SLIDES PREPARED ELSEWHERE | 1 | 0 | 1 |
| | A Total | | | 3,050 | 2,669 | 381 |
| Q4 | M | 99242 | OFFICE CONSULTATION, 3 KEY COMPONENTS: EXPAND PROB FOCUS HX;EXPAND PROB | 675 | 664 | 11 |
| Q4 | M | 99243 | OFFICE CONSULTATION, 3 KEY COMPONENTS: DETAILED HX; DETAILED HX; DETAILED EXAM; MED | 936 | 907 | 29 |
| Q4 | M | 99212 | OFFICE/OP VISIT, EST PT, 2 KEY COMPONENTS: PROB FOCUS HX; PROB FOCUS EX | 364 | 307 | 57 |
| Q4 | M | 99203 | OFFICE/OP VISIT, NEW PT, 3 KEY COMPONENTS: DETAILED HX; DETAILED EXAM; | 55 | 35 | 20 |
| Q4 | M | 99202 | OFFICE/OP VISIT, NEW PT, 3 KEY COMPONENTS: EXPAND PROB FOCUS HX; EXPAND | 32 | 20 | 12 |
| Q4 | M | 99214 | OFFICE/OP VISIT, EST PT, 2 KEY COMPONENTS: DETAILED HX; DETAILED EXAM; | 32 | 20 | 12 |
| . | . | . | . | . | . | . |
| . | . | . | . | . | . | . |
| . | . | . | . | . | . | . |
| Q4 | M | 99395 | PERIODIC COMPREHENSIVE PREVENTIVE MEDICINE E&M W/HX/ EXAM, EST PT; 18-39 | 2 | 0 | 2 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | |
|---|---|---|---|---|---|---|
| Q4 | M | 99204 | OFFICE/OP VISIT, NEW PT, 3 KEY COMPONENTS: COMPREHENSIVE HX;COMPREHENSIV | 1 | 0 | 1 |
| Q4 | M | 99241 | OFFICE CONSULTATION, 3 KEY COMPONENTS: PROB FOCUS HX; PROB FOCUS EXAM; | 1 | 1 | 0 |
| Q4 | M | 99213 | OFFICE/OP VISIT, EST PT, 2 KEY COMPONENTS: EXPAND PROB HX; EXPAND PROB | 995 | 742 | 253 |
| | M Total | | | 3,117 | 2,703 | 414 |
| Q4 | P | Q5N | TOPICAL ANTINEOPLASTIC & PREMALIGNANT LESION AGNTS | 676 | 656 | 20 |
| Q4 | P | J3301 | Injection, triamcinolone acetonide, per 10 mg | 12 | 8 | 4 |
| . | . | . | . | . | . | . |
| . | . | . | . | . | . | . |
| . | . | . | . | . | . | . |
| Q4 | P | L9B | VITAMIN A DERIVATIVES | 172 | 77 | 95 |
| | P Total | | | 4,275 | 1,518 | 2,757 |
| Q4 | R | 76942 | US GUIDANCE, NEEDLE PLACEMENT, RADIOLOGICAL S&I | 1 | 0 | 1 |
| | R Total | | | 1 | 0 | 1 |
| Q4 | S | 11401 | EXCISE, BENIGN SKIN LESION, INCL MARGINS, EXCEPT SKIN TAG, TRUNK/ARMS/L | 388 | 378 | 10 |
| Q4 | S | 11402 | EXCISE, BENIGN SKIN LESION, INCL MARGINS, EXCEPT SKIN TAG, TRUNK/ARMS/L | 199 | 194 | 5 |
| Q4 | S | 11400 | EXCISE, BENIGN SKIN LESION, INCL MARGINS, EXCEPT SKIN TAG, TRUNK/ARMS/L | 191 | 190 | 1 |
| Q4 | S | 11300 | SHAVING SKIN LESION, TRUNK/ARMS/LEGS; DIAMETER 0.5 CM/< | 479 | 473 | 6 |
| Q4 | S | 11441 | EXCISE, BENIGN SKIN LESION, INCL MARGINS, FACE/EARS/EYELIDS/NOSE/LIPS/M | 69 | 67 | 2 |
| Q4 | S | 11421 | EXCISE BEN SKIN LESION W/MARG, EXCEPT SKIN TAG SCALP/NECK/HANDS/FEET/GE | 68 | 68 | 0 |
| Q4 | S | 11440 | EXCISE, BENIGN SKIN LESION, INCL MARGINS, FACE/EARS/EYELIDS/NOSE/LIPS/M | 93 | 92 | 1 |
| Q4 | S | 12031 | LAYER CLOSURE, WOUNDS, SCALP/AXILLAE/TRUNK/EXTREMITIES; 2 CM/< | 47 | 44 | 3 |
| Q4 | S | 11100 | BX, SKIN, SUBQ/MUCOUS MEMBRANE; SINGLE LESION | 358 | 334 | 24 |
| Q4 | S | 11422 | EXCISE BEN SKIN LESION W/MARG, EXCEPT SKIN TAG SCALP/NECK/HANDS/FEET/GE | 34 | 34 | 0 |
| Q4 | S | 11420 | EXCISE BENIGN SKIN LESION W/MARG, EXCPT SKIN TAG SCALP/NECK/HANDS/FEET/ | 55 | 55 | 0 |
| Q4 | S | 12032 | LAYER CLOSURE, WOUNDS, SCALP/AXILLAE/TRUNK/EXTREMITIES; 2.6-7.5 CM | 27 | 26 | 1 |
| Q4 | S | 13101 | REPAIR, COMPLEX, TRUNK; 2.6 TO 7.5 CM | 8 | 8 | 0 |
| Q4 | S | 11442 | EXCISE, BENIGN SKIN LESION, INCL MARGINS, FACE/EARS/EYELIDS/NOSE/LIPS/M | 19 | 18 | 1 |
| Q4 | S | 11307 | SHAVING SKIN LESION, SCALP/NECK/HANDS/FEET/GENITALIA; DIAMETER 1.1-2.0 | 35 | 35 | 0 |
| Q4 | S | 11312 | SHAVING SKIN LESION, FACE/EARS/EYELIDS/NOSE/LIPS/MUCOUS MEMBRANE; DIAME | 34 | 34 | 0 |
| Q4 | S | 67810 | BX, EYELID | 18 | 18 | 0 |
| Q4 | S | 11403 | EXCISE, BENIGN SKIN LESION, INCL MARGINS, EXCEPT SKIN TAG, TRUNK/ARMS/L | 34 | 33 | 1 |
| Q4 | S | 11406 | EXCISE, BENIGN SKIN LESION, INCL MARGINS, EXCEPT SKIN TAG, TRUNK/ARMS/L | 7 | 6 | 1 |
| Q4 | S | 40490 | BX, LIP | 13 | 13 | 0 |
| Q4 | S | 11310 | SHAVING SKIN LESION, FACE/EARS/EYELIDS/NOSE/LIPS/MUCOUS MEMBRANE; DIAME | 133 | 124 | 9 |
| Q4 | S | 11308 | SHAVING SKIN LESION, SCALP/NECK/HANDS/FEET/GENITALIA; DIAMETER > 2.0 CM | 9 | 9 | 0 |
| Q4 | S | 11303 | SHAVING SKIN LESION, TRUNK/ARMS/LEGS; DIAMETER >2.0 CM | 12 | 11 | 1 |
| Q4 | S | 11305 | SHAVING SKIN LESION, SCALP/NECK/HANDS/FEET/GENITALIA; DIAMETER 0.5 CM/< | 147 | 143 | 4 |
| Q4 | S | 13131 | REPAIR, COMPLEX, FOREHEAD/CHEEKS/CHIN/MOUTH/NECK/AXILLAE/GENITALIA/HAND | 2 | 2 | 0 |
| Q4 | S | 11101 | BX, SKIN, SUBQ/MUCOUS MEMBRANE (SEP PROC); ADD'L LESION | 124 | 118 | 6 |
| Q4 | S | 12051 | LAYER CLOSURE, WOUNDS, FACE/EARS/EYELIDS/NOSE/LIPS/MUCOUS MEMBRANES; 2. | 4 | 3 | 1 |
| . | . | . | . | . | . | . |
| . | . | . | . | . | . | . |
| . | . | . | . | . | . | . |
| Q4 | S | 17106 | DESTRUCTION, CUTANEOUS VASCULAR PROLIFERATIVE LESIONS; <10 SQ CM | 2 | 2 | 0 |
| Q4 | S | 54056 | DESTRUCTION, PENILE LESION, SIMPLE; CRYOSURGERY | 1 | 1 | 0 |
| Q4 | S | 11404 | EXCISE, BENIGN SKIN LESION, INCL MARGINS, EXCEPT SKIN TAG, TRUNK/ARMS/L | 5 | 4 | 1 |
| Q4 | S | 11443 | EXCISE, BENIGN SKIN LESION, INCL MARGINS, FACE/EARS/EYELIDS/NOSE/LIPS/M | 1 | 1 | 0 |
| Q4 | S | 11302 | SHAVING SKIN LESION, TRUNK/ARMS/LEGS; DIAMETER 1.1-2.0 CM | 92 | 87 | 5 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | |
|---|---|---|---|---|---|
| Q4 | S | 11306 | SHAVING SKIN LESION, SCALP/NECK/HANDS/FEET/GENITALIA; DIAMETER 0.6-1.0 | 117 | 113 | 4 |
| Q4 | S | 11311 | SHAVING SKIN LESION, FACE/EARS/EYELIDS/NOSE/LIPS/ MUCOUS MEMBRANE; DIAME | 83 | 82 | 1 |
| Q4 | S | 11301 | SHAVING SKIN LESION, TRUNK/ARMS/LEGS; DIAMETER 0.6-1.0 CM | 338 | 334 | 4 |
| Q4 | S | 17000 | DESTRUCTION, BENIGN/PREMALIG LESIONS, EXCEPT SKIN TAGS/ CUTANEOUS VASC P | 612 | 589 | 23 |
| | S Total | | | 5,038 | 4,893 | 145 |
| | Q4 Total | | | 15,481 | 11,783 | 3,698 |
| | Grand Total | | | 78,530 | 58,652 | 19,878 |

| quartile | category | services | Expected Svcs | Stratum episodes | Total Costs | Your Costs | Others Costs | Expected Costs | Total Cost Difference | Total Costs per stratum episodes |
|---|---|---|---|---|---|---|---|---|---|---|
| Q1 | A | 00300 | .58 | 6,455 | $580 | $580 | $0 | $167 | $413 | $0 |
| Q1 | A | 94720 | .58 | 6,455 | $165 | $165 | $0 | $48 | $117 | $0 |
| Q1 | A | 94240 | .29 | 6,455 | $125 | $125 | $0 | $36 | $89 | $0 |
| Q1 | A | 94010 | .29 | 6,455 | $124 | $124 | $0 | $36 | $88 | $0 |
| Q1 | A | A4646 | .87 | 6,455 | $149 | $0 | $149 | $63 | $86 | $0 |
| Q1 | A | 99601 | .29 | 6,455 | $95 | $95 | $0 | $27 | $68 | $0 |
| . | . | . | . | . | . | . | . | . | . | . |
| . | . | . | . | . | . | . | . | . | . | . |
| Q1 | A | 88321 | 4.04 | 6,455 | $85 | $0 | $85 | $344 | ($259) | $0 |
| Q1 | A | 88342 | 9.24 | 6,455 | $476 | $476 | $0 | $1,370 | ($894) | $0 |
| Q1 | A | 88305 | 3105.38 | 6,455 | $62,122 | $53,278 | $8,844 | $96,026 | ($33,904) | $10 |
| | A Total | | 3435.95 | | $66,375 | $55,690 | $10,685 | $100,909 | ($34,534) | $10 |
| Q1 | M | 99213 | 1967.28 | 6,455 | $130,482 | $121,036 | $9,446 | $108,522 | $21,960 | $20 |
| Q1 | M | 99214 | 33.78 | 6,455 | $3,973 | $2,734 | $1,239 | $3,067 | $906 | $1 |
| Q1 | M | 99205 | .29 | 6,455 | $164 | $0 | $164 | $47 | $117 | $0 |
| . | . | . | . | . | . | . | . | . | . | . |
| . | . | . | . | . | . | . | . | . | . | . |
| Q1 | M | 99241 | 30.31 | 6,455 | $53 | $53 | $0 | $1,607 | ($1,554) | $0 |
| Q1 | M | 99202 | 28.58 | 6,455 | $119 | $0 | $119 | $1,901 | ($1,782) | $0 |
| Q1 | M | 99203 | 46.19 | 6,455 | $1,020 | $302 | $718 | $4,896 | ($3,876) | $0 |
| Q1 | M | 99212 | 378.50 | 6,455 | $9,866 | $8,935 | $931 | $14,840 | ($4,974) | $2 |
| Q1 | M | 99242 | 625.35 | 6,455 | $32,863 | $31,514 | $1,349 | $60,757 | ($27,894) | $5 |
| Q1 | M | 99243 | 1231.06 | 6,455 | $69,132 | $65,789 | $3,343 | $158,856 | ($89,724) | $11 |
| | M Total | | 4371.37 | | $249,522 | $230,790 | $18,732 | $357,088 | ($107,566) | $39 |
| Q1 | P | L9B | 993.17 | 6,455 | $4,900 | $4,397 | $503 | $2,414 | $2,486 | $1 |
| Q1 | P | H3A | 3742.56 | 6,455 | $5,607 | $1,073 | $4,534 | $4,803 | $804 | $1 |
| . | . | . | . | . | . | . | . | . | . | . |
| . | . | . | . | . | . | . | . | . | . | . |
| Q1 | P | J9A | 48.50 | 6,455 | $8 | $0 | $8 | $15 | ($7) | $0 |
| Q1 | P | H0A | 15.88 | 6,455 | $10 | $0 | $10 | $28 | ($18) | $0 |
| Q1 | P | S2B | 1127.42 | 6,455 | $1,355 | $468 | $887 | $1,485 | ($130) | $0 |
| | P Total | | 7386.96 | | $20,728 | $13,487 | $7,241 | $16,845 | $3,883 | $3 |
| Q1 | R | 76942 | .58 | 6,455 | $39 | $0 | $39 | $57 | ($18) | $0 |
| | R Total | | .58 | | $39 | $0 | $39 | $57 | ($18) | $0 |
| Q1 | S | 17000 | 1277.26 | 6,455 | $86,301 | $84,932 | $1,369 | $79,652 | $6,649 | $13 |
| Q1 | S | 11300 | 472.33 | 6,455 | $24,845 | $24,100 | $745 | $20,778 | $4,067 | $4 |
| Q1 | S | 17004 | 9.82 | 6,455 | $858 | $858 | $0 | $594 | $264 | $0 |
| Q1 | S | 54060 | .29 | 6,455 | $278 | $278 | $0 | $80 | $198 | $0 |
| . | . | . | . | . | . | . | . | . | . | . |
| . | . | . | . | . | . | . | . | . | . | . |
| Q1 | S | 11442 | 16.46 | 6,455 | $396 | $198 | $198 | $2,828 | ($2,432) | $0 |
| Q1 | S | 11421 | 35.22 | 6,455 | $676 | $676 | $0 | $4,224 | ($3,548) | $0 |
| Q1 | S | 11400 | 147.82 | 6,455 | $10,040 | $9,466 | $574 | $13,774 | ($3,734) | $2 |
| Q1 | S | 11101 | 183.62 | 6,455 | $3,596 | $3,242 | $354 | $7,559 | ($3,963) | $1 |
| Q1 | S | 11100 | 511.02 | 6,455 | $39,576 | $38,139 | $1,437 | $43,864 | ($4,288) | $6 |
| Q1 | S | 11310 | 209.03 | 6,455 | $7,985 | $7,608 | $377 | $12,363 | ($4,378) | $1 |
| Q1 | S | 11403 | 34.36 | 6,455 | $825 | $646 | $179 | $5,610 | ($4,785) | $0 |
| Q1 | S | 12031 | 33.49 | 6,455 | $899 | $713 | $186 | $5,685 | ($4,786) | $0 |
| Q1 | S | 11441 | 43.88 | 6,455 | $1,496 | $797 | $699 | $6,482 | ($4,986) | $0 |
| Q1 | S | 11440 | 78.82 | 6,455 | $1,751 | $1,358 | $393 | $9,266 | ($7,515) | $0 |
| Q1 | S | 11301 | 786.45 | 6,455 | $39,819 | $39,200 | $619 | $48,630 | ($8,811) | $6 |
| Q1 | S | 11302 | 164.28 | 6,455 | $4,274 | $4,274 | $0 | $13,253 | ($8,979) | $1 |
| Q1 | S | 11402 | 153.31 | 6,455 | $9,737 | $9,105 | $632 | $21,014 | ($11,277) | $2 |
| Q1 | S | 11306 | 240.21 | 6,455 | $3,848 | $3,631 | $217 | $15,227 | ($11,379) | $1 |
| Q1 | S | 11311 | 218.84 | 6,455 | $5,715 | $5,430 | $285 | $17,184 | ($11,469) | $1 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | | | | |
|---|---|---|---|---|---|---|---|---|---|---|
| Q1 | S | 11401 | 278.89 | 6,455 | $10,989 | $10,532 | $457 | $29,553 | ($18,564) | $2 |
| | S Total | | 7399.95 | | $280,871 | $271,549 | $9,322 | $397,845 | ($116,974) | $44 |
| | Q1 Total | | 22594.81 | | $617,535 | $571,516 | $46,019 | $872,743 | ($255,208) | $96 |
| Q2 | A | 88305 | 2137.44 | 4,443 | $87,190 | $74,527 | $12,663 | $66,095 | $21,095 | $20 |
| Q2 | A | 88342 | 6.36 | 4,443 | $1,587 | $793 | $794 | $943 | $644 | $0 |
| Q2 | A | 00820 | .20 | 4,443 | $315 | $0 | $315 | $63 | $252 | $0 |
| . | . | . | . | . | . | . | . | . | . | . |
| . | . | . | . | . | . | . | . | . | . | . |
| Q2 | A | 80053 | 24.24 | 4,443 | $110 | $0 | $110 | $121 | ($11) | $0 |
| Q2 | A | 84460 | 12.52 | 4,443 | $34 | $0 | $34 | $51 | ($17) | $0 |
| Q2 | A | 84443 | 9.54 | 4,443 | $35 | $0 | $35 | $67 | ($32) | $0 |
| Q2 | A | 80050 | 5.37 | 4,443 | $28 | $0 | $28 | $75 | ($47) | $0 |
| | A Total | | 2348.48 | | $91,878 | $76,951 | $14,927 | $69,078 | $22,800 | $21 |
| Q2 | M | 99242 | 430.43 | 4,443 | $43,318 | $40,616 | $2,702 | $41,819 | $1,499 | $10 |
| Q2 | M | 99204 | 2.19 | 4,443 | $586 | $0 | $586 | $315 | $271 | $0 |
| Q2 | M | 99245 | .40 | 4,443 | $234 | $0 | $234 | $94 | $140 | $0 |
| . | . | . | . | . | . | . | . | . | . | . |
| . | . | . | . | . | . | . | . | . | . | . |
| Q2 | M | 99241 | 20.87 | 4,443 | $159 | $106 | $53 | $1,106 | ($947) | $0 |
| Q2 | M | 99203 | 31.80 | 4,443 | $1,289 | $205 | $1,084 | $3,370 | ($2,081) | $0 |
| Q2 | M | 99212 | 260.52 | 4,443 | $7,280 | $5,990 | $1,290 | $10,215 | ($2,935) | $2 |
| Q2 | M | 99243 | 847.35 | 4,443 | $100,552 | $97,581 | $2,971 | $109,341 | ($8,789) | $23 |
| Q2 | M | 99213 | 1354.08 | 4,443 | $55,484 | $43,371 | $12,113 | $74,696 | ($19,212) | $12 |
| | M Total | | 3013.20 | | $213,438 | $188,618 | $24,820 | $246,083 | ($32,645) | $48 |
| Q2 | P | S2B | 776.00 | 4,443 | $1,316 | $238 | $1,078 | $1,022 | $294 | $0 |
| Q2 | P | Z2G | 404.60 | 4,443 | $3,074 | $2,775 | $299 | $2,800 | $274 | $1 |
| . | . | . | . | . | . | . | . | . | . | . |
| . | . | . | . | . | . | . | . | . | . | . |
| Q2 | P | J7050 | 2.19 | 4,443 | $7 | $7 | $0 | $9 | ($2) | $0 |
| Q2 | P | Z2A | 22.65 | 4,443 | $26 | $18 | $8 | $45 | ($19) | $0 |
| Q2 | P | L9B | 683.60 | 4,443 | $669 | $552 | $117 | $1,662 | ($993) | $0 |
| | P Total | | 5062.41 | | $11,384 | $7,127 | $4,257 | $11,354 | $30 | $3 |
| Q2 | S | 11100 | 351.74 | 4,443 | $51,962 | $50,826 | $1,136 | $30,192 | $21,770 | $12 |
| Q2 | S | 11302 | 113.07 | 4,443 | $17,768 | $17,591 | $177 | $9,122 | $8,646 | $4 |
| Q2 | S | 11101 | 126.39 | 4,443 | $13,545 | $13,367 | $178 | $5,203 | $8,342 | $3 |
| Q2 | S | 11301 | 541.32 | 4,443 | $38,844 | $37,832 | $1,012 | $33,472 | $5,372 | $9 |
| Q2 | S | 11305 | 151.62 | 4,443 | $10,542 | $10,043 | $499 | $6,011 | $4,531 | $2 |
| Q2 | S | 11312 | 23.45 | 4,443 | $5,154 | $5,154 | $0 | $2,311 | $2,843 | $1 |
| Q2 | S | 11300 | 325.11 | 4,443 | $16,356 | $15,573 | $783 | $14,302 | $2,054 | $4 |
| Q2 | S | 11311 | 150.63 | 4,443 | $13,139 | $12,949 | $190 | $11,828 | $1,311 | $3 |
| Q2 | S | 11400 | 101.75 | 4,443 | $10,317 | $10,210 | $107 | $9,481 | $836 | $2 |
| Q2 | S | 11603 | .40 | 4,443 | $324 | $324 | $0 | $64 | $260 | $0 |
| Q2 | S | 11307 | 19.67 | 4,443 | $2,010 | $2,010 | $0 | $1,789 | $221 | $0 |
| . | . | . | . | . | . | . | . | . | . | . |
| Q2 | S | 40490 | 4.57 | 4,443 | $411 | $411 | $0 | $514 | ($103) | $0 |
| Q2 | S | 11900 | 4.57 | 4,443 | $104 | $104 | $0 | $216 | ($112) | $0 |
| Q2 | S | 11310 | 143.87 | 4,443 | $8,226 | $7,886 | $340 | $8,510 | ($284) | $2 |
| Q2 | S | 17004 | 6.76 | 4,443 | $66 | $66 | $0 | $409 | ($343) | $0 |
| Q2 | S | 11420 | 21.86 | 4,443 | $1,573 | $1,573 | $0 | $1,956 | ($383) | $0 |
| . | . | . | . | . | . | . | . | . | . | . |
| Q2 | S | 11442 | 11.33 | 4,443 | $412 | $230 | $182 | $1,946 | ($1,534) | $0 |
| Q2 | S | 11306 | 165.34 | 4,443 | $8,946 | $8,558 | $388 | $10,481 | ($1,535) | $2 |
| Q2 | S | 11421 | 24.24 | 4,443 | $992 | $992 | $0 | $2,907 | ($1,915) | $0 |
| Q2 | S | 11440 | 54.25 | 4,443 | $4,240 | $4,030 | $210 | $6,378 | ($2,138) | $1 |
| Q2 | S | 12032 | 19.67 | 4,443 | $1,562 | $1,120 | $442 | $4,287 | ($2,725) | $0 |
| Q2 | S | 11403 | 23.65 | 4,443 | $914 | $914 | $0 | $3,862 | ($2,948) | $0 |
| Q2 | S | 11441 | 30.21 | 4,443 | $1,481 | $1,143 | $338 | $4,462 | ($2,981) | $0 |
| Q2 | S | 11401 | 191.96 | 4,443 | $17,276 | $16,281 | $995 | $20,341 | ($3,065) | $4 |
| Q2 | S | 11402 | 105.52 | 4,443 | $11,261 | $10,858 | $403 | $14,464 | ($3,203) | $3 |
| Q2 | S | 17000 | 879.14 | 4,443 | $45,979 | $43,698 | $2,281 | $54,825 | ($8,846) | $10 |
| | S Total | | 5091.23 | | $294,660 | $283,572 | $11,088 | $273,829 | $20,831 | $66 |
| | Q2 Total | | 15515.33 | | $611,360 | $556,268 | $55,092 | $600,343 | $11,017 | $138 |
| Q3 | A | 0551 | 1.74 | 7,788 | $425 | $425 | $0 | $148 | $277 | $0 |
| Q3 | A | 88321 | 4.88 | 7,788 | $680 | $595 | $85 | $415 | $265 | $0 |
| Q3 | A | 88342 | 11.15 | 7,788 | $1,890 | $951 | $939 | $1,653 | $237 | $0 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | | | | |
|---|---|---|---|---|---|---|---|---|---|---|
| Q3 | A | 0490 | 2.09 | 7,788 | $336 | $336 | $0 | $117 | $219 | $0 |
| . | . | . | . | . | . | . | . | . | . | . |
| . | . | . | . | . | . | . | . | . | . | . |
| . | . | . | . | . | . | . | . | . | . | . |
| Q3 | A | AS | 2.09 | 7,788 | $284 | $219 | $65 | $473 | ($189) | $0 |
| Q3 | A | 88305 | 3746.66 | 7,788 | $94,768 | $79,088 | $15,680 | $115,856 | ($21,088) | $12 |
| | | A Total | 4150.72 | | $102,204 | $83,082 | $19,122 | $121,893 | ($19,689) | $13 |
| Q3 | M | 99243 | 1485.29 | 7,788 | $259,400 | $255,556 | $3,844 | $191,661 | $67,739 | $33 |
| Q3 | M | 99213 | 2373.53 | 7,788 | $134,726 | $113,540 | $21,186 | $130,933 | $3,793 | $17 |
| Q3 | M | 99241 | 36.57 | 7,788 | $5,300 | $5,247 | $53 | $1,938 | $3,362 | $1 |
| Q3 | M | 99212 | 456.66 | 7,788 | $20,119 | $17,403 | $2,716 | $17,905 | $2,214 | $3 |
| Q3 | M | 99203 | 55.73 | 7,788 | $7,797 | $5,422 | $2,375 | $5,907 | $1,890 | $1 |
| Q3 | M | 99202 | 34.48 | 7,788 | $3,054 | $2,264 | $790 | $2,294 | $760 | $0 |
| . | . | . | . | . | . | . | . | . | . | . |
| . | . | . | . | . | . | . | . | . | . | . |
| . | . | . | . | . | . | . | . | . | . | . |
| Q3 | M | 99204 | 3.83 | 7,788 | $293 | $0 | $293 | $551 | ($258) | $0 |
| Q3 | M | 99244 | 5.22 | 7,788 | $554 | $185 | $369 | $963 | ($409) | $0 |
| Q3 | M | 99214 | 40.75 | 7,788 | $2,071 | $265 | $1,806 | $3,701 | ($1,630) | $0 |
| Q3 | M | 99242 | 754.49 | 7,788 | $68,631 | $66,197 | $2,434 | $73,303 | ($4,672) | $9 |
| | | M Total | 5281.41 | | $504,876 | $466,125 | $38,751 | $431,288 | $73,588 | $65 |
| Q3 | p | L1B | 31.35 | 7,788 | $582 | $582 | $0 | $351 | $231 | $0 |
| Q3 | p | L1A | 1.04 | 7,788 | $161 | $161 | $0 | $56 | $105 | $0 |
| Q3 | p | Z2A | 39.71 | 7,788 | $112 | $0 | $112 | $79 | $33 | $0 |
| . | . | . | . | . | . | . | . | . | . | . |
| . | . | . | . | . | . | . | . | . | . | . |
| . | . | . | . | . | . | . | . | . | . | . |
| Q3 | p | Z2G | 709.20 | 7,788 | $4,246 | $3,962 | $284 | $4,907 | ($661) | $1 |
| Q3 | p | H3A | 4515.42 | 7,788 | $4,958 | $1,420 | $3,538 | $5,794 | ($836) | $1 |
| Q3 | p | Q5N | 928.65 | 7,788 | $2,375 | $2,375 | $0 | $4,279 | ($1,904) | $0 |
| | | P Total | 8895.00 | | $16,796 | $10,593 | $6,203 | $20,356 | ($3,560) | $2 |
| Q3 | S | 11306 | 289.81 | 7,788 | $31,883 | $31,670 | $213 | $18,371 | $13,512 | $4 |
| Q3 | S | 11311 | 264.04 | 7,788 | $34,032 | $33,524 | $508 | $20,732 | $13,300 | $4 |
| Q3 | S | 17000 | 1541.02 | 7,788 | $107,753 | $106,108 | $1,645 | $96,101 | $11,652 | $14 |
| Q3 | S | 11301 | 948.86 | 7,788 | $69,328 | $66,961 | $2,367 | $58,672 | $10,656 | $9 |
| Q3 | S | 11403 | 41.45 | 7,788 | $13,183 | $12,672 | $511 | $6,769 | $6,414 | $2 |
| Q3 | S | 11440 | 95.09 | 7,788 | $15,293 | $13,920 | $1,373 | $11,179 | $4,114 | $2 |
| Q3 | S | 11310 | 252.19 | 7,788 | $18,610 | $18,126 | $484 | $14,916 | $3,694 | $2 |
| Q3 | S | 11404 | 11.84 | 7,788 | $4,994 | $4,161 | $833 | $2,324 | $2,670 | $1 |
| Q3 | S | 17106 | 4.88 | 7,788 | $4,362 | $4,362 | $0 | $1,792 | $2,570 | $1 |
| . | . | . | . | . | . | . | . | . | . | . |
| . | . | . | . | . | . | . | . | . | . | . |
| . | . | . | . | . | . | . | . | . | . | . |
| Q3 | S | 11441 | 52.95 | 7,788 | $9,204 | $9,043 | $161 | $7,821 | $1,383 | $1 |
| Q3 | S | 12031 | 40.41 | 7,788 | $7,821 | $7,252 | $569 | $6,859 | $962 | $1 |
| Q3 | S | 11402 | 184.96 | 7,788 | $26,296 | $25,237 | $1,059 | $25,354 | $942 | $3 |
| Q3 | S | 11302 | 198.20 | 7,788 | $16,910 | $16,582 | $328 | $15,990 | $920 | $2 |
| Q3 | S | 54056 | 2.44 | 7,788 | $1,000 | $1,000 | $0 | $390 | $610 | $0 |
| Q3 | S | 11424 | 2.09 | 7,788 | $919 | $919 | $0 | $464 | $455 | $0 |
| Q3 | S | 67810 | 9.75 | 7,788 | $2,057 | $2,057 | $0 | $1,658 | $399 | $0 |
| . | . | . | . | . | . | . | . | . | . | . |
| . | . | . | . | . | . | . | . | . | . | . |
| . | . | . | . | . | . | . | . | . | . | . |
| Q3 | S | 11901 | 3.83 | 7,788 | $343 | $343 | $0 | $208 | $135 | $0 |
| Q3 | S | 11401 | 336.49 | 7,788 | $35,760 | $34,110 | $1,650 | $35,656 | $104 | $5 |
| Q3 | S | 11426 | .70 | 7,788 | $282 | $282 | $0 | $182 | $100 | $0 |
| Q3 | S | 17004 | 11.84 | 7,788 | $814 | $814 | $0 | $717 | $97 | $0 |
| Q3 | S | 11444 | .70 | 7,788 | $280 | $280 | $0 | $204 | $76 | $0 |
| . | . | . | . | . | . | . | . | . | . | . |
| . | . | . | . | . | . | . | . | . | . | . |
| . | . | . | . | . | . | . | . | . | . | . |
| Q3 | S | 11305 | 265.78 | 7,788 | $6,227 | $5,943 | $284 | $10,537 | ($4,310) | $1 |
| Q3 | S | 11101 | 221.54 | 7,788 | $4,223 | $3,697 | $526 | $9,120 | ($4,897) | $1 |
| Q3 | S | 11400 | 178.35 | 7,788 | $11,277 | $10,908 | $369 | $16,619 | ($5,342) | $1 |
| Q3 | S | 11330 | 569.87 | 7,788 | $11,209 | $10,330 | $879 | $25,069 | ($13,860) | $1 |
| Q3 | S | 11100 | 616.55 | 7,788 | $31,241 | $28,008 | $3,233 | $52,922 | ($21,681) | $4 |
| | | S Total | 8974.42 | | $518,752 | $499,077 | $19,675 | $489,127 | $29,625 | $67 |
| | Q3 Total | | 27301.54 | | $1,142,628 | $1,058,877 | $83,751 | $1,062,664 | $79,964 | $147 |
| Q4 | A | 88305 | 1766.53 | 3,672 | $88,522 | $80,632 | $7,890 | $54,625 | $33,897 | $24 |
| Q4 | A | AS | .99 | 3,672 | $513 | $513 | $0 | $223 | $290 | $0 |
| Q4 | A | ER | .66 | 3,672 | $305 | $305 | $0 | $81 | $224 | $0 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | | | |
|---|---|---|---|---|---|---|---|---|---|
| Q4 | A | S0630 | 1.81 | 3,672 | $216 | $216 | $0 | $75 | $141 | $0 |
| . | . | . | . | . | . | . | . | . | . | . |
| . | . | . | . | . | . | . | . | . | . | . |
| . | . | . | . | . | . | . | . | . | . | . |
| Q4 | A | 85025 | 20.86 | 3,672 | $39 | $0 | $39 | $64 | ($25) | $0 |
| Q4 | A | 84460 | 10.35 | 3,672 | $13 | $0 | $13 | $43 | ($30) | $0 |
| Q4 | A | 80053 | 20.04 | 3,672 | $70 | $0 | $70 | $100 | ($30) | $0 |
| Q4 | A | 80061 | 15.11 | 3,672 | $64 | $0 | $64 | $121 | ($57) | $0 |
| Q4 | A | 88321 | 2.30 | 3,672 | $85 | $0 | $85 | $195 | ($110) | $0 |
| | | A Total | 1945.71 | | $92,174 | $83,419 | $8,755 | $57,213 | $34,961 | $25 |
| Q4 | M | 99242 | 355.74 | 3,672 | $65,629 | $64,578 | $1,051 | $34,562 | $31,067 | $18 |
| Q4 | M | 99243 | 700.30 | 3,672 | $121,141 | $117,517 | $3,624 | $90,367 | $30,774 | $33 |
| Q4 | M | 99212 | 215.31 | 3,672 | $14,137 | $11,867 | $2,270 | $8,442 | $5,695 | $4 |
| Q4 | M | 99203 | 26.28 | 3,672 | $6,851 | $4,826 | $2,025 | $2,785 | $4,066 | $2 |
| Q4 | M | 99202 | 16.26 | 3,672 | $2,474 | $1,740 | $734 | $1,082 | $1,392 | $1 |
| Q4 | M | 99214 | 19.22 | 3,672 | $3,077 | $1,766 | $1,311 | $1,745 | $1,332 | $1 |
| . | . | . | . | . | . | . | . | . | . | . |
| . | . | . | . | . | . | . | . | . | . | . |
| . | . | . | . | . | . | . | . | . | . | . |
| Q4 | M | 99395 | 2.96 | 3,672 | $112 | $0 | $112 | $166 | ($54) | $0 |
| Q4 | M | 99204 | 1.81 | 3,672 | $147 | $0 | $147 | $260 | ($113) | $0 |
| Q4 | M | 99241 | 17.24 | 3,672 | $53 | $53 | $0 | $914 | ($861) | $0 |
| Q4 | M | 99213 | 1119.11 | 3,672 | $55,194 | $41,218 | $13,976 | $61,734 | ($6,540) | $15 |
| | | M Total | 2486.87 | | $271,026 | $244,855 | $26,171 | $203,021 | $68,005 | $74 |
| Q4 | P | Q5N | 437.85 | 3,672 | $3,602 | $3,515 | $87 | $2,017 | $1,585 | $1 |
| Q4 | P | J3301 | 3.45 | 3,672 | $80 | $60 | $20 | $33 | $47 | $0 |
| . | . | . | . | . | . | . | . | . | . | . |
| . | . | . | . | . | . | . | . | . | . | . |
| . | . | . | . | . | . | . | . | . | . | . |
| Q4 | P | L9B | 564.97 | 3,672 | $427 | $159 | $268 | $1,373 | ($946) | $0 |
| | | P Total | 4131.53 | | $9,627 | $6,095 | $3,532 | $9,359 | $268 | $3 |
| Q4 | R | 76942 | .33 | 3,672 | $158 | $0 | $158 | $32 | $126 | $0 |
| | | R Total | .33 | | $158 | $0 | $158 | $32 | $126 | $0 |
| Q4 | S | 11401 | 158.65 | 3,672 | $38,337 | $37,510 | $827 | $16,812 | $21,525 | $10 |
| Q4 | S | 11402 | 87.21 | 3,672 | $25,492 | $24,873 | $619 | $11,954 | $13,538 | $7 |
| Q4 | S | 11400 | 84.09 | 3,672 | $16,076 | $15,974 | $102 | $7,836 | $8,240 | $4 |
| Q4 | S | 11300 | 268.69 | 3,672 | $19,559 | $19,344 | $215 | $11,820 | $7,739 | $5 |
| Q4 | S | 11441 | 24.96 | 3,672 | $10,271 | $10,038 | $233 | $3,687 | $6,584 | $3 |
| Q4 | S | 11421 | 20.04 | 3,672 | $8,103 | $8,103 | $0 | $2,403 | $5,700 | $2 |
| Q4 | S | 11440 | 44.84 | 3,672 | $10,809 | $10,686 | $123 | $5,271 | $5,538 | $3 |
| Q4 | S | 12031 | 19.05 | 3,672 | $8,025 | $7,589 | $436 | $3,234 | $4,791 | $2 |
| Q4 | S | 11100 | 290.70 | 3,672 | $29,152 | $27,305 | $1,847 | $24,953 | $4,199 | $8 |
| Q4 | S | 11422 | 10.35 | 3,672 | $4,979 | $4,979 | $0 | $1,475 | $3,504 | $1 |
| Q4 | S | 11420 | 18.07 | 3,672 | $4,806 | $4,806 | $0 | $1,617 | $3,189 | $1 |
| Q4 | S | 12032 | 16.26 | 3,672 | $5,932 | $5,770 | $162 | $3,543 | $2,389 | $2 |
| Q4 | S | 13101 | 1.31 | 3,672 | $2,554 | $2,554 | $0 | $419 | $2,135 | $1 |
| Q4 | S | 11442 | 9.36 | 3,672 | $3,483 | $3,315 | $168 | $1,609 | $1,874 | $1 |
| Q4 | S | 11307 | 16.26 | 3,672 | $3,126 | $3,126 | $0 | $1,479 | $1,647 | $1 |
| Q4 | S | 11312 | 19.38 | 3,672 | $3,459 | $3,459 | $0 | $1,910 | $1,549 | $1 |
| Q4 | S | 67810 | 4.60 | 3,672 | $2,138 | $2,138 | $0 | $782 | $1,356 | $1 |
| Q4 | S | 11403 | 19.54 | 3,672 | $4,510 | $4,312 | $198 | $3,191 | $1,319 | $1 |
| Q4 | S | 11406 | 2.14 | 3,672 | $1,591 | $1,339 | $252 | $498 | $1,093 | $0 |
| Q4 | S | 40490 | 3.78 | 3,672 | $1,473 | $1,473 | $0 | $425 | $1,048 | $0 |
| Q4 | S | 11310 | 118.91 | 3,672 | $8,001 | $7,555 | $446 | $7,033 | $968 | $2 |
| Q4 | S | 11308 | 1.81 | 3,672 | $926 | $926 | $0 | $186 | $740 | $0 |
| Q4 | S | 11303 | 5.26 | 3,672 | $1,196 | $1,104 | $92 | $527 | $669 | $0 |
| Q4 | S | 11305 | 125.31 | 3,672 | $5,579 | $5,417 | $162 | $4,968 | $611 | $2 |
| Q4 | S | 13131 | .33 | 3,672 | $630 | $630 | $0 | $103 | $527 | $0 |
| Q4 | S | 11101 | 104.45 | 3,672 | $4,817 | $4,592 | $225 | $4,300 | $517 | $1 |
| Q4 | S | 12051 | 1.97 | 3,672 | $904 | $672 | $232 | $432 | $472 | $0 |
| . | . | . | . | . | . | . | . | . | . | . |
| . | . | . | . | . | . | . | . | . | . | . |
| . | . | . | . | . | . | . | . | . | . | . |
| Q4 | S | 17106 | 2.30 | 3,672 | $782 | $782 | $0 | $845 | ($63) | $0 |
| Q4 | S | 54056 | 1.15 | 3,672 | $121 | $121 | $0 | $184 | ($63) | $0 |
| Q4 | S | 11404 | 5.58 | 3,672 | $846 | $737 | $109 | $1,096 | ($250) | $0 |
| Q4 | S | 11443 | 2.46 | 3,672 | $222 | $222 | $0 | $518 | ($296) | $0 |
| Q4 | S | 11302 | 93.45 | 3,672 | $6,952 | $6,621 | $331 | $7,539 | ($587) | $2 |
| Q4 | S | 11306 | 136.64 | 3,672 | $8,064 | $7,920 | $144 | $8,662 | ($598) | $2 |
| Q4 | S | 11311 | 124.49 | 3,672 | $6,633 | $6,593 | $40 | $9,775 | ($3,142) | $2 |
| Q4 | S | 11301 | 447.38 | 3,672 | $20,447 | $20,270 | $177 | $27,664 | ($7,217) | $6 |
| Q4 | S | 17000 | 726.58 | 3,672 | $35,855 | $34,605 | $1,250 | $45,311 | ($9,456) | $10 |
| | | S Total | 4235.33 | | $316,052 | $307,155 | $8,897 | $231,346 | $84,706 | $86 |
| | Q4 Total | | 12799.77 | | $689,037 | $641,524 | $47,513 | $500,971 | $188,066 | $188 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| Grand Total | 78211.45 | $3,060,560 | $2,828,185 | $232,375 | $3,036,722 | $23,838 | $568 |
|---|---|---|---|---|---|---|---|

| quartile | category | services | Difference per stratum episodes | Your costs per svc | Other costs per svc | Spec costs per svc | episodes this service occurred |
|---|---|---|---|---|---|---|---|
| Q1 | A | 00300 | $0 | $290 | $0 | $290 | 2 |
| Q1 | A | 94720 | $0 | $83 | $0 | $83 | 2 |
| Q1 | A | 94240 | $0 | $125 | $0 | $125 | 1 |
| Q1 | A | 94010 | $0 | $124 | $0 | $124 | 1 |
| Q1 | A | A4646 | $0 | $0 | $75 | $73 | 2 |
| Q1 | A | 99601 | $0 | $95 | $0 | $95 | 1 |
| . | . | . | . | . | . | . | . |
| . | . | . | . | . | . | . | . |
| Q1 | A | 88321 | ($0) | $0 | $85 | $85 | 1 |
| Q1 | A | 88342 | ($0) | $159 | $0 | $148 | 2 |
| Q1 | A | 88305 | ($5) | $31 | $31 | $31 | 1,403 |
| | A Total | | ($5) | | | | |
| Q1 | M | 99213 | $3 | $55 | $55 | $55 | 2,261 |
| Q1 | M | 99214 | $0 | $88 | $89 | $91 | 45 |
| Q1 | M | 99205 | $0 | $0 | $164 | $164 | 1 |
| . | . | . | . | . | . | . | . |
| . | . | . | . | . | . | . | . |
| Q1 | M | 99241 | ($0) | $53 | $0 | $53 | 1 |
| Q1 | M | 99202 | ($0) | $0 | $60 | $67 | 2 |
| Q1 | M | 99203 | ($1) | $101 | $103 | $106 | 10 |
| Q1 | M | 99212 | ($1) | $39 | $39 | $39 | 249 |
| Q1 | M | 99242 | ($4) | $96 | $96 | $97 | 339 |
| Q1 | M | 99243 | ($14) | $129 | $129 | $129 | 529 |
| | M Total | | ($17) | | | | |
| Q1 | P | L9B | $0 | $3 | $3 | $2 | 79 |
| Q1 | P | H3A | $0 | $1 | $1 | $1 | 233 |
| . | . | . | . | . | . | . | . |
| . | . | . | . | . | . | . | . |
| Q1 | P | J9A | ($0) | $0 | $0 | $0 | 2 |
| Q1 | P | H0A | ($0) | $0 | $0 | $2 | 1 |
| Q1 | P | S2B | ($0) | $2 | $1 | $1 | 21 |
| | P Total | | $1 | | | | |
| Q1 | R | 76942 | ($0) | $0 | $39 | $99 | 1 |
| | R Total | | ($0) | | | | |
| Q1 | S | 17000 | $1 | $64 | $60 | $62 | 1,215 |
| Q1 | S | 11300 | $1 | $47 | $50 | $44 | 398 |
| Q1 | S | 17004 | $0 | $66 | $0 | $61 | 13 |
| Q1 | S | 54060 | $0 | $278 | $0 | $278 | 1 |
| . | . | . | . | . | . | . | . |
| . | . | . | . | . | . | . | . |
| Q1 | S | 11442 | ($0) | $198 | $99 | $172 | 3 |
| Q1 | S | 11421 | ($1) | $135 | $0 | $120 | 5 |
| Q1 | S | 11400 | ($1) | $106 | $115 | $93 | 88 |
| Q1 | S | 11101 | ($1) | $38 | $39 | $41 | 83 |
| Q1 | S | 11100 | ($1) | $85 | $85 | $86 | 458 |
| Q1 | S | 11310 | ($1) | $64 | $63 | $59 | 105 |
| Q1 | S | 11403 | ($1) | $162 | $179 | $163 | 4 |
| Q1 | S | 12031 | ($1) | $178 | $186 | $170 | 5 |
| Q1 | S | 11441 | ($1) | $133 | $140 | $148 | 10 |
| Q1 | S | 11440 | ($1) | $136 | $131 | $118 | 12 |
| Q1 | S | 11301 | ($1) | $68 | $52 | $62 | 462 |
| Q1 | S | 11302 | ($1) | $85 | $0 | $81 | 45 |
| Q1 | S | 11402 | ($2) | $145 | $158 | $137 | 64 |
| Q1 | S | 11306 | ($2) | $77 | $72 | $63 | 43 |
| Q1 | S | 11311 | ($2) | $89 | $95 | $79 | 60 |
| Q1 | S | 11401 | ($3) | $113 | $91 | $106 | 92 |
| | S Total | | ($18) | | | | |
| Q1 Total | | | ($40) | | | | |
| Q2 | A | 88305 | $5 | $31 | $31 | $31 | 1,760 |
| Q2 | A | 88342 | $0 | $159 | $159 | $148 | 7 |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | |
|---|---|---|---|---|---|---|---|
| Q2 | A | 00820 | $0 | $0 | $315 | $315 | 1 |
| . | . | . | . | . | . | . | . |
| . | . | . | . | . | . | . | . |
| . | . | . | . | . | . | . | . |
| Q2 | A | 80053 | ($0) | $0 | $5 | $5 | 21 |
| Q2 | A | 84460 | ($0) | $0 | $3 | $4 | 10 |
| Q2 | A | 84443 | ($0) | $0 | $7 | $7 | 5 |
| Q2 | A | 80050 | ($0) | $0 | $14 | $14 | 2 |
| | A Total | | $5 | | | | |
| Q2 | M | 99242 | $0 | $97 | $97 | $97 | 440 |
| Q2 | M | 99204 | $0 | $0 | $147 | $144 | 4 |
| Q2 | M | 99245 | $0 | $0 | $234 | $237 | 1 |
| . | . | . | . | . | . | . | . |
| . | . | . | . | . | . | . | . |
| . | . | . | . | . | . | . | . |
| Q2 | M | 99241 | ($0) | $53 | $53 | $53 | 3 |
| Q2 | M | 99203 | ($0) | $103 | $99 | $106 | 13 |
| Q2 | M | 99212 | ($1) | $40 | $39 | $39 | 173 |
| Q2 | M | 99243 | ($2) | $129 | $129 | $129 | 767 |
| Q2 | M | 99213 | ($4) | $56 | $54 | $55 | 959 |
| | M Total | | ($7) | | | | |
| Q2 | P | S2B | $0 | $2 | $1 | $1 | 18 |
| Q2 | P | Z2G | $0 | $7 | $5 | $7 | 17 |
| . | . | . | . | . | . | . | . |
| . | . | . | . | . | . | . | . |
| . | . | . | . | . | . | . | . |
| Q2 | P | J7050 | ($0) | $7 | $0 | $4 | 1 |
| Q2 | P | Z2A | ($0) | $3 | $4 | $2 | 3 |
| Q2 | P | L9B | ($0) | $2 | $2 | $2 | 9 |
| | P Total | | $0 | | | | |
| Q2 | S | 11100 | $5 | $90 | $87 | $86 | 574 |
| Q2 | S | 11302 | $2 | $75 | $89 | $81 | 183 |
| Q2 | S | 11101 | $2 | $44 | $36 | $41 | 181 |
| Q2 | S | 11301 | $1 | $58 | $60 | $62 | 437 |
| Q2 | S | 11305 | $1 | $37 | $45 | $40 | 126 |
| Q2 | S | 11312 | $1 | $101 | $0 | $99 | 47 |
| Q2 | S | 11300 | $0 | $44 | $46 | $44 | 247 |
| Q2 | S | 11311 | $0 | $78 | $95 | $79 | 137 |
| Q2 | S | 11400 | $0 | $106 | $107 | $93 | 92 |
| Q2 | S | 11603 | $0 | $162 | $0 | $162 | 2 |
| Q2 | S | 11307 | $0 | $87 | $0 | $91 | 20 |
| . | . | . | . | . | . | . | . |
| . | . | . | . | . | . | . | . |
| . | . | . | . | . | . | . | . |
| Q2 | S | 40490 | ($0) | $103 | $0 | $112 | 3 |
| Q2 | S | 11900 | ($0) | $52 | $0 | $47 | 2 |
| Q2 | S | 11310 | ($0) | $58 | $68 | $59 | 104 |
| Q2 | S | 17004 | ($0) | $66 | $0 | $61 | 1 |
| Q2 | S | 11420 | ($0) | $105 | $0 | $89 | 15 |
| . | . | . | . | . | . | . | . |
| . | . | . | . | . | . | . | . |
| . | . | . | . | . | . | . | . |
| Q2 | S | 11442 | ($0) | $115 | $182 | $172 | 3 |
| Q2 | S | 11306 | ($0) | $62 | $78 | $63 | 104 |
| Q2 | S | 11421 | ($0) | $124 | $0 | $120 | 7 |
| Q2 | S | 11440 | ($0) | $122 | $105 | $118 | 29 |
| Q2 | S | 12032 | ($1) | $224 | $221 | $218 | 7 |
| Q2 | S | 11403 | ($1) | $183 | $0 | $163 | 5 |
| Q2 | S | 11441 | ($1) | $163 | $169 | $148 | 9 |
| Q2 | S | 11401 | ($1) | $120 | $111 | $106 | 129 |
| Q2 | S | 11402 | ($1) | $157 | $134 | $137 | 70 |
| Q2 | S | 17000 | ($2) | $61 | $63 | $62 | 707 |
| | S Total | | $5 | | | | |
| | Q2 Total | | $2 | | | | |
| Q3 | A | 0551 | $0 | $85 | $0 | $85 | 1 |
| Q3 | A | 88321 | $0 | $85 | $85 | $85 | 8 |
| Q3 | A | 88342 | $0 | $159 | $117 | $148 | 7 |
| Q3 | A | 0490 | $0 | $56 | $0 | $56 | 1 |
| . | . | . | . | . | . | . | . |
| . | . | . | . | . | . | . | . |
| . | . | . | . | . | . | . | . |
| Q3 | A | AS | ($0) | $219 | $65 | $226 | 2 |
| Q3 | A | 88305 | ($3) | $31 | $31 | $31 | 2,048 |
| | A Total | | ($3) | | | | |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | |
|---|---|---|---|---|---|---|---|
| Q3 | M | 99243 | $9 | $129 | $128 | $129 | 2,004 |
| Q3 | M | 99213 | $0 | $55 | $53 | $55 | 2,351 |
| Q3 | M | 99241 | $0 | $53 | $53 | $53 | 100 |
| Q3 | M | 99212 | $0 | $40 | $38 | $39 | 488 |
| Q3 | M | 99203 | $0 | $95 | $95 | $106 | 82 |
| Q3 | M | 99202 | $0 | $61 | $56 | $67 | 51 |
| . | . | . | . | . | . | . | . |
| . | . | . | . | . | . | . | . |
| Q3 | M | 99204 | ($0) | $0 | $147 | $144 | 2 |
| Q3 | M | 99244 | ($0) | $185 | $185 | $184 | 3 |
| Q3 | M | 99214 | ($0) | $88 | $90 | $91 | 23 |
| Q3 | M | 99242 | ($1) | $97 | $97 | $97 | 699 |
| | M Total | | $9 | | | | |
| Q3 | p | L1B | $0 | $10 | $0 | $11 | 2 |
| Q3 | p | L1A | $0 | $54 | $0 | $54 | 1 |
| Q3 | p | Z2A | $0 | $0 | $2 | $2 | 1 |
| . | . | . | . | . | . | . | . |
| . | . | . | . | . | . | . | . |
| Q3 | p | Z2G | ($0) | $8 | $5 | $7 | 22 |
| Q3 | p | H3A | ($0) | $2 | $1 | $1 | 272 |
| Q3 | p | Q5N | ($0) | $4 | $0 | $5 | 16 |
| | P Total | | ($0) | | | | |
| Q3 | S | 11306 | $2 | $61 | $71 | $63 | 283 |
| Q3 | S | 11311 | $2 | $77 | $85 | $79 | 297 |
| Q3 | S | 17000 | $1 | $63 | $59 | $62 | 1,580 |
| Q3 | S | 11301 | $1 | $61 | $62 | $62 | 742 |
| Q3 | S | 11403 | $1 | $178 | $128 | $163 | 69 |
| Q3 | S | 11440 | $1 | $117 | $106 | $118 | 108 |
| Q3 | S | 11310 | $0 | $57 | $48 | $59 | 251 |
| Q3 | S | 11404 | $0 | $198 | $208 | $196 | 24 |
| Q3 | S | 17106 | $0 | $364 | $0 | $367 | 12 |
| . | . | . | . | . | . | . | . |
| . | . | . | . | . | . | . | . |
| Q3 | S | 11441 | $0 | $146 | $161 | $148 | 58 |
| Q3 | S | 12031 | $0 | $169 | $142 | $170 | 44 |
| Q3 | S | 11402 | $0 | $136 | $132 | $137 | 177 |
| Q3 | S | 11302 | $0 | $89 | $82 | $81 | 174 |
| Q3 | S | 54056 | $0 | $167 | $0 | $160 | 6 |
| Q3 | S | 11424 | $0 | $230 | $0 | $222 | 4 |
| Q3 | S | 67810 | $0 | $257 | $0 | $170 | 7 |
| . | . | . | . | . | . | . | . |
| . | . | . | . | . | . | . | . |
| Q3 | S | 11901 | $0 | $49 | $0 | $54 | 7 |
| Q3 | S | 11401 | $0 | $108 | $92 | $106 | 270 |
| Q3 | S | 11426 | $0 | $282 | $0 | $262 | 1 |
| Q3 | S | 17004 | $0 | $54 | $0 | $61 | 15 |
| Q3 | S | 11444 | $0 | $280 | $0 | $294 | 1 |
| . | . | . | . | . | . | . | . |
| . | . | . | . | . | . | . | . |
| Q3 | S | 11305 | ($1) | $37 | $41 | $40 | 119 |
| Q3 | S | 11101 | ($1) | $39 | $38 | $41 | 78 |
| Q3 | S | 11400 | ($1) | $87 | $74 | $93 | 102 |
| Q3 | S | 11300 | ($2) | $43 | $42 | $44 | 189 |
| Q3 | S | 11100 | ($3) | $86 | $77 | $86 | 350 |
| | S Total | | $4 | | | | |
| Q3 Total | | | $10 | | | | |
| Q4 | A | 88305 | $9 | $31 | $31 | $31 | 1,581 |
| Q4 | A | AS | $0 | $257 | $0 | $226 | 2 |
| Q4 | A | ER | $0 | $153 | $0 | $123 | 2 |
| Q4 | A | S0630 | $0 | $43 | $0 | $41 | 5 |
| . | . | . | . | . | . | . | . |
| . | . | . | . | . | . | . | . |
| Q4 | A | 85025 | ($0) | $0 | $3 | $3 | 13 |
| Q4 | A | 84460 | ($0) | $0 | $4 | $4 | 3 |
| Q4 | A | 80053 | ($0) | $0 | $5 | $5 | 14 |
| Q4 | A | 80061 | ($0) | $0 | $8 | $8 | 8 |
| Q4 | A | 88321 | ($0) | $0 | $85 | $85 | 1 |
| | A Total | | $10 | | | | |

TABLE A8-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682

| | | | | | | | |
|---|---|---|---|---|---|---|---|
| Q4 | M | 99242 | $8 | $97 | $96 | $97 | 672 |
| Q4 | M | 99243 | $8 | $130 | $125 | $129 | 931 |
| Q4 | M | 99212 | $2 | $39 | $40 | $39 | 331 |
| Q4 | M | 99203 | $1 | $138 | $101 | $106 | 55 |
| Q4 | M | 99202 | $0 | $87 | $61 | $67 | 32 |
| Q4 | M | 99214 | $0 | $88 | $109 | $91 | 31 |
| . | . | . | . | . | . | . | . |
| . | . | . | . | . | . | . | . |
| . | . | . | . | . | . | . | . |
| Q4 | M | 99395 | ($0) | $0 | $56 | $56 | 2 |
| Q4 | M | 99204 | ($0) | $0 | $147 | $144 | 1 |
| Q4 | M | 99241 | ($0) | $53 | $0 | $53 | 1 |
| Q4 | M | 99213 | ($2) | $56 | $55 | $55 | 939 |
| | M Total | | $19 | | | | |
| Q4 | P | Q5N | $0 | $5 | $4 | $5 | 29 |
| Q4 | P | J3301 | $0 | $8 | $5 | $10 | 10 |
| . | . | . | . | . | . | . | . |
| . | . | . | . | . | . | . | . |
| . | . | . | . | . | . | . | . |
| Q4 | P | L9B | ($0) | $2 | $3 | $2 | 9 |
| | P Total | | $0 | | | | |
| Q4 | R | 76942 | $0 | $0 | $158 | $99 | 1 |
| | R Total | | $0 | | | | |
| Q4 | S | 11401 | $6 | $99 | $83 | $106 | 270 |
| Q4 | S | 11402 | $4 | $128 | $124 | $137 | 169 |
| Q4 | S | 11400 | $2 | $84 | $102 | $93 | 151 |
| Q4 | S | 11300 | $2 | $41 | $36 | $44 | 264 |
| Q4 | S | 11441 | $2 | $150 | $117 | $148 | 61 |
| Q4 | S | 11421 | $2 | $119 | $0 | $120 | 62 |
| Q4 | S | 11440 | $2 | $116 | $123 | $118 | 74 |
| Q4 | S | 12031 | $1 | $172 | $145 | $170 | 44 |
| Q4 | S | 11100 | $1 | $82 | $77 | $86 | 355 |
| Q4 | S | 11422 | $1 | $146 | $0 | $143 | 32 |
| Q4 | S | 11420 | $1 | $87 | $0 | $89 | 45 |
| Q4 | S | 12032 | $1 | $222 | $162 | $218 | 27 |
| Q4 | S | 13101 | $1 | $319 | $0 | $319 | 8 |
| Q4 | S | 11442 | $1 | $184 | $168 | $172 | 19 |
| Q4 | S | 11307 | $0 | $89 | $0 | $91 | 33 |
| Q4 | S | 11312 | $0 | $102 | $0 | $99 | 33 |
| Q4 | S | 67810 | $0 | $119 | $0 | $170 | 16 |
| Q4 | S | 11403 | $0 | $131 | $198 | $163 | 32 |
| Q4 | S | 11406 | $0 | $223 | $252 | $233 | 7 |
| Q4 | S | 40490 | $0 | $113 | $0 | $112 | 12 |
| Q4 | S | 11310 | $0 | $61 | $50 | $59 | 100 |
| Q4 | S | 11308 | $0 | $103 | $0 | $103 | 9 |
| Q4 | S | 11303 | $0 | $100 | $92 | $100 | 10 |
| Q4 | S | 11305 | $0 | $38 | $41 | $40 | 101 |
| Q4 | S | 13131 | $0 | $315 | $0 | $315 | 2 |
| Q4 | S | 11101 | $0 | $39 | $38 | $41 | 95 |
| Q4 | S | 12051 | $0 | $224 | $232 | $219 | 4 |
| . | . | . | . | . | . | . | . |
| . | . | . | . | . | . | . | . |
| . | . | . | . | . | . | . | . |
| Q4 | S | 17106 | ($0) | $391 | $0 | $367 | 2 |
| Q4 | S | 54056 | ($0) | $121 | $0 | $160 | 1 |
| Q4 | S | 11404 | ($0) | $184 | $109 | $196 | 5 |
| Q4 | S | 11443 | ($0) | $222 | $0 | $210 | 1 |
| Q4 | S | 11302 | ($0) | $76 | $66 | $81 | 77 |
| Q4 | S | 11306 | ($0) | $70 | $36 | $63 | 91 |
| Q4 | S | 11311 | ($1) | $80 | $40 | $79 | 74 |
| Q4 | S | 11301 | ($2) | $61 | $44 | $62 | 250 |
| Q4 | S | 17000 | ($3) | $59 | $54 | $62 | 552 |
| | S Total | | $23 | | | | |
| | Q4 Total | | $51 | | | | |
| | Grand Total | | $24 | | | | |

TABLE A9

Dermatology
Dates of Service Jan. 1, 2003-Dec. 31, 2004 paid Dec. 31, 2004
Total Role benign neoplasm of the skin without actinic keratoses diagnosis 702.xx
etg 0682
Cost driver threshold $2 (rounded value)

| quartile | category | services | service description | Total Svcs | Your Svcs |
|---|---|---|---|---|---|
| Q1 | A | 88305 | LEVEL IV—SURGICAL PATHOLOGY, GROSS & MICROSCOPIC EXAM | 2,008 | 1,723 |
| | A Total | | | 2,008 | 1,723 |
| Q1 | M | 99213 | OFFICE/OP VISIT, EST PT, 2 KEY COMPONENTS: EXPAND PROB HX; EXPAND PROB | 2,356 | 2,184 |
| Q1 | M | 99212 | OFFICE/OP VISIT, EST PT, 2 KEY COMPONENTS: PROB FOCUS HX; PROB FOCUS EX | 253 | 229 |
| Q1 | M | 99242 | OFFICE CONSULTATION, 3 KEY COMPONENTS: EXPAND PROB FOCUS HX;EXPAND PROB | 341 | 327 |
| Q1 | M | 99243 | OFFICE CONSULTATION, 3 KEY COMPONENTS: DETAILED HX; DETAILED EXAM; MED | 536 | 510 |
| | M Total | | | 3,486 | 3,250 |
| Q1 | S | 17000 | DESTRUCTION, BENIGN/PREMALIG LESIONS, EXCEPT SKIN TAGS/ CUTANEOUS VASC P | 1,343 | 1,320 |
| Q1 | S | 11300 | SHAVING SKIN LESION, TRUNK/ARMS/LEGS; DIAMETER 0.5 CM/< | 524 | 509 |
| Q1 | S | 11400 | EXCISE, BENIGN SKIN LESION, INCL MARGINS, EXCEPT SKIN TAG, TRUNK/ARMS/L | 94 | 89 |
| Q1 | S | 11100 | BX, SKIN, SUBQ/MUCOUS MEMBRANE; SINGLE LESION | 465 | 448 |
| Q1 | S | 11301 | SHAVING SKIN LESION, TRUNK/ARMS/LEGS; DIAMETER 0.6-1.0 CM | 585 | 573 |
| Q1 | S | 11402 | EXCISE, BENIGN SKIN LESION, INCL MARGINS, EXCEPT SKIN TAG, TRUNK/ARMS/L | 67 | 63 |
| Q1 | S | 11401 | EXCISE, BENIGN SKIN LESION, INCL MARGINS, EXCEPT SKIN TAG, TRUNK/ARMS/L | 98 | 93 |
| | S Total | | | 3,176 | 3,095 |
| | Q1 Total | | | 8,670 | 8,068 |
| Q2 | A | 88305 | LEVEL IV—SURGICAL PATHOLOGY, GROSS & MICROSCOPIC EXAM | 2,823 | 2,414 |
| | A Total | | | 2,823 | 2,414 |
| Q2 | M | 99242 | OFFICE CONSULTATION, 3 KEY COMPONENTS: EXPAND PROB FOCUS HX;EXPAND PROB | 445 | 417 |
| Q2 | M | 99212 | OFFICE/OP VISIT, EST PT, 2 KEY COMPONENTS: PROB FOCUS HX; PROB FOCUS EX | 183 | 150 |
| Q2 | M | 99243 | OFFICE CONSULTATION, 3 KEY COMPONENTS: DETAILED HX; DETAILED EXAM; MED | 779 | 756 |
| Q2 | M | 99213 | OFFICE/OP VISIT, EST PT, 2 KEY COMPONENTS: EXPAND PROB HX; EXPAND PROB | 999 | 776 |
| | M Total | | | 2,406 | 2,099 |
| Q2 | S | 11100 | BX, SKIN, SUBQ/MUCOUS MEMBRANE; SINGLE LESION | 580 | 567 |
| Q2 | S | 11302 | SHAVING SKIN LESION, TRUNK/ARMS/LEGS; DIAMETER 1.1-2.0 CM | 236 | 234 |
| Q2 | S | 11101 | BX, SKIN, SUBQ/MUCOUS MEMBRANE (SEP PROC); ADDL LESION | 307 | 302 |
| Q2 | S | 11301 | SHAVING SKIN LESION, TRUNK/ARMS/LEGS; DIAMETER 0.6-1.0 CM | 671 | 654 |
| Q2 | S | 11305 | SHAVING SKIN LESION, SCALP/NECK/HANDS/FEET/GENITALIA; DIAMETER 0.5 CM/< | 285 | 274 |
| Q2 | S | 11300 | SHAVING SKIN LESION, TRUNK/ARMS/LEGS; DIAMETER 0.5 CM/< | 374 | 357 |
| Q2 | S | 11311 | SHAVING SKIN LESION, FACE/EARS/EYELIDS/NOSE/LIPS/MUCOUS MEMBRANE; DIAME | 167 | 165 |
| Q2 | S | 11400 | EXCISE, BENIGN SKIN LESION, INCL MARGINS, EXCEPT SKIN TAG, TRUNK/ARMS/L | 97 | 96 |
| Q2 | S | 11310 | SHAVING SKIN LESION, FACE/EARS/EYELIDS/NOSE/LIPS/MUCOUS MEMBRANE; DIAME | 140 | 135 |
| Q2 | S | 11306 | SHAVING SKIN LESION, SCALP/NECK/HANDS/FEET/GENITALIA; DIAMETER 0.6-1.0 | 144 | 139 |
| Q2 | S | 11401 | EXCISE, BENIGN SKIN LESION, INCL MARGINS, EXCEPT SKIN TAG, TRUNK/ARMS/L | 145 | 136 |
| Q2 | S | 11402 | EXCISE, BENIGN SKIN LESION, INCL MARGINS, EXCEPT SKIN TAG, TRUNK/ARMS/L | 72 | 69 |
| Q2 | S | 17000 | DESTRUCTION, BENIGN/PREMALIG LESIONS, EXCEPT SKIN TAGS/ CUTANEOUS VASC P | 758 | 722 |
| | S Total | | | 3,976 | 3,850 |
| | Q2 Total | | | 9,205 | 8,363 |
| Q3 | A | 88305 | LEVEL IV—SURGICAL PATHOLOGY, GROSS & MICROSCOPIC EXAM | 3,056 | 2,549 |
| | A Total | | | 3,056 | 2,549 |
| Q3 | M | 99243 | OFFICE CONSULTATION, 3 KEY COMPONENTS: DETAILED HX: DETAILED EXAM; MED | 2,013 | 1,983 |
| Q3 | M | 99213 | OFFICE/OP VISIT, EST PT, 2 KEY COMPONENTS: EXPAND PROB HX; EXPAND PROB | 2,464 | 2,063 |
| Q3 | M | 99212 | OFFICE/OP VISIT, EST PT, 2 KEY COMPONENTS: PROB FOCUS HX; PROB FOCUS EX | 511 | 439 |
| Q3 | M | 99242 | OFFICE CONSULTATION, 3 KEY COMPONENTS: EXPAND PROB FOCUS HX; EXPAND PROB | 705 | 680 |
| | M Total | | | 5,693 | 5,165 |
| Q3 | S | 11306 | SHAVING SKIN LESION, SCALP/NECK/HANDS/FEET/GENITALIA; DIAMETER 0.6-1.0 | 521 | 518 |

TABLE A9-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682
Cost driver threshold $2 (rounded value)

| | | | | | |
|---|---|---|---|---|---|
| Q3 | S | 11311 | SHAVING SKIN LESION, FACE/EARS/EYELIDS/NOSE/LIPS/MUCOUS MEMBRANE; DIAME | 444 | 438 |
| Q3 | S | 17000 | DESTRUCTION, BENIGN/PREMALIG LESIONS, EXCEPT SKIN TAGS/ CUTANEOUS VASC P | 1,711 | 1,683 |
| Q3 | S | 11301 | SHAVING SKIN LESION, TRUNK/ARMS/LEGS; DIAMETER 0.6-1.0 CM | 1,130 | 1,092 |
| Q3 | S | 11403 | EXCISE, BENIGN SKIN LESION, INCL MARGINS, EXCEPT SKIN TAG, TRUNK/ARMS/L | 75 | 71 |
| Q3 | S | 11440 | EXCISE, BENIGN SKIN LESION, INCL MARGINS, FACE/EARS/EYELIDS/ NOSE/LIPS/M | 132 | 119 |
| Q3 | S | 11310 | SHAVING SKIN LESION, FACE/EARS/EYELIDS/NOSE/LIPS/MUCOUS MEMBRANE; DIAME | 327 | 317 |
| Q3 | S | 11402 | EXCISE, BENIGN SKIN LESION, INCL MARGINS, EXCEPT SKIN TAG, TRUNK/ARMS/L | 193 | 185 |
| Q3 | S | 11302 | SHAVING SKIN LESION, TRUNK/ARMS/LEGS; DIAMETER 1.1-2.0 CM | 191 | 187 |
| Q3 | S | 11401 | EXCISE, BENIGN SKIN LESION, INCL MARGINS, EXCEPT SKIN TAG, TRUNK/ARMS/L | 335 | 317 |
| Q3 | S | 11100 | BX, SKIN, SUBQ/MUCOUS MEMBRANE; SINGLE LESION | 367 | 325 |
| | S Total | | | 5,426 | 5,252 |
| | Q3 Total | | | 14,175 | 12,966 |
| Q4 | A | 88305 | LEVEL IV—SURGICAL PATHOLOGY, GROSS & MICROSCOPIC EXAM | 2,869 | 2,614 |
| | A Total | | | 2,869 | 2,614 |
| Q4 | M | 99242 | OFFICE CONSULTATION, 3 KEY COMPONENTS: EXPAND PROB FOCUS HX;EXPAND PROB | 675 | 664 |
| Q4 | M | 99243 | OFFICE CONSULTATION, 3 KEY COMPONENTS: DETAILED HX; DETAILED HX; DETAILED EXAM; MED | 936 | 907 |
| Q4 | M | 99212 | OFFICE/OP VISIT, EST PT, 2 KEY COMPONENTS: PROB FOCUS HX; PROB FOCUS EX | 364 | 307 |
| Q4 | M | 99203 | OFFICE/OP VISIT, NEW PT, 3 KEY COMPONENTS: DETAILED HX; DETAILED EXAM; | 55 | 35 |
| Q4 | M | 99213 | OFFICE/OP VISIT, EST PT, 2 KEY COMPONENTS: EXPAND PROB HX; EXPAND PROB | 995 | 742 |
| | M Total | | | 3,025 | 2,655 |
| Q4 | S | 11401 | EXCISE, BENIGN SKIN LESION, INCL MARGINS, EXCEPT SKIN TAG, TRUNK/ARMS/L | 388 | 378 |
| Q4 | S | 11402 | EXCISE, BENIGN SKIN LESION, INCL MARGINS, EXCEPT SKIN TAG, TRUNK/ARMS/L | 199 | 194 |
| Q4 | S | 11400 | EXCISE, BENIGN SKIN LESION, INCL MARGINS, EXCEPT SKIN TAG, TRUNK/ARMS/L | 191 | 190 |
| Q4 | S | 11300 | SHAVING SKIN LESION, TRUNK/ARMS/LEGS; DIAMETER 0.5 CM/< | 479 | 473 |
| Q4 | S | 11441 | EXCISE, BENIGN SKIN LESION, INCL MARGINS, FACE/EARS/EYELIDS/ NOSE/LIPS/M | 69 | 67 |
| Q4 | S | 11421 | EXCISE BEN SKIN LESION W/MARG, EXCEPT SKIN TAG SCALP/NECK/ HANDS/FEET/GE | 68 | 68 |
| Q4 | S | 11440 | EXCISE, BENIGN SKIN LESION, INCL MARGINS, FACE/EARS/ EYELIDS/NOSE/LIPS/M | 93 | 92 |
| Q4 | S | 12031 | LAYER CLOSURE, WOUNDS, SCALP/AXILLAE/TRUNK/EXTREMITIES; 2.5 CM/< | 47 | 44 |
| Q4 | S | 11100 | BX, SKIN, SUBQ/MUCOUS MEMBRANE; SINGLE LESION | 358 | 334 |
| Q4 | S | 12032 | LAYER CLOSURE, WOUNDS, SCALP/AXILLAE/TRUNK/EXTREMITIES; 2.6-7.5 CM | 27 | 26 |
| Q4 | S | 11310 | SHAVING SKIN LESION, FACE/EARS/EYELIDS/NOSE/LIPS/MUCOUS MEMBRANE; DIAME | 133 | 124 |
| Q4 | S | 11305 | SHAVING SKIN LESION, SCALP/NECK/HANDS/FEET/GENITALIA; DIAMETER 0.5 CM/< | 147 | 143 |
| Q4 | S | 11302 | SHAVING SKIN LESION, TRUNK/ARMS/LEGS; DIAMETER 1.1-2.0 CM | 92 | 87 |
| Q4 | S | 11306 | SHAVING SKIN LESION, SCALP/NECK/HANDS/FEET/GENITALIA; DIAMETER 0.6-1.0 | 117 | 113 |
| Q4 | S | 11311 | SHAVING SKIN LESION, FACE/EARS/EYELIDS/NOSE/LIPS/MUCOUS MEMBRANE; DIAME | 83 | 82 |
| Q4 | S | 11301 | SHAVING SKIN LESION, TRUNK/ARMS/LEGS; DIAMETER 0.6-1.0 CM | 338 | 334 |
| Q4 | S | 17000 | DESTRUCTION, BENIGN/PREMALIG LESIONS, EXCEPT SKIN TAGS/ CUTANEOUS VASC P | 612 | 589 |
| | S Total | | | 3,441 | 3,338 |
| | Q4 Total | | | 9,335 | 8,607 |
| | Grand Total | | | 41,385 | 38,004 |

| quartile | category | services | Other Svcs | Expected Svcs | Quartile episodes | Total Costs | Your Costs | Others Costs | Expected Costs | Total Cost Difference |
|---|---|---|---|---|---|---|---|---|---|---|
| Q1 | A | 88305 | 285 | 3105.38 | 6,455 | $62,122 | $53,278 | $8,844 | $96,026 | ($33,904) |
| | A Total | | 285 | | | $62,122 | $53,278 | $8,844 | $96,026 | ($33,904) |
| Q1 | M | 99213 | 172 | 1967.28 | 6,455 | $130,482 | $121,036 | $9,446 | $108,522 | $21,960 |
| Q1 | M | 99212 | 24 | 378.50 | 6,455 | $9,866 | $8,935 | $931 | $14,840 | ($4,974) |

TABLE A9-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682
Cost driver threshold $2 (rounded value)

| | | | | | | | | | | |
|---|---|---|---|---|---|---|---|---|---|---|
| Q1 | M | 99242 | 14 | 625.35 | 6,455 | $32,863 | $31,514 | $1,349 | $60,757 | ($27,894) |
| Q1 | M | 99243 | 26 | 1231.06 | 6,455 | $69,132 | $65,789 | $3,343 | $158,856 | ($89,724) |
| | M Total | | 236 | | | $242,343 | $227,274 | $15,069 | $342,975 | ($100,632) |
| Q1 | S | 17000 | 23 | 1277.26 | 6,455 | $86,301 | $84,932 | $1,369 | $79,652 | $6,649 |
| Q1 | S | 11300 | 15 | 472.33 | 6,455 | $24,845 | $24,100 | $745 | $20,778 | $4,067 |
| Q1 | S | 11400 | 5 | 147.82 | 6,455 | $10,040 | $9,466 | $574 | $13,774 | ($3,734) |
| Q1 | S | 11100 | 17 | 511.02 | 6,455 | $39,576 | $38,139 | $1,437 | $43,864 | ($4,288) |
| Q1 | S | 11301 | 12 | 786.45 | 6,455 | $39,819 | $39,200 | $619 | $48,630 | ($8,811) |
| Q1 | S | 11402 | 4 | 153.31 | 6,455 | $9,737 | $9,105 | $632 | $21,014 | ($11,277) |
| Q1 | S | 11401 | 5 | 278.89 | 6,455 | $10,989 | $10,532 | $457 | $29,553 | ($18,564) |
| | S Total | | 81 | | | $221,307 | $215,474 | $5,833 | $257,266 | ($35,959) |
| | Q1 Total | | 602 | | | $525,772 | $496,026 | $29,746 | $696,267 | ($170,495) |
| Q2 | A | 88305 | 409 | 2137.44 | 4,443 | $87,190 | $74,527 | $12,663 | $66,095 | $21,095 |
| | A Total | | 409 | | | $87,190 | $74,527 | $12,663 | $66,095 | $21,095 |
| Q2 | M | 99242 | 28 | 430.43 | 4,443 | $43,318 | $40,616 | $2,702 | $41,819 | $1,499 |
| Q2 | M | 99212 | 33 | 260.52 | 4,443 | $7,280 | $5,990 | $1,290 | $10,215 | ($2,935) |
| Q2 | M | 99243 | 23 | 847.35 | 4,443 | $100,552 | $97,581 | $2,971 | $109,341 | ($8,789) |
| Q2 | M | 99213 | 223 | 1354.08 | 4,443 | $55,484 | $43,371 | $12,113 | $74,696 | ($19,212) |
| | M Total | | 307 | | | $206,634 | $187,558 | $19,076 | $236,071 | ($29,437) |
| Q2 | S | 11100 | 13 | 351.74 | 4,443 | $51,962 | $50,826 | $1,136 | $30,192 | $21,770 |
| Q2 | S | 11302 | 2 | 113.07 | 4,443 | $17,768 | $17,591 | $177 | $9,122 | $8,646 |
| Q2 | S | 11101 | 5 | 126.39 | 4,443 | $13,545 | $13,367 | $178 | $5,203 | $8,342 |
| Q2 | S | 11301 | 17 | 541.32 | 4,443 | $38,844 | $37,832 | $1,012 | $33,472 | $5,372 |
| Q2 | S | 11305 | 11 | 151.62 | 4,443 | $10,542 | $10,043 | $499 | $6,011 | $4,531 |
| Q2 | S | 11300 | 17 | 325.11 | 4,443 | $16,356 | $15,573 | $783 | $14,302 | $2,054 |
| Q2 | S | 11311 | 2 | 150.63 | 4,443 | $13,139 | $12,949 | $190 | $11,828 | $1,311 |
| Q2 | S | 11400 | 1 | 101.75 | 4,443 | $10,317 | $10,210 | $107 | $9,481 | $836 |
| Q2 | S | 11310 | 5 | 143.87 | 4,443 | $8,226 | $7,886 | $340 | $8,510 | ($284) |
| Q2 | S | 11306 | 5 | 165.34 | 4,443 | $8,946 | $8,558 | $388 | $10,481 | ($1,535) |
| Q2 | S | 11401 | 9 | 191.96 | 4,443 | $17,276 | $16,281 | $995 | $20,341 | ($3,065) |
| Q2 | S | 11402 | 3 | 105.52 | 4,443 | $11,261 | $10,858 | $403 | $14,464 | ($3,203) |
| Q2 | S | 17000 | 36 | 879.14 | 4,443 | $45,979 | $43,698 | $2,281 | $54,825 | ($8,846) |
| | S Total | | 126 | | | $264,161 | $255,672 | $8,489 | $228,231 | $35,930 |
| | Q2 Total | | 842 | | | $557,985 | $517,757 | $40,228 | $530,397 | $27,588 |
| Q3 | A | 88305 | 507 | 3746.66 | 7,788 | $94,768 | $79,088 | $15,680 | $115,856 | ($21,088) |
| | A Total | | 507 | | | $94,768 | $79,088 | $15,680 | $115,856 | ($21,088) |
| Q3 | M | 99243 | 30 | 1485.29 | 7,788 | $259,400 | $255,556 | $3,844 | $191,661 | $67,739 |
| Q3 | M | 99213 | 401 | 2373.53 | 7,788 | $134,726 | $113,540 | $21,186 | $130,933 | $3,793 |
| Q3 | M | 99212 | 72 | 456.66 | 7,788 | $20,119 | $17,403 | $2,716 | $17,905 | $2,214 |
| Q3 | M | 99242 | 25 | 754.49 | 7,788 | $68,631 | $66,197 | $2,434 | $73,303 | ($4,672) |
| | M Total | | 528 | | | $482,876 | $452,696 | $30,180 | $413,802 | $69,074 |
| Q3 | S | 11306 | 3 | 289.81 | 7,788 | $31,883 | $31,670 | $213 | $18,371 | $13,512 |
| Q3 | S | 11311 | 6 | 264.04 | 7,788 | $34,032 | $33,524 | $508 | $20,732 | $13,300 |
| Q3 | S | 17000 | 28 | 1541.02 | 7,788 | $107,753 | $106,108 | $1,645 | $96,101 | $11,652 |
| Q3 | S | 11301 | 38 | 948.86 | 7,788 | $69,328 | $66,961 | $2,367 | $58,672 | $10,656 |
| Q3 | S | 11403 | 4 | 41.45 | 7,788 | $13,183 | $12,672 | $511 | $6,769 | $6,414 |
| Q3 | S | 11440 | 13 | 95.09 | 7,788 | $15,293 | $13,920 | $1,373 | $11,179 | $4,114 |
| Q3 | S | 11310 | 10 | 252.19 | 7,788 | $18,610 | $18,126 | $484 | $14,916 | $3,694 |
| Q3 | S | 11402 | 8 | 184.96 | 7,788 | $26,296 | $25,237 | $1,059 | $25,354 | $942 |
| Q3 | S | 11302 | 4 | 198.20 | 7,788 | $16,910 | $16,582 | $328 | $15,990 | $920 |
| Q3 | S | 11401 | 18 | 336.49 | 7,788 | $35,760 | $34,110 | $1,650 | $35,656 | $104 |
| Q3 | S | 11100 | 42 | 616.55 | 7,788 | $31,241 | $28,008 | $3,233 | $52,922 | ($21,681) |
| | S Total | | 174 | | | $400,289 | $386,918 | $13,371 | $356,662 | $43,627 |
| | Q3 Total | | 1,209 | | | $977,933 | $918,702 | $59,231 | $886,320 | $91,613 |
| Q4 | A | 88305 | 255 | 1766.53 | 3,672 | $88,522 | $80,632 | $7,890 | $54,625 | $33,897 |
| | A Total | | 255 | | | $88,522 | $80,632 | $7,890 | $54,625 | $33,897 |
| Q4 | M | 99242 | 11 | 355.74 | 3,672 | $65,629 | $64,578 | $1,051 | $34,562 | $31,067 |
| Q4 | M | 99243 | 29 | 700.30 | 3,672 | $121,141 | $117,517 | $3,624 | $90,367 | $30,774 |
| Q4 | M | 99212 | 57 | 215.31 | 3,672 | $14,137 | $11,867 | $2,270 | $8,442 | $5,695 |
| Q4 | M | 99203 | 20 | 26.28 | 3,672 | $6,851 | $4,826 | $2,025 | $2,785 | $4,066 |
| Q4 | M | 99213 | 253 | 1119.11 | 3,672 | $55,194 | $41,218 | $13,976 | $61,734 | ($6,540) |
| | M Total | | 370 | | | $262,952 | $240,006 | $22,946 | $197,890 | $65,062 |
| Q4 | S | 11401 | 10 | 158.65 | 3,672 | $38,337 | $37,510 | $827 | $16,812 | $21,525 |
| Q4 | S | 11402 | 5 | 87.21 | 3,672 | $25,492 | $24,873 | $619 | $11,954 | $13,538 |
| Q4 | S | 11400 | 1 | 84.09 | 3,672 | $16,076 | $15,974 | $102 | $7,836 | $8,240 |
| Q4 | S | 11300 | 6 | 268.69 | 3,672 | $19,559 | $19,344 | $215 | $11,820 | $7,739 |
| Q4 | S | 11441 | 2 | 24.96 | 3,672 | $10,271 | $10,038 | $233 | $3,687 | $6,584 |
| Q4 | S | 11421 | 0 | 20.04 | 3,672 | $8,103 | $8,103 | $0 | $2,403 | $5,700 |
| Q4 | S | 11440 | 1 | 44.84 | 3,672 | $10,809 | $10,686 | $123 | $5,271 | $5,538 |
| Q4 | S | 12031 | 3 | 19.05 | 3,672 | $8,025 | $7,589 | $436 | $3,234 | $4,791 |
| Q4 | S | 11100 | 24 | 290.70 | 3,672 | $29,152 | $27,305 | $1,847 | $24,953 | $4,199 |
| Q4 | S | 12032 | 1 | 16.26 | 3,672 | $5,932 | $5,770 | $162 | $3,543 | $2,389 |
| Q4 | S | 11310 | 9 | 118.91 | 3,672 | $8,001 | $7,555 | $446 | $7,033 | $968 |

TABLE A9-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682
Cost driver threshold $2 (rounded value)

| | | | | | | | | | |
|---|---|---|---|---|---|---|---|---|---|
| Q4 | S | 11305 | 4 | 125.31 | 3,672 | $5,579 | $5,417 | $162 | $4,968 | $611 |
| Q4 | S | 11302 | 5 | 93.45 | 3,672 | $6,952 | $6,621 | $331 | $7,539 | ($587) |
| Q4 | S | 11306 | 4 | 136.64 | 3,672 | $8,064 | $7,920 | $144 | $8,662 | ($598) |
| Q4 | S | 11311 | 1 | 124.49 | 3,672 | $6,633 | $6,593 | $40 | $9,775 | ($3,142) |
| Q4 | S | 11301 | 4 | 447.38 | 3,672 | $20,447 | $20,270 | $177 | $27,664 | ($7,217) |
| Q4 | S | 17000 | 23 | 726.58 | 3,672 | $35,855 | $34,605 | $1,250 | $45,311 | ($9,456) |
| | S Total | | 103 | | | $263,287 | $256,173 | $7,114 | $202,465 | $60,822 |
| | Q4 Total | | 728 | | | $614,761 | $576,811 | $37,950 | $454,980 | $159,781 |
| | Grand Total | | 3,381 | | | $2,676,451 | $2,509,296 | $167,155 | $2,567,965 | $108,486 |

| quartile | category | services | Total Costs per stratum episodes | Difference per stratum episodes | Your costs per svc | Other costs per svc | Spec costs per svc | episodes this service occurred |
|---|---|---|---|---|---|---|---|---|
| Q1 | A | 88305 | $10 | ($5) | $31 | $31 | $31 | 11,403 |
| | A Total | | $10 | ($5) | | | | 1,403 |
| Q1 | M | 99213 | $20 | $3 | $55 | $55 | $55 | 2,261 |
| Q1 | M | 99212 | $2 | ($1) | $39 | $39 | $39 | 249 |
| Q1 | M | 99242 | $5 | ($4) | $96 | $96 | $97 | 339 |
| Q1 | M | 99243 | $11 | ($14) | $129 | $129 | $129 | 529 |
| | M Total | | $38 | ($16) | | | | 3,378 |
| Q1 | S | 17000 | $13 | $1 | $64 | $60 | $62 | 1,215 |
| Q1 | S | 11300 | $4 | $1 | $47 | $50 | $44 | 398 |
| Q1 | S | 11400 | $2 | ($1) | $106 | $115 | $93 | 88 |
| Q1 | S | 11100 | $6 | ($1) | $85 | $85 | $86 | 458 |
| Q1 | S | 11301 | $6 | ($1) | $68 | $52 | $62 | 462 |
| Q1 | S | 11402 | $2 | ($2) | $145 | $158 | $137 | 64 |
| Q1 | S | 11401 | $2 | ($3) | $113 | $91 | $106 | 92 |
| | S Total | | $34 | ($6) | | | | 2,777 |
| | Q1 Total | | $81 | ($26) | | | | 7,558 |
| Q2 | A | 88305 | $20 | $5 | $31 | $31 | $31 | 1,760 |
| | A Total | | $20 | $5 | | | | 1,760 |
| Q2 | M | 99242 | $10 | $0 | $97 | $97 | $97 | 440 |
| Q2 | M | 99212 | $2 | ($1) | $40 | $39 | $39 | 173 |
| Q2 | M | 99243 | $23 | ($2) | $129 | $129 | $129 | 767 |
| Q2 | M | 99213 | $12 | ($4) | $56 | $54 | $55 | 959 |
| | M Total | | $47 | ($7) | | | | 2,339 |
| Q2 | S | 11100 | $12 | $5 | $90 | $87 | $86 | 574 |
| Q2 | S | 11302 | $4 | $2 | $75 | $89 | $81 | 183 |
| Q2 | S | 11101 | $3 | $2 | $44 | $36 | $41 | 181 |
| Q2 | S | 11301 | $9 | $1 | $58 | $60 | $62 | 437 |
| Q2 | S | 11305 | $2 | $1 | $37 | $45 | $40 | 126 |
| Q2 | S | 11300 | $4 | $0 | $44 | $46 | $44 | 247 |
| Q2 | S | 11311 | $3 | $0 | $78 | $95 | $79 | 137 |
| Q2 | S | 11400 | $2 | $0 | $106 | $107 | $93 | 92 |
| Q2 | S | 11310 | $2 | ($0) | $58 | $68 | $59 | 104 |
| Q2 | S | 11306 | $2 | ($0) | $62 | $78 | $63 | 104 |
| Q2 | S | 11401 | $4 | ($1) | $120 | $111 | $106 | 129 |
| Q2 | S | 11402 | $3 | ($1) | $157 | $134 | $137 | 70 |
| Q2 | S | 17000 | $10 | ($2) | $61 | $63 | $62 | 707 |
| | S Total | | $59 | $8 | | | | 3,091 |
| | Q2 Total | | $126 | $6 | | | | 7,190 |
| Q3 | A | 88305 | $12 | ($3) | $31 | $31 | $31 | 2,048 |
| | A Total | | $12 | ($3) | | | | 2,048 |
| Q3 | M | 99243 | $33 | $9 | $129 | $128 | $129 | 2,004 |
| Q3 | M | 99213 | $17 | $0 | $55 | $53 | $55 | 2,351 |
| Q3 | M | 99212 | $3 | $0 | $40 | $38 | $39 | 488 |
| Q3 | M | 99242 | $9 | ($1) | $97 | $97 | $97 | 699 |
| | M Total | | $62 | $9 | | | | 5,542 |
| Q3 | S | 11306 | $4 | $2 | $61 | $71 | $63 | 283 |
| Q3 | S | 11311 | $4 | $2 | $77 | $85 | $79 | 297 |
| Q3 | S | 17000 | $14 | $1 | $63 | $59 | $62 | 1,580 |
| Q3 | S | 11301 | $9 | $1 | $61 | $62 | $62 | 742 |
| Q3 | S | 11403 | $2 | $1 | $178 | $128 | $163 | 69 |
| Q3 | S | 11440 | $2 | $1 | $117 | $106 | $118 | 108 |
| Q3 | S | 11310 | $2 | $0 | $57 | $48 | $59 | 251 |
| Q3 | S | 11402 | $3 | $0 | $136 | $132 | $137 | 177 |
| Q3 | S | 11302 | $2 | $0 | $89 | $82 | $81 | 174 |
| Q3 | S | 11401 | $5 | $0 | $108 | $92 | $106 | 270 |
| Q3 | S | 11100 | $4 | ($3) | $86 | $77 | $86 | 350 |
| | S Total | | $51 | $6 | | | | 4,301 |
| | Q3 Total | | $126 | $12 | | | | 11,891 |

TABLE A9-continued

Dermatology
Dates of Service Jan. 1, 2003-Dec. 31, 2004 paid Dec. 31, 2004
Total Role benign neoplasm of the skin without actinic keratoses diagnosis 702.xx
etg 0682
Cost driver threshold $2 (rounded value)

| | | | | | | | | |
|---|---|---|---|---|---|---|---|---|
| Q4 | A | 88305 | $24 | $9 | $31 | $31 | $31 | 1,581 |
| | A Total | | $24 | $9 | | | | 1,581 |
| Q4 | M | 99242 | $18 | $8 | $97 | $96 | $97 | 672 |
| Q4 | M | 99243 | $33 | $8 | $130 | $125 | $129 | 931 |
| Q4 | M | 99212 | $4 | $2 | $39 | $40 | $39 | 331 |
| Q4 | M | 99203 | $2 | $1 | $138 | $101 | $106 | 55 |
| Q4 | M | 99213 | $15 | ($2) | $56 | $55 | $55 | 939 |
| | M Total | | $72 | $18 | | | | 2,928 |
| Q4 | S | 11401 | $10 | $6 | $99 | $83 | $106 | 270 |
| Q4 | S | 11402 | $7 | $4 | $128 | $124 | $137 | 169 |
| Q4 | S | 11400 | $4 | $2 | $84 | $102 | $93 | 151 |
| Q4 | S | 11300 | $5 | $2 | $41 | $36 | $44 | 264 |
| Q4 | S | 11441 | $3 | $2 | $150 | $117 | $148 | 61 |
| Q4 | S | 11421 | $2 | $2 | $119 | $0 | $120 | 62 |
| Q4 | S | 11440 | $3 | $2 | $116 | $123 | $118 | 74 |
| Q4 | S | 12031 | $2 | $1 | $172 | $145 | $170 | 44 |
| Q4 | S | 11100 | $8 | $1 | $82 | $77 | $86 | 355 |
| Q4 | S | 12032 | $2 | $1 | $222 | $162 | $218 | 27 |
| Q4 | S | 11310 | $2 | $0 | $61 | $50 | $59 | 100 |
| Q4 | S | 11305 | $2 | $0 | $38 | $41 | $40 | 101 |
| Q4 | S | 11302 | $2 | ($0) | $76 | $66 | $81 | 77 |
| Q4 | S | 11306 | $2 | ($0) | $70 | $36 | $63 | 91 |
| Q4 | S | 11311 | $2 | ($1) | $80 | $40 | $79 | 74 |
| Q4 | S | 11301 | $6 | ($2) | $61 | $44 | $62 | 250 |
| Q4 | S | 17000 | $10 | ($3) | $59 | $54 | $62 | 552 |
| | S Total | | $72 | $17 | | | | 2,722 |
| | Q4 Total | | $167 | $44 | | | | 7,231 |
| | Grand Total | | $500 | $35 | | | | 33,870 |

TABLE A10

Dermatology
Dates of Service Jan. 1, 2003-Dec. 31, 2004 paid Dec. 31, 2004
Total role benign neoplasm of the skin, without actinic keratoses
etg 0682

| Provider ID | category | services | service description | Total Svcs |
|---|---|---|---|---|
| CCP010000014 | A | 88305 | LEVEL IV—SURGICAL PATHOLOGY, GROSS & MICROSCOPIC EXAM | 645 |
| CCP010000014 | A | S0630 | Removal of sutures by a physician other than the physician who originall | 3 |
| CCP010000014 | A | A4649 | Surgical supply; miscellaneous | 1 |
| CCP010000014 | A | 88307 | LEVEL V—SURGICAL PATHOLOGY, GROSS & MICROSCOPIC EXAM | 1 |
| CCP010000014 | A | 93000 | ELECTROCARDIOGRAM, ROUTINE W/AT LEAST 12 LEADS; W/INTERPRETATION & REPO | 2 |
| CCP010000014 | A | A4550 | Surgical trays | 1 |
| CCP010000014 | A | 88312 | SPECIAL STAINS; GROUP I, MICROORGANISMS, EACH | 4 |
| CCP010000014 | A | 86644 | ANTIBODY; CYTOMEGALOVIRUS (CMV) | 1 |
| CCP010000014 | A | 86777 | ANTIBODY; TOXOPLASMA | 1 |
| CCP010000014 | A | 82947 | GLUCOSE; QUANTITATIVE, BLOOD (EXCEPT REAGENT STRIP) | 2 |
| CCP010000014 | A | 86140 | C-REACTIVE PROTEIN | 2 |
| CCP010000014 | A | 85025 | BLOOD COUNT; COMPLETE CBC, AUTOMATED (HGB, HCT, RBC, WBC, & PLATELET) & | 7 |
| CCP010000014 | A | 80003 | | 1 |
| CCP010000014 | A | 80005 | | 1 |
| CCP010000014 | A | 82040 | ALBUMIN; SERUM | 1 |
| CCP010000014 | A | 80051 | ELECTROLYTE PANEL | 1 |
| CCP010000014 | A | 85651 | SEDIMENTATION RATE, ERYTHROCYTE; NON-AUTOMATED | 2 |
| CCP010000014 | A | 84450 | TRANSFERASE; ASPARTATE AMINO (AST) (SGOT) | 2 |
| CCP010000014 | A | 82565 | CREATININE; BLOOD | 1 |
| CCP010000014 | A | 85730 | THROMBOPLASTIN TIME, PARTIAL (PTT); PLASMA/WHOLE BLOOD | 1 |
| CCP010000014 | A | 85652 | SEDIMENTATION RATE, ERYTHROCYTE; AUTOMATED | 1 |
| CCP010000014 | A | 85014 | BLOOD COUNT; HEMATOCRIT | 1 |
| CCP010000014 | A | 80053 | COMPREHENSIVE METABOLIC PANEL | 5 |
| CCP010000014 | A | 80048 | BASIC METABOLIC PANEL | 3 |
| CCP010000014 | A | 80050 | GENERAL HEALTH PANEL | 1 |
| CCP010000014 | A | 85027 | BLOOD COUNT; COMPLETE CBC, AUTOMATED (HGB, HCT, RBC, WBC, & PLATELET) | 2 |
| CCP010000014 | A | 82270 | BLOOD, OCCULT, BY PEROXIDASE ACTIVITY, QUALITATIVE; FECES, 1-3 SIMULTAN | 1 |
| CCP010000014 | A | 88304 | LEVEL III—SURGICAL PATHOLOGY, GROSS & MICROSCOPIC EXAM | 3 |
| CCP010000014 | A | 80061 | LIPID PANEL | 2 |
| | A Total | | | 699 |
| CCP010000014 | M | 99243 | OFFICE CONSULTATION, 3 KEY COMPONENTS: DETAILED HX; DETAILED EXAM; MED | 255 |

TABLE A10-continued

Dermatology
Dates of Service Jan. 1, 2003-Dec. 31, 2004 paid Dec. 31, 2004
Total role benign neoplasm of the skin, without actinic keratoses
etg 0682

| | | | | |
|---|---|---|---|---|
| CCP010000014 | M | 99203 | OFFICE/OP VISIT, NEW PT, 3 KEY COMPONENTS: DETAILED HX; DETAILED EXAM: | 33 |
| CCP010000014 | M | 99242 | OFFICE CONSULTATION, 3 KEY COMPONENTS: EXPAND PROB FOCUS HX; EXPAND PROB | 129 |
| CCP010000014 | M | 99213 | OFFICE/OP VISIT, EST PT, 2 KEY COMPONENTS: EXPAND PROB HX; EXPAND PROB | 320 |
| CCP010000014 | M | 99202 | OFFICE/OP VISIT, NEW PT, 3 KEY COMPONENTS: EXPAND PROB FOCUS HX; EXPAND | 15 |
| CCP010000014 | M | 99214 | OFFICE/OP VISIT, EST PT, 2 KEY COMPONENTS: DETAILED HX; DETAILED EXAM; | 8 |
| CCP010000014 | M | 99211 | OFFICE/OP VISIT, EST PT, NOT REQUIRING PHYSICIAN PRESENCE, TYPICALLY 5 | 2 |
| CCP010000014 | M | 99395 | PERIODIC COMPREHENSIVE PREVENTIVE MEDICINE E&M W/HX/EXAM, EST PT; 18-39 | 1 |
| CCP010000014 | M | 99396 | PERIODIC COMPREHENSIVE PREVENTIVE MEDICINE E&M W/HX/EXAM, EST PT; 40-64 | 1 |
| CCP010000014 | M | 99212 | OFFICE/OP VISIT, EST PT, 2 KEY COMPONENTS: PROB FOCUS HX; PROB FOCUS EX | 32 |
| | M Total | | | 796 |
| CCP010000014 | P | J3301 | Injection, triamcinolone acetonide, per 10 mg | 1 |
| CCP010000014 | P | Z2A | ANTIHISTAMINES | 1 |
| CCP010000014 | P | S2B | NSAIDS, CYCLOOXYGENASE INHIBITOR—TYPE | 157 |
| CCP010000014 | P | L9B | VITAMIN A DERIVATIVES | 55 |
| CCP010000014 | P | H3A | ANALGESICS, NARCOTICS | 502 |
| CCP010000014 | P | Z2G | IMMUNOMODULATORS | 28 |
| | P Total | | | 744 |
| CCP010000014 | S | 11401 | EXCISE, BENIGN SKIN LESION, INCL MARGINS, EXCEPT SKIN TAG, TRUNK/ARMS/L | 131 |
| CCP010000014 | S | 11400 | EXCISE, BENIGN SKIN LESION, INCL MARGINS, EXCEPT SKIN TAG, TRUNK/ARMS/L | 113 |
| CCP010000014 | S | 11441 | EXCISE, BENIGN SKIN LESION, INCL MARGINS, FACE/EARS/EYELIDS/NOSE/LIPS/M | 42 |
| CCP010000014 | S | 11440 | EXCISE, BENIGN SKIN LESION, INCL MARGINS, FACE/EARS/EYELIDS/NOSE/LIPS/M | 48 |
| CCP010000014 | S | 11421 | EXCISE BEN SKIN LESION W/MARG, EXCEPT SKIN TAG SCALP/NECK/HANDS/FEET/GE | 35 |
| CCP010000014 | S | 11402 | EXCISE, BENIGN SKIN LESION, INCL MARGINS, EXCEPT SKIN TAG, TRUNK/ARMS/L | 39 |
| CCP010000014 | S | 11420 | EXCISE BENIGN SKIN LESION W/MARG, EXCPT SKIN TAG SCALP/NECK/HANDS/FEET/ | 34 |
| CCP010000014 | S | 11422 | EXCISE BEN SKIN LESION W/MARG, EXCEPT SKIN TAG SCALP/NECK/HANDS/FEET/GE | 12 |
| CCP010000014 | S | 11442 | EXCISE, BENIGN SKIN LESION, INCL MARGINS, FACE/EARS/EYELIDS/NOSE/LIPS/M | 9 |
| CCP010000014 | S | 11307 | SHAVING SKIN LESION, SCALP/NECK/HANDS/FEET/GENITALIA; DIAMETER 1.1-2.0 | 12 |
| CCP010000014 | S | 11306 | SHAVING SKIN LESION, SCALP/NECK/HANDS/FEET/GENITALIA; DIAMETER 0.6-1.0 | 41 |
| CCP010000014 | S | 11308 | SHAVING SKIN LESION, SCALP/NECK/HANDS/FEET/GENITALIA; DIAMETER >2.0 CM | 7 |
| CCP010000014 | S | 11303 | SHAVING SKIN LESION, TRUNK/ARMS/LEGS; DIAMETER >2.0 CM | 6 |
| CCP010000014 | S | 11446 | EXCISE, BENIGN SKIN LESION, INCL MARGINS, FACE/EARS/EYELIDS/NOSE/LIPS/M | 1 |
| CCP010000014 | S | 11444 | EXCISE, BENIGN SKIN LESION, INCL MARGINS, FACE/EARS/EYELIDS/NOSE/LIPS/M | 1 |
| CCP010000014 | S | 11312 | SHAVING SKIN LESION, FACE/EARS/EYELIDS/NOSE/LIPS/MUCOUS MEMBRANE; DIAME | 7 |
| CCP010000014 | S | 11423 | EXCISE BEN SKIN LESION W/MARG, EXCEPT SKIN TAG SCALP/NECK/HANDS/FEET/GE | 2 |
| CCP010000014 | S | 11424 | EXCISE BEN SKIN LESION W/MARG, EXCEPT SKIN TAG SCALP/NECK/HANDS/FEET/GE | 1 |
| CCP010000014 | S | 11443 | EXCISE, BENIGN SKIN LESION, INCL MARGINS, FACE/EARS/EYELIDS/NOSE/LIPS/M | 1 |
| CCP010000014 | S | 11900 | INJECTION, INTRALESIONAL; UP TO & INCL 7 LESIONS | 2 |
| CCP010000014 | S | 11403 | EXCISE, BENIGN SKIN LESION, INCL MARGINS, EXCEPT SKIN TAG, TRUNK/ARMS/L | 5 |
| CCP010000014 | S | 11310 | SHAVING SKIN LESION, FACE/EARS/EYELIDS/NOSE/LIPS/MUCOUS MEMBRANE; DIAME | 22 |
| CCP010000014 | S | 11101 | BX, SKIN, SUBQ/MUCOUS MEMBRANE (SEP PROC); ADD'L LESION | 19 |
| CCP010000014 | S | 11305 | SHAVING SKIN LESION, SCALP/NECK/HANDS/FEET/GENITALIA; DIAMETER 0.5 CM/< | 22 |
| CCP010000014 | S | 12032 | LAYER CLOSURE, WOUNDS, SCALP/AXILLAE/TRUNK/EXTREMITIES; 2.6-7.5 CM | 1 |
| CCP010000014 | S | 17003 | DESTRUCTION, BENIGN/PREMALIG LESIONS, EXCEPT SKIN TAGS/CUTANEOUS VASC P | 31 |
| CCP010000014 | S | 11302 | SHAVING SKIN LESION, TRUNK/ARMS/LEGS; DIAMETER 1.1-2.0 CM | 8 |
| CCP010000014 | S | 11311 | SHAVING SKIN LESION, FACE/EARS/EYELIDS/NOSE/LIPS/MUCOUS MEMBRANE; DIAME | 15 |
| CCP010000014 | S | 11300 | SHAVING SKIN LESION, TRUNK/ARMS/LEGS; DIAMETER 0.5 CM/< | 30 |
| CCP010000014 | S | 11301 | SHAVING SKIN LESION, TRUNK/ARMS/LEGS; DIAMETER 0.6-1.0 CM | 77 |
| CCP010000014 | S | 11100 | BX, SKIN, SUBQ/MUCOUS MEMBRANE; SINGLE LESION | 29 |
| CCP010000014 | S | 17110 | DESTRUCTION, FLAT WARTS, MOLLUSCUM CONTAGIOSUM/MILIA; UP TO 14 LESIONS | 8 |
| CCP010000014 | S | 17000 | DESTRUCTION, BENIGN/PREMALIG LESIONS, EXCEPT SKIN TAGS/CUTANEOUS VASC P | 7 |
| | S Total | | | 818 |
| CCP010000014 Total | | | | 3,057 |

| Provider ID | category | services | Your Svcs | Other Svcs | Expected Svcs | Practitioner episodes | Total Costs | Your Costs | Others Costs | Expected Costs |
|---|---|---|---|---|---|---|---|---|---|---|
| CCP010000014 | A | 88305 | 638 | 7 | 451.73 | 939 | $19,902 | $19,685 | $217 | $13,969 |
| CCP010000014 | A | S0630 | 3 | 0 | .46 | 939 | $148 | $148 | $0 | $19 |
| CCP010000014 | A | A4649 | 1 | 0 | .04 | 939 | $73 | $73 | $0 | $3 |
| CCP010000014 | A | 88307 | 1 | 0 | .08 | 939 | $68 | $68 | $0 | $6 |
| CCP010000014 | A | 93000 | 0 | 2 | .71 | 939 | $79 | $0 | $79 | $22 |
| CCP010000014 | A | A4550 | 1 | 0 | .04 | 939 | $49 | $49 | $0 | $2 |
| CCP010000014 | A | 88312 | 4 | 0 | 2.60 | 939 | $64 | $64 | $0 | $42 |
| CCP010000014 | A | 86644 | 0 | 1 | .17 | 939 | $14 | $0 | $14 | $2 |
| CCP010000014 | A | 86777 | 0 | 1 | .04 | 939 | $8 | $0 | $8 | $0 |
| CCP010000014 | A | 82947 | 0 | 2 | 1.13 | 939 | $8 | $0 | $8 | $3 |
| CCP010000014 | A | 86140 | 0 | 2 | .21 | 939 | $6 | $0 | $6 | $1 |
| CCP010000014 | A | 85025 | 0 | 7 | 5.33 | 939 | $21 | $0 | $21 | $16 |
| CCP010000014 | A | 80003 | 0 | 1 | .08 | 939 | $5 | $0 | $5 | $0 |
| CCP010000014 | A | 80005 | 0 | 1 | .08 | 939 | $5 | $0 | $5 | $0 |
| CCP010000014 | A | 82040 | 0 | 1 | .17 | 939 | $5 | $0 | $5 | $1 |
| CCP010000014 | A | 80051 | 0 | 1 | .08 | 939 | $4 | $0 | $4 | $0 |
| CCP010000014 | A | 85651 | 0 | 2 | .21 | 939 | $4 | $0 | $4 | $0 |
| CCP010000014 | A | 84450 | 0 | 2 | 1.01 | 939 | $6 | $0 | $6 | $3 |

TABLE A10-continued

Dermatology
Dates of Service Jan. 1, 2003-Dec. 31, 2004 paid Dec. 31, 2004
Total role benign neoplasm of the skin, without actinic keratoses
etg 0682

| | | | | | | | | | |
|---|---|---|---|---|---|---|---|---|---|
| CCP010000014 | A | 82565 | 0 | 1 | .55 | 939 | $5 | $0 | $5 | $2 |
| CCP010000014 | A | 85730 | 0 | 1 | .25 | 939 | $3 | $0 | $3 | $1 |
| CCP010000014 | A | 85652 | 0 | 1 | .17 | 939 | $2 | $0 | $2 | $0 |
| CCP010000014 | A | 85014 | 0 | 1 | .50 | 939 | $2 | $0 | $2 | $1 |
| CCP010000014 | A | 80053 | 0 | 5 | 5.12 | 939 | $25 | $0 | $25 | $26 |
| CCP010000014 | A | 80048 | 0 | 3 | 3.40 | 939 | $9 | $0 | $9 | $11 |
| CCP010000014 | A | 80050 | 0 | 1 | 1.13 | 939 | $14 | $0 | $14 | $16 |
| CCP010000014 | A | 85027 | 0 | 2 | 3.19 | 939 | $4 | $0 | $4 | $7 |
| CCP010000014 | A | 82270 | 0 | 1 | 1.72 | 939 | $2 | $0 | $2 | $6 |
| CCP010000014 | A | 88304 | 3 | 0 | 3.49 | 939 | $45 | $45 | $0 | $53 |
| CCP010000014 | A | 80061 | 0 | 2 | 3.86 | 939 | $16 | $0 | $16 | $31 |
| | A Total | | 651 | 48 | 487.60 | | $20,596 | $20,132 | $464 | $14,243 |
| CCP010000014 | M | 99243 | 252 | 3 | 179.08 | 939 | $33,762 | $33,384 | $378 | $23,109 |
| CCP010000014 | M | 99203 | 29 | 4 | 6.72 | 939 | $4,725 | $4,241 | $484 | $712 |
| CCP010000014 | M | 99242 | 127 | 2 | 90.97 | 939 | $12,829 | $12,653 | $176 | $8,838 |
| CCP010000014 | M | 99213 | 266 | 54 | 286.18 | 939 | $18,609 | $15,059 | $3,550 | $15,787 |
| CCP010000014 | M | 99202 | 15 | 0 | 4.16 | 939 | $1,395 | $1,395 | $0 | $277 |
| CCP010000014 | M | 99214 | 1 | 7 | 4.91 | 939 | $904 | $88 | $816 | $446 |
| CCP010000014 | M | 99211 | 0 | 2 | .46 | 939 | $70 | $0 | $70 | $11 |
| CCP010000014 | M | 99395 | 0 | 1 | .76 | 939 | $56 | $0 | $56 | $42 |
| CCP010000014 | M | 99396 | 0 | 1 | 2.10 | 939 | $56 | $0 | $56 | $118 |
| CCP010000014 | M | 99212 | 23 | 9 | 55.06 | 939 | $1,328 | $912 | $416 | $2,159 |
| | M Total | | 713 | 83 | 630.40 | | $73,734 | $67,732 | $6,002 | $51,498 |
| CCP010000014 | P | J3301 | 1 | 0 | .88 | 939 | $25 | $25 | $0 | $9 |
| CCP010000014 | P | Z2A | 1 | 0 | 4.79 | 939 | $5 | $5 | $0 | $10 |
| CCP010000014 | P | S2B | 20 | 137 | 164.00 | 939 | $65 | $15 | $50 | $216 |
| CCP010000014 | P | L9B | 0 | 55 | 144.47 | 939 | $191 | $0 | $191 | $351 |
| CCP010000014 | P | H3A | 60 | 442 | 544.43 | 939 | $483 | $83 | $400 | $699 |
| CCP010000014 | P | Z2G | 0 | 28 | 85.51 | 939 | $134 | $0 | $134 | $592 |
| | P Total | | 82 | 662 | 944.08 | | $903 | $128 | $775 | $1,876 |
| CCP010000014 | S | 11401 | 128 | 3 | 40.57 | 939 | $14,782 | $14,574 | $208 | $4,299 |
| CCP010000014 | S | 11400 | 113 | 0 | 21.50 | 939 | $10,270 | $10,270 | $0 | $2,004 |
| CCP010000014 | S | 11441 | 41 | 1 | 6.38 | 939 | $6,485 | $6,337 | $148 | $943 |
| CCP010000014 | S | 11440 | 48 | 0 | 11.47 | 939 | $6,017 | $6,017 | $0 | $1,348 |
| CCP010000014 | S | 11421 | 35 | 0 | 5.12 | 939 | $4,541 | $4,541 | $0 | $614 |
| CCP010000014 | S | 11402 | 39 | 0 | 22.30 | 939 | $6,600 | $6,600 | $0 | $3,057 |
| CCP010000014 | S | 11420 | 34 | 0 | 4.62 | 939 | $2,950 | $2,950 | $0 | $413 |
| CCP010000014 | S | 11422 | 12 | 0 | 2.65 | 939 | $2,034 | $2,034 | $0 | $377 |
| CCP010000014 | S | 11442 | 9 | 0 | 2.39 | 939 | $1,912 | $1,912 | $0 | $411 |
| CCP010000014 | S | 11307 | 12 | 0 | 4.16 | 939 | $1,106 | $1,106 | $0 | $378 |
| CCP010000014 | S | 11306 | 41 | 0 | 34.94 | 939 | $2,887 | $2,887 | $0 | $2,215 |
| CCP010000014 | S | 11308 | 7 | 0 | .46 | 939 | $696 | $696 | $0 | $48 |
| CCP010000014 | S | 11303 | 6 | 0 | 1.34 | 939 | $549 | $549 | $0 | $135 |
| CCP010000014 | S | 11446 | 1 | 0 | .04 | 939 | $371 | $371 | $0 | $16 |
| CCP010000014 | S | 11444 | 1 | 0 | .08 | 939 | $307 | $307 | $0 | $25 |
| CCP010000014 | S | 11312 | 7 | 0 | 4.96 | 939 | $766 | $766 | $0 | $488 |
| CCP010000014 | S | 11423 | 2 | 0 | .97 | 939 | $390 | $390 | $0 | $170 |
| CCP010000014 | S | 11424 | 1 | 0 | .25 | 939 | $244 | $244 | $0 | $56 |
| CCP010000014 | S | 11443 | 1 | 0 | .63 | 939 | $222 | $222 | $0 | $132 |
| CCP010000014 | S | 11900 | 2 | 0 | .97 | 939 | $55 | $55 | $0 | $46 |
| CCP010000014 | S | 11403 | 5 | 0 | 5.00 | 939 | $755 | $755 | $0 | $816 |
| CCP010000014 | S | 11310 | 21 | 1 | 30.41 | 939 | $1,435 | $1,365 | $70 | $1,798 |
| CCP010000014 | S | 11101 | 19 | 0 | 26.71 | 939 | $734 | $734 | $0 | $1,100 |
| CCP010000014 | S | 11305 | 22 | 0 | 32.04 | 939 | $850 | $850 | $0 | $1,270 |
| CCP010000014 | S | 12032 | 1 | 0 | 4.16 | 939 | $223 | $223 | $0 | $906 |
| CCP010000014 | S | 17003 | 28 | 3 | 305.24 | 939 | $87 | $60 | $27 | $1,221 |
| CCP010000014 | S | 11302 | 8 | 0 | 23.90 | 939 | $683 | $683 | $0 | $1,928 |
| CCP010000014 | S | 11311 | 15 | 0 | 31.83 | 939 | $1,233 | $1,233 | $0 | $2,500 |
| CCP010000014 | S | 11300 | 30 | 0 | 68.71 | 939 | $1,300 | $1,300 | $0 | $3,023 |
| CCP010000014 | S | 11301 | 77 | 0 | 114.40 | 939 | $4,307 | $4,307 | $0 | $7,074 |
| CCP010000014 | S | 11100 | 28 | 1 | 74.34 | 939 | $2,608 | $2,524 | $84 | $6,381 |
| CCP010000014 | S | 17110 | 8 | 0 | 111.59 | 939 | $507 | $507 | $0 | $6,256 |
| CCP010000014 | S | 17000 | 6 | 1 | 185.80 | 939 | $454 | $396 | $58 | $11,587 |
| | S Total | | 808 | 10 | 1179.94 | | $78,360 | $77,765 | $595 | $63,034 |
| CCP010000014 Total | | | 2,254 | 803 | 3242.02 | | $173,593 | $165,757 | $7,836 | $130,651 |

| Provider ID | category | services | Total Cost Difference | Total Costs per stratum episodes | Difference per stratum episodes | Your costs per svc | Other costs per svc | Spec costs per svc | episodes this service occurred |
|---|---|---|---|---|---|---|---|---|---|
| CCP010000014 | A | 88305 | $5,933 | $21 | $6 | $31 | $31 | $31 | 349 |
| CCP010000014 | A | S0630 | $129 | $0 | $0 | $49 | $0 | $41 | 3 |
| CCP010000014 | A | A4649 | $70 | $0 | $0 | $73 | $0 | $73 | 1 |
| CCP010000014 | A | 88307 | $62 | $0 | $0 | $68 | $0 | $68 | 1 |

TABLE A10-continued

Dermatology
Dates of Service Jan. 1, 2003-Dec. 31, 2004 paid Dec. 31, 2004
Total role benign neoplasm of the skin, without actinic keratoses
etg 0682

| | | | | | | | | |
|---|---|---|---|---|---|---|---|---|
| CCP010000014 | A | 93000 | $57 | $0 | $0 | $0 | $40 | $31 | 2 |
| CCP010000014 | A | A4550 | $47 | $0 | $0 | $49 | $0 | $49 | 1 |
| CCP010000014 | A | 88312 | $22 | $0 | $0 | $16 | $0 | $16 | 2 |
| CCP010000014 | A | 86644 | $12 | $0 | $0 | $0 | $14 | $14 | 1 |
| CCP010000014 | A | 86777 | $8 | $0 | $0 | $0 | $8 | $8 | 1 |
| CCP010000014 | A | 82947 | $5 | $0 | $0 | $0 | $4 | $2 | 2 |
| CCP010000014 | A | 86140 | $5 | $0 | $0 | $0 | $3 | $3 | 2 |
| CCP010000014 | A | 85025 | $5 | $0 | $0 | $0 | $3 | $3 | 7 |
| CCP010000014 | A | 80003 | $5 | $0 | $0 | $0 | $5 | $5 | 1 |
| CCP010000014 | A | 80005 | $5 | $0 | $0 | $0 | $5 | $5 | 1 |
| CCP010000014 | A | 82040 | $4 | $0 | $0 | $0 | $5 | $6 | 1 |
| CCP010000014 | A | 80051 | $4 | $0 | $0 | $0 | $4 | $4 | 1 |
| CCP010000014 | A | 85651 | $4 | $0 | $0 | $0 | $2 | $2 | 2 |
| CCP010000014 | A | 84450 | $3 | $0 | $0 | $0 | $3 | $3 | 1 |
| CCP010000014 | A | 82565 | $3 | $0 | $0 | $0 | $5 | $4 | 1 |
| CCP010000014 | A | 85730 | $2 | $0 | $0 | $0 | $3 | $3 | 1 |
| CCP010000014 | A | 85652 | $2 | $0 | $0 | $0 | $2 | $2 | 1 |
| CCP010000014 | A | 85014 | $1 | $0 | $0 | $0 | $2 | $2 | 1 |
| CCP010000014 | A | 80053 | ($1) | $0 | ($0) | $0 | $5 | $5 | 5 |
| CCP010000014 | A | 80048 | ($2) | $0 | ($0) | $0 | $3 | $3 | 3 |
| CCP010000014 | A | 80050 | ($2) | $0 | ($0) | $0 | $14 | $14 | 1 |
| CCP010000014 | A | 85027 | ($3) | $0 | ($0) | $0 | $2 | $2 | 2 |
| CCP010000014 | A | 82270 | ($4) | $0 | ($0) | $0 | $2 | $3 | 1 |
| CCP010000014 | A | 88304 | ($8) | $0 | ($0) | $15 | $0 | $15 | 3 |
| CCP010000014 | A | 80061 | ($15) | $0 | ($0) | $0 | $8 | $8 | 2 |
| | A Total | | $6,353 | $22 | $7 | | | | |
| CCP010000014 | M | 99243 | $10,653 | $36 | $11 | $132 | $126 | $129 | 254 |
| CCP010000014 | M | 99203 | $4,013 | $5 | $4 | $146 | $121 | $106 | 33 |
| CCP010000014 | M | 99242 | $3,991 | $14 | $4 | $100 | $88 | $97 | 129 |
| CCP010000014 | M | 99213 | $2,822 | $20 | $3 | $57 | $66 | $55 | 311 |
| CCP010000014 | M | 99202 | $1,118 | $1 | $1 | $93 | $0 | $67 | 15 |
| CCP010000014 | M | 99214 | $458 | $1 | $0 | $88 | $117 | $91 | 8 |
| CCP010000014 | M | 99211 | $59 | $0 | $0 | $0 | $35 | $24 | 2 |
| CCP010000014 | M | 99395 | $14 | $0 | $0 | $0 | $56 | $56 | 1 |
| CCP010000014 | M | 99396 | ($62) | $0 | ($0) | $0 | $56 | $56 | 1 |
| CCP010000014 | M | 99212 | ($831) | $1 | ($1) | $40 | $46 | $39 | 32 |
| | M Total | | $22,236 | $79 | $24 | | | | |
| CCP010000014 | P | J3301 | $16 | $0 | $0 | $25 | $0 | $10 | 1 |
| CCP010000014 | P | Z2A | ($5) | $0 | ($0) | $5 | $0 | $2 | 1 |
| CCP010000014 | P | S2B | ($151) | $0 | ($0) | $1 | $0 | $1 | 6 |
| CCP010000014 | P | L9B | ($160) | $0 | ($0) | $0 | $3 | $2 | 3 |
| CCP010000014 | P | H3A | ($216) | $1 | ($0) | $1 | $1 | $1 | 35 |
| CCP010000014 | P | Z2G | ($458) | $0 | ($0) | $0 | $5 | $7 | 1 |
| | P Total | | ($973) | $1 | ($1) | | | | |
| CCP010000014 | S | 11401 | $10,483 | $16 | $11 | $114 | $69 | $106 | 100 |
| CCP010000014 | S | 11400 | $8,266 | $11 | $9 | $91 | $0 | $93 | 90 |
| CCP010000014 | S | 11441 | $5,542 | $7 | $6 | $155 | $148 | $148 | 38 |
| CCP010000014 | S | 11440 | $4,669 | $6 | $5 | $125 | $0 | $118 | 38 |
| CCP010000014 | S | 11421 | $3,927 | $5 | $4 | $130 | $0 | $120 | 31 |
| CCP010000014 | S | 11402 | $3,543 | $7 | $4 | $169 | $0 | $137 | 38 |
| CCP010000014 | S | 11420 | $2,537 | $3 | $3 | $87 | $0 | $89 | 27 |
| CCP010000014 | S | 11422 | $1,657 | $2 | $2 | $170 | $0 | $143 | 12 |
| CCP010000014 | S | 11442 | $1,501 | $2 | $2 | $212 | $0 | $172 | 9 |
| CCP010000014 | S | 11307 | $728 | $1 | $1 | $92 | $0 | $91 | 10 |
| CCP010000014 | S | 11306 | $672 | $3 | $1 | $70 | $0 | $63 | 28 |
| CCP010000014 | S | 11308 | $648 | $1 | $1 | $99 | $0 | $103 | 7 |
| CCP010000014 | S | 11303 | $414 | $1 | $0 | $92 | $0 | $100 | 4 |
| CCP010000014 | S | 11446 | $355 | $0 | $0 | $371 | $0 | $371 | 1 |
| CCP010000014 | S | 11444 | $282 | $0 | $0 | $307 | $0 | $294 | 1 |
| CCP010000014 | S | 11312 | $278 | $1 | $0 | $109 | $0 | $99 | 7 |
| CCP010000014 | S | 11423 | $220 | $0 | $0 | $195 | $0 | $175 | 2 |
| CCP010000014 | S | 11424 | $188 | $0 | $0 | $244 | $0 | $222 | 1 |
| CCP010000014 | S | 11443 | $90 | $0 | $0 | $222 | $0 | $210 | 1 |
| CCP010000014 | S | 11900 | $9 | $0 | $0 | $28 | $0 | $47 | 2 |
| CCP010000014 | S | 11403 | ($61) | $1 | ($0) | $151 | $0 | $163 | 5 |
| CCP010000014 | S | 11310 | ($363) | $2 | ($0) | $65 | $70 | $59 | 17 |
| CCP010000014 | S | 11101 | ($366) | $1 | ($0) | $39 | $0 | $41 | 16 |
| CCP010000014 | S | 11305 | ($420) | $1 | ($0) | $39 | $0 | $40 | 14 |
| CCP010000014 | S | 12032 | ($683) | $0 | ($1) | $223 | $0 | $218 | 1 |
| CCP010000014 | S | 17003 | ($1,134) | $0 | ($1) | $2 | $9 | $4 | 7 |
| CCP010000014 | S | 11302 | ($1,245) | $1 | ($1) | $85 | $0 | $81 | 7 |
| CCP010000014 | S | 11311 | ($1,267) | $1 | ($1) | $82 | $0 | $79 | 12 |
| CCP010000014 | S | 11300 | ($1,723) | $1 | ($2) | $43 | $0 | $44 | 18 |
| CCP010000014 | S | 11301 | ($2,767) | $5 | ($3) | $56 | $0 | $62 | 48 |

TABLE A10-continued

Dermatology
Dates of Service Jan. 1, 2003-Dec. 31, 2004 paid Dec. 31, 2004
Total role benign neoplasm of the skin, without actinic keratoses
etg 0682

| | | | | | | | | | |
|---|---|---|---|---|---|---|---|---|---|
| CCP010000014 | S | 11100 | ($3,773) | $3 | ($4) | $90 | $84 | $86 | 29 |
| CCP010000014 | S | 17110 | ($5,749) | $1 | ($6) | $63 | $0 | $56 | 8 |
| CCP010000014 | S | 17000 | ($11,133) | $0 | ($12) | $66 | $58 | $62 | 7 |
| | S Total | | $15,326 | $83 | $16 | | | | |
| CCP010000014 Total | | | $42,942 | $185 | | | $46 | | |

TABLE A11

Dermatology
Dates of Service Jan. 1, 2003-Dec. 31, 2004 paid Dec. 31, 2004
Total role MPPT Meta Drilldown all etg's

| Provider ID | category | services | service description | Total Svcs |
|---|---|---|---|---|
| CCP010000014 | A | 88305 | LEVEL IV—SURGICAL PATHOLOGY, GROSS & MICROSCOPIC EXAM | 762 |
| CCP010000014 | A | CL | Clinic/TreatmDermatology/Testing | 28 |
| CCP010000014 | A | AS | Ambulatory Surgery | 2 |
| CCP010000014 | A | 93000 | ELECTROCARDIOGRAM, ROUTINE W/AT LEAST 12 LEADS; W/INTERPRETATION & REPO | 7 |
| CCP010000014 | A | 82627 | DEHYDROEPIANDROSTERONE-SULFATE (DHEA-S) | 12 |
| CCP010000014 | A | 00300 | ANESTHESIA, HEAD, NECK, POST TRUNK INTEGUMENTARY, MUSCLES/NERVES | 1 |
| CCP010000014 | A | 84402 | TESTOSTERONE; FREE | 8 |
| CCP010000014 | A | S0630 | Removal of sutures by a physician other than the physician who originall | 3 |
| CCP010000014 | A | 83550 | IRON BINDING CAPACITY | 21 |
| CCP010000014 | A | 88312 | SPECIAL STAINS; GROUP I, MICROORGANISMS, EACH | 27 |
| CCP010000014 | A | 95024 | ALLERGY TESTS, INTRADERMAL, ALLERGENIC EXTRACTS, SPECIFY NUMBER | 22 |
| CCP010000014 | A | 95004 | ALLERGY TESTS, PERCUTANEOUS, ALLERGENIC EXTRACTS, SPECIFY NUMBER | 44 |
| CCP010000014 | A | 86376 | MICROSOMAL ANTIBODIES, EACH | 8 |
| CCP010000014 | A | 84443 | THYROID STIMULATING HORMONE (TSH) | 34 |
| CCP010000014 | A | 86038 | ANTINUCLEAR ANTIBODIES (ANA) | 26 |
| CCP010000014 | A | ER | Emergency | 6 |
| CCP010000014 | A | A4550 | Surgical trays | 2 |
| CCP010000014 | A | 93017 | CARDIOVASCULAR STRESS TEST W/ECG MONITOR; TRACING ONLY, W/O INTERPRETAT | 1 |
| CCP010000014 | A | 84403 | TESTOSTERONE; TOTAL | 9 |
| CCP010000014 | A | 80053 | COMPREHENSIVE METABOLIC PANEL | 41 |
| CCP010000014 | A | 85652 | SEDIMENTATION RATE, ERYTHROCYTE; AUTOMATED | 38 |
| CCP010000014 | A | 87101 | CULTURE, FUNGI (MOLD/YEAST) ISOLATION, W/PRESUMPTIVE ID OF ISOLATES; SK | 24 |
| CCP010000014 | A | 88307 | LEVEL V—SURGICAL PATHOLOGY, GROSS & MICROSCOPIC EXAM | 1 |
| CCP010000014 | A | A4649 | Surgical supply; miscellaneous | 1 |
| CCP010000014 | A | 86235 | EXTRACTABLE NUCLEAR ANTIGEN, ANTIBODY TO, ANY METHOD, EACH ANTIBODY | 19 |
| CCP010000014 | A | 86618 | ANTIBODY; BORRELIA BURGDORFERI (LYME DISEASE) | 5 |
| CCP010000014 | A | 83540 | IRON | 22 |
| CCP010000014 | A | 80076 | HEPATIC FUNCTION PANEL | 24 |
| CCP010000014 | A | 86644 | ANTIBODY; CYTOMEGALOVIRUS (CMV) | 3 |
| CCP010000014 | A | 83735 | MAGNESIUM | 7 |
| CCP010000014 | A | 80050 | GENERAL HEALTH PANEL | 9 |
| CCP010000014 | A | 83498 | HYDROXYPROGESTERONE, 17-D | 3 |
| CCP010000014 | A | 86665 | ANTIBODY; EPSTEIN-BARR (EB) VIRUS, VIRAL CAPSID (VCA) | 4 |
| CCP010000014 | A | 86617 | ANTIBODY; BORRELIA BURGDORFERI (LYME DISEASE) CONFIRMATORY TEST | 1 |
| CCP010000014 | A | 86039 | ANTINUCLEAR ANTIBODIES (ANA); TITER | 5 |
| CCP010000014 | A | 93005 | ELECTROCARDIOGRAM, ROUTINE W/AT LEAST 12 LEADS; TRACING ONLY W/O INTER | 1 |
| CCP010000014 | A | 82550 | CREATINE KINASE (CK), (CPK); TOTAL | 7 |
| CCP010000014 | A | 87620 | INFECTIOUS AGENT, NUCLEIC ACID (DNA/RNA); HUMAN PAPILLOMAVIRUS, DIRECT | 1 |
| CCP010000014 | A | 86431 | RHEUMATOID FACTOR; QUANTITATIVE | 5 |
| CCP010000014 | A | 85021 | | 1 |
| CCP010000014 | A | 86580 | SKIN TEST; TUBERCULOSIS, INTRADERMAL | 2 |
| CCP010000014 | A | 87107 | CULTURE, FUNGI, DEFINITIVE ID, EACH ORGANISM; MOLD | 2 |
| CCP010000014 | A | 93010 | ELECTROCARDIOGRAM, ROUTINE W/AT LEAST 12 LEADS; INTERPRETATION & REPORT | 1 |
| CCP010000014 | A | 86777 | ANTIBODY; TOXOPLASMA | 1 |
| CCP010000014 | A | 85023 | | 3 |
| CCP010000014 | A | 82728 | FERRITIN | 4 |
| CCP010000014 | A | 82947 | GLUCOSE; QUANTITATIVE, BLOOD (EXCEPT REAGENT STRIP) | 6 |
| CCP010000014 | A | 80005 | | 1 |
| CCP010000014 | A | 84450 | TRANSFERASE; ASPARTATE AMINO (AST) (SGOT) | 6 |
| CCP010000014 | A | 86787 | ANTIBODY; VARICELLA-ZOSTER | 1 |
| CCP010000014 | A | 85014 | BLOOD COUNT; HEMATOCRIT | 3 |
| CCP010000014 | A | 86140 | C-REACTIVE PROTEIN | 2 |
| CCP010000014 | A | 83036 | HEMOGLOBIN; GLYCATED | 3 |
| CCP010000014 | A | 86765 | ANTIBODY; RUBEOLA | 1 |
| CCP010000014 | A | 85651 | SEDIMENTATION RATE, ERYTHROCYTE; NON-AUTOMATED | 9 |

TABLE A11-continued

Dermatology
Dates of Service Jan. 1, 2003-Dec. 31, 2004 paid Dec. 31, 2004
Total role MPPT Meta Drilldown all etg's

| | | | | |
|---|---|---|---|---|
| CCP010000014 | A | 85008 | BLOOD COUNT; BLOOD SMEAR, MICROSCOP EXAM W/O MANUAL DIFFERENTIAL WBC CO | 1 |
| CCP010000014 | A | 80003 | | 1 |
| CCP010000014 | A | 85730 | THROMBOPLASTIN TIME, PARTIAL (PTT); PLASMA/WHOLE BLOOD | 2 |
| CCP010000014 | A | 82950 | GLUCOSE; POST GLUCOSE DOSE (INCLUDES GLUCOSE) | 1 |
| CCP010000014 | A | 80051 | ELECTROLYTE PANEL | 1 |
| CCP010000014 | A | 87206 | SMEAR, PRIME SRCE, W/INTERPR; FLUORESC &/OR ACID FAST STAIN, BACTERIA/F | 1 |
| CCP010000014 | A | 81050 | VOLUME MEASUREMENT, TIMED COLLECTION, EACH | 1 |
| CCP010000014 | A | 83002 | GONADOTROPIN; LUTEINIZING HORMONE (LH) | 1 |
| CCP010000014 | A | 84146 | PROLACTIN | 1 |
| CCP010000014 | A | 85025 | BLOOD COUNT; COMPLETE CBC, AUTOMATED (HGB, HCT, RBC, WBC, & PLATELET) & | 46 |
| CCP010000014 | A | 86308 | HETEROPHILE ANTIBODIES; SCREENING | 1 |
| CCP010000014 | A | 81003 | URINALYSIS, DIP STICK/TABLET REAGENT; AUTOMATED, W/O MICROSCOPY | 1 |
| CCP010000014 | A | 84478 | TRIGLYCERIDES | 10 |
| CCP010000014 | A | 81000 | URINALYSIS, DIP STICK/TABLET REAGENT; NON-AUTOMATED W/MICROSCOPY | 2 |
| CCP010000014 | A | 81002 | URINALYSIS, DIP STICK/TABLET REAGENT; NON-AUTOMATED, W/O MICROSCOPY | 3 |
| CCP010000014 | A | 83615 | LACTATE DEHYDROGENASE (LD), (LDH) | 2 |
| CCP010000014 | A | 87210 | SMEAR, PRIMARY SOURCE W/INTERPRETATION; WET MOUNT, FOR INFECTIOUS AGENT | 27 |
| CCP010000014 | A | 84436 | THYROXINE; TOTAL | 1 |
| CCP010000014 | A | 82565 | CREATININE; BLOOD | 1 |
| CCP010000014 | A | 81001 | URINALYSIS, DIP STICK/TABLET REAGENT; AUTOMATED W/O MICROSCOPY | 1 |
| CCP010000014 | A | 83001 | GONADOTROPIN; FOLLICLE STIMULATING HORMONE (FSH) | 1 |
| CCP010000014 | A | 87081 | CULTURE, PRESUMPTIVE, PATHOGENIC ORGANISMS, SCREENING ONLY | 5 |
| CCP010000014 | A | 86162 | COMPLEMENT; TOTAL HEMOLYTIC (CH50) | 1 |
| CCP010000014 | A | 82248 | BILIRUBIN; DIRECT | 1 |
| CCP010000014 | A | 82270 | BLOOD, OCCULT, BY PEROXIDASE ACTIVITY, QUALITATIVE; FECES, 1-3 SIMULTAN | 2 |
| CCP010000014 | A | 85027 | BLOOD COUNT; COMPLETE CBC, AUTOMATED (HGB, HCT, RBC, WBC, & PLATELET) | 15 |
| CCP010000014 | A | 82040 | ALBUMIN; SERUM | 2 |
| CCP010000014 | A | 80048 | BASIC METABOLIC PANEL | 9 |
| CCP010000014 | A | 87106 | CULTURE, FUNGI, DEFINITIVE ID, EACH ORGANISM; YEAST | 2 |
| CCP010000014 | A | 87186 | SUSCEPT STUDIES, ANTIMICROB AGNT; MICRODILUT/AGAR DILUT (MIC/BRKPNT), E | 3 |
| CCP010000014 | A | 80061 | LIPID PANEL | 15 |
| CCP010000014 | A | 84439 | THYROXINE; FREE | 2 |
| CCP010000014 | A | 86225 | DEOXYRIBONUCLEIC ACID (DNA) ANTIBODY; NATIVE/DOUBLE STRANDED | 2 |
| CCP010000014 | A | 84460 | TRANSFERASE; ALANINE AMINO (ALT) (SGPT) | 1 |
| CCP010000014 | A | 86160 | COMPLEMENT; ANTIGEN, EACH COMPONENT | 1 |
| CCP010000014 | A | 87252 | VIRUS ISOLATION; TISSUE CULTURE INOCULATION, OBSERVATION & PRESUMPTIVE | 2 |
| CCP010000014 | A | 87070 | CULTURE, BACTERIAL; ANY OTHER SOURCE EXCEPT URINE/BLOOD/STOOL, AEROBIC, | 12 |
| CCP010000014 | A | 88304 | LEVEL III—SURGICAL PATHOLOGY, GROSS & MICROSCOPIC EXAM | 13 |
| CCP010000014 | A | 95044 | PATCH/APPLICATION TEST(S) (SPECIFY NUMBER) | 216 |
| | A Total | | | 1,700 |
| CCP010000014 | M | 99243 | OFFICE CONSULTATION, 3 KEY COMPONENTS: DETAILED HX; DETAILED EXAM; MED | 671 |
| CCP010000014 | M | 99213 | OFFICE/OP VISIT, EST PT, 2 KEY COMPONENTS: EXPAND PROB HX; EXPAND PROB | 1,565 |
| CCP010000014 | M | 99203 | OFFICE/OP VISIT, NEW PT, 3 KEY COMPONENTS: DETAILED HX; DETAILED EXAM; | 77 |
| CCP010000014 | M | 99202 | OFFICE/OP VISIT, NEW PT, 3 KEY COMPONENTS: EXPAND PROB FOCUS HX; EXPAND | 40 |
| CCP010000014 | M | 99214 | OFFICE/OP VISIT, EST PT, 2 KEY COMPONENTS: DETAILED HX; DETAILED EXAM; | 36 |
| CCP010000014 | M | 96910 | PHOTOCHEMOTHERAPY; TAR & UVB/PETROLATUM & UVB | 23 |
| CCP010000014 | M | 99245 | OFFICE CONSULTATION, 3 KEY COMPONENTS: COMPREHENSIVE HX; COMPREHENSIVE E | 1 |
| CCP010000014 | M | 99385 | INITIAL COMPREHENSIVE PREVENTIVE MEDICINE E&M W/HX/EXAM, NEW PT; 18-39 | 3 |
| CCP010000014 | M | 99211 | OFFICE/OP VISIT, EST PT, NOT REQUIRING PHYSICIAN PRESENCE, TYPICALLY 5 | 4 |
| CCP010000014 | M | 99215 | OFFICE/OP VISIT, EST PT, 2 KEY COMPONENTS: COMPREHENSIVE HX; COMPREHENSIV | 2 |
| CCP010000014 | M | 99204 | OFFICE/OP VISIT, NEW PT, 3 KEY COMPONENTS: COMPREHENSIVE HX; COMPREHENSIV | 2 |
| CCP010000014 | M | 99201 | OFFICE/OP VISIT, NEW PT, 3 KEY COMPONENTS: PROB FOCUS HX; PROB FOCUS EX | 1 |
| CCP010000014 | M | 99386 | INITIAL COMPREHENSIVE PREVENTIVE MEDICINE E&M W/HX/EXAM, NEW PT; 40-64 | 1 |
| CCP010000014 | M | 99395 | PERIODIC COMPREHENSIVE PREVENTIVE MEDICINE E&M W/HX/EXAM, EST PT; 18-39 | 3 |
| CCP010000014 | M | 99396 | PERIODIC COMPREHENSIVE PREVENTIVE MEDICINE E&M W/HX/EXAM, EST PT; 40-64 | 5 |
| CCP010000014 | M | 99394 | PERIODIC COMPREHENSIVE PREVENTIVE MEDICINE E&M W/HX/EXAM, EST PT; 12-17 | 1 |
| CCP010000014 | M | 92012 | OPHTHALMOLOGICAL MEDICAL EXAM & EVAL; INTERMEDIATE, ESTABLISHED PATIENT | 2 |
| CCP010000014 | M | 99241 | OFFICE CONSULTATION, 3 KEY COMPONENTS: PROB FOCUS HX; PROB FOCUS EXAM; | 2 |
| CCP010000014 | M | 99242 | OFFICE CONSULTATION, 3 KEY COMPONENTS: EXPAND PROB FOCUS HX; EXPAND PROB | 274 |
| CCP010000014 | M | 99212 | OFFICE/OP VISIT, EST PT, 2 KEY COMPONENTS: PROB FOCUS HX; PROB FOCUS EX | 172 |
| | M Total | | | 2,885 |
| CCP010000014 | P | Q5P | TOPICAL ANTI-INFLAMMATORY STEROIDAL | 12,473 |
| CCP010000014 | P | W1D | MACROLIDES | 3,320 |
| CCP010000014 | P | Z2E | IMMUNOSUPPRESSIVES | 150 |
| CCP010000014 | P | J3301 | Injection, triamcinolone acetonide, per 10 mg | 27 |
| CCP010000014 | P | Q5H | TOPICAL LOCAL ANESTHETICS | 390 |
| CCP010000014 | P | P4L | BONE RESORPTION INHIBITORS | 360 |
| CCP010000014 | P | Q5W | TOPICAL ANTIBIOTICS | 4,872 |
| CCP010000014 | P | H3D | ANALGESIC/ANTIPYRETICS, SALICYLATES | 98 |
| CCP010000014 | P | W1Q | QUINOLONES | 28 |
| CCP010000014 | P | Q8F | OTIC PREPARATIONS, ANTI-INFLAMMATORY-ANTIBIOTICS | 5 |
| CCP010000014 | P | Q4F | VAGINAL ANTIFUNGALS | 17 |
| CCP010000014 | P | W1W | CEPHALOSPORINS—1ST GENERATION | 1,011 |

TABLE A11-continued

Dermatology
Dates of Service Jan. 1, 2003-Dec. 31, 2004 paid Dec. 31, 2004
Total role MPPT Meta Drilldown all etg's

| | | | | |
|---|---|---|---|---:|
| CCP010000014 | P | J1030 | Injection, methylprednisolone acetate, 40 mg | 4 |
| CCP010000014 | P | W3A | ANTIFUNGAL ANTIBIOTICS | 30 |
| CCP010000014 | P | L5G | ROSACEA AGENTS, TOPICAL | 1,839 |
| CCP010000014 | P | J9A | INTESTINAL MOTILITY STIMULANTS | 51 |
| CCP010000014 | P | J9260 | Methotrexate sodium, 50 mg | 1 |
| CCP010000014 | P | H2U | TRICYCLIC ANTIDEPRESSANTS & REL. NON-SEL. RU-INHIB | 360 |
| CCP010000014 | P | H4B | ANTICONVULSANTS | 338 |
| CCP010000014 | P | Q5R | TOPICAL ANTIPARASITICS | 20 |
| CCP010000014 | P | H6J | ANTIEMETIC/ANTIVERTIGO AGENTS | 20 |
| CCP010000014 | P | Q8W | EAR PREPARATIONS, ANTIBIOTICS | 5 |
| CCP010000014 | P | S2A | COLCHICINE | 60 |
| CCP010000014 | P | H0A | LOCAL ANESTHETICS | 5 |
| CCP010000014 | P | D1A | PERIODONTAL COLLAGENASE INHIBITORS | 30 |
| CCP010000014 | P | Z4B | LEUKOTRIENE RECEPTOR ANTAGONISTS | 255 |
| CCP010000014 | P | U6W | BULK CHEMICALS | 30 |
| CCP010000014 | P | J5F | ANAPHYLAXIS THERAPY AGENTS | 21 |
| CCP010000014 | P | S2B | NSAIDS, CYCLOOXYGENASE INHIBITOR—TYPE | 2,954 |
| CCP010000014 | P | L3P | ANTIPRURITICS, TOPICAL | 20 |
| CCP010000014 | P | H3A | ANALGESICS, NARCOTICS | 994 |
| CCP010000014 | P | W4E | ANAEROBIC ANTIPROTOZOAL-ANTIBACTERIAL AGENTS | 45 |
| CCP010000014 | P | P5A | GLUCOCORTICOIDS | 632 |
| CCP010000014 | P | 0 | | 15 |
| CCP010000014 | P | W1A | PENICILLINS | 1,289 |
| CCP010000014 | P | W3B | ANTIFUNGAL AGENTS | 473 |
| CCP010000014 | P | V1B | ANTIMETABOLITES | 277 |
| CCP010000014 | P | L5E | ANTISEBORRHEIC AGENTS | 60 |
| CCP010000014 | P | W1K | LINCOSAMIDES | 52 |
| CCP010000014 | P | Z2A | ANTIHISTAMINES | 5,696 |
| CCP010000014 | P | R1H | POTASSIUM SPARING DIURETICS | 30 |
| CCP010000014 | P | L2A | EMOLLIENTS | 110 |
| CCP010000014 | P | CL | Clinic/TreatmDermatology/Testing | 1 |
| CCP010000014 | P | L9A | TOPICAL AGENTS, MISCELLANEOUS | 30 |
| CCP010000014 | P | W5A | ANTIVIRALS, GENERAL | 353 |
| CCP010000014 | P | Q5F | TOPICAL ANTIFUNGALS | 2,015 |
| CCP010000014 | P | L1B | ACNE AGENTS, SYSTEMIC | 90 |
| CCP010000014 | P | Q5S | TOPICAL SULFONAMIDES | 245 |
| CCP010000014 | P | L5A | KERATOLYTICS | 202 |
| CCP010000014 | P | Q5K | TOPICAL IMMUNOSUPPRESSIVE AGENTS | 1,041 |
| CCP010000014 | P | Z2G | IMMUNOMODULATORS | 70 |
| CCP010000014 | P | W1C | TETRACYCLINES | 18,225 |
| CCP010000014 | P | L9B | VITAMIN A DERIVATIVES | 1,010 |
| CCP010000014 | P | L5H | ACNE AGENTS, TOPICAL | 240 |
| CCP010000014 | P | L5F | ANTIPSORIATICS AGENTS | 310 |
| | P Total | | | 62,299 |
| CCP010000014 | R | 73630 | RADIOLOGIC EXAM, FOOT; COMPLETE, 3+ VIEWS | 3 |
| CCP010000014 | R | 73130 | RADIOLOGIC EXAM, HAND; 3+ VIEWS | 2 |
| | R Total | | | 5 |
| CCP010000014 | S | 11400 | EXCISE, BENIGN SKIN LESION, INCL MARGINS, EXCEPT SKIN TAG, TRUNK/ARMS/L | 124 |
| CCP010000014 | S | 11441 | EXCISE, BENIGN SKIN LESION, INCL MARGINS, FACE/EARS/EYELIDS/NOSE/LIPS/M | 46 |
| CCP010000014 | S | 11440 | EXCISE, BENIGN SKIN LESION, INCL MARGINS, FACE/EARS/EYELIDS/NOSE/LIPS/M | 50 |
| CCP010000014 | S | 11402 | EXCISE, BENIGN SKIN LESION, INCL MARGINS, EXCEPT SKIN TAG, TRUNK/ARMS/L | 88 |
| CCP010000014 | S | 11421 | EXCISE BEN SKIN LESION W/MARG, EXCEPT SKIN TAG SCALP/NECK/HANDS/FEET/GE | 35 |
| CCP010000014 | S | 11420 | EXCISE BENIGN SKIN LESION W/MARG, EXCPT SKIN TAG SCALP/NECK/HANDS/FEET/ | 36 |
| CCP010000014 | S | 11442 | EXCISE, BENIGN SKIN LESION, INCL MARGINS, FACE/EARS/EYELIDS/NOSE/LIPS/M | 11 |
| CCP010000014 | S | 11422 | EXCISE BEN SKIN LESION W/MARG, EXCEPT SKIN TAG SCALP/NECK/HANDS/FEET/GE | 14 |
| CCP010000014 | S | 11641 | EXCISION, MALIGNANT LESION, INCL MARGINS, FACE/EARS/EYELIDS/NOSE/LIPS/M | 8 |
| CCP010000014 | S | 11306 | SHAVING SKIN LESION, SCALP/NECK/HANDS/FEET/GENITALIA; DIAMETER 0.6-1.0 | 44 |
| CCP010000014 | S | 11643 | EXCISION, MALIGNANT LESION, INCL MARGINS, FACE/EARS/EYELIDS/NOSE/LIPS/M | 3 |
| CCP010000014 | S | 14040 | ADJACENT TISSUE TRANSFER, FOREHEAD/CHEEKS/CHIN/MOUTH/NECK/AXILLAE/GENIT | 2 |
| CCP010000014 | S | 11308 | SHAVING SKIN LESION, SCALP/NECK/HANDS/FEET/GENITALIA; DIAMETER >2.0 CM | 7 |
| CCP010000014 | S | 11307 | SHAVING SKIN LESION, SCALP/NECK/HANDS/FEET/GENITALIA; DIAMETER 1.1-2.0 | 12 |
| CCP010000014 | S | 11603 | EXCISION, MALIGNANT LESION, INCL MARGINS, TRUNK/ARMS/LEGS; EXCISED DIAM | 4 |
| CCP010000014 | S | 11303 | SHAVING SKIN LESION, TRUNK/ARMS/LEGS; DIAMETER >2.0 CM | 6 |
| CCP010000014 | S | 11644 | EXCISION, MALIGNANT LESION, INCL MARGINS, FACE/EARS/EYELIDS/NOSE/LIPS/M | 1 |
| CCP010000014 | S | 11446 | EXCISE, BENIGN SKIN LESION, INCL MARGINS, FACE/EARS/EYELIDS/NOSE/LIPS/M | 1 |
| CCP010000014 | S | 11622 | EXCISION, MALIGNANT LESION, INCL MARGINS, SCALP/NECK/HANDS/FEET/GENITAL | 2 |
| CCP010000014 | S | 11444 | EXCISE, BENIGN SKIN LESION, INCL MARGINS, FACE/EARS/EYELIDS/NOSE/LIPS/M | 1 |
| CCP010000014 | S | 14020 | ADJACENT TISSUE TRANSFER/REARRANGEMENT, SCALP, ARMS &/OR LEGS; DEFECT 1 | 1 |
| CCP010000014 | S | 11770 | EXCISION, PILONIDAL CYST/SINUS; SIMPLE | 1 |
| CCP010000014 | S | 13132 | REPAIR, COMPLEX, FOREHEAD/CHEEKS/CHIN/MOUTH/NECK/AXILLAE/GENITALIA/HAND | 1 |
| CCP010000014 | S | 11312 | SHAVING SKIN LESION, FACE/EARS/EYELIDS/NOSE/LIPS/MUCOUS MEMBRANE; DIAME | 7 |
| CCP010000014 | S | 17110 | DESTRUCTION, FLAT WARTS, MOLLUSCUM CONTAGIOSUM/MILIA; UP TO 14 LESIONS | 250 |
| CCP010000014 | S | 11623 | EXCISION, MALIGNANT LESION, INCL MARGINS, SCALP/NECK/HANDS/FEET/GENITAL | 1 |
| CCP010000014 | S | 11424 | EXCISE BEN SKIN LESION W/MARG, EXCEPT SKIN TAG SCALP/NECK/HANDS/FEET/GE | 1 |

TABLE A11-continued

Dermatology
Dates of Service Jan. 1, 2003-Dec. 31, 2004 paid Dec. 31, 2004
Total role MPPT Meta Drilldown all etg's

| | | | | |
|---|---|---|---|---|
| CCP010000014 | S | 11621 | EXCISION, MALIGNANT LESION, INCL MARGINS, SCALP/NECK/HANDS/FEET/GENITAL | 2 |
| CCP010000014 | S | 11730 | AVULSION, NAIL PLATE, PARTIAL/COMPLETE, SIMPLE; SINGLE | 3 |
| CCP010000014 | S | 11900 | INJECTION, INTRALESIONAL; UP TO & INCL 7 LESIONS | 35 |
| CCP010000014 | S | 11640 | EXCISION, MALIGNANT LESION, INCL MARGINS, FACE/EARS/EYELIDS/NOSE/LIPS/M | 1 |
| CCP010000014 | S | 56605 | BX, VULVA/PERINEUM (SEP PROC); 1 LESION | 1 |
| CCP010000014 | S | 11732 | AVULSION, NAIL PLATE, PARTIAL/COMPLETE, SIMPLE; ADD'L NAIL PLATE | 2 |
| CCP010000014 | S | 20550 | INJECTION(S); SINGLE TENDON SHEATH, LIGAMENT, APONEUROSIS | 1 |
| CCP010000014 | S | 11443 | EXCISE, BENIGN SKIN LESION, INCL MARGINS, FACE/EARS/EYELIDS/NOSE/LIPS/M | 1 |
| CCP010000014 | S | 11423 | EXCISE BEN SKIN LESION W/MARG, EXCEPT SKIN TAG SCALP/NECK/HANDS/FEET/GE | 2 |
| CCP010000014 | S | 11601 | EXCISION, MALIGNANT LESION, INCL MARGINS, TRUNK/ARMS/LEGS; EXCISED DIAM | 1 |
| CCP010000014 | S | 11602 | EXCISION, MALIGNANT LESION, INCL MARGINS, TRUNK/ARMS/LEGS; EXCISED DIAM | 3 |
| CCP010000014 | S | 10060 | INCISION & DRAINAGE, ABSCESS; SIMPLE/SINGLE | 5 |
| CCP010000014 | S | 11642 | EXCISION, MALIGNANT LESION, INCL MARGINS, FACE/EARS/EYELIDS/NOSE/LIPS/M | 1 |
| CCP010000014 | S | 11403 | EXCISE, BENIGN SKIN LESION, INCL MARGINS, EXCEPT SKIN TAG, TRUNK/ARMS/L | 5 |
| CCP010000014 | S | 17111 | DESTRUCTION, FLAT WARTS, MOLLUSCUM CONTAGIOSUM/MILIA; 15 + | 2 |
| CCP010000014 | S | 11310 | SHAVING SKIN LESION, FACE/EARS/EYELIDS/NOSE/LIPS/MUCOUS MEMBRANE; DIAME | 23 |
| CCP010000014 | S | 11305 | SHAVING SKIN LESION, SCALP/NECK/HANDS/FEET/GENITALIA; DIAMETER 0.5 CM/< | 22 |
| CCP010000014 | S | 11101 | BX, SKIN, SUBQ/MUCOUS MEMBRANE (SEP PROC); ADD'L LESION | 22 |
| CCP010000014 | S | 12032 | LAYER CLOSURE, WOUNDS, SCALP/AXILLAE/TRUNK/EXTREMITIES; 2.6-7.5 CM | 1 |
| CCP010000014 | S | 11901 | INJECTION, INTRALESIONAL; >7 LESIONS | 4 |
| CCP010000014 | S | 11302 | SHAVING SKIN LESION, TRUNK/ARMS/LEGS; DIAMETER 1.1-2.0 CM | 8 |
| CCP010000014 | S | 11311 | SHAVING SKIN LESION, FACE/EARS/EYELIDS/NOSE/LIPS/MUCOUS MEMBRANE; DIAME | 16 |
| CCP010000014 | S | 11300 | SHAVING SKIN LESION, TRUNK/ARMS/LEGS; DIAMETER 0.5 CM/< | 31 |
| CCP010000014 | S | 17003 | DESTRUCTION, BENIGN/PREMALIG LESIONS, EXCEPT SKIN TAGS/CUTANEOUS VASC P | 245 |
| CCP010000014 | S | 17304 | CHEMOSURGERY (MOHS MICROGRAPHIC TECHNIQUE); 1ST STAGE, FRESH TISSUE, TO | 1 |
| CCP010000014 | S | 11301 | SHAVING SKIN LESION, TRUNK/ARMS/LEGS; DIAMETER 0.6-1.0 CM | 80 |
| CCP010000014 | S | 11100 | BX, SKIN, SUBQ/MUCOUS MEMBRANE; SINGLE LESION | 35 |
| CCP010000014 | S | 17000 | DESTRUCTION, BENIGN/PREMALIG LESIONS, EXCEPT SKIN TAGS/CUTANEOUS VASC P | 47 |
| | S Total | | | 1,493 |
| CCP010000014 | T | 0421 | PHYSICAL THEAPY VISIT CHARGE | 3 |
| | T Total | | | 3 |
| CCP010000014 Total | | | | 68,385 |

| Provider ID | category | services | Your Svcs | Other Svcs | Expected Svcs | Practitioner episodes | Total Costs | Your Costs | Others Costs | Expected Costs |
|---|---|---|---|---|---|---|---|---|---|---|
| CCP010000014 | A | 88305 | 748 | 14 | 509.99 | 2,540 | $23,516 | $23,083 | $433 | $15,764 |
| CCP010000014 | A | CL | 26 | 2 | 16.33 | 2,540 | $1,221 | $543 | $678 | $580 |
| CCP010000014 | A | AS | 0 | 2 | 1.94 | 2,540 | $1,198 | $0 | $1,198 | $755 |
| CCP010000014 | A | 93000 | 0 | 7 | 3.88 | 2,540 | $311 | $0 | $311 | $115 |
| CCP010000014 | A | 82627 | 4 | 8 | 3.60 | 2,540 | $264 | $88 | $176 | $79 |
| CCP010000014 | A | 00300 | 0 | 1 | .45 | 2,540 | $360 | $0 | $360 | $178 |
| CCP010000014 | A | 84402 | 2 | 6 | 2.87 | 2,540 | $224 | $56 | $168 | $81 |
| CCP010000014 | A | S0630 | 3 | 0 | .55 | 2,540 | $148 | $148 | $0 | $21 |
| CCP010000014 | A | 83550 | 8 | 13 | 4.15 | 2,540 | $147 | $56 | $91 | $29 |
| CCP010000014 | A | 88312 | 26 | 1 | 19.65 | 2,540 | $432 | $416 | $16 | $315 |
| CCP010000014 | A | 95024 | 0 | 22 | 2.11 | 2,540 | $125 | $0 | $125 | $13 |
| CCP010000014 | A | 95004 | 0 | 44 | 12.59 | 2,540 | $166 | $0 | $166 | $54 |
| CCP010000014 | A | 86376 | 4 | 4 | 1.00 | 2,540 | $128 | $64 | $64 | $16 |
| CCP010000014 | A | 84443 | 14 | 20 | 18.03 | 2,540 | $238 | $98 | $140 | $128 |
| CCP010000014 | A | 86038 | 6 | 20 | 13.87 | 2,540 | $208 | $48 | $160 | $112 |
| CCP010000014 | A | ER | 3 | 3 | 6.89 | 2,540 | $1,048 | $435 | $613 | $953 |
| CCP010000014 | A | A4550 | 1 | 1 | .07 | 2,540 | $98 | $49 | $49 | $3 |
| CCP010000014 | A | 93017 | 0 | 1 | .07 | 2,540 | $93 | $0 | $93 | $7 |
| CCP010000014 | A | 84403 | 2 | 7 | 4.98 | 2,540 | $180 | $40 | $140 | $104 |
| CCP010000014 | A | 80053 | 13 | 28 | 26.64 | 2,540 | $205 | $65 | $140 | $134 |
| CCP010000014 | A | 85652 | 16 | 22 | 5.16 | 2,540 | $76 | $32 | $44 | $11 |
| CCP010000014 | A | 87101 | 7 | 17 | 15.95 | 2,540 | $191 | $56 | $135 | $127 |
| CCP010000014 | A | 88307 | 1 | 0 | .10 | 2,540 | $68 | $68 | $0 | $7 |
| CCP010000014 | A | A4649 | 1 | 0 | .07 | 2,540 | $73 | $73 | $0 | $13 |
| CCP010000014 | A | 86235 | 8 | 11 | 11.24 | 2,540 | $141 | $60 | $81 | $81 |
| CCP010000014 | A | 86618 | 1 | 4 | 1.25 | 2,540 | $60 | $12 | $48 | $15 |
| CCP010000014 | A | 83540 | 8 | 14 | 8.30 | 2,540 | $66 | $24 | $42 | $25 |
| CCP010000014 | A | 80076 | 8 | 16 | 11.49 | 2,540 | $72 | $24 | $48 | $34 |
| CCP010000014 | A | 86644 | 0 | 3 | .35 | 2,540 | $42 | $0 | $42 | $5 |
| CCP010000014 | A | 83735 | 0 | 7 | 1.04 | 2,540 | $35 | $0 | $35 | $5 |
| CCP010000014 | A | 80050 | 2 | 7 | 6.68 | 2,540 | $126 | $28 | $98 | $97 |
| CCP010000014 | A | 83498 | 0 | 3 | 1.21 | 2,540 | $48 | $0 | $48 | $19 |
| CCP010000014 | A | 86665 | 0 | 4 | .69 | 2,540 | $32 | $0 | $32 | $6 |
| CCP010000014 | A | 86617 | 0 | 1 | .24 | 2,540 | $32 | $0 | $32 | $8 |
| CCP010000014 | A | 86039 | 2 | 3 | 2.39 | 2,540 | $45 | $18 | $27 | $21 |
| CCP010000014 | A | 93005 | 1 | 0 | .73 | 2,540 | $54 | $54 | $0 | $38 |
| CCP010000014 | A | 82550 | 0 | 7 | 3.88 | 2,540 | $28 | $0 | $28 | $16 |
| CCP010000014 | A | 87620 | 0 | 1 | .03 | 2,540 | $12 | $0 | $12 | $0 |
| CCP010000014 | A | 86431 | 1 | 4 | 2.18 | 2,540 | $20 | $4 | $16 | $9 |

TABLE A11-continued

Dermatology
Dates of Service Jan. 1, 2003-Dec. 31, 2004 paid Dec. 31, 2004
Total role MPPT Meta Drilldown all etg's

| | | | | | | | | | | |
|---|---|---|---|---|---|---|---|---|---|---|
| CCP010000014 | A | 85021 | 1 | 0 | .07 | 2,540 | $11 | $11 | $0 | $0 |
| CCP010000014 | A | 86580 | 0 | 2 | .93 | 2,540 | $18 | $0 | $18 | $8 |
| CCP010000014 | A | 87107 | 0 | 2 | .28 | 2,540 | $10 | $0 | $10 | $1 |
| CCP010000014 | A | 93010 | 1 | 0 | 1.25 | 2,540 | $31 | $31 | $0 | $23 |
| CCP010000014 | A | 86777 | 0 | 1 | .10 | 2,540 | $8 | $0 | $8 | $1 |
| CCP010000014 | A | 85023 | 0 | 3 | .66 | 2,540 | $9 | $0 | $9 | $2 |
| CCP010000014 | A | 82728 | 0 | 4 | 3.18 | 2,540 | $32 | $0 | $32 | $25 |
| CCP010000014 | A | 82947 | 1 | 5 | 4.64 | 2,540 | $16 | $2 | $14 | $10 |
| CCP010000014 | A | 80005 | 0 | 1 | .21 | 2,540 | $5 | $0 | $5 | $1 |
| CCP010000014 | A | 84450 | 0 | 6 | 4.29 | 2,540 | $20 | $0 | $20 | $16 |
| CCP010000014 | A | 86787 | 0 | 1 | .62 | 2,540 | $10 | $0 | $10 | $6 |
| CCP010000014 | A | 85014 | 1 | 2 | 2.11 | 2,540 | $9 | $5 | $4 | $5 |
| CCP010000014 | A | 86140 | 0 | 2 | .86 | 2,540 | $6 | $0 | $6 | $3 |
| CCP010000014 | A | 83036 | 0 | 3 | 2.39 | 2,540 | $15 | $0 | $15 | $12 |
| CCP010000014 | A | 86765 | 0 | 1 | .80 | 2,540 | $15 | $0 | $15 | $12 |
| CCP010000014 | A | 85651 | 4 | 5 | 7.30 | 2,540 | $18 | $8 | $10 | $16 |
| CCP010000014 | A | 85008 | 0 | 1 | .03 | 2,540 | $2 | $0 | $2 | $0 |
| CCP010000014 | A | 80003 | 0 | 1 | .62 | 2,540 | $5 | $0 | $5 | $3 |
| CCP010000014 | A | 85730 | 0 | 2 | 1.38 | 2,540 | $6 | $0 | $6 | $4 |
| CCP010000014 | A | 82950 | 0 | 1 | .21 | 2,540 | $2 | $0 | $2 | $0 |
| CCP010000014 | A | 80051 | 0 | 1 | .62 | 2,540 | $4 | $0 | $4 | $2 |
| CCP010000014 | A | 87206 | 0 | 1 | .76 | 2,540 | $5 | $0 | $5 | $4 |
| CCP010000014 | A | 81050 | 0 | 1 | .52 | 2,540 | $2 | $0 | $2 | $1 |
| CCP010000014 | A | 83002 | 0 | 1 | .93 | 2,540 | $12 | $0 | $12 | $11 |
| CCP010000014 | A | 84146 | 0 | 1 | .97 | 2,540 | $11 | $0 | $11 | $11 |
| CCP010000014 | A | 85025 | 12 | 34 | 44.91 | 2,540 | $138 | $36 | $102 | $138 |
| CCP010000014 | A | 86308 | 0 | 1 | .59 | 2,540 | $4 | $0 | $4 | $4 |
| CCP010000014 | A | 81003 | 0 | 1 | 1.56 | 2,540 | $1 | $0 | $1 | $2 |
| CCP010000014 | A | 84478 | 4 | 6 | 10.21 | 2,540 | $30 | $12 | $18 | $31 |
| CCP010000014 | A | 81000 | 1 | 1 | 3.25 | 2,540 | $16 | $6 | $10 | $17 |
| CCP010000014 | A | 81002 | 2 | 1 | 3.70 | 2,540 | $12 | $8 | $4 | $14 |
| CCP010000014 | A | 83615 | 0 | 2 | 2.42 | 2,540 | $6 | $0 | $6 | $9 |
| CCP010000014 | A | 87210 | 27 | 0 | 29.82 | 2,540 | $201 | $201 | $0 | $205 |
| CCP010000014 | A | 84436 | 1 | 0 | 1.76 | 2,540 | $4 | $4 | $0 | $8 |
| CCP010000014 | A | 82565 | 0 | 1 | 2.15 | 2,540 | $5 | $0 | $5 | $9 |
| CCP010000014 | A | 81001 | 0 | 1 | 3.22 | 2,540 | $2 | $0 | $2 | $6 |
| CCP010000014 | A | 83001 | 0 | 1 | 1.56 | 2,540 | $8 | $0 | $8 | $12 |
| CCP010000014 | A | 87081 | 0 | 5 | 6.12 | 2,540 | $20 | $0 | $20 | $25 |
| CCP010000014 | A | 86162 | 1 | 0 | 1.38 | 2,540 | $15 | $15 | $0 | $21 |
| CCP010000014 | A | 82248 | 0 | 1 | 4.22 | 2,540 | $2 | $0 | $2 | $9 |
| CCP010000014 | A | 82270 | 0 | 2 | 3.49 | 2,540 | $4 | $0 | $4 | $11 |
| CCP010000014 | A | 85027 | 3 | 12 | 18.72 | 2,540 | $30 | $6 | $24 | $39 |
| CCP010000014 | A | 82040 | 0 | 2 | 3.81 | 2,540 | $10 | $0 | $10 | $21 |
| CCP010000014 | A | 80048 | 0 | 9 | 12.11 | 2,540 | $27 | $0 | $27 | $38 |
| CCP010000014 | A | 87106 | 2 | 0 | 4.91 | 2,540 | $8 | $8 | $0 | $20 |
| CCP010000014 | A | 87186 | 1 | 2 | 5.47 | 2,540 | $15 | $5 | $10 | $28 |
| CCP010000014 | A | 80061 | 2 | 13 | 17.16 | 2,540 | $120 | $16 | $104 | $137 |
| CCP010000014 | A | 84439 | 1 | 1 | 4.50 | 2,540 | $16 | $8 | $8 | $36 |
| CCP010000014 | A | 86225 | 0 | 2 | 3.74 | 2,540 | $24 | $0 | $24 | $45 |
| CCP010000014 | A | 84460 | 0 | 1 | 6.57 | 2,540 | $5 | $0 | $5 | $26 |
| CCP010000014 | A | 86160 | 0 | 1 | 2.73 | 2,540 | $13 | $0 | $13 | $35 |
| CCP010000014 | A | 87252 | 1 | 1 | 3.74 | 2,540 | $30 | $15 | $15 | $56 |
| CCP010000014 | A | 87070 | 2 | 10 | 17.58 | 2,540 | $74 | $12 | $62 | $111 |
| CCP010000014 | A | 88304 | 12 | 1 | 18.03 | 2,540 | $198 | $183 | $15 | $272 |
| CCP010000014 | A | 95044 | 216 | 0 | 437.81 | 2,540 | $1,722 | $1,722 | $0 | $3,460 |
| | A Total | | 1,212 | 488 | 1435.61 | | $34,573 | $27,956 | $6,617 | $25,003 |
| CCP010000014 | M | 99243 | 653 | 18 | 456.36 | 2,540 | $88,094 | $85,793 | $2,301 | $58,791 |
| CCP010000014 | M | 99213 | 1,282 | 283 | 1434.71 | 2,540 | $92,196 | $73,944 | $18,252 | $78,728 |
| CCP010000014 | M | 99203 | 64 | 13 | 19.27 | 2,540 | $10,618 | $9,211 | $1,407 | $1,958 |
| CCP010000014 | M | 99202 | 39 | 1 | 18.58 | 2,540 | $3,687 | $3,618 | $69 | $1,183 |
| CCP010000014 | M | 99214 | 1 | 35 | 29.13 | 2,540 | $3,458 | $88 | $3,370 | $2,578 |
| CCP010000014 | M | 96910 | 23 | 0 | 12.35 | 2,540 | $1,255 | $1,255 | $0 | $637 |
| CCP010000014 | M | 99245 | 0 | 1 | .48 | 2,540 | $239 | $0 | $239 | $110 |
| CCP010000014 | M | 99385 | 0 | 3 | .76 | 2,540 | $168 | $0 | $168 | $43 |
| CCP010000014 | M | 99211 | 0 | 4 | 2.94 | 2,540 | $140 | $0 | $140 | $67 |
| CCP010000014 | M | 99215 | 0 | 2 | 1.49 | 2,540 | $259 | $0 | $259 | $189 |
| CCP010000014 | M | 99204 | 0 | 2 | 1.63 | 2,540 | $294 | $0 | $294 | $235 |
| CCP010000014 | M | 99201 | 0 | 1 | .28 | 2,540 | $61 | $0 | $61 | $11 |
| CCP010000014 | M | 99386 | 0 | 1 | .35 | 2,540 | $56 | $0 | $56 | $19 |
| CCP010000014 | M | 99395 | 0 | 3 | 2.84 | 2,540 | $168 | $0 | $168 | $159 |
| CCP010000014 | M | 99396 | 0 | 5 | 5.02 | 2,540 | $280 | $0 | $280 | $281 |
| CCP010000014 | M | 99394 | 0 | 1 | 1.25 | 2,540 | $56 | $0 | $56 | $70 |
| CCP010000014 | M | 92012 | 0 | 2 | 1.00 | 2,540 | $20 | $0 | $20 | $43 |
| CCP010000014 | M | 99241 | 0 | 2 | 12.52 | 2,540 | $126 | $0 | $126 | $665 |
| CCP010000014 | M | 99242 | 265 | 9 | 293.29 | 2,540 | $27,510 | $26,602 | $908 | $28,438 |

TABLE A11-continued

Dermatology
Dates of Service Jan. 1, 2003-Dec. 31, 2004 paid Dec. 31, 2004
Total role MPPT Meta Drilldown all etg's

| | | | | | | | | | | |
|---|---|---|---|---|---|---|---|---|---|---|
| CCP010000014 | M | 99212 | 118 | 54 | 329.10 | 2,540 | $7,450 | $5,009 | $2,441 | $12,820 |
| | M Total | | 2,445 | 440 | 2622.76 | | $236,135 | $205,520 | $30,615 | $187,026 |
| CCP010000014 | P | Q5P | 10,881 | 1,592 | 10633.52 | 2,540 | $33,903 | $32,099 | $1,804 | $22,958 |
| CCP010000014 | P | W1D | 2,915 | 405 | 1519.47 | 2,540 | $7,180 | $6,449 | $731 | $2,298 |
| CCP010000014 | P | Z2E | 150 | 0 | 92.83 | 2,540 | $1,024 | $1,024 | $0 | $356 |
| CCP010000014 | P | J3301 | 27 | 0 | 23.32 | 2,540 | $672 | $672 | $0 | $177 |
| CCP010000014 | P | Q5H | 315 | 75 | 252.95 | 2,540 | $1,153 | $783 | $370 | $757 |
| CCP010000014 | P | P4L | 90 | 270 | 208.60 | 2,540 | $824 | $201 | $623 | $462 |
| CCP010000014 | P | Q5W | 4,277 | 595 | 4063.45 | 2,540 | $5,507 | $4,650 | $857 | $5,255 |
| CCP010000014 | P | H3D | 0 | 98 | 32.90 | 2,540 | $194 | $0 | $194 | $49 |
| CCP010000014 | P | W1Q | 28 | 0 | 16.09 | 2,540 | $276 | $276 | $0 | $152 |
| CCP010000014 | P | Q8F | 0 | 5 | .21 | 2,540 | $73 | $0 | $73 | $5 |
| CCP010000014 | P | Q4F | 3 | 14 | .86 | 2,540 | $68 | $37 | $31 | $5 |
| CCP010000014 | P | W1W | 912 | 99 | 590.98 | 2,540 | $645 | $450 | $195 | $595 |
| CCP010000014 | P | J1030 | 4 | 0 | .48 | 2,540 | $32 | $32 | $0 | $6 |
| CCP010000014 | P | W3A | 30 | 0 | 88.05 | 2,540 | $224 | $224 | $0 | $199 |
| CCP010000014 | P | L5G | 1,680 | 159 | 1932.06 | 2,540 | $5,162 | $4,643 | $519 | $5,142 |
| CCP010000014 | P | J9A | 0 | 51 | 21.04 | 2,540 | $25 | $0 | $25 | $8 |
| CCP010000014 | P | J9260 | 1 | 0 | .38 | 2,540 | $15 | $15 | $0 | $2 |
| CCP010000014 | P | H2U | 30 | 330 | 202.71 | 2,540 | $48 | $5 | $43 | $36 |
| CCP010000014 | P | H4B | 0 | 338 | 153.76 | 2,540 | $102 | $0 | $102 | $91 |
| CCP010000014 | P | Q5R | 20 | 0 | 37.16 | 2,540 | $159 | $159 | $0 | $151 |
| CCP010000014 | P | H6J | 6 | 14 | 24.32 | 2,540 | $104 | $75 | $29 | $108 |
| CCP010000014 | P | Q8W | 0 | 5 | 8.62 | 2,540 | $18 | $0 | $18 | $25 |
| CCP010000014 | P | S2A | 0 | 60 | 81.65 | 2,540 | $10 | $0 | $10 | $23 |
| CCP010000014 | P | H0A | 0 | 5 | 23.73 | 2,540 | $16 | $0 | $16 | $33 |
| CCP010000014 | P | D1A | 30 | 0 | 47.05 | 2,540 | $65 | $65 | $0 | $100 |
| CCP010000014 | P | Z4B | 90 | 165 | 245.96 | 2,540 | $622 | $201 | $421 | $662 |
| CCP010000014 | P | U6W | 30 | 0 | 58.92 | 2,540 | $16 | $16 | $0 | $62 |
| CCP010000014 | P | J5F | 21 | 0 | 22.80 | 2,540 | $181 | $181 | $0 | $234 |
| CCP010000014 | P | S2B | 396 | 2,558 | 2552.63 | 2,540 | $4,147 | $646 | $3,501 | $4,206 |
| CCP010000014 | P | L3P | 20 | 0 | 44.74 | 2,540 | $72 | $72 | $0 | $135 |
| CCP010000014 | P | H3A | 287 | 707 | 867.53 | 2,540 | $1,068 | $450 | $618 | $1,136 |
| CCP010000014 | P | W4E | 22 | 23 | 110.61 | 2,540 | $31 | $15 | $16 | $104 |
| CCP010000014 | P | P5A | 405 | 227 | 663.78 | 2,540 | $281 | $97 | $184 | $355 |
| CCP010000014 | P | 0 | 15 | 0 | 70.10 | 2,540 | $48 | $48 | $0 | $186 |
| CCP010000014 | P | W1A | 911 | 378 | 1254.69 | 2,540 | $1,343 | $632 | $711 | $1,483 |
| CCP010000014 | P | W3B | 440 | 33 | 265.96 | 2,540 | $1,191 | $1,122 | $69 | $1,339 |
| CCP010000014 | P | V1B | 189 | 88 | 397.09 | 2,540 | $251 | $215 | $36 | $400 |
| CCP010000014 | P | L5E | 0 | 60 | 175.04 | 2,540 | $16 | $0 | $16 | $247 |
| CCP010000014 | P | W1K | 42 | 10 | 97.57 | 2,540 | $220 | $194 | $26 | $475 |
| CCP010000014 | P | Z2A | 3,004 | 2,692 | 6474.40 | 2,540 | $11,822 | $6,103 | $5,719 | $12,298 |
| CCP010000014 | P | R1H | 0 | 30 | 458.54 | 2,540 | $18 | $0 | $18 | $552 |
| CCP010000014 | P | L2A | 0 | 110 | 494.80 | 2,540 | $168 | $0 | $168 | $723 |
| CCP010000014 | P | CL | 1 | 0 | 16.33 | 2,540 | $7 | $7 | $0 | $580 |
| CCP010000014 | P | L9A | 0 | 30 | 388.75 | 2,540 | $84 | $0 | $84 | $975 |
| CCP010000014 | P | W5A | 336 | 17 | 475.66 | 2,540 | $946 | $721 | $225 | $2,237 |
| CCP010000014 | P | Q5F | 1,471 | 544 | 2635.63 | 2,540 | $3,772 | $2,899 | $873 | $5,211 |
| CCP010000014 | P | L1B | 90 | 0 | 220.98 | 2,540 | $829 | $829 | $0 | $3,145 |
| CCP010000014 | P | Q5S | 245 | 0 | 1525.67 | 2,540 | $507 | $507 | $0 | $3,118 |
| CCP010000014 | P | L5A | 90 | 112 | 1990.61 | 2,540 | $167 | $72 | $95 | $3,311 |
| CCP010000014 | P | Q5K | 831 | 210 | 1927.36 | 2,540 | $4,333 | $3,669 | $664 | $8,103 |
| CCP010000014 | P | Z2G | 0 | 70 | 608.80 | 2,540 | $564 | $0 | $564 | $4,562 |
| CCP010000014 | P | W1C | 16,856 | 1,369 | 18512.14 | 2,540 | $21,875 | $20,225 | $1,650 | $28,915 |
| CCP010000014 | P | L9B | 805 | 205 | 4351.76 | 2,540 | $3,079 | $2,548 | $531 | $12,860 |
| CCP010000014 | P | L5H | 85 | 155 | 3074.00 | 2,540 | $592 | $201 | $391 | $10,413 |
| CCP010000014 | P | L5F | 130 | 180 | 2401.95 | 2,540 | $1,495 | $665 | $830 | $11,897 |
| | P Total | | 48,211 | 14,088 | 72441.02 | | $117,244 | $94,194 | $23,050 | $158,917 |
| CCP010000014 | R | 73630 | 0 | 3 | .55 | 2,540 | $90 | $0 | $90 | $14 |
| CCP010000014 | R | 73130 | 0 | 2 | .35 | 2,540 | $62 | $0 | $62 | $9 |
| | R Total | | 0 | 5 | .90 | | $152 | $0 | $152 | $23 |
| CCP010000014 | S | 11401 | 133 | 3 | 38.06 | 2,540 | $15,321 | $15,113 | $208 | $4,022 |
| CCP010000014 | S | 11400 | 123 | 1 | 20.59 | 2,540 | $11,236 | $11,130 | $106 | $1,914 |
| CCP010000014 | S | 11441 | 45 | 1 | 7.16 | 2,540 | $7,057 | $6,909 | $148 | $1,042 |
| CCP010000014 | S | 11440 | 50 | 0 | 12.46 | 2,540 | $6,222 | $6,222 | $0 | $1,458 |
| CCP010000014 | S | 11402 | 88 | 0 | 24.39 | 2,540 | $7,823 | $7,823 | $0 | $3,155 |
| CCP010000014 | S | 11421 | 35 | 0 | 6.68 | 2,540 | $4,541 | $4,541 | $0 | $771 |
| CCP010000014 | S | 11420 | 36 | 0 | 5.05 | 2,540 | $3,087 | $3,087 | $0 | $443 |
| CCP010000014 | S | 11442 | 10 | 1 | 3.77 | 2,540 | $2,277 | $2,094 | $183 | $624 |
| CCP010000014 | S | 11422 | 14 | 0 | 6.02 | 2,540 | $2,280 | $2,280 | $0 | $820 |
| CCP010000014 | S | 11641 | 8 | 0 | 1.31 | 2,540 | $1,549 | $1,549 | $0 | $259 |
| CCP010000014 | S | 11306 | 44 | 0 | 35.19 | 2,540 | $3,015 | $3,015 | $0 | $2,244 |
| CCP010000014 | S | 11643 | 3 | 0 | .59 | 2,540 | $839 | $839 | $0 | $175 |
| CCP010000014 | S | 14040 | 0 | 2 | .59 | 2,540 | $1,008 | $0 | $1,008 | $372 |
| CCP010000014 | S | 11308 | 7 | 0 | 1.11 | 2,540 | $696 | $696 | $0 | $119 |

TABLE A11-continued

Dermatology
Dates of Service Jan. 1, 2003-Dec. 31, 2004 paid Dec. 31, 2004
Total role MPPT Meta Drilldown all etg's

| | | | | | | | | | |
|---|---|---|---|---|---|---|---|---|---|
| CCP010000014 | S | 11307 | 12 | 0 | 6.82 | 2,540 | $1,106 | $1,106 | $0 | $587 |
| CCP010000014 | S | 11603 | 4 | 0 | 1.80 | 2,540 | $749 | $749 | $0 | $290 |
| CCP010000014 | S | 11303 | 6 | 0 | 1.31 | 2,540 | $549 | $549 | $0 | $132 |
| CCP010000014 | S | 11644 | 1 | 0 | .03 | 2,540 | $392 | $392 | $0 | $14 |
| CCP010000014 | S | 11446 | 1 | 0 | .03 | 2,540 | $371 | $371 | $0 | $13 |
| CCP010000014 | S | 11622 | 2 | 0 | .76 | 2,540 | $434 | $434 | $0 | $131 |
| CCP010000014 | S | 11444 | 1 | 0 | .10 | 2,540 | $307 | $307 | $0 | $30 |
| CCP010000014 | S | 14020 | 0 | 1 | .07 | 2,540 | $306 | $0 | $306 | $32 |
| CCP010000014 | S | 11770 | 0 | 1 | .03 | 2,540 | $229 | $0 | $229 | $8 |
| CCP010000014 | S | 13132 | 0 | 1 | .62 | 2,540 | $447 | $0 | $447 | $242 |
| CCP010000014 | S | 11312 | 7 | 0 | 5.71 | 2,540 | $766 | $766 | $0 | $561 |
| CCP010000014 | S | 17110 | 239 | 11 | 284.37 | 2,540 | $15,800 | $15,183 | $617 | $15,602 |
| CCP010000014 | S | 11623 | 1 | 0 | .21 | 2,540 | $244 | $244 | $0 | $47 |
| CCP010000014 | S | 11424 | 1 | 0 | .35 | 2,540 | $244 | $244 | $0 | $73 |
| CCP010000014 | S | 11621 | 2 | 0 | .38 | 2,540 | $188 | $188 | $0 | $54 |
| CCP010000014 | S | 11730 | 0 | 3 | 1.28 | 2,540 | $231 | $0 | $231 | $101 |
| CCP010000014 | S | 11900 | 35 | 0 | 20.14 | 2,540 | $1,075 | $1,075 | $0 | $956 |
| CCP010000014 | S | 11640 | 1 | 0 | .38 | 2,540 | $167 | $167 | $0 | $62 |
| CCP010000014 | S | 56605 | 0 | 1 | .48 | 2,540 | $125 | $0 | $125 | $44 |
| CCP010000014 | S | 11732 | 0 | 2 | .24 | 2,540 | $68 | $0 | $68 | $9 |
| CCP010000014 | S | 20550 | 0 | 1 | .38 | 2,540 | $57 | $0 | $57 | $25 |
| CCP010000014 | S | 11443 | 1 | 0 | .93 | 2,540 | $222 | $222 | $0 | $199 |
| CCP010000014 | S | 11423 | 2 | 0 | 2.18 | 2,540 | $390 | $390 | $0 | $371 |
| CCP010000014 | S | 11601 | 1 | 0 | .86 | 2,540 | $91 | $91 | $0 | $128 |
| CCP010000014 | S | 11602 | 3 | 0 | 3.60 | 2,540 | $491 | $491 | $0 | $542 |
| CCP010000014 | S | 10060 | 3 | 2 | 9.13 | 2,540 | $815 | $396 | $419 | $933 |
| CCP010000014 | S | 11642 | 1 | 0 | 1.49 | 2,540 | $245 | $245 | $0 | $367 |
| CCP010000014 | S | 11403 | 5 | 0 | 6.78 | 2,540 | $755 | $755 | $0 | $1,115 |
| CCP010000014 | S | 17111 | 0 | 2 | 9.06 | 2,540 | $88 | $0 | $88 | $454 |
| CCP010000014 | S | 11310 | 22 | 1 | 31.21 | 2,540 | $1,474 | $1,404 | $70 | $1,875 |
| CCP010000014 | S | 11305 | 22 | 0 | 33.11 | 2,540 | $850 | $850 | $0 | $1,315 |
| CCP010000014 | S | 11101 | 22 | 0 | 33.42 | 2,540 | $871 | $871 | $0 | $1,360 |
| CCP010000014 | S | 12032 | 1 | 0 | 5.71 | 2,540 | $223 | $223 | $0 | $1,197 |
| CCP010000014 | S | 11901 | 4 | 0 | 17.99 | 2,540 | $195 | $195 | $0 | $1,180 |
| CCP010000014 | S | 11302 | 8 | 0 | 24.57 | 2,540 | $683 | $683 | $0 | $1,978 |
| CCP010000014 | S | 11311 | 16 | 0 | 33.32 | 2,540 | $1,328 | $1,328 | $0 | $2,660 |
| CCP010000014 | S | 11300 | 31 | 0 | 63.18 | 2,540 | $1,331 | $1,331 | $0 | $2,783 |
| CCP010000014 | S | 17003 | 242 | 3 | 688.83 | 2,540 | $1,018 | $991 | $27 | $2,706 |
| CCP010000014 | S | 17304 | 0 | 1 | 4.50 | 2,540 | $649 | $0 | $649 | $2,820 |
| CCP010000014 | S | 11301 | 80 | 0 | 107.50 | 2,540 | $4,469 | $4,469 | $0 | $6,709 |
| CCP010000014 | S | 11100 | 33 | 2 | 115.35 | 2,540 | $3,220 | $3,053 | $167 | $9,826 |
| CCP010000014 | S | 17000 | 44 | 3 | 454.90 | 2,540 | $3,145 | $2,955 | $190 | $28,738 |
| | S Total | | 1,450 | 43 | 2136.09 | | $113,359 | $108,016 | $5,343 | $105,691 |
| CCP010000014 | T | 0421 | 3 | 0 | .45 | 2,540 | $375 | $375 | $0 | $42 |
| | T Total | | 3 | 0 | .45 | | $375 | $375 | $0 | $42 |
| CCP010000014 Total | | | 53,321 | 15,064 | 78636.83 | | $501,838 | $436,061 | $65,777 | $476,702 |

| Provider ID | category | services | Total Cost Difference | Total Costs per stratum episodes | Difference per stratum episodes | Your costs per svc | Other costs per svc | Spec costs per svc | episodes this service occurred |
|---|---|---|---|---|---|---|---|---|---|
| CCP010000014 | A | 88305 | $7,752 | $9 | $3 | $31 | $31 | $31 | 414 |
| CCP010000014 | A | CL | $641 | $0 | $0 | $21 | $339 | $36 | 9 |
| CCP010000014 | A | AS | $443 | $0 | $0 | $0 | $599 | $390 | 2 |
| CCP010000014 | A | 93000 | $196 | $0 | $0 | $0 | $44 | $30 | 7 |
| CCP010000014 | A | 82627 | $185 | $0 | $0 | $22 | $22 | $22 | 11 |
| CCP010000014 | A | 00300 | $182 | $0 | $0 | $0 | $360 | $396 | 1 |
| CCP010000014 | A | 84402 | $143 | $0 | $0 | $28 | $28 | $28 | 8 |
| CCP010000014 | A | S0630 | $127 | $0 | $0 | $49 | $0 | $38 | 3 |
| CCP010000014 | A | 83550 | $118 | $0 | $0 | $7 | $7 | $7 | 21 |
| CCP010000014 | A | 88312 | $117 | $0 | $0 | $16 | $16 | $16 | 15 |
| CCP010000014 | A | 95024 | $112 | $0 | $0 | $0 | $6 | $6 | 1 |
| CCP010000014 | A | 95004 | $112 | $0 | $0 | $0 | $4 | $4 | 1 |
| CCP010000014 | A | 86376 | $112 | $0 | $0 | $16 | $16 | $16 | 8 |
| CCP010000014 | A | 84443 | $110 | $0 | $0 | $7 | $7 | $7 | 34 |
| CCP010000014 | A | 86038 | $96 | $0 | $0 | $8 | $8 | $8 | 26 |
| CCP010000014 | A | ER | $95 | $0 | $0 | $145 | $204 | $138 | 6 |
| CCP010000014 | A | A4550 | $95 | $0 | $0 | $49 | $49 | $49 | 2 |
| CCP010000014 | A | 93017 | $86 | $0 | $0 | $0 | $93 | $100 | 1 |
| CCP010000014 | A | 84403 | $76 | $0 | $0 | $20 | $20 | $21 | 9 |
| CCP010000014 | A | 80053 | $71 | $0 | $0 | $5 | $5 | $5 | 31 |
| CCP010000014 | A | 85652 | $65 | $0 | $0 | $2 | $2 | $2 | 38 |
| CCP010000014 | A | 87101 | $64 | $0 | $0 | $8 | $8 | $8 | 22 |
| CCP010000014 | A | 88307 | $61 | $0 | $0 | $68 | $0 | $68 | 1 |
| CCP010000014 | A | A4649 | $60 | $0 | $0 | $73 | $0 | $187 | 1 |

TABLE A11-continued

Dermatology
Dates of Service Jan. 1, 2003-Dec. 31, 2004 paid Dec. 31, 2004
Total role MPPT Meta Drilldown all etg's

| | | | | | | | | |
|---|---|---|---|---|---|---|---|---|
| CCP010000014 | A | 86235 | $60 | $0 | $0 | $8 | $7 | $7 | 9 |
| CCP010000014 | A | 86618 | $45 | $0 | $0 | $12 | $12 | $12 | 5 |
| CCP010000014 | A | 83540 | $41 | $0 | $0 | $3 | $3 | $3 | 22 |
| CCP010000014 | A | 80076 | $38 | $0 | $0 | $3 | $3 | $3 | 22 |
| CCP010000014 | A | 86644 | $37 | $0 | $0 | $0 | $14 | $14 | 3 |
| CCP010000014 | A | 83735 | $30 | $0 | $0 | $0 | $5 | $5 | 3 |
| CCP010000014 | A | 80050 | $29 | $0 | $0 | $14 | $14 | $15 | 9 |
| CCP010000014 | A | 83498 | $29 | $0 | $0 | $0 | $16 | $16 | 3 |
| CCP010000014 | A | 86665 | $26 | $0 | $0 | $0 | $8 | $8 | 1 |
| CCP010000014 | A | 86617 | $24 | $0 | $0 | $0 | $32 | $32 | 1 |
| CCP010000014 | A | 86039 | $24 | $0 | $0 | $9 | $9 | $9 | 5 |
| CCP010000014 | A | 93005 | $16 | $0 | $0 | $54 | $0 | $52 | 1 |
| CCP010000014 | A | 82550 | $12 | $0 | $0 | $0 | $4 | $4 | 4 |
| CCP010000014 | A | 87620 | $12 | $0 | $0 | $0 | $12 | $12 | 1 |
| CCP010000014 | A | 86431 | $11 | $0 | $0 | $4 | $4 | $4 | 5 |
| CCP010000014 | A | 85021 | $11 | $0 | $0 | $11 | $0 | $7 | 1 |
| CCP010000014 | A | 86580 | $10 | $0 | $0 | $0 | $9 | $9 | 2 |
| CCP010000014 | A | 87107 | $9 | $0 | $0 | $0 | $5 | $5 | 2 |
| CCP010000014 | A | 93010 | $8 | $0 | $0 | $31 | $0 | $18 | 1 |
| CCP010000014 | A | 86777 | $7 | $0 | $0 | $0 | $8 | $8 | 1 |
| CCP010000014 | A | 85023 | $7 | $0 | $0 | $0 | $3 | $3 | 3 |
| CCP010000014 | A | 82728 | $7 | $0 | $0 | $0 | $8 | $8 | 4 |
| CCP010000014 | A | 82947 | $6 | $0 | $0 | $2 | $3 | $2 | 6 |
| CCP010000014 | A | 80005 | $4 | $0 | $0 | $0 | $5 | $5 | 1 |
| CCP010000014 | A | 84450 | $4 | $0 | $0 | $0 | $3 | $4 | 5 |
| CCP010000014 | A | 86787 | $4 | $0 | $0 | $0 | $10 | $10 | 1 |
| CCP010000014 | A | 85014 | $4 | $0 | $0 | $5 | $2 | $3 | 3 |
| CCP010000014 | A | 86140 | $3 | $0 | $0 | $0 | $3 | $3 | 2 |
| CCP010000014 | A | 83036 | $3 | $0 | $0 | $0 | $5 | $5 | 3 |
| CCP010000014 | A | 86765 | $3 | $0 | $0 | $0 | $15 | $15 | 1 |
| CCP010000014 | A | 85651 | $2 | $0 | $0 | $2 | $2 | $2 | 9 |
| CCP010000014 | A | 85008 | $2 | $0 | $0 | $0 | $2 | $2 | 1 |
| CCP010000014 | A | 80003 | $2 | $0 | $0 | $0 | $5 | $5 | 1 |
| CCP010000014 | A | 85730 | $2 | $0 | $0 | $0 | $3 | $3 | 2 |
| CCP010000014 | A | 82950 | $2 | $0 | $0 | $0 | $2 | $2 | 1 |
| CCP010000014 | A | 80051 | $2 | $0 | $0 | $0 | $4 | $4 | 1 |
| CCP010000014 | A | 87206 | $1 | $0 | $0 | $0 | $5 | $5 | 1 |
| CCP010000014 | A | 81050 | $1 | $0 | $0 | $0 | $2 | $2 | 1 |
| CCP010000014 | A | 83002 | $1 | $0 | $0 | $0 | $12 | $12 | 1 |
| CCP010000014 | A | 84146 | $0 | $0 | $0 | $0 | $11 | $11 | 1 |
| CCP010000014 | A | 85025 | ($0) | $0 | ($0) | $3 | $3 | $3 | 39 |
| CCP010000014 | A | 86308 | ($0) | $0 | $0 | $0 | $4 | $7 | 1 |
| CCP010000014 | A | 81003 | ($1) | $0 | ($0) | $0 | $1 | $1 | 1 |
| CCP010000014 | A | 84478 | ($1) | $0 | ($0) | $3 | $3 | $3 | 8 |
| CCP010000014 | A | 81000 | ($1) | $0 | ($0) | $6 | $10 | $5 | 2 |
| CCP010000014 | A | 81002 | ($2) | $0 | ($0) | $4 | $4 | $4 | 3 |
| CCP010000014 | A | 83615 | ($3) | $0 | ($0) | $0 | $3 | $4 | 2 |
| CCP010000014 | A | 87210 | ($4) | $0 | ($0) | $7 | $0 | $7 | 27 |
| CCP010000014 | A | 84436 | ($4) | $0 | ($0) | $4 | $0 | $4 | 1 |
| CCP010000014 | A | 82565 | ($4) | $0 | ($0) | $0 | $5 | $4 | 1 |
| CCP010000014 | A | 81001 | ($4) | $0 | ($0) | $0 | $2 | $2 | 1 |
| CCP010000014 | A | 83001 | ($4) | $0 | ($0) | $0 | $8 | $8 | 1 |
| CCP010000014 | A | 87081 | ($5) | $0 | ($0) | $0 | $4 | $4 | 5 |
| CCP010000014 | A | 86162 | ($6) | $0 | ($0) | $15 | $0 | $15 | 1 |
| CCP010000014 | A | 82248 | ($7) | $0 | ($0) | $0 | $2 | $2 | 1 |
| CCP010000014 | A | 82270 | ($7) | $0 | ($0) | $0 | $2 | $3 | 2 |
| CCP010000014 | A | 85027 | ($9) | $0 | ($0) | $2 | $2 | $2 | 15 |
| CCP010000014 | A | 82040 | ($11) | $0 | ($0) | $0 | $5 | $5 | 2 |
| CCP010000014 | A | 80048 | ($11) | $0 | ($0) | $0 | $3 | $3 | 9 |
| CCP010000014 | A | 87106 | ($12) | $0 | ($0) | $4 | $0 | $4 | 2 |
| CCP010000014 | A | 87186 | ($13) | $0 | ($0) | $5 | $5 | $5 | 3 |
| CCP010000014 | A | 80061 | ($17) | $0 | ($0) | $8 | $8 | $8 | 14 |
| CCP010000014 | A | 84439 | ($20) | $0 | ($0) | $8 | $8 | $8 | 2 |
| CCP010000014 | A | 86225 | ($21) | $0 | ($0) | $0 | $12 | $12 | 2 |
| CCP010000014 | A | 84460 | ($21) | $0 | ($0) | $0 | $5 | $4 | 1 |
| CCP010000014 | A | 86160 | ($22) | $0 | ($0) | $0 | $13 | $13 | 1 |
| CCP010000014 | A | 87252 | ($26) | $0 | ($0) | $15 | $15 | $15 | 2 |
| CCP010000014 | A | 87070 | ($37) | $0 | ($0) | $6 | $6 | $6 | 12 |
| CCP010000014 | A | 88304 | ($74) | $0 | ($0) | $15 | $15 | $15 | 9 |
| CCP010000014 | A | 95044 | ($1,738) | $1 | ($1) | $8 | $0 | $8 | 9 |
| | A Total | | $9,570 | $14 | $4 | | | | |
| CCP010000014 | M | 99243 | $29,303 | $35 | $12 | $131 | $128 | $129 | 666 |
| CCP010000014 | M | 99213 | $13,468 | $36 | $5 | $58 | $64 | $55 | 1,303 |
| CCP010000014 | M | 99203 | $8,660 | $4 | $3 | $144 | $108 | $102 | 76 |
| CCP010000014 | M | 99202 | $2,504 | $1 | $1 | $93 | $69 | $64 | 40 |

TABLE A11-continued

Dermatology
Dates of Service Jan. 1, 2003-Dec. 31, 2004 paid Dec. 31, 2004
Total role MPPT Meta Drilldown all etg's

| | | | | | | | | |
|---|---|---|---|---|---|---|---|---|
| CCP010000014 | M | 99214 | $880 | $1 | $0 | $88 | $96 | $89 | 34 |
| CCP010000014 | M | 96910 | $618 | $0 | $0 | $55 | $0 | $52 | 5 |
| CCP010000014 | M | 99245 | $129 | $0 | $0 | $0 | $239 | $228 | 1 |
| CCP010000014 | M | 99385 | $125 | $0 | $0 | $0 | $56 | $56 | 3 |
| CCP010000014 | M | 99211 | $73 | $0 | $0 | $0 | $35 | $23 | 4 |
| CCP010000014 | M | 99215 | $70 | $0 | $0 | $0 | $130 | $127 | 2 |
| CCP010000014 | M | 99204 | $59 | $0 | $0 | $0 | $147 | $144 | 2 |
| CCP010000014 | M | 99201 | $50 | $0 | $0 | $0 | $61 | $41 | 1 |
| CCP010000014 | M | 99386 | $37 | $0 | $0 | $0 | $56 | $56 | 1 |
| CCP010000014 | M | 99395 | $9 | $0 | $0 | $0 | $56 | $56 | 3 |
| CCP010000014 | M | 99396 | ($1) | $0 | ($0) | $0 | $56 | $56 | 5 |
| CCP010000014 | M | 99394 | ($14) | $0 | ($0) | $0 | $56 | $56 | 1 |
| CCP010000014 | M | 92012 | ($23) | $0 | ($0) | $0 | $10 | $43 | 2 |
| CCP010000014 | M | 99241 | ($539) | $0 | ($0) | $0 | $63 | $53 | 2 |
| CCP010000014 | M | 99242 | ($928) | $11 | ($0) | $100 | $101 | $97 | 273 |
| CCP010000014 | M | 99212 | ($5,370) | $3 | ($2) | $42 | $45 | $39 | 164 |
| | M Total | | $49,109 | $93 | $19 | | | | |
| CCP010000014 | P | Q5P | $10,945 | $13 | $4 | $3 | $1 | $2 | 415 |
| CCP010000014 | P | W1D | $4,882 | $3 | $2 | $2 | $2 | $2 | 98 |
| CCP010000014 | P | Z2E | $668 | $0 | $0 | $7 | $0 | $4 | 3 |
| CCP010000014 | P | J3301 | $495 | $0 | $0 | $25 | $0 | $8 | 25 |
| CCP010000014 | P | Q5H | $396 | $0 | $0 | $2 | $5 | $3 | 17 |
| CCP010000014 | P | P4L | $362 | $0 | $0 | $2 | $2 | $2 | 1 |
| CCP010000014 | P | Q5W | $252 | $2 | $0 | $1 | $1 | $1 | 140 |
| CCP010000014 | P | H3D | $145 | $0 | $0 | $0 | $2 | $2 | 2 |
| CCP010000014 | P | W1Q | $124 | $0 | $0 | $10 | $0 | $9 | 2 |
| CCP010000014 | P | Q8F | $68 | $0 | $0 | $0 | $15 | $24 | 1 |
| CCP010000014 | P | Q4F | $63 | $0 | $0 | $12 | $2 | $6 | 1 |
| CCP010000014 | P | W1W | $50 | $0 | $0 | $0 | $2 | $1 | 33 |
| CCP010000014 | P | J1030 | $26 | $0 | $0 | $8 | $0 | $12 | 3 |
| CCP010000014 | P | W3A | $25 | $0 | $0 | $7 | $0 | $2 | 1 |
| CCP010000014 | P | L5G | $20 | $2 | $0 | $3 | $3 | $3 | 71 |
| CCP010000014 | P | J9A | $17 | $0 | $0 | $0 | $0 | $0 | 2 |
| CCP010000014 | P | J9260 | $13 | $0 | $0 | $15 | $0 | $5 | 1 |
| CCP010000014 | P | H2U | $12 | $0 | $0 | $0 | $0 | $0 | 4 |
| CCP010000014 | P | H4B | $11 | $0 | $0 | $0 | $0 | $1 | 5 |
| CCP010000014 | P | Q5R | $8 | $0 | $0 | $8 | $0 | $4 | 5 |
| CCP010000014 | P | H6J | ($4) | $0 | ($0) | $13 | $2 | $4 | 4 |
| CCP010000014 | P | Q8W | ($7) | $0 | ($0) | $0 | $4 | $3 | 1 |
| CCP010000014 | P | S2A | ($13) | $0 | ($0) | $0 | $0 | $0 | 1 |
| CCP010000014 | P | H0A | ($17) | $0 | ($0) | $0 | $3 | $1 | 1 |
| CCP010000014 | P | D1A | ($35) | $0 | ($0) | $2 | $0 | $2 | 1 |
| CCP010000014 | P | Z4B | ($40) | $0 | ($0) | $2 | $3 | $3 | 2 |
| CCP010000014 | P | U6W | ($46) | $0 | ($0) | $1 | $0 | $1 | 1 |
| CCP010000014 | P | J5F | ($53) | $0 | ($0) | $9 | $0 | $10 | 2 |
| CCP010000014 | P | S2B | ($59) | $2 | ($0) | $2 | $1 | $2 | 60 |
| CCP010000014 | P | L3P | ($63) | $0 | ($0) | $4 | $0 | $3 | 2 |
| CCP010000014 | P | H3A | ($68) | $0 | ($0) | $2 | $1 | $1 | 64 |
| CCP010000014 | P | W4E | ($73) | $0 | ($0) | $1 | $1 | $1 | 6 |
| CCP010000014 | P | P5A | ($74) | $0 | ($0) | $0 | $1 | $1 | 28 |
| CCP010000014 | P | 0 | ($138) | $0 | ($0) | $3 | $0 | $3 | 1 |
| CCP010000014 | P | W1A | ($140) | $1 | ($0) | $1 | $2 | $1 | 81 |
| CCP010000014 | P | W3B | ($148) | $0 | ($0) | $3 | $2 | $5 | 19 |
| CCP010000014 | P | V1B | ($149) | $0 | ($0) | $1 | $0 | $1 | 7 |
| CCP010000014 | P | L5E | ($231) | $0 | ($0) | $0 | $0 | $1 | 2 |
| CCP010000014 | P | W1K | ($255) | $0 | ($0) | $5 | $3 | $5 | 9 |
| CCP010000014 | P | Z2A | ($476) | $5 | ($0) | $2 | $2 | $2 | 121 |
| CCP010000014 | P | R1H | ($534) | $0 | ($0) | $0 | $1 | $1 | 1 |
| CCP010000014 | P | L2A | ($555) | $0 | ($0) | $0 | $2 | $1 | 4 |
| CCP010000014 | P | CL | ($573) | $0 | ($0) | $7 | $0 | $36 | 1 |
| CCP010000014 | P | L9A | ($891) | $0 | ($0) | $0 | $3 | $3 | 1 |
| CCP010000014 | P | W5A | ($1,291) | $0 | ($1) | $2 | $13 | $5 | 8 |
| CCP010000014 | P | Q5F | ($1,439) | $1 | ($1) | $2 | $2 | $2 | 90 |
| CCP010000014 | P | L1B | ($2,316) | $0 | ($1) | $9 | $0 | $14 | 1 |
| CCP010000014 | P | Q5S | ($2,611) | $0 | ($1) | $2 | $0 | $2 | 7 |
| CCP010000014 | P | L5A | ($3,144) | $0 | ($1) | $1 | $1 | $2 | 7 |
| CCP010000014 | P | Q5K | ($3,770) | $2 | ($1) | $4 | $3 | $4 | 35 |
| CCP010000014 | P | Z2G | ($3,998) | $0 | ($2) | $0 | $8 | $7 | 3 |
| CCP010000014 | P | W1C | ($7,040) | $9 | ($3) | $1 | $1 | $2 | 272 |
| CCP010000014 | P | L9B | ($9,781) | $1 | ($4) | $3 | $3 | $3 | 40 |
| CCP010000014 | P | L5H | ($9,821) | $0 | ($4) | $2 | $3 | $3 | 8 |
| CCP010000014 | P | L5F | ($10,402) | $1 | ($4) | $5 | $5 | $5 | 11 |
| | P Total | | ($41,673) | $46 | ($16) | | | | |
| CCP010000014 | R | 73630 | $76 | $0 | $0 | $0 | $30 | $24 | 2 |
| CCP010000014 | R | 73130 | $53 | $0 | $0 | $0 | $31 | $26 | 1 |

TABLE A11-continued

Dermatology
Dates of Service Jan. 1, 2003-Dec. 31, 2004 paid Dec. 31, 2004
Total role MPPT Meta Drilldown all etg's

|  |  |  |  |  |  |  |  |  |
|---|---|---|---|---|---|---|---|---|
|  | R Total |  | $129 | $0 | $0 |  |  |  |
| CCP010000014 | S | 11401 | $11,299 | $6 | $4 | $114 | $69 | $106 | 105 |
| CCP010000014 | S | 11400 | $9,322 | $4 | $4 | $90 | $106 | $93 | 101 |
| CCP010000014 | S | 11441 | $6,015 | $3 | $2 | $154 | $148 | $145 | 42 |
| CCP010000014 | S | 11440 | $4,764 | $2 | $2 | $124 | $0 | $117 | 39 |
| CCP010000014 | S | 11402 | $4,668 | $3 | $2 | $89 | $0 | $129 | 47 |
| CCP010000014 | S | 11421 | $3,770 | $2 | $1 | $130 | $0 | $115 | 31 |
| CCP010000014 | S | 11420 | $2,644 | $1 | $1 | $86 | $0 | $88 | 29 |
| CCP010000014 | S | 11442 | $1,653 | $1 | $1 | $209 | $183 | $166 | 11 |
| CCP010000014 | S | 11422 | $1,460 | $1 | $1 | $163 | $0 | $136 | 13 |
| CCP010000014 | S | 11641 | $1,290 | $1 | $1 | $194 | $0 | $197 | 8 |
| CCP010000014 | S | 11306 | $771 | $1 | $0 | $69 | $0 | $64 | 31 |
| CCP010000014 | S | 11643 | $664 | $0 | $0 | $280 | $0 | $297 | 3 |
| CCP010000014 | S | 14040 | $636 | $0 | $0 | $0 | $504 | $633 | 1 |
| CCP010000014 | S | 11308 | $577 | $0 | $0 | $99 | $0 | $108 | 7 |
| CCP010000014 | S | 11307 | $519 | $0 | $0 | $92 | $0 | $86 | 10 |
| CCP010000014 | S | 11603 | $459 | $0 | $0 | $187 | $0 | $161 | 3 |
| CCP010000014 | S | 11303 | $417 | $0 | $0 | $92 | $0 | $100 | 4 |
| CCP010000014 | S | 11644 | $378 | $0 | $0 | $392 | $0 | $392 | 1 |
| CCP010000014 | S | 11446 | $358 | $0 | $0 | $371 | $0 | $371 | 1 |
| CCP010000014 | S | 11622 | $303 | $0 | $0 | $217 | $0 | $172 | 2 |
| CCP010000014 | S | 11444 | $277 | $0 | $0 | $307 | $0 | $289 | 1 |
| CCP010000014 | S | 14020 | $274 | $0 | $0 | $0 | $306 | $459 | 1 |
| CCP010000014 | S | 11770 | $221 | $0 | $0 | $0 | $229 | $229 | 1 |
| CCP010000014 | S | 13132 | $205 | $0 | $0 | $0 | $447 | $389 | 1 |
| CCP010000014 | S | 11312 | $205 | $0 | $0 | $109 | $0 | $98 | 7 |
| CCP010000014 | S | 17110 | $198 | $6 | $0 | $64 | $56 | $55 | 137 |
| CCP010000014 | S | 11623 | $197 | $0 | $0 | $244 | $0 | $228 | 1 |
| CCP010000014 | S | 11424 | $171 | $0 | $0 | $244 | $0 | $212 | 1 |
| CCP010000014 | S | 11621 | $134 | $0 | $0 | $94 | $0 | $143 | 1 |
| CCP010000014 | S | 11730 | $130 | $0 | $0 | $0 | $77 | $79 | 2 |
| CCP010000014 | S | 11900 | $119 | $0 | $0 | $31 | $0 | $47 | 32 |
| CCP010000014 | S | 11640 | $105 | $0 | $0 | $167 | $0 | $164 | 1 |
| CCP010000014 | S | 56605 | $81 | $0 | $0 | $0 | $125 | $90 | 1 |
| CCP010000014 | S | 11732 | $59 | $0 | $0 | $0 | $34 | $36 | 1 |
| CCP010000014 | S | 20550 | $32 | $0 | $0 | $0 | $57 | $67 | 1 |
| CCP010000014 | S | 11443 | $23 | $0 | $0 | $222 | $0 | $213 | 1 |
| CCP010000014 | S | 11423 | $19 | $0 | $0 | $195 | $0 | $170 | 2 |
| CCP010000014 | S | 11601 | ($37) | $0 | ($0) | $91 | $0 | $148 | 1 |
| CCP010000014 | S | 11602 | ($51) | $0 | ($0) | $164 | $0 | $151 | 3 |
| CCP010000014 | S | 10060 | ($118) | $0 | ($0) | $132 | $210 | $102 | 4 |
| CCP010000014 | S | 11642 | ($122) | $0 | ($0) | $245 | $0 | $247 | 1 |
| CCP010000014 | S | 11403 | ($360) | $0 | ($0) | $151 | $0 | $164 | 5 |
| CCP010000014 | S | 17111 | ($366) | $0 | ($0) | $0 | $44 | $50 | 1 |
| CCP010000014 | S | 11310 | ($401) | $1 | ($0) | $64 | $70 | $60 | 18 |
| CCP010000014 | S | 11305 | ($465) | $0 | ($0) | $39 | $0 | $40 | 14 |
| CCP010000014 | S | 11101 | ($489) | $0 | ($0) | $40 | $0 | $41 | 19 |
| CCP010000014 | S | 12032 | ($974) | $0 | ($0) | $223 | $0 | $210 | 1 |
| CCP010000014 | S | 11901 | ($985) | $0 | ($0) | $49 | $0 | $66 | 4 |
| CCP010000014 | S | 11302 | ($1,295) | $0 | ($1) | $85 | $0 | $81 | 7 |
| CCP010000014 | S | 11311 | ($1,332) | $1 | ($1) | $83 | $0 | $80 | 13 |
| CCP010000014 | S | 11300 | ($1,452) | $1 | ($1) | $43 | $0 | $44 | 19 |
| CCP010000014 | S | 17003 | ($1,688) | $0 | ($1) | $4 | $9 | $4 | 38 |
| CCP010000014 | S | 17304 | ($2,171) | $0 | ($1) | $0 | $649 | $627 | 1 |
| CCP010000014 | S | 11301 | ($2,240) | $2 | ($1) | $56 | $0 | $62 | 50 |
| CCP010000014 | S | 11100 | ($6,606) | $1 | ($3) | $93 | $84 | $85 | 35 |
| CCP010000014 | S | 17000 | ($25,593) | $1 | ($10) | $67 | $63 | $63 | 44 |
|  | S Total |  | $7,668 | $45 | $3 |  |  |  |  |
| CCP010000014 | T | 0421 | $333 | $0 | $0 | $125 | $0 | $94 | 1 |
|  | T Total |  | $333 | $0 | $0 |  |  |  |  |
| CCP010000014 Total |  |  | $25,136 | $198 |  |  | $10 |  |  |

TABLE B1

Allergy
Dates of service Jan. 1, 2003-Dec. 31, 2004 paid Dec. 31, 2004
Actual physician names and IDs removed
Allergic Rhinitis etg 0332

| doctor | id list | total role episode count | Responsible expense | total role expense | Responsible average per episode | Total role expense per episode | cost rank | QUINTILE |
|---|---|---|---|---|---|---|---|---|
| 1 | CCP010000013 | 181 | $93,363 | $115,782 | $516 | $640 | 1 | Q1 |
| 2 | CCP010000004 | 127 | $72,348 | $84,166 | $570 | $663 | 2 | Q1 |
| 3 | CCP010000011 | 164 | $100,182 | $113,283 | $611 | $691 | 3 | Q1 |
| 4 | CCP010000007 | 76 | $36,371 | $52,780 | $479 | $694 | 4 | Q2 |
| 5 | CCP010000015 | 194 | $93,695 | $135,933 | $483 | $701 | 5 | Q2 |
| 6 | CCP010000005 | 80 | $42,292 | $56,626 | $529 | $708 | 6 | Q2 |
| 7 | CCP010000009 | 603 | $329,485 | $430,038 | $546 | $713 | 7 | Q3 |
| 8 | CCP010000001 | 140 | $88,318 | $100,009 | $631 | $714 | 8 | Q3 |
| 9 | CCP010000008 | 200 | $89,377 | $143,388 | $447 | $717 | 9 | Q3 |
| 10 | CCP010000003 | 65 | $36,455 | $48,193 | $561 | $741 | 10 | Q4 |
| 11 | CCP010000002 | 160 | $68,220 | $119,405 | $426 | $746 | 11 | Q4 |
| 12 | CCP010000010 | 206 | $128,860 | $155,119 | $626 | $753 | 12 | Q4 |
| 13 | CCP010000014 | 149 | $95,622 | $118,949 | $642 | $798 | 13 | Q4 |
| 14 | CCP010000012 | 109 | $74,708 | $90,000 | $685 | $826 | 14 | Q5 |
| 15 | CCP010000006 | 65 | $44,481 | $54,945 | $684 | $845 | 15 | Q5 |
| 16 | CCP010000016 | 63 | $43,554 | $55,351 | $691 | $879 | 16 | Q5 |

Note:
physician 10 assigned to Q4 because total costs per episode were more similar to Q4 than to Q3.

TABLE B2

Total Role Allergic Rhinitis ETGno 0332 by quintile
Each doctor with greater than or equal to 50 episodes
(3 doctors per Quintile, 4 in Q4)

| quintile | category | services | PROC_DESC | Total Svcs | Your Svcs | Other Svcs |
|---|---|---|---|---|---|---|
| Q1 | A | 95004 | ALLERGY TESTS, PERCUTANEOUS, ALLERGENIC EXTRACTS, SPECIFY NUMBER | 5,249 | 5,249 | 0 |
| Q1 | A | 95024 | ALLERGY TESTS, INTRADERMAL, ALLERGENIC EXTRACTS, SPECIFY NUMBER | 1,809 | 1,809 | 0 |
| Q1 | A | 94150 | VITAL CAPACITY, TOTAL (SEP PROC) | 10 | 0 | 10 |
| Q1 | A | 86003 | ALLERGEN SPECIFIC IGE; QUANTITATIVE/SEMIQUANTITATIVE, EACH ALLERGEN | 167 | 0 | 167 |
| Q1 | A | 82785 | GAMMAGLOBULIN; IGE | 13 | 0 | 13 |
| . | . | . | . | . | . | . |
| Q1 | A | 80053 | COMPREHENSIVE METABOLIC PANEL | 5 | 0 | 5 |
| Q1 | A | 90782 | THERAPEUTIC/PROPHYLACTIC/DX INJECTION (SPECIFY MATL INJECTED); SUBQ/IM | 2 | 0 | 2 |
| Q1 | A | 95010 | ALLERGY TESTS, PERCUTANEOUS, SEQUENTIAL/INCREMENTAL, SPECIFY NUMBER | 16 | 16 | 0 |
| Q1 | A | 95015 | ALLERGY TESTS, INTRADERMAL, SEQUENTIAL/INCREMENTAL, SPECIFY | 16 | 16 | 0 |
| Q1 | A | ER | Emergency | 2 | 2 | 0 |
| | A Total | | | 7,390 | 7,123 | 267 |
| Q1 | M | 99244 | OFFICE CONSULTATION, 3 KEY COMPONENTS: COMPREHENSIVE HX; COMPREHENSIVE E | 49 | 46 | 3 |
| Q1 | M | 99214 | OFFICE/OP VISIT, EST PT, 2 KEY COMPONENTS: DETAILED HX; DETAILED HX; DETAILED EXAM; | 168 | 158 | 10 |
| Q1 | M | 95145 | PROFES SVC, SUPERVIS, PREPARA, PROVISION, ANTIGEN, ALLERGEN IMMUNOTHERA | 80 | 80 | 0 |
| . | . | . | . | . | . | . |
| Q1 | M | 99211 | OFFICE/OP VISIT, EST PT, NOT REQUIRING PHYSICIAN PRESENCE, TYPICALLY 5 | 11 | 0 | 11 |
| Q1 | M | 99212 | OFFICE/OP VISIT, EST PT, 2 KEY COMPONENTS: PROB FOCUS HX; PROB FOCUS EX | 8 | 3 | 5 |
| Q1 | M | 99243 | OFFICE CONSULTATION, 3 KEY COMPONENTS: DETAILED HX; DETAILED EXAM; MED | 35 | 35 | 0 |
| Q1 | M | 99213 | OFFICE/OP, VISIT, EST PT, 2 KEY COMPONENTS: EXPAND PROB HX; EXPAND PROB | 259 | 125 | 134 |
| Q1 | M | 95147 | PROFESSIONAL SVC, SUPERVISION, PROVISION, ANTIGENS, ALLERGEN IMMUNOTHER | 20 | 20 | 0 |

TABLE B2-continued

Total Role Allergic Rhinitis ETGno 0332 by quintile
Each doctor with greater than or equal to 50 episodes
(3 doctors per Quintile, 4 in Q4)

| Q1 | M | 95115 | PROFESSIONAL SVC, ALLERGEN IMMUNOTHERAPY NON-PROVISION EXTRACTS; SINGLE | 222 | 171 | 51 |
|---|---|---|---|---|---|---|
| Q1 | M | 95165 | PROFES SVC, SUPERVIS, PREPARA, PROVISION, ANTIGENS, ALLERGEN IMMUNOTHER | 5,342 | 5,012 | 330 |
| Q1 | M | 95117 | PROFESSIONAL SVC, ALLERGEN IMMUNOTHERAPY NON-PROVISION EXTRACTS; 2+ INJ | 3,059 | 2,391 | 668 |
| | M Total | | | 9,275 | 8,041 | 1,234 |
| Q1 | P | Q7P | NASAL ANTI-INFLAMMATORY STEROIDS | 24,703 | 21,712 | 2,991 |
| Q1 | P | Z4B | LEUKOTRIENE RECEPTOR ANTAGONISTS | 2,080 | 1,660 | 420 |
| Q1 | P | Z2A | ANTIHISTAMINES | 22,109 | 16,777 | 5,332 |
| Q1 | P | Q7E | NASAL ANTIHISTAMINE | 550 | 550 | 0 |
| Q1 | P | Q7A | NOSE PREPARATIONS, MISCELLANEOUS (RX) | 30 | 30 | 0 |
| Q1 | P | B3J | EXPECTORANTS | 49 | 0 | 49 |
| Q1 | P | P5A | GLUCOCORTICOIDS | 42 | 30 | 12 |
| Q1 | P | Q6R | EYE ANTIHISTAMINES | 448 | 313 | 135 |
| Q1 | P | B3K | COUGH AND/OR COLD PREPARATIONS | 108 | 30 | 78 |
| | P Total | | | 50,119 | 41,102 | 9,017 |
| Q1 | R | 76375 | CORONAL/SAGITTAL/MULTIPLANAR/OBLIQUE/3D/HOLOGRAPHIC CT/MRI OTHER RECONS | 1 | 0 | 1 |
| Q1 | R | 70210 | RADIOLOGIC EXAM, SINUSES, PARANASAL, <3 VIEWS | 2 | 1 | 1 |
| Q1 | R | 70486 | CT SCAN, MAXILLOFACIAL AREA; W/O CONTRAST MATL | 1 | 0 | 1 |
| Q1 | R | 71020 | RADIOLOGIC EXAM, CHEST, 2 VIEWS, FRONTAL & LATERAL | 3 | 0 | 3 |
| | R Total | | | 7 | 1 | 6 |
| Q1 | S | 31231 | NASAL ENDOSCOPY, DX, UNILAT/BILAT (SEP PROC) | 2 | 2 | 0 |
| | S Total | | | 2 | 2 | 0 |
| | Q1 Total | | | 66,793 | 56,269 | 10,524 |
| Q2 | A | 95004 | ALLERGY TESTS, PERCUTANEOUS, ALLERGENIC EXTRACTS, SPECIFY NUMBER | 3,812 | 3,812 | 0 |
| Q2 | A | 95010 | ALLERGY TESTS, PERCUTANEOUS, SEQUENTIAL/INCREMENTAL, SPECIFY NUMBER | 90 | 90 | 0 |
| Q2 | A | 95024 | ALLERGY TESTS, INTRADERMAL, ALLERGENIC EXTRACTS, SPECIFY NUMBER | 1,539 | 1,539 | 0 |
| Q2 | A | 95015 | ALLERGY TESTS, INTRADERMAL, SEQUENTIAL/INCREMENTAL, SPECIFY NUMBER | 81 | 81 | 0 |
| Q2 | A | 87799 | INFECTIOUS AGENT, NUCLEIC ACID (DNA/RNA), NOS; QUANTIFICATION EA ORGAN | 1 | 1 | 0 |
| Q2 | A | 95070 | INHALATION BRONCHIAL CHALLENGE TESTS; W/HISTAMINE/METHACHOLINE | 1 | 1 | 0 |
| Q2 | A | 90782 | THERAPEUTIC/PROPHYLACTIC/DX INJECTION (SPECIFY MATL INJECTED); SUBQ/IM | 15 | 0 | 15 |
| Q2 | A | 85025 | BLOOD COUNT; COMPLETE CBC, AUTOMATED (HGB, HCT, RBC, WBC, & PLATELET) & | 11 | 1 | 10 |
| . | . | . | . | . | . | . |
| . | . | . | . | . | . | . |
| . | . | . | . | . | . | . |
| Q2 | A | CL | Clinic/Treatment/Testing | 1 | 0 | 1 |
| Q2 | A | 94010 | SPIROMETRY W/GRAPHIC RECORD/VITAL CAPACITY/FLOW RATE W/WO MAXIMAL VOLUN | 5 | 4 | 1 |
| Q2 | A | ER | Emergency | 1 | 0 | 1 |
| | A Total | | | 5,651 | 5,532 | 119 |
| Q2 | M | 95165 | PROFES SVC, SUPERVIS, PREPARA, PROVISION, ANTIGENS, ALLERGEN IMMUNOTHER | 6,420 | 6,300 | 120 |
| Q2 | M | 95115 | PROFESSIONAL SVC, ALLERGEN IMMUNOTHERAPY NON-PROVISION EXTRACTS; SINGLE | 577 | 231 | 346 |
| Q2 | M | 99242 | OFFICE CONSULTATION, 3 KEY COMPONENTS: EXPAND PROB FOCUS HX;EXPAND PROB | 22 | 22 | 0 |
| Q2 | M | 99215 | OFFICE/OP VISIT, EST PT, 2 KEY COMPONENTS: COMPREHENSIVE HX; COMPREHENSIV | 5 | 4 | 1 |
| Q2 | M | 99205 | OFFICE/OP VISIT, NEW PT, 3 KEY COMPONENTS: COMPREHENSIVE HX; COMPREHENSIV | 1 | 1 | 0 |
| Q2 | M | 99396 | PERIODIC COMPREHENSIVE PREVENTIVE MEDICINE E&M W/HX/EXAM, EST PT; 40-64 | 5 | 0 | 5 |
| . | . | . | . | . | . | . |
| . | . | . | . | . | . | . |
| . | . | . | . | . | . | . |
| Q2 | M | 95145 | PROFES SVC, SUPERVIS, PREPARA, PROVISION, ANTIGEN, ALLERGEN IMMUNOTHERA | 30 | 20 | 10 |
| Q2 | M | 95147 | PROFESSIONAL SVC, SUPERVISION, PROVISION, ANTIGENS, ALLERGEN IMMUNOTHER | 20 | 10 | 10 |
| Q2 | M | 99214 | OFFICE/OP VISIT, EST PT, 2 KEY COMPONENTS: DETAILED HX; DETAILED EXAM; | 67 | 48 | 19 |
| Q2 | M | 99213 | OFFICE/OP VISIT, EST PT, 2 KEY COMPONENTS: EXPAND PROB HX; EXPAND PROB | 172 | 57 | 115 |
| Q2 | M | 99244 | OFFICE CONSULTATION, 3 KEY COMPONENTS: COMPREHENSIVE HX; COMPREHENSIVE E | 6 | 6 | 0 |

TABLE B2-continued

Total Role Allergic Rhinitis ETGno 0332 by quintile
Each doctor with greater than or equal to 50 episodes
(3 doctors per Quintile, 4 in Q4)

| | | | | | | |
|---|---|---|---|---|---|---|
| Q2 | M | 95117 | PROFESSIONAL SVC, ALLERGEN IMMUNOTHERAPY NON-PROVISION EXTRACTS; 2+ INJ | 2,823 | 1,081 | 1,742 |
| | M Total | | | 10,225 | 7,814 | 2,411 |
| Q2 | P | Z4B | LEUKOTRIENE RECEPTOR ANTAGONISTS | 1,124 | 690 | 434 |
| Q2 | P | Q6R | EYE ANTIHISTAMINES | 437 | 191 | 246 |
| . | . | . | . | . | . | . |
| . | . | . | . | . | . | . |
| . | . | . | . | . | . | . |
| Q2 | P | B3J | EXPECTORANTS | 85 | 30 | 55 |
| Q2 | P | P5A | GLUCOCORTICOIDS | 10 | 0 | 10 |
| Q2 | P | Z2A | ANTIHISTAMINES | 13,602 | 8,778 | 4,824 |
| Q2 | P | Q7P | NASAL ANTI-INFLAMMATORY STEROIDS | 7,740 | 4,472 | 3,268 |
| | P Total | | | 23,853 | 14,740 | 9,113 |
| Q2 | R | 70486 | CT SCAN, MAXILLOFACIAL AREA; W/O CONTRAST MATL | 3 | 1 | 2 |
| Q2 | R | 70250 | RADIOLOGIC EXAM, SKULL; <4 VIEWS | 1 | 1 | 0 |
| Q2 | R | 71020 | RADIOLOGIC EXAM, CHEST, 2 VIEWS, FRONTAL & LATERAL | 3 | 1 | 2 |
| | R Total | | | 7 | 3 | 4 |
| Q2 Total | | | | 39,736 | 28,089 | 11,647 |
| Q3 | A | 94010 | SPIROMETRY W/GRAPHIC RECORD/VITAL CAPACITY/FLOW RATE W/WO MAXIMAL VOLUN | 36 | 32 | 4 |
| Q3 | A | A0427 | Ambulance service, advanced life support, emergency transport, level 1 ( | 1 | 1 | 0 |
| Q3 | A | A0429 | Ambulance service, basic life support, emergency transport (BLS —emerge | 1 | 1 | 0 |
| Q3 | A | A0432 | Paramedic intercept (PI), rural area, transport furnished by a volunteer | 1 | 1 | 0 |
| . | . | . | . | . | . | . |
| . | . | . | . | . | . | . |
| . | . | . | . | . | . | . |
| Q3 | A | 94150 | VITAL CAPACITY, TOTAL (SEP PROC) | 4 | 0 | 4 |
| Q3 | A | 82785 | GAMMAGLOBULIN; IGE | 3 | 2 | 1 |
| Q3 | A | ER | Emergency | 9 | 5 | 4 |
| Q3 | A | 86003 | ALLERGEN SPECIFIC IGE; QUANTITATIVE/SEMIQUANTITATIVE, EACH ALLERGEN | 41 | 32 | 9 |
| Q3 | A | 95015 | ALLERGY TESTS, INTRADERMAL, SEQUENTIAL/INCREMENTAL, SPECIFY NUMBER | 6 | 6 | 0 |
| Q3 | A | 95024 | ALLERGY TESTS, INTRADERMAL, ALLERGENIC EXTRACTS, SPECIFY NUMBER | 2,969 | 2,880 | 89 |
| Q3 | A | 95004 | ALLERGY TESTS, PERCUTANEOUS, ALLERGENIC EXTRACTS, SPECIFY NUMBER | 5,661 | 5,465 | 196 |
| | A Total | | | 8,969 | 8,458 | 511 |
| Q3 | M | 95117 | PROFESSIONAL SVC, ALLERGEN IMMUNOTHERAPY NON-PROVISION EXTRACTS; 2+ INJ | 11,361 | 7,460 | 3,901 |
| Q3 | M | 95165 | PROFES SVC, SUPERVIS, PREPARA, PROVISION, ANTIGENS, ALLERGEN IMMUNOTHER | 19,554 | 19,034 | 520 |
| Q3 | M | 95115 | PROFESSIONAL SVC, ALLERGEN IMMUNOTHERAPY NON-PROVISION EXTRACTS; SINGLE | 1,224 | 487 | 737 |
| Q3 | M | 99212 | OFFICE/OP VISIT, EST PT, 2 KEY COMPONENTS: PROB FOCUS HX; PROB FOCUS EX | 73 | 57 | 16 |
| Q3 | M | 99213 | OFFICE/OP VISIT, EST PT, 2 KEY COMPONENTS: EXPAND PROB HX; EXPAND PROB | 572 | 314 | 258 |
| . | . | . | . | . | . | . |
| . | . | . | . | . | . | . |
| . | . | . | . | . | . | . |
| Q3 | M | 99211 | OFFICE/OP VISIT, EST PT, NOT REQUIRING PHYSICIAN PRESENCE, TYPICALLY 5 | 55 | 4 | 51 |
| Q3 | M | 99215 | OFFICE/OP VISIT, EST PT, 2 KEY COMPONENTS: COMPREHENSIVE HX; COMPREHENSIV | 2 | 2 | 0 |
| Q3 | M | 99242 | OFFICE CONSULTATION, 3 KEY COMPONENTS: EXPAND PROB FOCUS HX;EXPAND PROB | 1 | 0 | 1 |
| Q3 | M | 99243 | OFFICE CONSULTATION, 3 KEY COMPONENTS: DETAILED HX; DETAILED EXAM; MED | 76 | 72 | 4 |
| Q3 | M | 99244 | OFFICE CONSULTATION, 3 KEY COMPONENTS: COMPREHENSIVE HX; COMPREHENSIVE E | 34 | 30 | 4 |
| Q3 | M | 95145 | PROFES SVC, SUPERVIS, PREPARA, PROVISION, ANTIGEN, ALLERGEN IMMUNOTHERA | 32 | 20 | 12 |
| Q3 | M | 95147 | PROFESSIONAL SVC, SUPERVISION, PROVISION, ANTIGENS, ALLERGEN IMMUNOTHERA | 29 | 29 | 0 |
| Q3 | M | 99214 | OFFICE/OP VISIT, EST PT, 2 KEY COMPONENTS: DETAILED HX; DETAILED EXAM; | 91 | 52 | 39 |
| | M Total | | | 33,135 | 27,561 | 5,574 |
| Q3 | P | B3J | EXPECTORANTS | 178 | 59 | 119 |
| Q3 | P | B3K | COUGH AND/OR COLD PREPARATIONS | 378 | 229 | 149 |
| Q3 | P | P5A | GLUCOCORTICOIDS | 34 | 20 | 14 |
| Q3 | P | Q6R | EYE ANTIHISTAMINES | 600 | 472 | 128 |
| Q3 | P | Q7E | NASAL ANTIHISTAMINE | 517 | 457 | 60 |
| Q3 | P | Z4B | LEUKOTRIENE RECEPTOR ANTAGONISTS | 1,620 | 750 | 870 |
| Q3 | P | Q7P | NASAL ANTI-INFLAMMATORY STEROIDS | 22,039 | 15,841 | 6,198 |

TABLE B2-continued

Total Role Allergic Rhinitis ETGno 0332 by quintile
Each doctor with greater than or equal to 50 episodes
(3 doctors per Quintile, 4 in Q4)

| | | | | | | |
|---|---|---|---|---|---|---|
| Q3 | P | Z2A | ANTIHISTAMINES | 29,922 | 19,060 | 10,862 |
| | | P Total | | 55,288 | 36,888 | 18,400 |
| Q3 | R | 70450 | CT SCAN, HEAD/BRAIN; W/O CONTRAST MATL | 2 | 0 | 2 |
| Q3 | R | 70160 | RADIOLOGIC EXAM, NASAL BONES, COMPLETE, MINIMUM, 3 VIEWS | 1 | 0 | 1 |
| Q3 | R | 71020 | RADIOLOGIC EXAM, CHEST, 2 VIEWS, FRONTAL & LATERAL | 4 | 1 | 3 |
| Q3 | R | 70486 | CT SCAN, MAXILLOFACIAL AREA; W/O CONTRAST MATL | 1 | 0 | 1 |
| | | R Total | | 8 | 1 | 7 |
| | Q3 Total | | | 97,400 | 72,908 | 24,492 |
| Q4 | A | 95004 | ALLERGY TESTS, PERCUTANEOUS, ALLERGENIC EXTRACTS, SPECIFY NUMBER | 5,563 | 5,477 | 86 |
| Q4 | A | CL | Clinic/Treatment/Testing | 1 | 1 | 0 |
| Q4 | A | 86003 | ALLERGEN SPECIFIC IGE; QUANTITATIVE/SEMIQUANTITATIVE, EACH ALLERGEN | 122 | 14 | 108 |
| Q4 | A | 94010 | SPIROMETRY W/GRAPHIC RECORD/VITAL CAPACITY/FLOW RATE W/WO IMMUNOTHER | 19 | 17 | 2 |
| Q4 | A | 92557 | COMPREHENSIVE AUDIOMETRY THRESHOLD VAL & SPEECH RECOGNITION | 1 | 0 | 1 |
| . | . | . | . | . | . | . |
| . | . | . | . | . | . | . |
| . | . | . | . | . | . | . |
| Q4 | A | 80053 | COMPREHENSIVE METABOLIC PANEL | 6 | 1 | 5 |
| Q4 | A | 80050 | GENERAL HEALTH PANEL | 2 | 1 | 1 |
| Q4 | A | 90782 | THERAPEUTIC/PROPHYLACTIC/DX INJECTION (SPECIFY MATL INJECTED); SUBQ/IM | 5 | 1 | 4 |
| Q4 | A | 95015 | ALLERGY TESTS, INTRADERMAL, SEQUENTIAL/INCREMENTAL, SPECIFY NUMBER | 20 | 20 | 0 |
| Q4 | A | 95010 | ALLERGY TESTS, PERCUTANEOUS, SEQUENTIAL/INCREMENTAL, SPECIFY NUMBER | 10 | 10 | 0 |
| Q4 | A | 95024 | ALLERGY TESTS, INTRADERMAL, ALLERGENIC EXTRACTS, SPECIFY NUMBER | 1,957 | 1,949 | 8 |
| | A Total | | | 7,822 | 7,505 | 317 |
| Q4 | M | 99214 | OFFICE/OP VISIT, EST PT, 2 KEY COMPONENTS: DETAILED HX; DETAILED EXAM; | 258 | 216 | 42 |
| Q4 | M | 95147 | PROFESSIONAL SVC, SUPERVISION, PROVISION, ANTIGENS, ALLERGEN IMMUNOTHER | 130 | 110 | 20 |
| Q4 | M | 95145 | PROFES SVC, SUPERVIS, PREPARA, PROVISION, ANTIGEN, ALLERGEN IMMUNOTHERA | 131 | 121 | 10 |
| Q4 | M | 99243 | OFFICE CONSULTATION, 3 KEY COMPONENTS: DETAILED HX; DETAILED EXAM; MED | 58 | 57 | 1 |
| Q4 | M | 99211 | OFFICE/OP VISIT, EST PT, NOT REQUIRING PHYSICIAN PRESENCE, TYPICALLY 5 | 61 | 2 | 59 |
| Q4 | M | 99215 | OFFICE/OP VISIT, EST PT, 2 KEY COMPONENTS: COMPREHENSIVE HX; COMPREHENSIV | 5 | 4 | 1 |
| . | . | . | . | . | . | . |
| . | . | . | . | . | . | . |
| . | . | . | . | . | . | . |
| Q4 | M | 99213 | OFFICE/OP VISIT, EST PT, 2 KEY COMPONENTS: EXPAND PROB HX; EXPAND PROB | 333 | 152 | 181 |
| Q4 | M | 99242 | OFFICE CONSULTATION, 3 KEY COMPONENTS: EXPAND PROB FOCUS H EXPAND PROB | 2 | 1 | 1 |
| Q4 | M | 99212 | OFFICE/OP VISIT, EST PT, 2 KEY COMPONENTS: PROB FOCUS HX; PROB | 10 | 3 | 7 |
| Q4 | M | ER | Emergency | 1 | 0 | 1 |
| Q4 | M | 95115 | PROFESSIONAL SVC, ALLERGEN IMMUNOTHERAPY NON-PROVISION EXTRACTS; SINGLE | 485 | 215 | 270 |
| Q4 | M | 95165 | PROFES SVC, SUPERVIS, PREPARA, PROVISION, ANTIGENS, ALLERGEN IMMUNOTHER | 9,894 | 9,014 | 880 |
| Q4 | M | 95117 | PROFESSIONAL SVC, ALLERGEN IMMUNOTHERAPY NON-PROVISION EXTRACTS; 2+ INJ | 5,667 | 3,234 | 2,433 |
| | M Total | | | 17,086 | 13,158 | 3,928 |
| Q4 | P | Z2A | ANTIHISTAMINES | 31,066 | 22,860 | 8,206 |
| Q4 | P | Q7E | NASAL ANTIHISTAMINE | 863 | 699 | 164 |
| Q4 | P | Q6R | EYE ANTIHISTAMINES | 694 | 565 | 129 |
| . | . | . | . | . | . | . |
| . | . | . | . | . | . | . |
| . | . | . | . | . | . | . |
| Q4 | P | B3J | EXPECTORANTS | 66 | 10 | 56 |
| Q4 | P | B3K | COUGH AND/OR COLD PREPARATIONS | 140 | 52 | 88 |
| Q4 | P | Z4B | LEUKOTRIENE RECEPTOR ANTAGONISTS | 930 | 690 | 240 |
| Q4 | P | Q7P | NASAL ANTI-INFLAMMATORY STEROIDS | 16,309 | 10,935 | 5,374 |
| | | P Total | | 50,241 | 35,915 | 14,326 |
| Q4 | R | 71020 | RADIOLOGIC EXAM, CHEST, 2 VIEWS, FRONTAL & LATERAL | 4 | 3 | 1 |
| Q4 | R | 70220 | RADIOLOGIC EXAM, SINUSES, PARANASAL, COMPLETE, MINIMUM, 3 VIEW | 1 | 0 | 1 |
| Q4 | R | 70486 | CT SCAN, MAXILLOFACIAL AREA; W/O CONTRAST MATL | 1 | 0 | 1 |
| | R Total | | | 6 | 3 | 3 |

TABLE B2-continued

Total Role Allergic Rhinitis ETGno 0332 by quintile
Each doctor with greater than or equal to 50 episodes
(3 doctors per Quintile, 4 in Q4)

| quintile | category | code | description | | | |
|---|---|---|---|---|---|---|
| Q4 | S | 31231 | NASAL ENDOSCOPY, DX, UNILAT/BILAT (SEP PROC) | 2 | 0 | 2 |
| | S Total | | | 2 | 0 | 2 |
| | Q4 Total | | | 75,157 | 56,581 | 18,576 |
| Q5 | A | 95024 | ALLERGY TESTS, INTRADERMAL, ALLERGENIC, EXTRACTS, SPECIFY NUMBER | 1,118 | 1,118 | 0 |
| Q5 | A | 95015 | ALLERGY TESTS, INTRADERMAL, SEQUENTIAL/INCREMENTAL, SPECIFY NUMBER | 27 | 27 | 0 |
| Q5 | A | ER | Emergency | 4 | 3 | 1 |
| Q5 | A | CL | Clinic/Treatment/Testing | 3 | 0 | 3 |
| Q5 | A | 90782 | THERAPEUTIC/PROPHYLACTIC/DX INJECTION (SPECIFY MATL INJECTED | 10 | 0 | 10 |
| . | . | . | . | . | . | . |
| . | . | . | . | . | . | . |
| . | . | . | . | . | . | . |
| Q5 | A | 95010 | ALLERGY TESTS, PERCUTANEOUS, SEQUENTIAL/INCREMENTAL, SPECIFY NUMBER | 7 | 7 | 0 |
| Q5 | A | 94010 | SPIROMETRY W/GRAPHIC RECORD/VITAL CAPACITY/FLOW RATE W/WO MAXIMAL VOLUN | 1 | 1 | 0 |
| Q5 | A | 95004 | ALLERGY TESTS, PERCUTANEOUS, ALLERGENIC EXTRACTS, SPECIFY NUMBER | 1,315 | 1,315 | 0 |
| | A Total | | | 2,612 | 2,475 | 137 |
| Q5 | M | 95165 | PROFES SVC, SUPERVIS, PREPARA, PROVISION, ANTIGENS, ALLERGEN IMMUNOTHER | 4,930 | 4,740 | 190 |
| Q5 | M | 95117 | PROFESSIONAL SVC, ALLERGEN IMMUNOTHERAPY NON-PROVISION EXTRACTS; 2+ INJ | 2,558 | 1,907 | 651 |
| Q5 | M | 95145 | PROFES SVC, SUPERVIS, PREPARA, PROVISION, ANTIGEN, ALLERGEN IMMUNOTHERA | 120 | 110 | 10 |
| Q5 | M | 95147 | PROFESSIONAL SVC, SUPERVISION, PROVISION, ANTIGENS, ALLERGEN IMMUNOTHER | 70 | 70 | 0 |
| Q5 | M | 95115 | PROFESSIONAL SVC, ALLERGEN IMMUNOTHERAPY NON-PROVISION EXTRACTS; SINGLE | 346 | 285 | 61 |
| Q5 | M | 99243 | OFFICE CONSULTATION, 3 KEY COMPONENTS: DETAILED HX; DETAILED EXAM; MED | 25 | 21 | 4 |
| Q5 | M | 99211 | OFFICE/OP VISIT, EST PT, NOT REQUIRING PHYSICIAN PRESENCE, TYPICALLY 5 | 33 | 0 | 33 |
| Q5 | M | 99212 | OFFICE/OP VISIT, EST PT, 2 KEY COMPONENTS: PROB FOCUS HX; PROB FOCUS EX | 18 | 13 | 5 |
| Q5 | M | 99204 | OFFICE/OP VISIT, NEW PT, 3 KEY COMPONENTS: COMPREHENSIVE HX;COMPREHENSIV | 1 | 0 | 1 |
| . | . | . | . | . | . | . |
| . | . | . | . | . | . | . |
| . | . | . | . | . | . | . |
| Q5 | M | 99213 | OFFICE/OP VISIT, EST PT, 2 KEY COMPONENTS: EXPAND PROB HX; EXPAND PROB | 140 | 77 | 63 |
| Q5 | M | 99214 | OFFICE/OP VISIT, EST PT, 2 KEY COMPONENTS: DETAILED HX; DETAILED EXAM; | 46 | 29 | 17 |
| Q5 | M | 99244 | OFFICE CONSULTATION, 3 KEY COMPONENTS: COMPREHENSIVE HX; COMPREHENSIVE E | 4 | 3 | 1 |
| | M Total | | | 8,299 | 7,258 | 1,041 |
| Q5 | P | Q7P | NASAL ANTI-INFLAMMATORY STEROIDS | 9,599 | 7,868 | 1,731 |
| Q5 | P | Z2A | ANTIHISTAMINES | 10,628 | 7,179 | 3,449 |
| Q5 | P | Q6R | EYE ANTIHISTAMINES | 474 | 440 | 34 |
| Q5 | P | B3K | COUGH AND/OR COLD PREPARATIONS | 304 | 238 | 66 |
| Q5 | P | Q7E | NASAL ANTIHISTAMINE | 464 | 396 | 68 |
| Q5 | P | P5A | GLUCOCORTICOIDS | 335 | 319 | 16 |
| Q5 | P | Q7A | NOSE PREPARATIONS, MISCELLANEOUS (RX) | 45 | 45 | 0 |
| Q5 | P | B3J | EXPECTORANTS | 49 | 0 | 49 |
| Q5 | P | Z4B | LEUKOTRIENE RECEPTOR ANTAGONISTS | 450 | 270 | 180 |
| | P Total | | | 22,348 | 16,755 | 5,593 |
| Q5 | R | 70220 | RADIOLOGIC EXAM, SINUSES, PARANASAL, COMPLETE, MINIMUM, 3 VIEWS | 1 | 0 | 1 |
| | R Total | | | 1 | 0 | 1 |
| Q5 | S | 30520 | SEPTOPLASTY/SUBMUCOUS RESECTION W/WO CARTILAGE SCORING/CONTOURING/GRAFT | 1 | 0 | 1 |
| Q5 | S | 31231 | NASAL ENDOSCOPY, DX, UNILAT/BILAT (SEP PROC) | 1 | 0 | 1 |
| | S Total | | | 2 | 0 | 2 |
| | Q5 Total | | | 33,262 | 26,488 | 6,774 |
| | Grand Total | | | 312,348 | 240,335 | 72,013 |

| quintile | category | services | Expected Svcs | quintile episodes | Total Costs | Your Costs | Other Costs | expected costs | Total Cost Difference | Total Cost Difference per Quintile Episode | Your costs per svc |
|---|---|---|---|---|---|---|---|---|---|---|---|
| Q1 | A | 95004 | 4068.32 | 472 | $20,676 | $20,676 | $0 | $15,973 | $4,703 | $10 | $4 |
| Q1 | A | 95024 | 1768.96 | 472 | $10,946 | $10,946 | $0 | $10,545 | $401 | $1 | $6 |

TABLE B2-continued

Total Role Allergic Rhinitis ETGno 0332 by quintile
Each doctor with greater than or equal to 50 episodes
(3 doctors per Quintile, 4 in Q4)

| | | | | | | | | | | | |
|---|---|---|---|---|---|---|---|---|---|---|---|
| Q1 | A | | 94150 | 2.64 | 472 | $258 | $0 | $258 | $59 | $199 | $0 | $0 |
| Q1 | A | | 86003 | 73.83 | 472 | $341 | $0 | $341 | $153 | $188 | $0 | $0 |
| Q1 | A | | 82785 | 3.96 | 472 | $169 | $0 | $169 | $51 | $118 | $0 | $0 |
| . | . | | . | . | . | . | . | . | . | . | . | . |
| . | . | | . | . | . | . | . | . | . | . | . | . |
| . | . | | . | . | . | . | . | . | . | . | . | . |
| Q1 | A | | 80053 | 8.85 | 472 | $25 | $0 | $25 | $48 | ($23) | ($0) | $0 |
| Q1 | A | | 90782 | 9.23 | 472 | $18 | $0 | $18 | $74 | ($56) | ($0) | $0 |
| Q1 | A | | 95010 | 23.17 | 472 | $390 | $390 | $0 | $557 | ($167) | ($0) | $24 |
| Q1 | A | | 95015 | 28.25 | 472 | $356 | $356 | $0 | $623 | ($267) | ($1) | $22 |
| Q1 | A | | ER | 5.09 | 472 | $365 | $365 | $0 | $855 | ($490) | ($1) | $183 |
| | A Total | | | 6075.92 | 472 | $35,004 | $33,715 | $1,289 | $29,993 | $5,011 | $11 | |
| Q1 | M | | 99244 | 22.98 | 472 | $9,045 | $8,491 | $554 | $4,228 | $4,817 | $10 | $185 |
| Q1 | M | | 99214 | 118.66 | 472 | $14,891 | $14,013 | $878 | $10,445 | $4,446 | $9 | $89 |
| Q1 | M | | 95145 | 74.02 | 472 | $1,730 | $1,730 | $0 | $1,590 | $140 | $0 | $22 |
| . | . | | . | . | . | . | . | . | . | . | . | . |
| . | . | | . | . | . | . | . | . | . | . | . | . |
| Q1 | M | | 99211 | 35.03 | 472 | $253 | $0 | $253 | $782 | ($529) | ($1) | $0 |
| Q1 | M | | 99212 | 22.04 | 472 | $308 | $120 | $188 | $883 | ($575) | ($1) | $40 |
| Q1 | M | | 99243 | 42.38 | 472 | $4,546 | $4,546 | $0 | $5,451 | ($905) | ($2) | $130 |
| Q1 | M | | 99213 | 278.00 | 472 | $14,137 | $7,000 | $7,137 | $15,176 | ($1,039) | ($2) | $56 |
| Q1 | M | | 95147 | 50.67 | 472 | $782 | $782 | $0 | $1,954 | ($1,172) | ($2) | $39 |
| Q1 | M | | 95115 | 537.55 | 472 | $3,408 | $2,736 | $672 | $8,582 | ($5,174) | ($11) | $16 |
| Q1 | M | | 95165 | 8690.38 | 472 | $60,093 | $56,357 | $3,736 | $91,309 | ($31,216) | ($66) | $11 |
| Q1 | M | | 95117 | 4796.85 | 472 | $63,856 | $50,048 | $13,808 | $100,110 | ($36,254) | ($77) | $21 |
| | M Total | | | 14680.78 | 472 | $173,957 | $145,823 | $28,134 | $241,259 | ($67,302) | ($143) | |
| Q1 | P | | Q7P | 15141.29 | 472 | $51,580 | $45,801 | $5,779 | $31,968 | $19,612 | $42 | $2 |
| Q1 | P | | Z4B | 1168.51 | 472 | $5,781 | $4,616 | $1,165 | $3,136 | $2,645 | $6 | $3 |
| Q1 | P | | Z2A | 20214.82 | 472 | $43,162 | $33,287 | $9,875 | $40,682 | $2,480 | $5 | $2 |
| Q1 | P | | Q7E | 530.20 | 472 | $1,108 | $1,108 | $0 | $1,059 | $49 | $0 | $2 |
| Q1 | P | | Q7A | 56.50 | 472 | $86 | $86 | $0 | $88 | ($2) | ($0) | $3 |
| Q1 | P | | B3J | 80.42 | 472 | $41 | $0 | $41 | $76 | ($35) | ($0) | $0 |
| Q1 | P | | P5A | 85.13 | 472 | $42 | $31 | $11 | $110 | ($68) | ($0) | $1 |
| Q1 | P | | Q6R | 499.69 | 472 | $1,479 | $1,076 | $403 | $1,618 | ($139) | ($0) | $3 |
| Q1 | P | | B3K | 233.55 | 472 | $181 | $58 | $123 | $491 | ($310) | ($1) | $2 |
| | P Total | | | 38010.13 | 472 | $103,460 | $86,063 | $17,397 | $79,227 | $24,233 | $51 | |
| Q1 | R | | 76375 | .19 | 472 | $147 | $0 | $147 | $28 | $119 | $0 | $0 |
| Q1 | R | | 70210 | .38 | 472 | $68 | $34 | $34 | $13 | $55 | $0 | $34 |
| Q1 | R | | 70486 | 1.13 | 472 | $249 | $0 | $249 | $234 | $15 | $0 | $0 |
| Q1 | R | | 71020 | 2.64 | 472 | $88 | $0 | $88 | $81 | $7 | $0 | $0 |
| | R Total | | | 4.33 | 472 | $552 | $34 | $518 | $356 | $196 | $0 | |
| Q1 | S | | 31231 | .94 | 472 | $258 | $258 | $0 | $121 | $137 | $0 | $129 |
| | S Total | | | .94 | | $258 | $258 | $0 | $121 | | | |
| | Q1 Total | | | 58772.10 | | $313,231 | $265,893 | $47,338 | $350,956 | | | |
| Q2 | A | | 95004 | 3008.14 | 349 | $15,167 | $15,167 | $0 | $11,811 | $3,356 | $10 | $4 |
| Q2 | A | | 95010 | 17.13 | 349 | $2,158 | $2,158 | $0 | $412 | $1,746 | $5 | $24 |
| Q2 | A | | 95024 | 1307.98 | 349 | $9,338 | $9,338 | $0 | $7,797 | $1,541 | $4 | $6 |
| Q2 | A | | 95015 | 20.89 | 349 | $1,779 | $1,779 | $0 | $461 | $1,318 | $4 | $22 |
| Q2 | A | | 87799 | .14 | 349 | $110 | $110 | $0 | $15 | $95 | $0 | $110 |
| Q2 | A | | 95070 | .14 | 349 | $91 | $91 | $0 | $13 | $78 | $0 | $91 |
| Q2 | A | | 90782 | 6.82 | 349 | $121 | $0 | $121 | $55 | $66 | $0 | $0 |
| Q2 | A | | 85025 | 6.27 | 349 | $56 | $26 | $30 | $22 | $34 | $0 | $26 |
| . | . | | . | . | . | . | . | . | . | . | . | . |
| . | . | | . | . | . | . | . | . | . | . | . | . |
| Q2 | A | | CL | .70 | 349 | $10 | $0 | $10 | $81 | ($71) | ($0) | $0 |
| Q2 | A | | 94010 | 11.00 | 349 | $200 | $166 | $34 | $428 | ($228) | ($1) | $42 |
| Q2 | A | | ER | 3.76 | 349 | $128 | $0 | $128 | $632 | ($504) | ($1) | $0 |
| | A Total | | | 4487.84 | 349 | $29,690 | $28,939 | $751 | $22,156 | $7,534 | $22 | |
| Q2 | M | | 95165 | 6425.72 | 349 | $71,708 | $70,368 | $1,340 | $67,514 | $4,194 | $12 | $11 |
| Q2 | M | | 95115 | 397.46 | 349 | $8,695 | $3,658 | $5,037 | $6,346 | $2,349 | $7 | $16 |
| Q2 | M | | 99242 | 3.76 | 349 | $2,146 | $2,146 | $0 | $367 | $1,779 | $5 | $98 |
| Q2 | M | | 99215 | 1.81 | 349 | $649 | $520 | $129 | $235 | $414 | $1 | $130 |
| Q2 | M | | 99205 | .14 | 349 | $187 | $187 | $0 | $26 | $161 | $0 | $187 |
| Q2 | M | | 99396 | 2.65 | 349 | $280 | $0 | $280 | $148 | $132 | $0 | $0 |
| . | . | | . | . | . | . | . | . | . | . | . | . |
| . | . | | . | . | . | . | . | . | . | . | . | . |
| Q2 | M | | 95145 | 54.73 | 349 | $618 | $437 | $181 | $1,175 | ($557) | ($2) | $22 |
| Q2 | M | | 95147 | 37.46 | 349 | $723 | $391 | $332 | $1,444 | ($721) | ($2) | $39 |
| Q2 | M | | 99214 | 87.74 | 349 | $5,906 | $4,260 | $1,646 | $7,723 | ($1,817) | ($5) | $89 |
| Q2 | M | | 99213 | 205.56 | 349 | $9,260 | $3,176 | $6,084 | $11,221 | ($1,961) | ($6) | $56 |
| Q2 | M | | 99244 | 16.99 | 349 | $1,107 | $1,107 | $0 | $3,126 | ($2,019) | ($6) | $185 |

TABLE B2-continued

Total Role Allergic Rhinitis ETGno 0332 by quintile
Each doctor with greater than or equal to 50 episodes
(3 doctors per Quintile, 4 in Q4)

| | | | | | | | | | | | |
|---|---|---|---|---|---|---|---|---|---|---|---|
| Q2 | M | 95117 | 3546.82 | 349 | $57,343 | $21,437 | $35,906 | $74,022 | ($16,679) | ($48) | $20 |
| | M Total | | 10864.68 | 349 | $164,820 | $111,782 | $53,038 | $179,759 | ($14,939) | ($43) | |
| Q2 | P | Z4B | 864.00 | 349 | $2,943 | $1,738 | $1,205 | $2,318 | $625 | $2 | $3 |
| Q2 | P | Q6R | 369.47 | 349 | $1,354 | $687 | $667 | $1,197 | $157 | $0 | $4 |
| . | . | . | . | . | . | . | . | . | . | . | . |
| . | . | . | . | . | . | . | . | . | . | . | . |
| . | . | . | . | . | . | . | . | . | . | . | . |
| Q2 | P | B3J | 59.47 | 349 | $49 | $12 | $37 | $56 | ($7) | ($0) | $0 |
| Q2 | P | P5A | 62.95 | 349 | $5 | $0 | $5 | $81 | ($76) | ($0) | $0 |
| Q2 | P | Z2A | 14946.98 | 349 | $27,153 | $18,039 | $9,114 | $30,080 | ($2,927) | ($8) | $2 |
| Q2 | P | Q7P | 11195.57 | 349 | $16,959 | $9,813 | $7,146 | $23,637 | ($6,678) | ($19) | $2 |
| | P Total | | 28107.31 | 349 | $50,034 | $31,259 | $18,775 | $58,583 | ($8,549) | ($24) | |
| Q2 | R | 70486 | .84 | 349 | $673 | $305 | $368 | $173 | $500 | $1 | $305 |
| Q2 | R | 70250 | .14 | 349 | $36 | $36 | $0 | $5 | $31 | $0 | $36 |
| Q2 | R | 71020 | 1.95 | 349 | $86 | $37 | $49 | $60 | $26 | $0 | $37 |
| | R Total | | 2.92 | | $795 | $378 | $417 | $238 | | | |
| | Q2 Total | | 43462.76 | | $245,339 | $172,358 | $72,981 | $260,737 | | | |
| Q3 | A | 94010 | 29.73 | 943 | $1,477 | $1,304 | $173 | $1,156 | $321 | $0 | $41 |
| Q3 | A | A0427 | .38 | 943 | $509 | $509 | $0 | $192 | $317 | $0 | $509 |
| Q3 | A | A0429 | .38 | 943 | $450 | $450 | $0 | $169 | $281 | $0 | $450 |
| Q3 | A | A0432 | .38 | 943 | $320 | $320 | $0 | $120 | $200 | $0 | $320 |
| . | . | . | . | . | . | . | . | . | . | . | . |
| . | . | . | . | . | . | . | . | . | . | . | . |
| . | . | . | . | . | . | . | . | . | . | . | . |
| Q3 | A | 94150 | 5.27 | 943 | $56 | $0 | $56 | $118 | ($62) | ($0) | $0 |
| Q3 | A | 82785 | 7.90 | 943 | $39 | $26 | $13 | $103 | ($64) | ($0) | $13 |
| Q3 | A | ER | 10.16 | 943 | $1,605 | $1,081 | $524 | $1,708 | ($103) | ($0) | $216 |
| Q3 | A | 86003 | 147.51 | 943 | $84 | $64 | $20 | $305 | ($221) | ($0) | $2 |
| Q3 | A | 95015 | 56.44 | 943 | $134 | $134 | $0 | $1,244 | ($1,110) | ($1) | $22 |
| Q3 | A | 95024 | 3534.18 | 943 | $17,535 | $17,005 | $530 | $21,068 | ($3,533) | ($4) | $6 |
| Q3 | A | 95004 | 8128.01 | 943 | $21,809 | $21,047 | $762 | $31,912 | ($10,103) | ($11) | $4 |
| | A Total | | 12131.44 | 943 | $45,294 | $42,185 | $3,109 | $59,238 | ($13,944) | ($15) | |
| Q3 | M | 95117 | 9583.53 | 943 | $238,744 | $155,699 | $83,045 | $200,007 | $38,737 | $41 | $21 |
| Q3 | M | 95165 | 17362.34 | 943 | $189,364 | $183,700 | $5,664 | $182,424 | $6,940 | $7 | $10 |
| Q3 | M | 95115 | 1073.95 | 943 | $20,048 | $7,790 | $12,258 | $17,146 | $2,902 | $3 | $16 |
| Q3 | M | 99212 | 44.03 | 943 | $2,948 | $2,280 | $668 | $1,764 | $1,184 | $1 | $40 |
| Q3 | M | 99213 | 555.41 | 943 | $31,343 | $17,307 | $14,036 | $30,320 | $1,023 | $1 | $55 |
| . | . | . | . | . | . | . | . | . | . | . | . |
| . | . | . | . | . | . | . | . | . | . | . | . |
| . | . | . | . | . | . | . | . | . | . | . | . |
| Q3 | M | 99211 | 69.99 | 943 | $1,206 | $92 | $1,114 | $1,563 | ($357) | ($0) | $23 |
| Q3 | M | 99215 | 4.89 | 943 | $259 | $259 | $0 | $634 | ($375) | ($0) | $130 |
| Q3 | M | 99242 | 10.16 | 943 | $97 | $0 | $97 | $990 | ($893) | ($1) | $0 |
| Q3 | M | 99243 | 84.67 | 943 | $9,639 | $9,120 | $519 | $10,891 | ($1,252) | ($1) | $127 |
| Q3 | M | 99244 | 45.91 | 943 | $6,240 | $5,501 | $739 | $8,447 | ($2,207) | ($2) | $183 |
| Q3 | M | 95145 | 147.88 | 943 | $712 | $428 | $284 | $3,176 | ($2,464) | ($3) | $21 |
| Q3 | M | 95147 | 101.22 | 943 | $1,115 | $1,115 | $0 | $3,903 | ($2,788) | ($3) | $38 |
| Q3 | M | 99214 | 237.07 | 943 | $7,871 | $4,463 | $3,408 | $20,868 | ($12,997) | ($14) | $86 |
| | M Total | | 29354.17 | 943 | $511,821 | $387,754 | $124,067 | $484,315 | $27,506 | $29 | |
| Q3 | P | B3J | 160.68 | 943 | $246 | $37 | $209 | $152 | $94 | $0 | $1 |
| Q3 | P | B3K | 466.61 | 943 | $815 | $482 | $333 | $981 | ($166) | ($0) | $2 |
| Q3 | P | P5A | 170.09 | 943 | $25 | $9 | $16 | $219 | ($194) | ($0) | $0 |
| Q3 | P | Q6R | 998.32 | 943 | $2,220 | $1,830 | $390 | $3,234 | ($1,014) | ($1) | $4 |
| Q3 | P | Q7E | 1059.28 | 943 | $961 | $855 | $106 | $2,115 | ($1,154) | ($1) | $2 |
| Q3 | P | Z4B | 2334.55 | 943 | $4,271 | $1,984 | $2,287 | $6,265 | ($1,994) | ($2) | $3 |
| Q3 | P | Q7P | 30250.51 | 943 | $45,664 | $31,993 | $13,671 | $63,868 | ($18,204) | ($19) | $2 |
| Q3 | P | Z2A | 40386.82 | 943 | $61,825 | $40,014 | $21,811 | $81,277 | ($19,452) | ($21) | $2 |
| | P Total | | 75826.83 | 943 | $116,027 | $77,204 | $38,823 | $158,111 | ($42,084) | ($45) | |
| Q3 | R | 70450 | .75 | 943 | $97 | $0 | $97 | $37 | $60 | $0 | $0 |
| Q3 | R | 70160 | .38 | 943 | $31 | $0 | $31 | $12 | $19 | $0 | $0 |
| Q3 | R | 71020 | 5.27 | 943 | $100 | $37 | $63 | $161 | ($61) | ($0) | $37 |
| Q3 | R | 70486 | 2.26 | 943 | $65 | $0 | $65 | $468 | ($403) | ($0) | $0 |
| | R Total | | 8.65 | 943 | $293 | $37 | $256 | $678 | ($385) | ($0) | |
| | Q3 Total | | 117321.09 | | $673,435 | $507,180 | $166,255 | $702,341 | | | |
| Q4 | A | 95004 | 4964.72 | 576 | $22,180 | $21,854 | $326 | $19,493 | $2,687 | $5 | $4 |
| Q4 | A | CL | 1.15 | 576 | $397 | $397 | $0 | $134 | $263 | $0 | $397 |
| Q4 | A | 86003 | 90.10 | 576 | $252 | $34 | $218 | $186 | $66 | $0 | $2 |
| Q4 | A | 94010 | 18.16 | 576 | $751 | $714 | $37 | $706 | $45 | $0 | $42 |
| Q4 | A | 92557 | .23 | 576 | $50 | $0 | $50 | $11 | $39 | $0 | $0 |
| . | . | . | . | . | . | . | . | . | . | . | . |
| . | . | . | . | . | . | . | . | . | . | . | . |
| . | . | . | . | . | . | . | . | . | . | . | . |
| Q4 | A | 80053 | 10.80 | 576 | $30 | $5 | $25 | $58 | ($28) | ($0) | $5 |
| Q4 | A | 80050 | 5.06 | 576 | $28 | $14 | $14 | $71 | ($43) | ($0) | $14 |
| Q4 | A | 90782 | 11.26 | 576 | $40 | $8 | $32 | $90 | ($50) | ($0) | $8 |

TABLE B2-continued

Total Role Allergic Rhinitis ETGno 0332 by quintile
Each doctor with greater than or equal to 50 episodes
(3 doctors per Quintile, 4 in Q4)

| | | | | | | | | | | | |
|---|---|---|---|---|---|---|---|---|---|---|---|
| Q4 | A | 95015 | 34.48 | 576 | $437 | $437 | $0 | $760 | ($323) | ($1) | $22 |
| Q4 | A | 95010 | 28.27 | 576 | $240 | $240 | $0 | $680 | ($440) | ($1) | $24 |
| Q4 | A | 95024 | 2158.74 | 576 | $11,920 | $11,873 | $47 | $12,869 | ($949) | ($2) | $6 |
| | A Total | | 7431.00 | 576 | $37,998 | $36,194 | $1,804 | $36,730 | $1,268 | $2 | |
| Q4 | M | 99214 | 144.80 | 576 | $22,778 | $19,093 | $3,685 | $12,746 | $10,032 | $17 | $88 |
| Q4 | M | 95147 | 61.83 | 576 | $5,015 | $4,267 | $748 | $2,384 | $2,631 | $5 | $39 |
| Q4 | M | 95145 | 90.33 | 576 | $2,803 | $2,589 | $214 | $1,940 | $863 | $1 | $21 |
| Q4 | M | 99243 | 51.72 | 576 | $7,502 | $7,373 | $129 | $6,653 | $849 | $1 | $129 |
| Q4 | M | 99211 | 42.75 | 576 | $1,353 | $46 | $1,307 | $955 | $398 | $1 | $23 |
| Q4 | M | 99215 | 2.99 | 576 | $648 | $518 | $130 | $388 | $260 | $0 | $130 |
| . | . | . | . | . | . | . | . | . | . | . | . |
| Q4 | M | 99213 | 339.26 | 576 | $18,313 | $8,455 | $9,858 | $18,520 | ($207) | ($0) | $56 |
| Q4 | M | 99242 | 6.21 | 576 | $194 | $97 | $97 | $605 | ($411) | ($1) | $97 |
| Q4 | M | 99212 | 26.89 | 576 | $410 | $116 | $294 | $1,078 | ($668) | ($1) | $39 |
| Q4 | M | ER | 6.21 | 576 | $253 | $0 | $253 | $1,043 | ($790) | ($1) | $0 |
| Q4 | M | 95115 | 655.99 | 576 | $7,881 | $3,440 | $4,441 | $10,473 | ($2,592) | ($5) | $16 |
| Q4 | M | 95165 | 10605.20 | 576 | $108,460 | $99,200 | $9,260 | $111,428 | ($2,968) | ($5) | $11 |
| Q4 | M | 95117 | 5853.78 | 576 | $118,104 | $67,266 | $50,838 | $122,168 | ($4,064) | ($7) | $21 |
| | M Total | | 17931.85 | 576 | $300,507 | $217,833 | $82,674 | $296,672 | $3,835 | $7 | |
| Q4 | P | Z2A | 24668.94 | 576 | $61,796 | $46,892 | $14,904 | $49,646 | $12,150 | $21 | $2 |
| Q4 | P | Q7E | 647.02 | 576 | $1,704 | $1,388 | $316 | $1,292 | $412 | $1 | $2 |
| Q4 | P | Q6R | 609.79 | 576 | $2,151 | $1,717 | $434 | $1,975 | $176 | $0 | $3 |
| . | . | . | . | . | . | . | . | . | . | . | . |
| Q4 | P | B3J | 98.15 | 576 | $49 | $8 | $41 | $93 | ($44) | ($0) | $1 |
| Q4 | P | B3K | 285.01 | 576 | $307 | $141 | $166 | $599 | ($292) | ($1) | $3 |
| Q4 | P | Z4B | 1425.98 | 576 | $2,445 | $1,860 | $585 | $3,827 | ($1,382) | ($2) | $3 |
| Q4 | P | Q7P | 18477.51 | 576 | $33,632 | $22,787 | $10,845 | $39,011 | ($5,379) | ($9) | $2 |
| | P Total | | 46390.75 | 576 | $102,446 | $75,013 | $27,433 | $96,705 | $5,741 | $10 | |
| Q4 | R | 71020 | 3.22 | 576 | $155 | $117 | $38 | $99 | $56 | $0 | $39 |
| Q4 | R | 70220 | .46 | 576 | $45 | $0 | $45 | $21 | $24 | $0 | $0 |
| Q4 | R | 70486 | 1.38 | 576 | $258 | $0 | $258 | $286 | ($28) | ($0) | $0 |
| | R Total | | 5.06 | 576 | $458 | $117 | $341 | $405 | $53 | $0 | |
| Q4 | S | 31231 | 1.15 | 576 | $257 | $0 | $257 | $148 | $109 | $0 | $0 |
| | S Total | | 1.15 | 576 | $257 | $0 | $257 | $148 | $109 | $0 | |
| | Q4 Total | | 71759.81 | | $441,666 | $329,157 | $112,509 | $430,660 | | | |
| Q5 | A | 95024 | 888.23 | 237 | $6,250 | $6,250 | $0 | $5,295 | $955 | $4 | $6 |
| Q5 | A | 95015 | 14.19 | 237 | $601 | $601 | $0 | $313 | $288 | $1 | $22 |
| Q5 | A | ER | 2.55 | 237 | $697 | $569 | $128 | $429 | $268 | $1 | $190 |
| Q5 | A | CL | .47 | 237 | $174 | $0 | $174 | $55 | $119 | $1 | $0 |
| Q5 | A | 90782 | 4.63 | 237 | $80 | $0 | $80 | $37 | $43 | $0 | $0 |
| . | . | . | . | . | . | . | . | . | . | . | . |
| Q5 | A | 95010 | 11.63 | 237 | $171 | $171 | $0 | $280 | ($109) | ($0) | $24 |
| Q5 | A | 94010 | 7.47 | 237 | $43 | $43 | $0 | $290 | ($247) | ($1) | $43 |
| Q5 | A | 95004 | 2042.78 | 237 | $4,974 | $4,974 | $0 | $8,020 | ($3,046) | ($13) | $4 |
| | A Total | | 3057.36 | 237 | $13,582 | $12,720 | $862 | $15,113 | ($1,531) | ($6) | |
| Q5 | M | 95165 | 4363.60 | 237 | $55,163 | $53,070 | $2,093 | $45,848 | $9,315 | $39 | $11 |
| Q5 | M | 95117 | 2408.59 | 237 | $53,467 | $40,047 | $13,420 | $50,267 | $3,200 | $14 | $21 |
| Q5 | M | 95145 | 37.17 | 237 | $2,577 | $2,363 | $214 | $798 | $1,779 | $8 | $21 |
| Q5 | M | 95147 | 25.44 | 237 | $2,737 | $2,737 | $0 | $981 | $1,756 | $7 | $39 |
| Q5 | M | 95115 | 269.91 | 237 | $5,533 | $4,560 | $973 | $4,309 | $1,224 | $5 | $16 |
| Q5 | M | 99243 | 21.28 | 237 | $3,243 | $2,724 | $519 | $2,737 | $506 | $2 | $130 |
| Q5 | M | 99211 | 17.59 | 237 | $759 | $0 | $759 | $393 | $366 | $2 | $0 |
| Q5 | M | 99212 | 11.07 | 237 | $714 | $520 | $194 | $443 | $271 | $1 | $40 |
| Q5 | M | 99204 | .47 | 237 | $147 | $0 | $147 | $77 | $70 | $0 | $0 |
| . | . | . | . | . | . | . | . | . | . | . | . |
| Q5 | M | 99213 | 139.59 | 237 | $7,521 | $4,220 | $3,301 | $7,620 | ($99) | ($0) | $55 |
| Q5 | M | 99214 | 59.58 | 237 | $4,009 | $2,568 | $1,441 | $5,245 | ($1,236) | ($5) | $89 |
| Q5 | M | 99244 | 11.54 | 237 | $738 | $553 | $185 | $2,123 | ($1,385) | ($6) | $184 |
| | M Total | | 7373.67 | 237 | $137,274 | $113,687 | $23,587 | $121,517 | $15,757 | $66 | |
| Q5 | P | Q7P | 7602.73 | 237 | $21,892 | $17,648 | $4,244 | $16,052 | $5,840 | $25 | $2 |
| Q5 | P | Z2A | 10150.24 | 237 | $22,057 | $14,835 | $7,222 | $20,427 | $1,630 | $7 | $2 |
| Q5 | P | Q6R | 250.90 | 237 | $1,389 | $1,293 | $96 | $813 | $576 | $2 | $3 |
| Q5 | P | B3K | 117.27 | 237 | $815 | $609 | $206 | $246 | $569 | $2 | $3 |
| Q5 | P | Q7E | 266.22 | 237 | $918 | $759 | $159 | $532 | $386 | $2 | $2 |
| Q5 | P | P5A | 42.75 | 237 | $405 | $381 | $24 | $55 | $350 | $1 | $1 |
| Q5 | P | Q7A | 28.37 | 237 | $75 | $75 | $0 | $44 | $31 | $0 | $2 |
| Q5 | P | B3J | 40.38 | 237 | $20 | $0 | $20 | $38 | ($18) | ($0) | $0 |

TABLE B2-continued

Total Role Allergic Rhinitis ETGno 0332 by quintile
Each doctor with greater than or equal to 50 episodes
(3 doctors per Quintile, 4 in Q4)

| | | | | | | | | | | |
|---|---|---|---|---|---|---|---|---|---|---|
| Q5 | P | Z4B | 586.73 | 237 | $1,208 | $736 | $472 | $1,574 | ($366) | ($2) | $3 |
| | P Total | | 19085.59 | 237 | $48,779 | $36,336 | $12,443 | $39,781 | $8,998 | $38 | |
| Q5 | R | 70220 | .19 | 237 | $45 | $0 | $45 | $9 | $36 | $0 | $0 |
| | R Total | | .19 | 237 | $45 | $0 | $45 | $9 | $36 | $0 | |
| Q5 | S | 30520 | .09 | 237 | $487 | $0 | $487 | $46 | $441 | $2 | $0 |
| Q5 | S | 31231 | .47 | 237 | $129 | $0 | $129 | $61 | $68 | $0 | $0 |
| | S Total | | .57 | 237 | $616 | $0 | $616 | $107 | $509 | $2 | |
| | Q5 Total | | 29517.38 | | $200,296 | $162,743 | $37,553 | $176,527 | | | |
| | Grand Total | | 320833.13 | | $1,873,967 | $1,437,331 | $436,636 | $1,921,220 | | | |

| quintile | category | services | Other costs per svc | Spec Costs per svc | Total Costs per episode | Your Avg Cost per Episode | other costs per episode | total episodes this service occurred |
|---|---|---|---|---|---|---|---|---|
| Q1 | A | 95004 | $0 | $4 | $44 | $44 | $0 | 147 |
| Q1 | A | 95024 | $0 | $6 | $23 | $23 | $0 | 85 |
| Q1 | A | 94150 | $26 | $22 | $1 | $0 | $1 | 1 |
| Q1 | A | 86003 | $2 | $2 | $1 | $0 | $1 | 14 |
| Q1 | A | 82785 | $13 | $13 | $0 | $0 | $0 | 13 |
| . | . | . | . | . | . | . | . | . |
| . | . | . | . | . | . | . | . | . |
| . | . | . | . | . | . | . | . | . |
| Q1 | A | 80053 | $5 | $5 | $0 | $0 | $0 | 5 |
| Q1 | A | 90782 | $9 | $8 | $0 | $0 | $0 | 1 |
| Q1 | A | 95010 | $0 | $24 | $1 | $1 | $0 | 2 |
| Q1 | A | 95015 | $0 | $22 | $1 | $1 | $0 | 2 |
| Q1 | A | ER | $0 | $168 | $1 | $1 | $0 | 2 |
| | A Total | | | | | | | |
| Q1 | M | 99244 | $185 | $184 | $19 | $18 | $1 | 47 |
| Q1 | M | 99214 | $88 | $88 | $32 | $30 | $2 | 124 |
| Q1 | M | 95145 | $0 | $21 | $4 | $4 | $0 | 5 |
| . | . | . | . | . | . | . | . | . |
| . | . | . | . | . | . | . | . | . |
| . | . | . | . | . | . | . | . | . |
| Q1 | M | 99211 | $23 | $22 | $1 | $0 | $1 | 1 |
| Q1 | M | 99212 | $38 | $40 | $1 | $0 | $0 | 7 |
| Q1 | M | 99243 | $0 | $129 | $10 | $10 | $0 | 35 |
| Q1 | M | 99213 | $53 | $55 | $30 | $15 | $15 | 148 |
| Q1 | M | 95147 | $0 | $39 | $2 | $2 | $0 | 2 |
| Q1 | M | 95115 | $13 | $16 | $7 | $6 | $1 | 18 |
| Q1 | M | 95165 | $11 | $11 | $127 | $119 | $8 | 176 |
| Q1 | M | 95117 | $21 | $21 | $135 | $106 | $29 | 167 |
| | M Total | | | | | | | |
| Q1 | P | Q7P | $2 | $2 | $109 | $97 | $12 | 209 |
| Q1 | P | Z4B | $3 | $3 | $12 | $10 | $2 | 13 |
| Q1 | P | Z2A | $2 | $2 | $91 | $71 | $21 | 194 |
| Q1 | P | Q7E | $0 | $2 | $2 | $2 | $0 | 5 |
| Q1 | P | Q7A | $0 | $2 | $0 | $0 | $0 | 1 |
| Q1 | P | B3J | $1 | $1 | $0 | $0 | $0 | 3 |
| Q1 | P | P5A | $1 | $1 | $0 | $0 | $0 | 3 |
| Q1 | P | Q6R | $3 | $3 | $3 | $2 | $1 | 19 |
| Q1 | P | B3K | $2 | $2 | $0 | $0 | $0 | 6 |
| | P Total | | | | | | | |
| Q1 | R | 76375 | $147 | $147 | $0 | $0 | $0 | 1 |
| Q1 | R | 70210 | $34 | $34 | $0 | $0 | $0 | 2 |
| Q1 | R | 70486 | $249 | $208 | $1 | $0 | $1 | 1 |
| Q1 | R | 71020 | $29 | $31 | $0 | $0 | $0 | 3 |
| | R Total | | | | | | | |
| Q1 | S | 31231 | $0 | $129 | $1 | $1 | $0 | 2 |
| | S Total | | | | | | | |
| | Q1 Total | | | | | | | |
| Q2 | A | 95004 | $0 | $4 | $43 | $43 | $0 | 63 |
| Q2 | A | 95010 | $0 | $24 | $6 | $6 | $0 | 6 |
| Q2 | A | 95024 | $0 | $6 | $27 | $27 | $0 | 44 |
| Q2 | A | 95015 | $0 | $22 | $5 | $5 | $0 | 6 |
| Q2 | A | 87799 | $0 | $110 | $0 | $0 | $0 | 1 |
| Q2 | A | 95070 | $0 | $91 | $0 | $0 | $0 | 1 |
| Q2 | A | 90782 | $8 | $8 | $0 | $0 | $0 | 8 |
| Q2 | A | 85025 | $3 | $4 | $0 | $0 | $0 | 5 |
| . | . | . | . | . | . | . | . | . |
| . | . | . | . | . | . | . | . | . |
| . | . | . | . | . | . | . | . | . |
| Q2 | A | CL | $10 | $116 | $0 | $0 | $0 | 1 |
| Q2 | A | 94010 | $34 | $39 | $1 | $0 | $0 | 5 |
| Q2 | A | ER | $128 | $168 | $0 | $0 | $0 | 1 |
| | A Total | | | | | | | |

TABLE B2-continued

Total Role Allergic Rhinitis ETGno 0332 by quintile
Each doctor with greater than or equal to 50 episodes
(3 doctors per Quintile, 4 in Q4)

| | | | | | | | | |
|---|---|---|---|---|---|---|---|---|
| Q2 | M | 95165 | $11 | $11 | $205 | $202 | $4 | 249 |
| Q2 | M | 95115 | $15 | $16 | $25 | $10 | $14 | 47 |
| Q2 | M | 99242 | $0 | $97 | $6 | $6 | $0 | 22 |
| Q2 | M | 99215 | $129 | $130 | $2 | $1 | $0 | 5 |
| Q2 | M | 99205 | $0 | $187 | $1 | $1 | $0 | 1 |
| Q2 | M | 99396 | $56 | $56 | $1 | $0 | $1 | 5 |
| . | . | . | . | . | . | . | . | . |
| . | . | . | . | . | . | . | . | . |
| . | . | . | . | . | . | . | . | . |
| Q2 | M | 95145 | $18 | $21 | $2 | $1 | $1 | 2 |
| Q2 | M | 95147 | $33 | $39 | $2 | $1 | $1 | 2 |
| Q2 | M | 99214 | $87 | $88 | $17 | $12 | $5 | 64 |
| Q2 | M | 99213 | $53 | $55 | $27 | $9 | $17 | 128 |
| Q2 | M | 99244 | $0 | $184 | $3 | $3 | $0 | 6 |
| Q2 | M | 95117 | $21 | $21 | $164 | $61 | $103 | 195 |
| | M Total | | | | | | | |
| Q2 | P | Z4B | $3 | $3 | $8 | $5 | $3 | 12 |
| Q2 | P | Q6R | $3 | $3 | $4 | $2 | $2 | 14 |
| . | . | . | . | . | . | . | . | . |
| . | . | . | . | . | . | . | . | . |
| . | . | . | . | . | . | . | . | . |
| Q2 | P | B3J | $1 | $1 | $0 | $0 | $0 | 7 |
| Q2 | P | P5A | $1 | $1 | $0 | $0 | $0 | 1 |
| Q2 | P | Z2A | $2 | $2 | $78 | $52 | $26 | 102 |
| Q2 | P | Q7P | $2 | $2 | $49 | $28 | $20 | 81 |
| | P Total | | | | | | | |
| Q2 | R | 70486 | $184 | $208 | $2 | $1 | $1 | 2 |
| Q2 | R | 70250 | $0 | $36 | $0 | $0 | $0 | 1 |
| Q2 | R | 71020 | $25 | $31 | $0 | $0 | $0 | 2 |
| | R Total | | | | | | | |
| Q2 Total | | | | | | | | |
| Q3 | A | 94010 | $43 | $39 | $2 | $1 | $0 | 36 |
| Q3 | A | A0427 | $0 | $509 | $1 | $1 | $0 | 1 |
| Q3 | A | A0429 | $0 | $450 | $0 | $0 | $0 | 1 |
| Q3 | A | A0432 | $0 | $320 | $0 | $0 | $0 | 1 |
| . | . | . | . | . | . | . | . | . |
| . | . | . | . | . | . | . | . | . |
| . | . | . | . | . | . | . | . | . |
| Q3 | A | 94150 | $14 | $22 | $0 | $0 | $0 | 2 |
| Q3 | A | 82785 | $13 | $13 | $0 | $0 | $0 | 3 |
| Q3 | A | ER | $131 | $168 | $2 | $1 | $1 | 9 |
| Q3 | A | 86003 | $2 | $2 | $0 | $0 | $0 | 7 |
| Q3 | A | 95015 | $0 | $22 | $0 | $0 | $0 | 1 |
| Q3 | A | 95024 | $6 | $6 | $19 | $18 | $1 | 101 |
| Q3 | A | 95004 | $4 | $4 | $23 | $22 | $1 | 110 |
| | A Total | | | | | | | |
| Q3 | M | 95117 | $21 | $21 | $253 | $165 | $88 | 689 |
| Q3 | M | 95165 | $11 | $11 | $201 | $195 | $6 | 768 |
| Q3 | M | 95115 | $17 | $16 | $21 | $8 | $13 | 110 |
| Q3 | M | 99212 | $42 | $40 | $3 | $2 | $1 | 60 |
| Q3 | M | 99213 | $54 | $55 | $33 | $18 | $15 | 381 |
| . | . | . | . | . | . | . | . | . |
| . | . | . | . | . | . | . | . | . |
| . | . | . | . | . | . | . | . | . |
| Q3 | M | 99211 | $22 | $22 | $1 | $0 | $1 | 15 |
| Q3 | M | 99215 | $0 | $130 | $0 | $0 | $0 | 2 |
| Q3 | M | 99242 | $97 | $97 | $0 | $0 | $0 | 1 |
| Q3 | M | 99243 | $130 | $129 | $10 | $10 | $1 | 75 |
| Q3 | M | 99244 | $185 | $184 | $7 | $6 | $1 | 34 |
| Q3 | M | 95145 | $24 | $21 | $1 | $0 | $0 | 3 |
| Q3 | M | 95147 | $0 | $39 | $1 | $1 | $0 | 3 |
| Q3 | M | 99214 | $87 | $88 | $8 | $5 | $4 | 77 |
| | M Total | | | | | | | |
| Q3 | P | B3J | $2 | $1 | $0 | $0 | $0 | 20 |
| Q3 | P | B3K | $2 | $2 | $1 | $1 | $0 | 17 |
| Q3 | P | P5A | $1 | $1 | $0 | $0 | $0 | 5 |
| Q3 | P | Q6R | $3 | $3 | $2 | $2 | $0 | 29 |
| Q3 | P | Q7E | $2 | $2 | $1 | $1 | $0 | 8 |
| Q3 | P | Z4B | $3 | $3 | $5 | $2 | $2 | 10 |
| Q3 | P | Q7P | $2 | $2 | $48 | $34 | $14 | 232 |
| Q3 | P | Z2A | $2 | $2 | $66 | $42 | $23 | 290 |
| | P Total | | | | | | | |
| Q3 | R | 70450 | $49 | $49 | $0 | $0 | $0 | 2 |
| Q3 | R | 70160 | $31 | $31 | $0 | $0 | $0 | 1 |
| Q3 | R | 71020 | $21 | $31 | $0 | $0 | $0 | 4 |

TABLE B2-continued

Total Role Allergic Rhinitis ETGno 0332 by quintile
Each doctor with greater than or equal to 50 episodes
(3 doctors per Quintile, 4 in Q4)

| | | | | | | | | |
|---|---|---|---|---|---|---|---|---|
| Q3 | R | 70486 | $65 | $208 | $0 | $0 | $0 | 1 |
| | R Total | | | | | | | |
| | Q3 Total | | | | | | | |
| Q4 | A | 95004 | $4 | $4 | $39 | $38 | $1 | 117 |
| Q4 | A | CL | $0 | $116 | $1 | $1 | $0 | 1 |
| Q4 | A | 86003 | $2 | $2 | $0 | $0 | $0 | 12 |
| Q4 | A | 94010 | $19 | $39 | $1 | $1 | $0 | 18 |
| Q4 | A | 92557 | $50 | $50 | $0 | $0 | $0 | 1 |
| . | . | . | . | . | . | . | . | . |
| . | . | . | . | . | . | . | . | . |
| . | . | . | . | . | . | . | . | . |
| Q4 | A | 80053 | $5 | $5 | $0 | $0 | $0 | 5 |
| Q4 | A | 80050 | $14 | $14 | $0 | $0 | $0 | 2 |
| Q4 | A | 90782 | $8 | $8 | $0 | $0 | $0 | 2 |
| Q4 | A | 95015 | $0 | $22 | $1 | $1 | $0 | 2 |
| Q4 | A | 95010 | $0 | $24 | $0 | $0 | $0 | 2 |
| Q4 | A | 95024 | $6 | $6 | $21 | $21 | $0 | 85 |
| | A Total | | | | | | | |
| Q4 | M | 99214 | $88 | $88 | $40 | $33 | $6 | 188 |
| Q4 | M | 95147 | $37 | $39 | $9 | $7 | $1 | 6 |
| Q4 | M | 95145 | $21 | $21 | $5 | $4 | $0 | 8 |
| Q4 | M | 99243 | $129 | $129 | $13 | $13 | $0 | 58 |
| Q4 | M | 99211 | $22 | $22 | $2 | $0 | $2 | 8 |
| Q4 | M | 99215 | $130 | $130 | $1 | $1 | $0 | 5 |
| . | . | . | . | . | . | . | . | . |
| . | . | . | . | . | . | . | . | . |
| . | . | . | . | . | . | . | . | . |
| Q4 | M | 99213 | $54 | $55 | $32 | $15 | $17 | 225 |
| Q4 | M | 99242 | $97 | $97 | $0 | $0 | $0 | 2 |
| Q4 | M | 99212 | $42 | $40 | $1 | $0 | $1 | 9 |
| Q4 | M | ER | $253 | $168 | $0 | $0 | $0 | 1 |
| Q4 | M | 95115 | $16 | $16 | $14 | $6 | $8 | 53 |
| Q4 | M | 95165 | $11 | $11 | $188 | $172 | $16 | 360 |
| Q4 | M | 95117 | $21 | $21 | $205 | $117 | $88 | 331 |
| | M Total | | | | | | | |
| Q4 | P | Z2A | $2 | $2 | $107 | $81 | $26 | 233 |
| Q4 | P | Q7E | $2 | $2 | $3 | $2 | $1 | 12 |
| Q4 | P | Q6R | $3 | $3 | $4 | $3 | $1 | 22 |
| . | . | . | . | . | . | . | . | . |
| . | . | . | . | . | . | . | . | . |
| . | . | . | . | . | . | . | . | . |
| Q4 | P | B3J | $1 | $1 | $0 | $0 | $0 | 7 |
| Q4 | P | B3K | $2 | $2 | $1 | $0 | $0 | 14 |
| Q4 | P | Z4B | $2 | $3 | $4 | $3 | $1 | 11 |
| Q4 | P | Q7P | $2 | $2 | $58 | $40 | $19 | 189 |
| | P Total | | | | | | | |
| Q4 | R | 71020 | $38 | $31 | $0 | $0 | $0 | 4 |
| Q4 | R | 70220 | $45 | $45 | $0 | $0 | $0 | 1 |
| Q4 | R | 70486 | $258 | $208 | $0 | $0 | $0 | 1 |
| | R Total | | | | | | | |
| Q4 | S | 31231 | $129 | $129 | $0 | $0 | $0 | 2 |
| | S Total | | | | | | | |
| | Q4 Total | | | | | | | |
| Q5 | A | 95024 | $0 | $6 | $26 | $26 | $0 | 42 |
| Q5 | A | 95015 | $0 | $22 | $3 | $3 | $0 | 1 |
| Q5 | A | ER | $128 | $168 | $3 | $2 | $1 | 4 |
| Q5 | A | CL | $58 | $116 | $1 | $0 | $1 | 1 |
| Q5 | A | 90782 | $8 | $8 | $0 | $0 | $0 | 2 |
| . | . | . | . | . | . | . | . | . |
| . | . | . | . | . | . | . | . | . |
| . | . | . | . | . | . | . | . | . |
| Q5 | A | 95010 | $0 | $24 | $1 | $1 | $0 | 1 |
| Q5 | A | 94010 | $0 | $39 | $0 | $0 | $0 | 1 |
| Q5 | A | 95004 | $0 | $4 | $21 | $21 | $0 | 42 |
| | A Total | | | | | | | |
| Q5 | M | 95165 | $11 | $11 | $233 | $224 | $9 | 149 |
| Q5 | M | 95117 | $21 | $21 | $226 | $169 | $57 | 137 |
| Q5 | M | 95145 | $21 | $21 | $11 | $10 | $1 | 7 |
| Q5 | M | 95147 | $0 | $39 | $12 | $12 | $0 | 6 |
| Q5 | M | 95115 | $16 | $16 | $23 | $19 | $4 | 32 |
| Q5 | M | 99243 | $130 | $129 | $14 | $11 | $2 | 24 |
| Q5 | M | 99211 | $23 | $22 | $3 | $0 | $3 | 3 |
| Q5 | M | 99212 | $39 | $40 | $3 | $2 | $1 | 15 |

TABLE B2-continued

Total Role Allergic Rhinitis ETGno 0332 by quintile
Each doctor with greater than or equal to 50 episodes
(3 doctors per Quintile, 4 in Q4)

| Q5 | M | 99204 | $147 | $163 | $1 | $0 | $1 | 1 |
|---|---|---|---|---|---|---|---|---|
| . | . | . | . | . | . | . | . | . |
| . | . | . | . | . | . | . | . | . |
| . | . | . | . | . | . | . | . | . |
| Q5 | M | 99213 | $52 | $55 | $32 | $18 | $14 | 98 |
| Q5 | M | 99214 | $85 | $88 | $17 | $11 | $6 | 40 |
| Q5 | M | 99244 | $185 | $184 | $3 | $2 | $1 | 4 |
| | M Total | | | | | | | |
| Q5 | P | Q7P | $2 | $2 | $92 | $74 | $18 | 93 |
| Q5 | P | Z2A | $2 | $2 | $93 | $63 | $30 | 97 |
| Q5 | P | Q6R | $3 | $3 | $6 | $5 | $0 | 14 |
| Q5 | P | B3K | $3 | $2 | $3 | $3 | $1 | 10 |
| Q5 | P | Q7E | $2 | $2 | $4 | $3 | $1 | 10 |
| Q5 | P | P5A | $2 | $1 | $2 | $2 | $0 | 7 |
| Q5 | P | Q7A | $0 | $2 | $0 | $0 | $0 | 2 |
| Q5 | P | B3J | $0 | $1 | $0 | $0 | $0 | 4 |
| Q5 | P | Z4B | $3 | $3 | $5 | $3 | $2 | 5 |
| | P Total | | | | | | | |
| Q5 | R | 70220 | $45 | $45 | $0 | $0 | $0 | 1 |
| | R Total | | | | | | | |
| Q5 | S | 30520 | $487 | $487 | $2 | $0 | $2 | 1 |
| Q5 | S | 31231 | $129 | $129 | $1 | $0 | $1 | 1 |
| | S Total | | | | | | | |
| Q5 Total | | | | | | | | |
| Grand Total | | | | | | | | |

TABLE B3

Allergy
Dates of service Jan. 1, 2003-Dec. 31, 2004 paid Dec. 31, 2004
Total Role Allergic Rhinitis ETGno 0332 by quintile
Each doctor with greater than or equal to 50 episodes
(3 doctors per Quintile, 4 in Q4)

| quintile | category | services | PROC_DESC | Total Cost Difference per Quintile Episode |
|---|---|---|---|---|
| Q1 | A | 95004 | ALLERGY TESTS, PERCUTANEOUS, ALLERGENIC EXTRACTS, SPECIFY NUMBER | $10 |
| | A Total | | | $10 |
| Q1 | M | 99244 | OFFICE CONSULTATION, 3 KEY COMPONENTS: COMPREHENSIVE HX; COMPREHENSIVE E | $10 |
| Q1 | M | 99214 | OFFICE/OP VISIT, EST PT, 2 KEY COMPONENTS: DETAILED HX: DETAILED EXAM; | $9 |
| Q1 | M | 99243 | OFFICE CONSULTATION, 3 KEY COMPONENTS: DETAILED HX; DETAILED EXAM; MED | ($2) |
| Q1 | M | 99213 | OFFICE/OP VISIT, EST PT, 2 KEY COMPONENTS: EXPAND PROB HX; EXPAND PROB | ($2) |
| Q1 | M | 95147 | PROFESSIONAL SVC, SUPERVISION, PROVISION, ANTIGENS, ALLERGEN IMMUNOTHER | ($2) |
| Q1 | M | 95115 | PROFESSIONAL SVC, ALLERGEN IMMUNOTHERAPY NON-PROVISION EXTRACTS; SINGLE | ($11) |
| Q1 | M | 95165 | PROFES SVC, SUPERVIS, PREPARA, PROVISION, ANTIGENS, ALLERGEN IMMUNOTHER | ($66) |
| Q1 | M | 95117 | PROFESSIONAL SVC, ALLERGEN IMMUNOTHERAPY NON-PROVISION EXTRACTS; 2+ INJ | ($77) |
| | M Total | | | ($141) |
| Q1 | P | Q7P | NASAL ANTI-INFLAMMATORY STEROIDS | $42 |
| Q1 | P | Z4B | LEUKOTRIENE RECEPTOR ANTAGONISTS | $6 |
| Q1 | P | Z2A | ANTIHISTAMINES | $5 |
| | P Total | | | $52 |
| | Q1 Total | | | |
| Q2 | A | 95004 | ALLERGY TESTS, PERCUTANEOUS, ALLERGENIC EXTRACTS, SPECIFY NUMBER | $10 |
| Q2 | A | 95010 | ALLERGY TESTS, PERCUTANEOUS, SEQUENTIAL/INCREMENTAL, SPECIFY NUMBER | $5 |

TABLE B3-continued

Allergy
Dates of service Jan. 1, 2003-Dec. 31, 2004 paid Dec. 31, 2004
Total Role Allergic Rhinitis ETGno 0332 by quintile
Each doctor with greater than or equal to 50 episodes
(3 doctors per Quintile, 4 in Q4)

| quintile | category | services | PROC_DESC | Total Cost Difference per Quintile Episode |
|---|---|---|---|---|
| Q2 | A | 95024 | ALLERGY TESTS, INTRADERMAL, ALLERGENIC EXTRACTS, SPECIFY NUMBER | $4 |
| Q2 | A | 95015 | ALLERGY TESTS, INTRADERMAL, SEQUENTIAL/INCREMENTAL, SPECIFY NUMBER | $4 |
| | A Total | | | $23 |
| Q2 | M | 95165 | PROFES SVC, SUPERVIS, PREPARA, PROVISION, ANTIGENS, ALLERGEN IMMUNOTHER | $12 |
| Q2 | M | 95115 | PROFESSIONAL SVC, ALLERGEN IMMUNOTHERAPY NON-PROVISION EXTRACTS; SINGLE | $7 |
| Q2 | M | 99242 | OFFICE CONSULTATION, 3 KEY COMPONENTS: EXPAND PROB FOCUS HX; EXPAND PROB | $5 |
| Q2 | M | 95145 | PROFES SVC, SUPERVIS, PREPARA, PROVISION, ANTIGEN, ALLERGEN IMMUNOTHERA | ($2) |
| Q2 | M | 95147 | PROFESSIONAL SVC, SUPERVISION, PROVISION, ANTIGENS, ALLERGEN IMMUNOTHER | ($2) |
| Q2 | M | 99214 | OFFICE/OP VISIT, EST PT, 2 KEY COMPONENTS: DETAILED HX; DETAILED EXAM; | ($5) |
| Q2 | M | 99213 | OFFICE/OP VISIT, EST PT, 2 KEY COMPONENTS: EXPAND PROB HX; EXPAND PROB | ($6) |
| Q2 | M | 99244 | OFFICE CONSULTATION, 3 KEY COMPONENTS: COMPREHENSIVE HX; COMPREHENSIVE E | ($6) |
| Q2 | M | 95117 | PROFESSIONAL SVC, ALLERGEN IMMUNOTHERAPY NON-PROVISION EXTRACTS; 2+ INJ | ($48) |
| | M Total | | | ($44) |
| Q2 | P | Z4B | LEUKOTRIENE RECEPTOR ANTAGONISTS | $2 |
| Q2 | P | Z2A | ANTIHISTAMINES | ($8) |
| Q2 | P | Q7P | NASAL ANTI-INFLAMMATORY STEROIDS | ($19) |
| | P Total | | | ($26) |
| | Q2 Total | | | |
| Q3 | A | 95015 | ALLERGY TESTS, INTRADERMAL, SEQUENTIAL/INCREMENTAL, SPECIFY NUMBER | ($1) |
| Q3 | A | 95024 | ALLERGY TESTS, INTRADERMAL, ALLERGENIC EXTRACTS, SPECIFY NUMBER | ($4) |
| Q3 | A | 95004 | ALLERGY TESTS, PERCUTANEOUS, ALLERGENIC EXTRACTS, SPECIFY NUMBER | ($11) |
| | A Total | | | ($16) |
| Q3 | M | 95117 | PROFESSIONAL SVC, ALLERGEN IMMUNOTHERAPY NON-PROVISION EXTRACTS; 2+ INJ | $41 |
| Q3 | M | 95165 | PROFES SVC, SUPERVIS, PREPARA, PROVISION, ANTIGENS, ALLERGEN IMMUNOTHER | $7 |
| Q3 | M | 95115 | PROFESSIONAL SVC, ALLERGEN IMMUNOTHERAPY NON-PROVISION EXTRACTS; SINGLE | $3 |
| Q3 | M | 99244 | OFFICE CONSULTATION, 3 KEY COMPONENTS: COMPREHENSIVE HX; COMPREHENSIVE E | ($2) |
| Q3 | M | 95145 | PROFES SVC, SUPERVIS, PREPARA, PROVISION, ANTIGEN, ALLERGEN IMMUNOTHERA | ($3) |
| Q3 | M | 95147 | PROFESSIONAL SVC, SUPERVISION. PROVISION. ANTIGENS, ALLERGEN IMMUNOTHER | ($3) |
| Q3 | M | 99214 | OFFICE/OP VISIT, EST PT, 2 KEY COMPONENTS: DETAILED HX; DETAILED EXAM; | ($14) |
| | M Total | | | $30 |
| Q3 | P | Z4B | LEUKOTRIENE RECEPTOR ANTAGONISTS | ($2) |
| Q3 | P | Q7P | NASAL ANTI-INFLAMMATORY STEROIDS | ($19) |
| Q3 | P | Z2A | ANTIHISTAMINES | ($21) |
| | P Total | | | ($42) |
| | Q3 Total | | | |
| Q4 | A | 95004 | ALLERGY TESTS, PERCUTANEOUS, ALLERGENIC EXTRACTS, SPECIFY NUMBER | $5 |
| Q4 | A | 95015 | ALLERGY TESTS, INTRADERMAL, SEQUENTIALINCREMENTAL, SPECIFY NUMBER | ($1) |

TABLE B3-continued

Allergy
Dates of service Jan. 1, 2003-Dec. 31, 2004 paid Dec. 31, 2004
Total Role Allergic Rhinitis ETGno 0332 by quintile
Each doctor with greater than or equal to 50 episodes
(3 doctors per Quintile, 4 in Q4)

| quintile | category | services | PROC_DESC | Total Cost Difference per Quintile Episode |
|---|---|---|---|---|
| Q4 | A | 95010 | ALLERGY TESTS, PERCUTANEOUS, SEQUENTIAL/INCREMENTAL, SPECIFY NUMBER | ($1) |
| Q4 | A | 95024 | ALLERGY TESTS, INTRADERMAL, ALLERGENIC EXTRACTS, SPECIFY NUMBER | ($2) |
| | A Total | | | $2 |
| Q4 | M | 99214 | OFFICE/OP VISIT, EST PT, 2 KEY COMPONENTS: DETAILED HX; DETAILED EXAM; | $17 |
| Q4 | M | 95147 | PROFESSIONAL SVC, SUPERVISION, PROVISION, ANTIGENS, ALLERGEN IMMUNOTHER | $5 |
| Q4 | M | 95145 | PROFES SVC, SUPERVIS, PREPARA, PROVISION. ANTIGEN, ALLERGEN IMMUNOTHERA | $1 |
| Q4 | M | 95115 | PROFESSIONAL SVC, ALLERGEN IMMUNOTHERAPY NON-PROVISION EXTRACTS; SINGLE | ($5) |
| Q4 | M | 95165 | PROFES SVC, SUPERVIS, PREPARA, PROVISION, ANTIGENS, ALLERGEN IMMUNOTHER | ($5) |
| Q4 | M | 95117 | PROFESSIONAL SVC, ALLERGEN IMMUNOTHERAPY NON-PROVISION EXTRACTS; 2+ INJ | ($7) |
| | M Total | | | $7 |
| Q4 | P | Z2A | ANTIHISTAMINES | $21 |
| Q4 | P | Z4B | LEUKOTRIENE RECEPTOR ANTAGONISTS | ($2) |
| Q4 | P | Q7P | NASAL ANTI-INFLAMMATORY STEROIDS | ($9) |
| | P Total | | | $9 |
| | Q4 Total | | | |
| Q5 | A | 95024 | ALLERGY TESTS, INTRADERMAL, ALLERGENIC EXTRACTS, SPECIFY NUMBER | $4 |
| Q5 | A | 95015 | ALLERGY TESTS, INTRADERMAL, SEQUENTIAL/INCREMENTAL, SPECIFY NUMBER | $1 |
| Q5 | A | 95004 | ALLERGY TESTS, PERCUTANEOUS, ALLERGENIC EXTRACTS, SPECIFY NUMBER | ($13) |
| | A Total | | | ($8) |
| Q5 | M | 95165 | PROFES SVC, SUPERVIS, PREPARA, PROVISION, ANTIGENS. ALLERGEN IMMUNOTHER | $39 |
| Q5 | M | 95117 | PROFESSIONAL SVC, ALLERGEN IMMUNOTHERAPY NON-PROVISION EXTRACTS; 2+ INJ | $14 |
| Q5 | M | 95145 | PROFES SVC, SUPERVIS, PREPARA, PROVISION, ANTIGEN, ALLERGEN IMMUNOTHERA | $8 |
| Q5 | M | 95147 | PROFESSIONAL SVC, SUPERVISION, PROVISION, ANTIGENS, ALLERGEN IMMUNOTHER | $7 |
| Q5 | M | 95115 | PROFESSIONAL SVC, ALLERGEN IMMUNOTHERAPY NON-PROVISION EXTRACTS; SINGLE | $5 |
| Q5 | M | 99243 | OFFICE CONSULTATION, 3 KEY COMPONENTS: DETAILED HX; DETAILED EXAM; MED | $2 |
| Q5 | M | 99211 | OFFICE/OP VISIT, EST PT, NOT REQUIRING PHYSICIAN PRESENCE, TYPICALLY 5 | $2 |
| Q5 | M | 99214 | OFFICE/OP VISIT, EST PT, 2 KEY COMPONENTS: DETAILED HX; DETAILED EXAM; | ($5) |
| Q5 | M | 99244 | OFFICE CONSULTATION, 3 KEY COMPONENTS: COMPREHENSIVE HX; COMPREHENSIVE E | ($6) |
| | M Total | | | $66 |
| Q5 | P | Q7P | NASAL ANTI-INFLAMMATORY STEROIDS | $25 |
| Q5 | P | Z2A | ANTIHISTAMINES | $7 |
| Q5 | P | Q6R | EYE ANTIHISTAMINES | $2 |
| Q5 | P | B3K | COUGH AND/OR COLD PREPARATIONS | $2 |
| Q5 | P | Q7E | NASAL ANTIHISTAMINE | $2 |
| Q5 | P | Z4B | LEUKOTRIENE RECEPTOR ANTAGONISTS | ($2) |
| | P Total | | | $36 |
| | Q5 Total | | | |

The invention claimed is:

1. A method of managing medical care performed by a group of medical practitioners, comprising the steps of:
compiling a plurality of episodes of care, each episode including services performed for that episode by medical practitioners;
selecting for analysis the episodes of care from the plurality of the episodes of care that correspond to a given condition;
preserving, with a computer, those services having a service value above a service value threshold defined such that only services that have a predetermined level of impact on the selected episodes of care are preserved;
sorting, with the computer, the medical practitioners into the two or more cost strata according to a predefined cost criterion, the sorting occurring such that each stratum includes at least one medical practitioner who provided at least one service performed in the selected episodes of care, the strata including a lower-cost practitioner stratum and higher-cost practitioner stratum;
listing the services associated with the medical practitioners for the selected episodes of care in each stratum with a service value being included with each of the services;
comparing the service values of the preserved services within the lower-cost practitioner stratum to the service values of corresponding preserved services within the higher-cost practitioner stratum; and
identifying the services which are cost drivers associated with the selected episodes of care that are at least partially responsible for differences in cost of the selected episodes of care between the lower-cost and higher-cost practitioner strata, the identification being performed by the computer and based on the step of comparing the preserved selected service values.

2. The method of managing medical care of claim 1, the step of preserving services comprising the steps of:
a) determining the service value threshold for each service by dividing the service values by the number of episodes in that stratum;
b) setting a minimum threshold for the service value threshold; and
c) preserving the services having a service value above the minimum threshold in a potential cost drivers table.

3. The method of managing medical care of claim 2, further comprising the step of generating a report comparing the service values for the services in the potential cost drivers table between the strata.

4. The method of managing medical care of claim 3, further comprising the step of listing services that differentiates the strata.

5. The method of managing medical care of claim 4, further comprising the step of providing the medical practitioners with a description of how to reduce the difference between the strata.

6. The method of claim 5, wherein the step of providing the medical practitioners with a description includes providing a medical practice pattern analysis report, comprising a table of a selected service value for a service for a plurality of strata, wherein the selected service value is greater than a threshold set to remove a plurality of other services having a lesser affect on a particular difference between the strata.

7. The method of claim 5, wherein the step of providing the medical practitioners with a description includes providing a medical method blueprint, comprising a plurality of cells, wherein each cell describes a treatment recommendation for a particular type of episode of care, wherein the recommendation is based on the medical practice pattern analysis that revealed a service as a driver for a difference between a plurality of stratified medical practitioners.

8. The method of managing medical care of claim 1, the service value being selected from the group consisting of the service cost total and the service utilization total.

9. The method of managing medical care of claim 1, the step of preserving services comprising the steps of:
a) determining an expected service value for each of the services in each strata; and
b) determining the service value threshold by subtracting the service values in each stratum from the expected service value and dividing the difference by the number of episodes in that stratum;
c) setting a minimum threshold for the service value threshold; and
d) preserving the services having a service value above the minimum threshold in a potential cost drivers table.

10. The method of managing medical care of claim 9, further comprising the step of generating a report that compares service values for the services in the potential cost drivers table between the strata.

11. The method of managing medical care of claim 10, further comprising the step of providing the medical practitioners with a description of how to reduce the difference between the strata.

12. The method of managing medical care of claim 9, the expected service value determination step comprising the steps of:
a) totaling the service values for each service for all the episodes to provide an analysis total of the service value;
b) determining an analysis average for the service values of each service by dividing the analysis total by the sum of the episodes in the analysis; and
c) multiplying the analysis average of the service value by the number of episodes in each stratum for each service to provide the expected service value.

13. The method of managing medical care of claim 1, wherein said step of compiling a plurality of episodes comprises:
a) tracking each service by episodes of care performed by a group of medical practitioners;
b) aggregating the services according to given characteristics; and
c) sorting the episodes of care into predefined conditions.

14. The method of managing medical care according to claim 13, wherein the cost criterion for separating the medical practitioners into strata further includes a criterion selected from the group consisting of the number of services performed, geographic region, specialty, type of practice, size of practice, and performance in another condition.

15. The method of managing medical care according to claim 1, the compiled episodes being selected from the group consisting of a complete episode treatment group, a combination of episode treatment groups, a subset of an episode treatment group, and a combination of subsets of a plurality of episode treatment groups.

16. The method of managing medical care according to claim 1, each of the medical practitioners being sorted into a separate stratum to provide an analysis comparing individual practitioners.

17. The method of managing medical care according to claim 16, wherein all the episodes related to a particular medical specialty are selected in the episode compiling step.

18. The method of managing medical care according to claim 1, wherein the medical practitioners having a particular service value are removed from the group.

19. The method of managing medical care according to claim 1, wherein the practitioners being attributed to the episodes are selected from the group consisting of the practitioner with the highest percentage cost of the episode, all practitioners in the episode responsible for costs that, in total, contributed more than a preset percentage of the total cost to the episode, all practitioners in the episode having professional fees that contributed more than a preset percentage of the total cost to the episode, a primary care physician associated with the episode, all practitioners with any involvement in the episode, the practitioner that performed a significant procedure in the episode, the practitioner that had the most face-to-face encounters with a patient associated with the episode, and combinations thereof.

20. The method of managing medical care according to claim 1, further comprising the step of analyzing the practice pattern of an individual practitioner in a total role drilldown analysis of a single medical condition.

21. The method of managing medical care according to claim 1, further comprising the step of analyzing the practice pattern of an individual practitioner in a total role meta-drilldown analysis including data from a plurality of medical conditions.

22. The method of managing medical care according to claim 1, the episodes being grouped into conditions by a grouper program and the compiled episodes being selected from the group consisting of a complete condition, a combination of conditions, a subset of a condition, and a combination of subsets of a plurality of conditions.

23. The method of managing medical care of claim 1, the step of preserving services comprising the steps of:
 a) equating the service value threshold for each service in each stratum to the selected service value in that stratum;
 b) setting the minimum threshold for the threshold parameter; and
 c) storing the services having a threshold parameter above the threshold in a potential cost drivers table.

24. The method of managing medical care of claim 1, the service value being the service cost total.

25. The method of managing medical care of claim 24, the step of preserving services comprising the steps of:
 a) determining the service value threshold for each service in each stratum by dividing the service cost total for all the episodes in that stratum by the service utilization total for all the episodes in that stratum;
 b) setting a minimum threshold for the service value threshold; and
 c) storing the services having a service value above the minimum threshold in a potential cost drivers table.

26. The method of managing medical care of claim 1, the step of preserving services comprising the steps of:
 a) determining an expected service value for each of the services; and
 b) determining the service value threshold by subtracting the service values from the expected service value;
 c) setting a minimum threshold for the service value threshold; and
 d) preserving the services having a service value above the minimum threshold in a potential cost drivers table.

27. The method of managing medical care of claim 26, further comprising the steps of:
 a) generating a report comparing the service values for the services in the potential cost drivers table between the strata;
 b) identifying the services that differentiate the strata; and
 c) providing the medical practitioners with a description of how to reduce the difference between the strata.

28. The method of managing medical care of claim 26, the service value being selected from the group consisting of the service cost total and the service utilization total.

29. The method of managing medical care of claim 26, the expected service value determination step comprising the steps of:
 a) totaling the service value for each service for all the episodes to provide an analysis total of the service value;
 b) determining an analysis average for the service value of each service by dividing the analysis total of the service value by the sum of the episodes in the analysis; and
 c) multiplying the analysis average of the service value by the number of episodes in each stratum for each service to provide the expected service value.

30. A method of managing medical care performed by a group of medical practitioners, comprising the steps of:
 compiling a plurality of episodes of care, each episode including a plurality of services performed for that episode by medical practitioners;
 selecting for analysis the episodes of care from the plurality of episodes of care that correspond to a given condition;
 sorting, with a computer, the medical practitioners into two or more cost strata according to a predefined cost criterion, the sorting occurring such that each stratum includes at least one medical practitioner who provided at least one service performed in the selected episodes of care, the strata including a lower-cost practitioner stratum and a higher-cost practitioner stratum;
 listing the services associated with the medical practitioners for the selected episodes of care in each stratum; and
 comparing, with the computer, an actual service value for the each service within the lower-cost and higher-cost practitioner strata to an expected service value for the service;
 identifying the services which are cost drivers associated with the selected episode of care that are at least partially responsible for differences in cost of the selected episodes of care between the lower-cost and higher-cost practitioner strata, the identification being performed by the computer and based on the step of comparing the actual service values within the lower-cost and higher-cost practitioner strata to the expected service value.

31. A method of managing medical care performed by a group of medical practitioners, comprising the steps of:
 compiling a plurality of episodes of care, each episode including services performed for that episode by medical practitioners;
 selecting for analysis the episodes of care from the plurality of episodes of care that correspond to a given condition;
 sorting, with a computer, the medical practitioners into the two or more cost strata according to a predefined cost criterion, the sorting occurring such that each stratum includes multiple medical practitioners who provided at least one service performed in the selected episode of care, the strata including a lower-cost practitioner stratum and a higher-cost practitioner stratum;
 associating, with the computer, each of the medical practitioners with all the services in the episodes that the medical practitioner had a role; and
 listing the services associated with the medical practitioners in each stratum;

comparing the service values of the selected services within the lower-cost practitioner stratum to the service values of corresponding services within the higher-cost practitioner stratum;

identifying the services which are cost drivers associated with the selected episodes of care that are at least partially responsible for differences in cost of the selected episodes of care between the lower-cost and higher-cost practitioner strata, the identification being performed by the computer and based on the step of comparing the service values.

\* \* \* \* \*

UNITED STATES PATENT AND TRADEMARK OFFICE
CERTIFICATE OF CORRECTION

| | | |
|---|---|---|
| PATENT NO. | : 7,818,181 B2 | Page 1 of 1 |
| APPLICATION NO. | : 11/392179 | |
| DATED | : October 19, 2010 | |
| INVENTOR(S) | : Robert A. Greene | |

It is certified that error appears in the above-identified patent and that said Letters Patent is hereby corrected as shown below:

On the Title page, Items (12) and (75) the inventor's name is erroneously spelled "Green." The proper spelling is "Greene."

Signed and Sealed this

Eighteenth Day of January, 2011

David J. Kappos
*Director of the United States Patent and Trademark Office*